(12) United States Patent
Kostrewa et al.

(10) Patent No.: US 6,391,605 B1
(45) Date of Patent: May 21, 2002

(54) MODIFIED PHYTASES

(75) Inventors: Dirk Kostrewa, Freiburg (DE); Luis Pasamontes, Trimbach (CH); Andrea Tomschy, Grenzach-Wyhlen (DE); Adolphus van Loon, Rheinfelden (CH); Kurt Vogel, Basel (CH); Markus Wyss, Liestal (CH)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/044,718

(22) Filed: Mar. 19, 1998

(30) Foreign Application Priority Data

Mar. 25, 1997 (EP) .............................................. 97810175

(51) Int. Cl.⁷ ............................ C12N 9/16; A61K 38/46
(52) U.S. Cl. ...................................... 435/196; 424/94.6
(58) Field of Search ......................... 435/196; 424/94.6

(56) References Cited

U.S. PATENT DOCUMENTS

| | | | |
|---|---|---|---|
| 5,436,156 | A | 7/1995 | Van Gorcom et al. |
| 5,443,979 | A | 8/1995 | Vanderbeke et al. |
| 5,863,533 | A | 1/1999 | Van Gorcom et al. |

FOREIGN PATENT DOCUMENTS

| | | |
|---|---|---|
| DE | 1 492 060 | 3/1969 |
| EP | 0 035 204 A2 | 9/1981 |
| EP | 299 108 B1 | 1/1989 |
| EP | 420 358 | 4/1991 |
| EP | 0 422 697 A1 | 4/1991 |
| EP | 619 369 A1 | 10/1994 |
| EP | 684 313 | 11/1995 |
| EP | 0 758 018 A1 | 2/1997 |
| EP | 747 483 | 5/1997 |
| EP | 0 897 010 A2 | 2/1999 |
| EP | 0 897 985 A2 | 2/1999 |
| EP | 98104858 | 2/1999 |
| WO | WO 91/14773 | 10/1991 |
| WO | 93/16175 | 8/1993 |
| WO | 94/03612 | 2/1994 |
| WO | WO 95/00662 | 1/1995 |
| WO | WO 98/54980 | 12/1998 |

OTHER PUBLICATIONS

Dox et al., J. Biol. Chem. 10:183–186 (1911).
Davis et al., Enzyme Microb. Technol. 5:377–382 (1983).
Lambrechts et al., Biotech, Lett. 14:61–66 (1992).
Shieh et al., Appl. Microbiol. 16:1348–1351 (1968).
Van Hartingsveldt et al., Gene 127:87–94 (1993).
Piddington et al., Gene 133:55–62 (1993).
Kraulis, J. Appl. Cryst. 24:946–950 (1991).
Merritt et al., Acta Cryst., 869–873 (1994).
Wodzinski et al., Advances in Applied Microbiology 42:263 (1996).
Mitchell et al., Microbiology 143:245–252 (1997).
Kostrewa et al., Nature Structural Biology 4:185–190 (1997).
Simons et al., Br. J. Nutr. 64:525–540 (1990).
Schoner et al., J. Anim. Physiol. a. Anim. Nutr. 66:248–255 (1991).
Jongbloed et al., J. Anim. Sci., 70:1159–1168 (1992).
Perney et al., Poultry Sci. 72:2106–2114 (1993).
Farrell et al., J. Anim. Physiol. a. Anim. Nutr. 69:278–283 (1993).
Broz et al., Br. Poultry Sci. 35:273–280 (1994).
Dungelhoef et al., Animal Feed Sci. Technol. 49:1–10 (1994).
Piccotti et al., J. Immunol. pp. 643–648 (1997).
Presentation by Dr. Luis Pasamontes at the Institute of Med. Microbiologie, Basel, Switzerland, Feb. 11, 1997.
Janecek, S., *Process Biochem.*, vol. 28, pp. 435–445 (1993).
Fersht, et al., *Curr. Opin. Struct. Biol.*, vol. 3, pp. 75–83 (1993).
Alber, T., *Annu. Rev. Biochem.*, vol. 58, pp. 765–798 (1989).
Matthews, B. W., *Curr. Opin. Struct. Biol.*, vol. 1, pp. 17–21 (1991).
Matthews, B. W., *Biochemistry*, vol. 26, No. 22, pp. 6885–6888 (1987).
Stuber et al., in *Immunological Methods*, eds. Lefkovits and Pernis, Academic Press Inc., vol. IV, pp 121–152 (1990).
Serrano, et al., *J. Mol. Biol.*, vol. 233, pp. 305–312 (1993).
Steipe, et al., *J. Mol. Biol.*, vol. 240, pp. 188–192 (1994).
Mullaney, et al., *Appl. Microbiol Biotechnol.*, vol. 35, pp. 611–614 (1991).
Lee C., et al., *Science*, vol. 239, pp. 1288–1291 (1988).
Conneely et al., *Biotechnology in the Feed Industry*, T.P. Lyons (ed.), Alltech Technical Publications, pp. 57–66 (1992).
Neurath et al., *The Proteins*, Academic Press, New York, p. 14 (1979).
Nunes, C., *Biol. Abstr.*, vol. 98 (10) Ref. No. 126043 (1994). Abstract.
Segueilha et al., *J. Fermentation and Bioeng.*, vol. 74 (1), pp. 7–11 (1992).
Yamada et al., *Agr. Biol. Chem.*, vol. 32, No. 10, pp. 1275–1282 (1968).
Pen et al., *Bio/Technology*, vol. 11, pp. 811–814 (1993).
Yamamoto et al., *Agr. Biol. Chem.*, vol. 36 (12), pp. 2097–2103 (1972).

(List continued on next page.)

*Primary Examiner*—Ponnathapu Achutamurthy
*Assistant Examiner*—Peter Tung
(74) *Attorney, Agent, or Firm*—Bryan Cave LLP

(57) ABSTRACT

A process for the production of a modified phytase with a desired property improved over the property of the corresponding unmodified phytase is disclosed, as well as modified phytases, polynucleotides encoding modified phytases, and animal feed including modified phytases.

24 Claims, 95 Drawing Sheets

OTHER PUBLICATIONS

Shieh et al., *Appl. Microbiol.,* vol. 16, No. 9, pp. 1348–1351 (1968).

Ullah, et al., "Identification of Active–Site Residues in *Aspergillus ficuum* Extracellular pH 2.5 Optimum Acid Phosphatase," *Biochemical and Biophysical Research Communications*, vol. 192, No. 2, pp. 754–759 (1993).

Derwent English language abstract of DE 1 492 060 (document B12) (1969).

Derwent accession no. XP–002120048, English language abstract of JP 09 065877 (1997).

Khare, et al., "Entrapment of Wheat Phytase in Polyacrylamide Gel and its Application in Soymilk Phytase Hydrolysis," *Biotechnol App. Biochem.*, vol. 19, pp. 193–198 (1994).

FIG. 1

```
  1 TCTGTAACCGATAGCGGACCGACTAGGCATCGTTGATCCACAATATCTCA    50

51 GACAATGCAACTCAGTCGAATATGAAGGGCTACAGCCAGCATTTAAATAC   100

101 GGCCGTCTAGGTCGGGCTCCGGGGATGAGGAGGAGCAGGCTCGTGTTCAT   150

151 TTCGGTCATGGCTTTTTTCACGGTCGCTCTTTCGCTTTATTACTTGCTAT   200
              M  A  F  F  T  V  A  L  S  L  Y  Y  L  L  S    15

201 CGAGgtgagatctctacaatatctgtctgcttagttgaattggtacttat   250
     R                                                   16

251 ctgtacagAGTCTCTGCTCAGGCCCCAGTGGTCCAGAATCATTCATGCAA   300
             V  S  A  Q  A  P  V  V  Q  N  H  S  C  N      30
                                    +

301 TACGGCGGACGGTGGATATCAATGCTTCCCCAATGTCTCTCATGTTTGGG   350
     T  A  D  G  G  Y  Q  C  F  P  N  V  S  H  V  W  G    47
                                 +

351 GTCAGTACTCGCCGTACTTCTCCATCGAGCAGGAGTCAGCTATCTCTGAG   400
     Q  Y  S  P  Y  F  S  I  E  Q  E  S  A  I  S  E       63

401 GACGTGCCTCATGGCTGTGAGGTTACCTTTGTGCAGGTGCTCTCGCGGCA   450
     D  V  P  H  G  C  E  V  T  F  V  Q  V  L  S  R  H    80

451 TGGGGCTAGGTATCCGACAGAGTCGAAGAGTAAGGCGTACTCGGGGTTGA   500
     G  A  R  Y  P  T  E  S  K  S  K  A  Y  S  G  L  I    97

501 TTGAAGCAATCCAGAAGAATGCTACCTCTTTTTGGGGACAGTATGCTTTT   550
     E  A  I  Q  K  N  A  T  S  F  W  G  Q  Y  A  F      113
                 +

551 CTGGAGAGTTATAACTATACCCTCGGCGCGGATGACTTGACTATCTTCGG   600
     L  E  S  Y  N  Y  T  L  G  A  D  D  L  T  I  F  G   130
              +

601 CGAGAACCAGATGGTTGATTCGGGTGCCAAGTTCTACCGACGGTATAAGA   650
     E  N  Q  M  V  D  S  G  A  K  F  Y  R  R  Y  K  N   147

651 ATCTCGCCAGGAAAAATACTCCTTTTATCCGTGCATCAGGGTCTGACCGT   700
     L  A  R  K  N  T  P  F  I  R  A  S  G  S  D  R     163
```

FIG. 4-1

```
701  GTCGTTGCGTCTGCGGAGAAGTTCATTAATGGATTTCGCAAGGCTCAGCT  750
      V  V  A  S  A  E  K  F  I  N  G  F  R  K  A  Q  L   180

751  CCACGACCATGGCTCCAAACGTGCTACGCCAGTTGTCAATGTGATTATCC  800
      H  D  H  G  S  K  R  A  T  P  V  V  N  V  I  I  P   197

801  CTGAAATCGATGGGTTTAACAACACCCTGGACCATAGCACGTGCGTATCT  850
      E  I  D  G  F  N  N  T  L  D  H  S  T  C  V  S      213
                                                 +

851  TTTGAGAATGATGAGCGGGCGGATGAAATTGAAGCCAATTTCACGGCAAT  900
      F  E  N  D  E  R  A  D  E  I  E  A  N  F  T  A  I   230
                                                       +

901  TATGGGACCTCCGATCCGCAAACGTCTGGAAAATGACCTCCCTGGCATCA  950
      M  G  P  P  I  R  K  R  L  E  N  D  L  P  G  I  K   247

951  AACTTACAAACGAGAATGTAATATATTTGATGGATATGTGCTCTTTCGAC 1000
      L  T  N  E  N  V  I  Y  L  M  D  M  C  S  F  D      263

1001 ACCATGGCGCGCACCGCCCACGGAACCGAGCTGTCTCCATTTTGTGCCAT 1050
      T  M  A  R  T  A  H  G  T  E  L  S  P  F  C  A  I   280

1051 CTTCACTGAAAAGGAGTGGCTGCAGTACGACTACCTTCAATCTCTATCAA 1100
      F  T  E  K  E  W  L  Q  Y  D  Y  L  Q  S  L  S  K   297

1101 AGTACTACGGCTACGGTGCCGGAAGCCCCCTTGGCCCAGCTCAGGGAATT 1150
      S  T  T  A  T  V  P  E  A  P  L  A  Q  L  R  E  F
      Y  Y  G  Y  G  A  G  S  P  L  G  P  A  Q  G  I     313

1151 GGCTTCACCAACGAGCTGATTGCCCGACTAACGCAATCGCCCGTCCAGGA 1200
      G  F  T  N  E  L  I  A  R  L  T  Q  S  P  V  Q  D   330

1201 CAACACAAGCACCAACCACACTCTAGACTCGAACCCAGCCACATTTCCGC 1250
      N  T  S  T  N  H  T  L  D  S  N  P  A  T  F  P  L   347
         +           +

1251 TCGACAGGAAGCTCTACGCCGACTTCTCCCACGACAATAGCATGATATCG 1300
      D  R  K  L  Y  A  D  F  S  H  D  N  S  M  I  S      363

1301 ATATTCTTCGCCATGGGTCTGTACAACGGCACCCAGCCGCTGTCAATGGA 1350
      I  F  F  A  M  G  L  Y  N  G  T  Q  P  L  S  M  D   380
                                +
```

FIG. 4-2

```
1351  TTCCGTGGAGTCGATCCAGGAGATGGACGGTTACGCGGCGTCTTGGACTG  1400
       S  V  E  S  I  Q  E  M  D  G  Y  A  A  S  W  T  V   397

1401  TTCCGTTTGGTGCGAGGGCTTACTTTGAGCTCATGCAGTGCGAGAAGAAG  1450
       P  F  G  A  R  A  Y  F  E  L  M  Q  C  E  K  K     413

1451  GAGCCGCTTGTGCGGGTATTAGTGAATGATCGCGTTGTTCCTCTTCATGG  1500
       E  P  L  V  R  V  L  V  N  D  R  V  V  P  L  H  G  430

1501  CTGCGCAGTTGACAAGTTTGGACGGTGCACTTTGGACGATTGGGTAGAGG  1550
       C  A  V  D  K  F  G  R  C  T  L  D  D  W  V  E  G   447

1551  GCTTGAATTTTGCAAGGAGCGGCGGGAACTGGAAGACTTGTTTTACCCTA  1600
       L  N  F  A  R  S  G  G  N  W  K  T  C  F  T  L     463

1601  TAAAGGGCGTTTGCTCATTCATAAGTGTTGTGCAGGTATAGGAAGGTTAG  1650

1651  GGAATTAGCTGTTTGGCTTTACTCTTATTAGACCAAGAATGATTTGTTTG  1700
1701  TTCTCAAGGCCTTCTAGCATATCGTCAAGTGGGATAAATCACCTATCCTC  1750
1751  CATGTGTAGGTGAACCCGCTCTTGCATCAACCTCTTGTGTTTCAGAGTAG  1800
1801  TTTCACCAAACATATCCTCGTGTCCTCTCTTCTGCTCTTCGGTCTCATAT  1850
1851  TACACTGTTCTCTATCTATATCGTCAACAAAACTACCACCCAAACACCAA  1900
1901  ATGTCACACTTTCCAGCACGAAATTTCTTCG  1931
```

FIG. 4-3

```
  1  TTCCACGCTGAAAGCCTGACTGCGATTTCCAAGCTGCATGCAGGCTGCTC    50
 51  AACTGCCTGCTTATCTTCATCAGACGCAGATACACAACCTGGTCTGTAGA   100
101  TGCACCCATGACGGACGAACGCACCGCTCTCTTGGCCTCCAGGGACCCGG   150
151  AGGTCGAGGGCGATGAGGTCGCGCCCTCGACGGCCTCCCAGTCCCTGTTG   200
201  CAGTTGAGATCTCGCTGCGAACGTCGACCGCAGATATGGTTGTCTTCGAC   250
251  GTTTTCTCGCCTTCGAGGAAGAATTGCTGCTGTGACGATGAGTCTGTTGT   300
                                           M  S  L  L     5

301  TGCTGGTGCTGTCCGGCGGGTTGGTCGCGTTATAgtatgctccttctctc   350
      L  V  L  S  G  G  L  V  A  L  Y                    16

351  tggtcatattgttttctgctaacgttctcataattgaagTGTCTCAAGAA   400
                                            V  S  R  N    20

401  ATCCGCATGTTGATAGCCACTCTTGCAATACAGTGGAAGGAGGGTATCAG   450
      P  H  V  D  S  H  S  C  N  T  V  E  G  G  Y  Q     36

451  TGTCGTCCAGAAATCTCCCACTCCTGGGGCCAGTATTCTCCATTCTTCTC   500
      C  R  P  E  I  S  H  S  W  G  Q  Y  S  P  F  F  S  53

501  CCTGGCAGACCAGTCGGAGATCTCGCCAGATGTCCCACAGAACTGCAAGA   550
      L  A  D  Q  S  E  I  S  P  D  V  P  Q  N  C  K  I  70

551  TTACGTTTGTCCAGCTGCTTTCTCGTCACGGCGCTAGATACCCTACGTCT   600
      T  F  V  Q  L  L  S  R  H  G  A  R  Y  P  T  S     86

601  TCCAAGACGGAGCTGTATTCGCAGCTGATCAGTCGGATTCAGAAGACGGC   650
      S  K  T  E  L  Y  S  Q  L  I  S  R  I  Q  K  T  A  103

651  GACTGCGTACAAAGGCTACTATGCCTTCTTGAAAGACTACAGATACCAGC   700
      T  A  Y  K  G  Y  Y  A  F  L  K  D  Y  R  Y  Q  L  120

701  TGGGAGCGAACGACCTGACGCCCTTTGGGGAAAACCAGATGATCCAGTTG   750
      G  A  N  D  L  T  P  F  G  E  N  Q  M  I  Q  L    136
```

FIG. 5-1

```
 751  GGCATCAAGTTTTATAACCATTACAAGAGTCTCGCCAGGAATGCCGTCCC   800
       G  I  K  F  Y  N  H  Y  K  S  L  A  R  N  A  V  P   153

801  ATTCGTTCGTTGCTCCGGCTCTGATCGGGTCATTGCCTCGGGGAGACTTT   850
       F  V  R  C  S  G  S  D  R  V  I  A  S  G  R  L  F   170

851  TCATCGAAGGTTTCCAGAGCGCCAAAGTGCTGGATCCTCATTCAGACAAG   900
       I  E  G  F  Q  S  A  K  V  L  D  P  H  S  D  K      186

901  CATGACGCTCCTCCCACGATCAACGTGATCATCGAGGAGGGTCCGTCCTA   950
       H  D  A  P  P  T  I  N  V  I  I  E  E  G  P  S  Y   203

951  CAATAACACGCTCGACACCGGCAGCTGTCCAGTCTTTGAGGACAGCAGCG  1000
       N  N  T  L  D  T  G  S  C  P  V  F  E  D  S  S  G   220
       +

1001  GGGGACATGACGCACAGGAAAAGTTCGCAAAGCAATTCGCACCAGCTATC  1050
       G  H  D  A  Q  E  K  F  A  K  Q  F  A  P  A  I      236

1051  CTGGAAAAGATCAAGGACCATCTTCCCGGCGTGGACCTGGCCGTGTCGGA  1100
       L  E  K  I  K  D  H  L  P  G  V  D  L  A  V  S  D   253

1101  TGTACCGTACTTGATGGACTTGTGTCCGTTTGAGACCTTGGCTCGCAACC  1150
       V  P  Y  L  M  D  L  C  P  F  E  T  L  A  R  N  H   270
                                                     +

1151  ACACAGACACGCTGTCTCCGTTCTGCGCTCTTTCCACGCAAGAGGAGTGG  1200
       T  D  T  L  S  P  F  C  A  L  S  T  Q  E  E  W      286

1201  CAAGCATATGACTACTACCAAAGTCTGGGGAAATACTATGGCAATGGCGG  1250
       Q  A  Y  D  Y  Y  Q  S  L  G  K  Y  Y  G  N  G  G   303

1251  GGGTAACCCGTTGGGGCCAGCCCAAGGCGTGGGGTTTGTCAACGAGTTGA  1300
       G  N  P  L  G  P  A  Q  G  V  G  F  V  N  E  L  I   320

1301  TTGCTCGCATGACCCATAGCCCTGTCCAGGACTACACCACGGTCAACCAC  1350
       A  R  M  T  H  S  P  V  Q  D  Y  T  T  V  N  H      336
                                                     +

1351  ACTCTTGACTCGAATCCGGCGACATTCCCTTTGAACGCGACGCTGTACGC  1400
       T  L  D  S  N  P  A  T  F  P  L  N  A  T  L  Y  A   353
                                              +
```

FIG. 5-2

```
1401  AGATTTCAGCCACGACAACACAATGACGTCAATTTTCGCGGCCTTGGGCC  1450
       D  F  S  H  D  N  T  M  T  S  I  F  A  A  L  G  L    370

1451  TGTACAACGGGACCGCGAAGCTGTCCACGACCGAGATCAAGTCCATTGAA  1500
       Y  N  G  T  A  K  L  S  T  T  E  I  K  S  I  E       386
       +

1501  GAGACGGACGGCTACTCGGCGGCGTGGACCGTTCCGTTCGGGGGGCGAGC  1550
       E  T  D  G  Y  S  A  A  W  T  V  P  F  G  G  R  A    403

1551  CTATATCGAGATGATGCAGTGTGATGATTCGGATGAGCCAGTCGTTCGGG  1600
       Y  I  E  M  M  Q  C  D  D  S  D  E  P  V  V  R  V    420

1601  TGCTGGTCAACGACCGGGTGGTGCCACTGCATGGCTGCGAGGTGGACTCC  1650
       L  V  N  D  R  V  V  P  L  H  G  C  E  V  D  S       436

1651  CTGGGGCGATGCAAACGAGACGACTTTGTCAGGGGACTGAGTTTTGCGCG  1700
       L  G  R  C  K  R  D  D  F  V  R  G  L  S  F  A  R    453

1701  ACAGGGTGGGAACTGGGAGGGGTGTTACGCTGCTTCTGAGTAGGTTTATT  1750
       Q  G  G  N  W  E  G  C  Y  A  A  S  E  *             466

1751  CAGCGAGTTTCGACCTTTCTATCCTTCAAACACTGCACAAAGACACACTG  1800
1801  CATGAAATGGTAACAGGCCTGGAGCGTTTTAGAAGGAAAAAGTT        1845
```

FIG. 5-3

```
  1  AGATTCAACGACGGAGGAATCGCAACCCTAATTGTCGGTATCATGGTGAC   50
                                                 M  V  T    3

51  TCTGACTTTCCTGCTTTCGGCGGCGTATCTGCTTTCTGGgtgagtggctt  100
      L  T  F  L  L  S  A  A  Y  L  L  S  G                 16

101  ggatctattgctcggatagggctgtggtgctgattctgaaacggagTAGA  150
                                                     R     17

151  GTGTCTGCGGCACCTAGTTCTGCTGGCTCCAAGTCCTGCGATACGGTAGA  200
      V  S  A  A  P  S  S  A  G  S  K  S  C  D  T  V  D    34

201  CCTCGGGTACCAGTGCTCCCCTGCGACTTCTCATCTATGGGCCAGTACT   250
      L  G  Y  Q  C  S  P  A  T  S  H  L  W  G  Q  Y  S    51

251  CGCCATTCTTTTCGCTCGAGGACGAGCTGTCCGTGTCGAGTAAGCTTCCC  300
      P  F  F  S  L  E  D  E  L  S  V  S  S  K  L  P       67

301  AAGGATTGCCGGATCACCTTGGTACAGGTGCTATCGCGCCATGGAGCGCG  350
      K  D  C  R  I  T  L  V  Q  V  L  S  R  H  G  A  R    84

351  GTACCCAACCAGCTCCAAGAGCAAAAAGTATAAGAAGCTTGTGACGGCGA  400
      Y  P  T  S  S  K  S  K  K  Y  K  K  L  V  T  A  I   101

401  TCCAGGCCAATGCCACCGACTTCAAGGGCAAGTTTGCCTTTTTGAAGACG  450
      Q  A  N  A  T  D  F  K  G  K  F  A  F  L  K  T      117
         +

451  TACAACTATACTCTGGGTGCGGATGACCTCACTCCCTTTGGGGAGCAGCA  500
      Y  N  Y  T  L  G  A  D  D  L  T  P  F  G  E  Q  Q   134
         +

501  GCTGGTGAACTCGGGCATCAAGTTCTACCAGAGGTACAAGGCTCTGGCGC  550
      L  V  N  S  G  I  K  F  Y  Q  R  Y  K  A  L  A  R   151

551  GCAGTGTGGTGCCGTTTATTCGCGCCTCAGGCTCGGACCGGGTTATTGCT  600
      S  V  V  P  F  I  R  A  S  G  S  D  R  V  I  A     167
```

FIG. 6-1

```
601  TCGGGAGAGAAGTTCATCGAGGGGTTCCAGCAGGCGAAGCTGGCTGATCC  650
      S  G  E  K  F  I  E  G  F  Q  Q  A  K  L  A  D  P   184

651  TGGCGCGACGAACCGCGCCGCTCCGGCGATTAGTGTGATTATTCCGGAGA  700
      G  A  T  N  R  A  A  P  A  I  S  V  I  I  P  E  S   201

701  GCGAGACGTTCAACAATACGCTGGACCACGGTGTGTGCACGAAGTTTGAG  750
      E  T  F  N  N  T  L  D  H  G  V  C  T  K  F  E      217
               +

751  GCGAGTCAGCTGGGAGATGAGGTTGCGGCCAATTTCACTGCGCTCTTTGC  800
      A  S  Q  L  G  D  E  V  A  A  N  F  T  A  L  F  A   234
                                 +

801  ACCCGACATCCGAGCTCGCGCCGAGAAGCATCTTCCTGGCGTGACGCTGA  850
      P  D  I  R  A  R  A  E  K  H  L  P  G  V  T  L  T   251

851  CAGACGAGGACGTTGTCAGTCTAATGGACATGTGTTCGTTTGATACGGTA  900
      D  E  D  V  V  S  L  M  D  M  C  S  F  D  T  V      267

901  GCGCGCACCAGCGACGCAAGTCAGCTGTCACCGTTCTGTCAACTCTTCAC  950
      A  R  T  S  D  A  S  Q  L  S  P  F  C  Q  L  F  T   284

951  TCACAATGAGTGGAAGAAGTACAACTACCTTCAGTCCTTGGGCAAGTACT 1000
      H  N  E  W  K  K  Y  N  Y  L  Q  S  L  G  K  Y  Y   301

1001 ACGGCTACGGCGCAGGCAACCCTCTGGGACCGGCTCAGGGGATAGGGTTC 1050
      G  Y  G  A  G  N  P  L  G  P  A  Q  G  I  G  F      317

1051 ACCAACGAGCTGATTGCCCGGTTGACTCGTTCGCCAGTGCAGGACCACAC 1100
      T  N  E  L  I  A  R  L  T  R  S  P  V  Q  D  H  T   334

1101 CAGCACTAACTCGACTCTAGTCTCCAACCCGGCCACCTTCCCGTTGAACG 1150
      S  T  N  S  T  L  V  S  N  P  A  T  F  P  L  N  A   351
         +                                         +

1151 CTACCATGTACGTCGACTTTTCACACGACAACAGCATGGTTTCCATCTTC 1200
      T  M  Y  V  D  F  S  H  D  N  S  M  V  S  I  F      367

1201 TTTGCATTGGGCCTGTACAACGGCACTGAACCCTTGTCCCGGACCTCGGT 1250
      F  A  L  G  L  Y  N  G  T  E  P  L  S  R  T  S  V   384
                      +
```

FIG. 6-2

```
1251  GGAAAGCGCCAAGGAATTGGATGGGTATTCTGCATCCTGGGTGGTGCCTT  1300
       E  S  A  K  E  L  D  G  Y  S  A  S  W  V  V  P  F   401

1301  TCGGCGCGCGAGCCTACTTCGAGACGATGCAATGCAAGTCGGAAAAGGAG  1350
       G  A  R  A  Y  F  E  T  M  Q  C  K  S  E  K  E     417

1351  CCTCTTGTTCGCGCTTTGATTAATGACCGGGTTGTGCCACTGCATGGCTG  1400
       P  L  V  R  A  L  I  N  D  R  V  V  P  L  H  G  C   434

1401  CGATGTGGACAAGCTGGGGCGATGCAAGCTGAATGACTTTGTCAAGGGAT  1450
       D  V  D  K  L  G  R  C  K  L  N  D  F  V  K  G  L   451

1451  TGAGTTGGGCCAGATCTGGGGGCAACTGGGGAGAGTGCTTTAGTTGAGAT  1500
       S  W  A  R  S  G  G  N  W  G  E  C  F  S  *        465

1501  GTCATTGTTATGCTATACTCCAATAGACCGTTGCTTAGCCATTCACTTCA  1550
1551  CTTTGCTCGAACCGCCTGCCG                               1571
```

FIG. 6-3

```
  1 ACGTCCCAGGTCGGGGACTACATCCGCTATGTGGTCCTCTACTTCGTCGG   50

51 AAGAATATACTGTCTCTTGTGGCTACCATGGGGGTTTTCGTCGTTCTATT  100
                            M  G  V  F  V  V  L  L      8

101 ATCTATCGCGACTCTGTTCGGCAGgtatgtgcaccgctctaggttcaact  150
     I  Y  R  D  S  V  R  Q                             16

151 cgcctggtaactgacaaacagcacagCACATCGGGCACTGCGCTGGGCCC  200
                              T  S  G  T  A  L  G  P    24

201 CCGTGGAAATCACAGCGACTGCACCTCAGTCGACCGGGGGTATCAATGCT  250
     R  G  N  H  S  D  C  T  S  V  D  R  G  Y  Q  C  F  41
        +

251 TCCCTGAGCTCTCCCATAAATGGGGTCTCTACGCGCCCTATTTCTCCCTC  300
     P  E  L  S  H  K  W  G  L  Y  A  P  Y  F  S  L     57

301 CAGGATGAATCTCCGTTTCCTCTGGACGTCCCGGATGACTGCCACATCAC  350
     Q  D  E  S  P  F  P  L  D  V  P  D  D  C  H  I  T  74

351 CTTTGTGCAGGTGCTGGCCCCGACATGGAGCGCGGTCTCCAACCGATAGCA  400
     F  V  Q  V  L  A  R  H  G  A  R  S  P  T  D  S  K  91

401 AGACAAAGGCGTATGCCGCGACTATTGCAGCCATCCAGAAGAATGCCACC  450
     T  K  A  Y  A  A  T  I  A  A  I  Q  K  N  A  T    107
                                              +

451 GCGTTGCCGGGCAAATACGCCTTCCTGAAGTCGTACAATTACTCCATGGG  500
     A  L  P  G  K  Y  A  F  L  K  S  Y  N  Y  S  M  G 124
                                         +

501 CTCCGAGAACCTGAACCCCTTCGGGCGGAACCAACTGCAAGATCTGGGCG  550
     S  E  N  L  N  P  F  G  R  N  Q  L  Q  D  L  G  A 141

551 CCCAGTTCTACCGTCGCTACGACACCCTCACCCGGCACATCAACCCTTTC  600
     Q  F  Y  R  R  Y  D  T  L  T  R  H  I  N  P  F    157

601 GTCCGGGCCGCGGATTCCTCCCGCGTCCACGAATCAGCCGAGAAGTTCGT  650
     V  R  A  A  D  S  S  R  V  H  E  S  A  E  K  F  V 174
```

FIG. 7-1

```
651  CGAGGGCTTCCAAAACGCCCGCCAAGGCGATCCTCACGCCAACCCTCACC  700
      E  G  F  Q  N  A  R  Q  G  D  P  H  A  N  P  H  Q    191

701  AGCCGTCGCCGCGCGTGGATGTAGTCATCCCCGAAGGCACCGCCTACAAC  750
      P  S  P  R  V  D  V  V  I  P  E  G  T  A  Y  N      207
                                                    +

751  AACACGCTCGAGCACAGCATCTGCACCGCCTTCGAGGCCAGCACCGTCGG  800
      N  T  L  E  H  S  I  C  T  A  F  E  A  S  T  V  G   224

801  CGACGCCGCGGCAGACAACTTCACTGCCGTGTTCGCGCCGGCGATCGCCA  850
      D  A  A  A  D  N  F  T  A  V  F  A  P  A  I  A  K   241
                  +

851  AGCGTCTGGAGGCCGATCTGCCCGGCGTGCAGCTGTCCGCCGACGACGTG  900
      R  L  E  A  D  L  P  G  V  Q  L  S  A  D  D  V      257

901  GTCAATCTGATGGCCATGTGTCCGTTCGAGACGGTCAGCCTGACCGACGA  950
      V  N  L  M  A  M  C  P  F  E  T  V  S  L  T  D  D   274

951  CGCGCACACGCTGTCGCCGTTCTGCGACCTCTTCACCGCCGCCGAGTGGA  1000
      A  H  T  L  S  P  F  C  D  L  F  T  A  A  E  W  T   291

1001 CGCAGTACAACTACCTGCTCTCGCTGGACAAGTACTACGGCTACGGCGGC  1050
      Q  Y  N  Y  L  L  S  L  D  K  Y  Y  G  Y  G  G      307

1051 GGCAATCCGCTGGGCCCCGTGCAGGGCGTGGGCTGGGCGAACGAGCTGAT  1100
      G  N  P  L  G  P  V  Q  G  V  G  W  A  N  E  L  I   324

1101 CGCGCGGCTGACGCGCTCCCCCGTCCACGACCACACCTGCGTCAACAACA  1150
      A  R  L  T  R  S  P  V  H  D  H  T  C  V  N  N  T   341
                                                    +

1151 CCCTCGACGCCAACCCCGGCCACCTTCCCGCTGAACGCCACCCTCTACGCG  1200
      L  D  A  N  P  A  T  F  P  L  N  A  T  L  Y  A      357
                              +

1201 GACTTTTCGCACGACAGTAACCTGGTGTCGATCTTCTGGGCGCTGGGTCT  1250
      D  F  S  H  D  S  N  L  V  S  I  F  W  A  L  G  L   374
```

FIG. 7-2

```
1251 GTACAACGGCACCAAGCCCCTGTCGCAGACCACCGTGGAGGATATCACCC 1300
      Y  N  G  T  K  P  L  S  Q  T  T  V  E  D  I  T  R   391
      +

1301 GGACGGACGGGTACGCGGCCGCCTGGACGGTGCCGTTTGCCGCCCGCGCC 1350
       T  D  G  Y  A  A  A  W  T  V  P  F  A  A  R  A    407

1351 TACATCGAGATGATGCAGTGTCGCGCGGAGAAGCAGCCGCTGGTGCGCGT 1400
      Y  I  E  M  M  Q  C  R  A  E  K  Q  P  L  V  R  V   424

1401 GCTGGTCAACGACCGTGTCATGCCGCTGCACGGCTGCGCGGTGGATAATC 1450
      L  V  N  D  R  V  M  P  L  H  G  C  A  V  D  N  L   441

1451 TGGGCAGGTGTAAACGGGACGACTTTGTGGAGGGACTGAGCTTTGCGCGG 1500
       G  R  C  K  R  D  D  F  V  E  G  L  S  F  A  R    457

1501 GCAGGAGGGAACTGGGCCGAGTGTTTCTGATGTACATGCTGTAGTTAGCT 1550
      A  G  G  N  W  A  E  C  F  *                        466

1551 TTGAGTCCTGAGGTACC                                    1567
```

FIG. 7-3

```
HEADER    PHOSOHOMONOESTERASE                                               1DIK   1
COMPND    PHYTASE (E.C.3.1.3.8)                                             1DIK   2
SOURCE    (Aspergillus ficuum)                                              1DIK   3
                                                                            1DIK   4
                                                                            1DIK   5
REMARK   2 RESOLUTION. 2.5 ANGSTROMS.                                       1DIK   6
REMARK   3                                                                  1DIK   7
REMARK   3 REFINEMENT.                                                      1DIK   8
REMARK   3    PROGRAM                     X-PLOR                            1DIK   9
REMARK   3    AUTHORS                     BRUENGER, A.T.                    1DIK  10
REMARK   3    R VALUE                     0.155                             1DIK  11
REMARK   3    FREE R VALUE                0.211                             1DIK  12
REMARK   3    RMSD BOND DISTANCES         0.009   ANGSTROMS                 1DIK  13
REMARK   3    RMSD BOND ANGLES            1.5     DEGREES                   1DIK  14
REMARK   3                                                                  1DIK  15
REMARK   3    NUMBER OF REFLECTIONS       17206                             1DIK  16
REMARK   3    RESOLUTION RANGE     20.0 -2.5   ANGSTROMS                    1DIK  17
REMARK   3    DATA CUTOFF                 0.      SIGMA (F)                 1DIK  18
REMARK   3                                                                  1DIK  19
REMARK   3    NUMBER OF PROTEIN ATOMS                       3369            1DIK  20
REMARK   3    NUMBER OF SOLVENT ATOMS                        115            1DIK  21
REMARK   3    NUMBER OF SULFATE ATOMS                          5            1DIK  22
REMARK   3                                                                  1DIK  23
REMARK   3 CONVENTIONAL RESTRAINED POSITIONAL AND TEMPERATURE FACTOR        1DIK  24
REMARK   3 REFINEMENT.                                                      1DIK  25
REMARK   3 THE STEREOCHEMICAL PARAMETERS FROM ENGH & HUBER WERE USED.       1DIK  26
REMARK   4                                                                  1DIK  27
REMARK   5                                                                  1DIK  42
REMARK   5 THE ASYMMETRIC UNIT OF THE CRYSTAL CONTAINS OF ONE               1DIK  43
REMARK   5 DEGLYCOSYLATED PROTEIN MONOMER.                                  1DIK  44
REMARK   6                                                                  1DIK  45
REMARK   6 THE AMINO ACIDS 249 - 252 ARE COMPLETELY DISORDERED.             1DIK  46
REMARK   6 THE FOLLOWING AMINO ACID SIDE CHAINS ARE DISORDERED:             1DIK  47
REMARK   6 GLU  43, LYS 70, GLU 77, GLN 81, LYS 94, GLN 392, GLN 395,       1DIK  48
REMARK   6 ARG 428                                                          1DIK  49
REMARK   6 THE ELECTRON DENSITY OF THE SULFATE IS NOT WELL DEFINED.         1DIK  50
SEQRES   1    434  SER CYS ASP THR VAL ASP GLN GLY TYR GLN CYS PHE SER     1DIK  51
SEQRES   2    434  GLU THR SER HIS LEU TRP GLY GLN TYR ALA PRO PHE PHE     1DIK  52
SEQRES   3    434  SER LEU ALA ASN GLU SER VAL ILE SER PRO GLU VAL PRO     1DIK  53
SEQRES   4    434  ALA GLY CYS ARG VAL THR PHE ALA GLN VAL LEU SER ARG     1DIK  54
SEQRES   5    434  HIS GLY ALA ARG TYR PRO THR ASP SER LYS GLY LYS LYS     1DIK  55
SEQRES   6    434  TYR SER ALA LEU ILE GLU GLU ILE GLN GLN ASN ALA THR     1DIK  56
SEQRES   7    434  THR PHE ASP GLY LYS TYR ALA PHE LEU LYS THR TYR ASN     1DIK  57
SEQRES   8    434  TYR SER LEU GLY ALA ASP ASP LEU THR PRO PHE GLY GLU     1DIK  58
SEQRES   9    434  GLN GLU LEU VAL ASN SER GLY ILE LYS PHE TYR GLN ARG     1DIK  59
SEQRES  10    434  TYR GLU SER LEU THR ARG ASN ILE VAL PRO PHE ILE ARG     1DIK  60
SEQRES  11    434  SER SER GLY SER SER ARG VAL ILE ALA SER GLY LYS LYS     1DIK  61
SEQRES  12    434  PHE ILE GLU GLY PHE GLN SER THR LYS LEU LYS ASP PRO     1DIK  62
SEQRES  13    434  ARG ALA GLN PRO GLY GLN SER SER PRO LYS ILE ASP VAL     1DIK  63
SEQRES  14    434  VAL ILE SER GLU ALA SER SER SER ASN ASN THR LEU ASP     1DIK  64
SEQRES  15    434  PRO GLY THR CYS THR VAL PHE GLU ASP SER GLU LEU ALA     1DIK  65
SEQRES  16    434  ASP THR VAL GLU ALA ASN PHE THR ALA THR PHE VAL PRO     1DIK  66
SEQRES  17    434  SER ILE ARG GLN ARG LEU GLU ASN ASP LEU SER GLY VAL     1DIK  67
SEQRES  18    434  THR LEU THR ASP THR GLU VAL THR TYR LEU MET ASP MET     1DIK  68
SEQRES  19    434  CYS SER PHE ASP THR ILE SER THR THR LYS LEU SER PRO     1DIK  69
SEQRES  20    434  PHE CYS ASP LEU PHE THR HIS ASP GLU TRP ILE ASN TYR     1DIK  70
SEQRES  21    434  ASP TYR LEU GLN SER LEU LYS LYS TYR TYR GLY HIS GLY     1DIK  71
SEQRES  22    434  ALA GLY ASN PRO LEU GLY PRO THR GLN GLY VAL GLY TYR     1DIK  72
SEQRES  23    434  ALA ASN GLU LEU ILE ALA ARG LEU THR HIS SER PRO VAL     1DIK  73
SEQRES  24    434  HIS ASP ASP THR SER SER ASN HIS THR LEU ASP SER SER     1DIK  74
SEQRES  25    434  PRO ALA THR PHE PRO LEU ASN SER THR LEU TYR ALA ASP     1DIK  75
SEQRES  26    434  PHE SER HIS ASP ASN GLY ILE ILE SER ILE LEU PHE ALA     1DIK  76
SEQRES  27    434  LEU GLY LEU TYR ASN GLY THR LYS PRO LEU SER THR THR     1DIK  77
SEQRES  28    434  THR VAL GLU ASN ILE THR GLN THR ASP GLY PHE SER SER     1DIK  78
SEQRES  29    434  ALA TRP THR VAL PRO PHE ALA SER ARG LEU TYR VAL GLU     1DIK  79
SEQRES  30    434  MET MET GLN CYS GLN ALA GLU GLN GLU PRO LEU VAL ARG     1DIK  80
```

FIG. 8-1

```
SEQRES  31    434  VAL LEU VAL ASN ASP ARG VAL VAL PRO LEU HIS GLY CYS      1DIK  81
SEQRES  32    434  PRO VAL ASP ALA LEU GLY ARG CYS THR ARG ASP SER PHE      1DIK  82
SEQRES  33    434  VAL ARG GLY LEU SER PHE ALA ARG SER GLY GLY ASP TRP      1DIK  83
SEQRES  34    434  ALA GLU CYS PHE ALA                                      1DIK  84
HET     SO4  201      5                                                     1DIK  85
FORMUL  2    SO4     O4 S1                                                  1DIK  86
FORMUL  3    HOH   *115 (H2 O1)                                             1DIK  87
SSBOND  1   CYS      8    CYS      17                                       1DIK  88
SSBOND  2   CYS     48    CYS     391                                       1DIK  89
SSBOND  3   CYS    192    CYS     442                                       1DIK  90
SSBOND  4   CYS    241    CYS     259                                       1DIK  91
SSBOND  5   CYS    413    CYS     421                                       1DIK  92
CRYST1    92.250   92.250  100.890   90.00   90.00  120.00 P 3 2 1     6    1DIK  93
ATOM       1  N   SER     7     -18.097  39.685   9.811  1.00 62.21         1DIK  94
ATOM       2  CA  SER     7     -17.205  40.761   9.300  1.00 63.47         1DIK  95
ATOM       3  C   SER     7     -16.157  41.230  10.307  1.00 63.25         1DIK  96
ATOM       4  O   SER     7     -15.210  41.924   9.918  1.00 63.40         1DIK  97
ATOM       5  CB  SER     7     -18.027  41.947   8.800  1.00 64.21         1DIK  98
ATOM       7  OG  SER     7     -18.983  41.499   7.850  1.00 69.41         1DIK  99
ATOM       8  N   CYS     8     -16.314  40.885  11.590  1.00 60.09         1DIK 100
ATOM       9  CA  CYS     8     -15.278  41.262  12.561  1.00 57.19         1DIK 101
ATOM      10  C   CYS     8     -14.528  40.052  13.134  1.00 54.36         1DIK 102
ATOM      11  O   CYS     8     -13.593  40.225  13.913  1.00 54.16         1DIK 103
ATOM      12  CB  CYS     8     -15.738  42.278  13.657  1.00 55.87         1DIK 104
ATOM      13  SG  CYS     8     -17.414  42.211  14.391  1.00 47.31         1DIK 105
ATOM      14  N   ASP     9     -14.945  38.838  12.748  1.00 49.46         1DIK 106
ATOM      15  CA  ASP     9     -14.217  37.609  13.109  1.00 44.53         1DIK 107
ATOM      16  C   ASP     9     -13.647  37.121  11.763  1.00 43.95         1DIK 108
ATOM      17  O   ASP     9     -14.380  36.543  10.956  1.00 45.30         1DIK 109
ATOM      18  CB  ASP     9     -15.112  36.512  13.687  1.00 36.86         1DIK 110
ATOM      19  CG  ASP     9     -14.324  35.205  13.981  1.00 43.08         1DIK 111
ATOM      20  OD1 ASP     9     -13.169  35.246  14.466  1.00 36.37         1DIK 112
ATOM      21  OD2 ASP     9     -14.860  34.107  13.725  1.00 53.20         1DIK 113
ATOM      22  N   THR    10     -12.360  37.357  11.515  1.00 39.20         1DIK 114
ATOM      23  CA  THR    10     -11.744  36.961  10.248  1.00 34.97         1DIK 115
ATOM      24  C   THR    10     -10.770  35.792  10.388  1.00 35.15         1DIK 116
ATOM      25  O   THR    10     -10.407  35.410  11.502  1.00 32.93         1DIK 117
ATOM      26  CB  THR    10     -10.988  38.148   9.605  1.00 32.39         1DIK 118
ATOM      27  OG1 THR    10      -9.967  38.612  10.500  1.00 36.02         1DIK 119
ATOM      28  CG2 THR    10     -11.937  39.286   9.319  1.00 24.30         1DIK 120
ATOM      29  N   VAL    11     -10.352  35.228   9.256  1.00 35.93         1DIK 121
ATOM      30  CA  VAL    11      -9.398  34.123   9.261  1.00 35.37         1DIK 122
ATOM      31  C   VAL    11      -8.050  34.591   9.798  1.00 36.90         1DIK 123
ATOM      32  O   VAL    11      -7.442  33.912  10.623  1.00 38.05         1DIK 124
ATOM      33  CB  VAL    11      -9.196  33.528   7.840  1.00 36.34         1DIK 125
ATOM      34  CG1 VAL    11      -7.982  32.584   7.806  1.00 29.66         1DIK 126
ATOM      35  CG2 VAL    11     -10.440  32.772   7.429  1.00 36.52         1DIK 127
ATOM      36  N   ASP    12      -7.585  35.749   9.334  1.00 36.93         1DIK 128
ATOM      37  CA  ASP    12      -6.298  36.277   9.774  1.00 35.36         1DIK 129
ATOM      38  C   ASP    12      -6.298  37.009  11.094  1.00 32.61         1DIK 130
ATOM      39  O   ASP    12      -5.449  36.757  11.930  1.00 31.31         1DIK 131
ATOM      40  CB  ASP    12      -5.698  37.195   8.712  1.00 44.11         1DIK 132
ATOM      41  CG  ASP    12      -4.974  36.428   7.629  1.00 54.17         1DIK 133
ATOM      42  OD1 ASP    12      -3.831  35.998   7.891  1.00 59.05         1DIK 134
ATOM      43  OD2 ASP    12      -5.540  36.252   6.523  1.00 57.68         1DIK 135
ATOM      44  N   GLN    13      -7.241  37.918  11.294  1.00 31.17         1DIK 136
ATOM      45  CA  GLN    13      -7.251  38.684  12.530  1.00 31.70         1DIK 137
ATOM      46  C   GLN    13      -7.944  38.049  13.741  1.00 30.12         1DIK 138
ATOM      47  O   GLN    13      -7.706  38.450  14.879  1.00 26.40         1DIK 139
ATOM      48  CB  GLN    13      -7.804  40.090  12.265  1.00 38.39         1DIK 140
ATOM      49  CG  GLN    13      -6.865  40.982  11.450  1.00 44.04         1DIK 141
ATOM      50  CD  GLN    13      -5.467  41.085  12.071  1.00 53.25         1DIK 142
ATOM      51  OE1 GLN    13      -5.251  41.806  13.055  1.00 56.16         1DIK 143
ATOM      52  NE2 GLN    13      -4.510  40.357  11.497  1.00 59.15         1DIK 144
ATOM      53  N   GLY    14      -8.792  37.057  13.520  1.00 26.13         1DIK 145
ATOM      54  CA  GLY    14      -9.476  36.460  14.648  1.00 23.53         1DIK 146
```

FIG. 8-2

```
ATOM    55  C   GLY    14    -10.684  37.301  15.001  1.00  23.28      1DIK 147
ATOM    56  O   GLY    14    -11.198  38.031  14.162  1.00  21.73      1DIK 148
ATOM    57  N   TYR    15    -11.137  37.211  16.241  1.00  26.17      1DIK 149
ATOM    58  CA  TYR    15    -12.312  37.944  16.682  1.00  27.82      1DIK 150
ATOM    59  C   TYR    15    -12.033  39.383  17.139  1.00  29.70      1DIK 151
ATOM    60  O   TYR    15    -11.437  39.617  18.200  1.00  30.97      1DIK 152
ATOM    61  CB  TYR    15    -12.986  37.154  17.786  1.00  27.03      1DIK 153
ATOM    62  CG  TYR    15    -14.380  37.607  18.120  1.00  31.13      1DIK 154
ATOM    63  CD1 TYR    15    -15.471  37.146  17.386  1.00  30.29      1DIK 155
ATOM    64  CD2 TYR    15    -14.620  38.456  19.203  1.00  29.69      1DIK 156
ATOM    65  CE1 TYR    15    -16.767  37.512  17.721  1.00  33.21      1DIK 157
ATOM    66  CE2 TYR    15    -15.912  38.829  19.549  1.00  30.40      1DIK 158
ATOM    67  CZ  TYR    15    -16.982  38.355  18.808  1.00  34.78      1DIK 159
ATOM    68  OH  TYR    15    -18.266  38.709  19.151  1.00  36.84      1DIK 160
ATOM    69  N   GLN    16    -12.482  40.336  16.327  1.00  28.71      1DIK 161
ATOM    70  CA  GLN    16    -12.293  41.760  16.583  1.00  31.69      1DIK 162
ATOM    71  C   GLN    16    -13.566  42.534  16.957  1.00  30.38      1DIK 163
ATOM    72  O   GLN    16    -13.543  43.754  17.038  1.00  35.26      1DIK 164
ATOM    73  CB  GLN    16    -11.616  42.419  15.367  1.00  32.17      1DIK 165
ATOM    74  CG  GLN    16    -10.250  41.819  14.974  1.00  34.26      1DIK 166
ATOM    75  CD  GLN    16     -9.212  41.894  16.098  1.00  40.25      1DIK 167
ATOM    76  OE1 GLN    16     -9.300  42.740  16.991  1.00  44.10      1DIK 168
ATOM    77  NE2 GLN    16     -8.227  41.003  16.060  1.00  37.91      1DIK 169
ATOM    78  N   CYS    17    -14.673  41.836  17.182  1.00  32.53      1DIK 170
ATOM    79  CA  CYS    17    -15.934  42.483  17.563  1.00  34.82      1DIK 171
ATOM    80  C   CYS    17    -15.880  42.811  19.062  1.00  32.69      1DIK 172
ATOM    81  O   CYS    17    -15.355  42.015  19.843  1.00  34.59      1DIK 173
ATOM    82  CB  CYS    17    -17.131  41.544  17.323  1.00  40.76      1DIK 174
ATOM    83  SG  CYS    17    -17.305  40.688  15.705  1.00  49.21      1DIK 175
ATOM    84  N   PHE    18    -16.413  43.965  19.464  1.00  28.18      1DIK 176
ATOM    85  CA  PHE    18    -16.446  44.383  20.882  1.00  26.43      1DIK 177
ATOM    86  C   PHE    18    -15.108  44.212  21.611  1.00  26.33      1DIK 178
ATOM    87  O   PHE    18    -15.098  43.898  22.798  1.00  30.47      1DIK 179
ATOM    88  CB  PHE    18    -17.499  43.579  21.665  1.00  20.51      1DIK 180
ATOM    89  CG  PHE    18    -18.754  43.278  20.892  1.00  19.05      1DIK 181
ATOM    90  CD1 PHE    18    -19.677  44.275  20.610  1.00  21.82      1DIK 182
ATOM    91  CD2 PHE    18    -19.014  41.988  20.447  1.00  16.40      1DIK 183
ATOM    92  CE1 PHE    18    -20.850  43.991  19.892  1.00  21.59      1DIK 184
ATOM    93  CE2 PHE    18    -20.180  41.691  19.729  1.00  19.40      1DIK 185
ATOM    94  CZ  PHE    18    -21.100  42.695  19.451  1.00  21.61      1DIK 186
ATOM    95  N   SER    19    -13.997  44.422  20.912  1.00  29.30      1DIK 187
ATOM    96  CA  SER    19    -12.648  44.228  21.461  1.00  30.72      1DIK 188
ATOM    97  C   SER    19    -12.361  44.754  22.857  1.00  31.50      1DIK 189
ATOM    98  O   SER    19    -11.619  44.128  23.617  1.00  32.76      1DIK 190
ATOM    99  CB  SER    19    -11.603  44.799  20.500  1.00  28.75      1DIK 191
ATOM   100  OG  SER    19    -11.757  46.201  20.381  1.00  33.48      1DIK 192
ATOM   101  N   GLU    20    -12.939  45.899  23.192  1.00  31.46      1DIK 193
ATOM   102  CA  GLU    20    -12.715  46.498  24.497  1.00  34.60      1DIK 194
ATOM   103  C   GLU    20    -13.323  45.653  25.626  1.00  33.63      1DIK 195
ATOM   104  O   GLU    20    -12.963  45.832  26.786  1.00  35.88      1DIK 196
ATOM   105  CB  GLU    20    -13.214  47.961  24.522  1.00  36.86      1DIK 197
ATOM   106  CG  GLU    20    -14.736  48.175  24.598  1.00  47.02      1DIK 198
ATOM   107  CD  GLU    20    -15.534  47.635  23.389  1.00  56.13      1DIK 199
ATOM   108  OE1 GLU    20    -15.103  47.815  22.218  1.00  56.48      1DIK 200
ATOM   109  OE2 GLU    20    -16.615  47.025  23.618  1.00  58.06      1DIK 201
ATOM   110  N   THR    21    -14.234  44.736  25.288  1.00  30.34      1DIK 202
ATOM   111  CA  THR    21    -14.861  43.832  26.267  1.00  27.14      1DIK 203
ATOM   112  C   THR    21    -14.525  42.355  25.983  1.00  26.26      1DIK 204
ATOM   113  O   THR    21    -14.048  41.641  26.868  1.00  24.39      1DIK 205
ATOM   114  CB  THR    21    -16.405  43.965  26.272  1.00  26.34      1DIK 206
ATOM   115  OG1 THR    21    -16.758  45.337  26.448  1.00  32.63      1DIK 207
ATOM   116  CG2 THR    21    -17.026  43.137  27.395  1.00  15.06      1DIK 208
ATOM   117  N   SER    22    -14.763  41.903  24.750  1.00  24.89      1DIK 209
ATOM   118  CA  SER    22    -14.533  40.506  24.377  1.00  21.13      1DIK 210
ATOM   119  C   SER    22    -13.105  40.015  24.621  1.00  20.85      1DIK 211
ATOM   120  O   SER    22    -12.896  38.837  24.919  1.00  19.87      1DIK 212
```

FIG. 8-3

```
ATOM   121  CB  SER  22  -14.924  40.282  22.918  1.00  16.59      1DIK 213
ATOM   122  OG  SER  22  -14.015  40.939  22.044  1.00  23.72      1DIK 214
ATOM   123  N   HIS  23  -12.126  40.911  24.497  1.00  20.46      1DIK 215
ATOM   124  CA  HIS  23  -10.726  40.555  24.708  1.00  20.05      1DIK 216
ATOM   125  C   HIS  23  -10.329  40.455  26.183  1.00  24.47      1DIK 217
ATOM   126  O   HIS  23   -9.196  40.084  26.496  1.00  25.61      1DIK 218
ATOM   127  CB  HIS  23   -9.800  41.536  23.982  1.00  17.77      1DIK 219
ATOM   128  CG  HIS  23   -9.861  41.426  22.484  1.00  24.57      1DIK 220
ATOM   129  ND1 HIS  23   -8.936  42.020  21.651  1.00  20.40      1DIK 221
ATOM   130  CD2 HIS  23  -10.746  40.795  21.670  1.00  23.97      1DIK 222
ATOM   131  CE1 HIS  23   -9.247  41.764  20.392  1.00  20.67      1DIK 223
ATOM   132  NE2 HIS  23  -10.340  41.022  20.376  1.00  23.06      1DIK 224
ATOM   133  N   LEU  24  -11.263  40.776  27.081  1.00  25.15      1DIK 225
ATOM   134  CA  LEU  24  -11.025  40.716  28.524  1.00  24.99      1DIK 226
ATOM   135  C   LEU  24  -11.739  39.538  29.210  1.00  27.65      1DIK 227
ATOM   136  O   LEU  24  -11.984  39.575  30.421  1.00  25.05      1DIK 228
ATOM   137  CB  LEU  24  -11.455  42.034  29.176  1.00  22.74      1DIK 229
ATOM   138  CG  LEU  24  -10.626  43.258  28.774  1.00  22.62      1DIK 230
ATOM   139  CD1 LEU  24  -11.264  44.509  29.324  1.00  23.25      1DIK 231
ATOM   140  CD2 LEU  24   -9.211  43.126  29.281  1.00  15.42      1DIK 232
ATOM   141  N   TRP  25  -12.062  38.496  28.437  1.00  26.64      1DIK 233
ATOM   142  CA  TRP  25  -12.744  37.317  28.961  1.00  21.87      1DIK 234
ATOM   143  C   TRP  25  -11.811  36.148  29.357  1.00  22.59      1DIK 235
ATOM   144  O   TRP  25  -12.283  35.040  29.625  1.00  22.32      1DIK 236
ATOM   145  CB  TRP  25  -13.804  36.845  27.951  1.00  22.87      1DIK 237
ATOM   146  CG  TRP  25  -14.977  37.813  27.754  1.00  25.99      1DIK 238
ATOM   147  CD1 TRP  25  -15.376  38.805  28.615  1.00  22.03      1DIK 239
ATOM   148  CD2 TRP  25  -15.880  37.877  26.626  1.00  23.51      1DIK 240
ATOM   149  NE1 TRP  25  -16.459  39.475  28.094  1.00  22.08      1DIK 241
ATOM   150  CE2 TRP  25  -16.792  38.931  26.877  1.00  24.34      1DIK 242
ATOM   151  CE3 TRP  25  -16.004  37.150  25.425  1.00  25.98      1DIK 243
ATOM   152  CZ2 TRP  25  -17.821  39.280  25.973  1.00  20.60      1DIK 244
ATOM   153  CZ3 TRP  25  -17.034  37.500  24.517  1.00  21.02      1DIK 245
ATOM   154  CH2 TRP  25  -17.923  38.555  24.804  1.00  20.24      1DIK 246
ATOM   155  N   GLY  26  -10.499  36.384  29.403  1.00  20.85      1DIK 247
ATOM   156  CA  GLY  26   -9.566  35.322  29.757  1.00  21.54      1DIK 248
ATOM   157  C   GLY  26   -9.676  34.138  28.806  1.00  21.52      1DIK 249
ATOM   158  O   GLY  26   -9.642  34.319  27.590  1.00  19.25      1DIK 250
ATOM   159  N   GLN  27   -9.819  32.927  29.346  1.00  23.90      1DIK 251
ATOM   160  CA  GLN  27   -9.946  31.740  28.503  1.00  24.89      1DIK 252
ATOM   161  C   GLN  27  -11.340  31.566  27.902  1.00  24.51      1DIK 253
ATOM   162  O   GLN  27  -11.600  30.573  27.226  1.00  25.98      1DIK 254
ATOM   163  CB  GLN  27   -9.535  30.455  29.245  1.00  23.84      1DIK 255
ATOM   164  CG  GLN  27  -10.472  29.995  30.323  1.00  21.01      1DIK 256
ATOM   165  CD  GLN  27  -10.344  30.823  31.573  1.00  27.35      1DIK 257
ATOM   166  OE1 GLN  27   -9.452  31.671  31.694  1.00  31.10      1DIK 258
ATOM   167  NE2 GLN  27  -11.231  30.588  32.517  1.00  32.00      1DIK 259
ATOM   168  N   TYR  28  -12.241  32.516  28.156  1.00  25.51      1DIK 260
ATOM   169  CA  TYR  28  -13.592  32.472  27.578  1.00  23.43      1DIK 261
ATOM   170  C   TYR  28  -13.647  33.499  26.433  1.00  24.19      1DIK 262
ATOM   171  O   TYR  28  -14.716  33.779  25.867  1.00  24.91      1DIK 263
ATOM   172  CB  TYR  28  -14.673  32.787  28.624  1.00  20.52      1DIK 264
ATOM   173  CG  TYR  28  -14.797  31.767  29.727  1.00  21.45      1DIK 265
ATOM   174  CD1 TYR  28  -14.609  30.402  29.480  1.00  25.41      1DIK 266
ATOM   175  CD2 TYR  28  -15.091  32.164  31.027  1.00  26.26      1DIK 267
ATOM   176  CE1 TYR  28  -14.711  29.462  30.506  1.00  24.86      1DIK 268
ATOM   177  CE2 TYR  28  -15.194  31.238  32.056  1.00  28.46      1DIK 269
ATOM   178  CZ  TYR  28  -15.005  29.895  31.793  1.00  29.76      1DIK 270
ATOM   179  OH  TYR  28  -15.113  28.997  32.827  1.00  35.18      1DIK 271
ATOM   180  N   ALA  29  -12.480  34.061  26.111  1.00  21.55      1DIK 272
ATOM   181  CA  ALA  29  -12.340  35.025  25.029  1.00  21.69      1DIK 273
ATOM   182  C   ALA  29  -12.102  34.251  23.725  1.00  22.47      1DIK 274
ATOM   183  O   ALA  29  -11.401  33.233  23.720  1.00  22.07      1DIK 275
ATOM   184  CB  ALA  29  -11.139  35.944  25.305  1.00  12.96      1DIK 276
ATOM   185  N   PRO  30  -12.709  34.697  22.612  1.00  24.01      1DIK 277
ATOM   186  CA  PRO  30  -12.509  34.027  21.319  1.00  20.94      1DIK 278
```

FIG. 8-4

```
ATOM    187  C   PRO    30     -11.099  34.409  20.841  1.00 19.17      1DIK 279
ATOM    188  O   PRO    30     -10.608  35.498  21.155  1.00 18.52      1DIK 280
ATOM    189  CB  PRO    30     -13.568  34.671  20.414  1.00 20.61      1DIK 281
ATOM    190  CG  PRO    30     -14.540  35.324  21.362  1.00 24.76      1DIK 282
ATOM    191  CD  PRO    30     -13.651  35.819  22.480  1.00 25.47      1DIK 283
ATOM    192  N   PHE    31     -10.438  33.533  20.093  1.00 20.80      1DIK 284
ATOM    193  CA  PHE    31      -9.102  33.861  19.596  1.00 19.54      1DIK 285
ATOM    194  C   PHE    31      -9.077  35.195  18.814  1.00 20.93      1DIK 286
ATOM    195  O   PHE    31      -9.957  35.482  17.984  1.00 20.23      1DIK 287
ATOM    196  CB  PHE    31      -8.552  32.723  18.692  1.00 17.50      1DIK 288
ATOM    197  CG  PHE    31      -7.448  33.165  17.750  1.00 19.27      1DIK 289
ATOM    198  CD1 PHE    31      -6.119  33.222  18.181  1.00 21.10      1DIK 290
ATOM    199  CD2 PHE    31      -7.747  33.579  16.435  1.00 18.79      1DIK 291
ATOM    200  CE1 PHE    31      -5.105  33.692  17.318  1.00 21.44      1DIK 292
ATOM    201  CE2 PHE    31      -6.741  34.050  15.564  1.00 14.12      1DIK 293
ATOM    202  CZ  PHE    31      -5.426  34.108  16.005  1.00 17.15      1DIK 294
ATOM    203  N   PHE    32      -8.067  36.005  19.097  1.00 18.45      1DIK 295
ATOM    204  CA  PHE    32      -7.844  37.244  18.368  1.00 20.59      1DIK 296
ATOM    205  C   PHE    32      -6.324  37.260  18.121  1.00 20.82      1DIK 297
ATOM    206  O   PHE    32      -5.536  36.921  19.002  1.00 23.47      1DIK 298
ATOM    207  CB  PHE    32      -8.350  38.480  19.131  1.00 19.12      1DIK 299
ATOM    208  CG  PHE    32      -7.872  38.573  20.560  1.00 23.83      1DIK 300
ATOM    209  CD1 PHE    32      -8.508  37.845  21.577  1.00 20.95      1DIK 301
ATOM    210  CD2 PHE    32      -6.806  39.406  20.896  1.00 19.92      1DIK 302
ATOM    211  CE1 PHE    32      -8.095  37.946  22.896  1.00 20.93      1DIK 303
ATOM    212  CE2 PHE    32      -6.382  39.517  22.219  1.00 22.76      1DIK 304
ATOM    213  CZ  PHE    32      -7.032  38.783  23.226  1.00 23.83      1DIK 305
ATOM    214  N   SER    33      -5.914  37.623  16.915  1.00 20.87      1DIK 306
ATOM    215  CA  SER    33      -4.504  37.635  16.571  1.00 22.19      1DIK 307
ATOM    216  C   SER    33      -3.672  38.690  17.284  1.00 23.15      1DIK 308
ATOM    217  O   SER    33      -4.041  39.870  17.320  1.00 23.04      1DIK 309
ATOM    218  CB  SER    33      -4.329  37.796  15.060  1.00 22.81      1DIK 310
ATOM    219  OG  SER    33      -2.947  37.792  14.729  1.00 25.39      1DIK 311
ATOM    220  N   LEU    34      -2.544  38.263  17.846  1.00 23.77      1DIK 312
ATOM    221  CA  LEU    34      -1.638  39.188  18.523  1.00 25.51      1DIK 313
ATOM    222  C   LEU    34      -0.492  39.605  17.606  1.00 26.78      1DIK 314
ATOM    223  O   LEU    34       0.501  40.148  18.084  1.00 26.99      1DIK 315
ATOM    224  CB  LEU    34      -1.063  38.572  19.796  1.00 23.17      1DIK 316
ATOM    225  CG  LEU    34      -2.087  38.252  20.887  1.00 25.71      1DIK 317
ATOM    226  CD1 LEU    34      -1.395  37.465  21.984  1.00 23.09      1DIK 318
ATOM    227  CD2 LEU    34      -2.712  39.528  21.427  1.00 19.78      1DIK 319
ATOM    228  N   ALA    35      -0.639  39.365  16.301  1.00 27.00      1DIK 320
ATOM    229  CA  ALA    35       0.390  39.711  15.319  1.00 31.06      1DIK 321
ATOM    230  C   ALA    35       0.835  41.166  15.428  1.00 35.74      1DIK 322
ATOM    231  O   ALA    35       2.025  41.455  15.344  1.00 39.04      1DIK 323
ATOM    232  CB  ALA    35      -0.103  39.434  13.915  1.00 24.83      1DIK 324
ATOM    233  N   ASN    36      -0.118  42.075  15.623  1.00 39.86      1DIK 325
ATOM    234  CA  ASN    36       0.181  43.506  15.737  1.00 41.12      1DIK 326
ATOM    235  C   ASN    36       0.815  43.897  17.057  1.00 40.64      1DIK 327
ATOM    236  O   ASN    36       1.319  45.010  17.188  1.00 42.67      1DIK 328
ATOM    237  CB  ASN    36      -1.084  44.349  15.538  1.00 43.24      1DIK 329
ATOM    238  CG  ASN    36      -1.671  44.193  14.156  1.00 49.12      1DIK 330
ATOM    239  OD1 ASN    36      -0.945  44.021  13.172  1.00 50.49      1DIK 331
ATOM    240  ND2 ASN    36      -2.995  44.246  14.066  1.00 56.59      1DIK 332
ATOM    241  N   GLU    37       0.784  43.000  18.039  1.00 39.04      1DIK 333
ATOM    242  CA  GLU    37       1.380  43.287  19.347  1.00 39.87      1DIK 334
ATOM    243  C   GLU    37       2.788  42.722  19.440  1.00 37.45      1DIK 335
ATOM    244  O   GLU    37       3.506  42.963  20.411  1.00 38.65      1DIK 336
ATOM    245  CB  GLU    37       0.530  42.693  20.478  1.00 43.47      1DIK 337
ATOM    246  CG  GLU    37      -0.796  43.401  20.721  1.00 47.80      1DIK 338
ATOM    247  CD  GLU    37      -0.616  44.863  21.087  1.00 51.75      1DIK 339
ATOM    248  OE1 GLU    37       0.084  45.166  22.088  1.00 51.94      1DIK 340
ATOM    249  OE2 GLU    37      -1.183  45.710  20.357  1.00 55.20      1DIK 341
ATOM    250  N   SER    38       3.174  41.961  18.425  1.00 35.62      1DIK 342
ATOM    251  CA  SER    38       4.482  41.340  18.389  1.00 34.02      1DIK 343
ATOM    252  C   SER    38       5.565  42.357  17.986  1.00 34.45      1DIK 344
```

FIG. 8-5

```
ATOM    253  O    SER    38       5.428  43.061  16.985  1.00  35.65      1DIK 345
ATOM    254  CB   SER    38       4.454  40.163  17.404  1.00  33.07      1DIK 346
ATOM    255  OG   SER    38       5.561  39.292  17.583  1.00  28.90      1DIK 347
ATOM    256  N    VAL    39       6.632  42.420  18.782  1.00  33.51      1DIK 348
ATOM    257  CA   VAL    39       7.767  43.305  18.541  1.00  33.30      1DIK 349
ATOM    258  C    VAL    39       8.539  42.760  17.327  1.00  33.54      1DIK 350
ATOM    259  O    VAL    39       9.024  43.520  16.490  1.00  34.06      1DIK 351
ATOM    260  CB   VAL    39       8.690  43.356  19.801  1.00  37.39      1DIK 352
ATOM    261  CG1  VAL    39       9.833  44.331  19.602  1.00  39.93      1DIK 353
ATOM    262  CG2  VAL    39       7.884  43.774  21.018  1.00  38.16      1DIK 354
ATOM    263  N    ILE    40       8.645  41.434  17.239  1.00  32.27      1DIK 355
ATOM    264  CA   ILE    40       9.323  40.766  16.127  1.00  29.21      1DIK 356
ATOM    265  C    ILE    40       8.262  40.386  15.083  1.00  28.46      1DIK 357
ATOM    266  O    ILE    40       7.195  39.885  15.440  1.00  26.34      1DIK 358
ATOM    267  CB   ILE    40      10.059  39.494  16.624  1.00  29.64      1DIK 359
ATOM    268  CG1  ILE    40      11.147  39.900  17.631  1.00  30.03      1DIK 360
ATOM    269  CG2  ILE    40      10.633  38.721  15.436  1.00  26.81      1DIK 361
ATOM    270  CD1  ILE    40      11.771  38.777  18.437  1.00  26.07      1DIK 362
ATOM    271  N    SER    41       8.548  40.626  13.806  1.00  29.09      1DIK 363
ATOM    272  CA   SER    41       7.594  40.302  12.737  1.00  30.76      1DIK 364
ATOM    273  C    SER    41       7.310  38.798  12.646  1.00  29.37      1DIK 365
ATOM    274  O    SER    41       8.234  37.990  12.552  1.00  28.10      1DIK 366
ATOM    275  CB   SER    41       8.113  40.802  11.386  1.00  29.99      1DIK 367
ATOM    276  OG   SER    41       7.148  40.555  10.379  1.00  32.70      1DIK 368
ATOM    227  N    PRO    42       6.021  38.410  12.664  1.00  31.46      1DIK 369
ATOM    278  CA   PRO    42       5.577  37.009  12.592  1.00  30.99      1DIK 370
ATOM    279  C    PRO    42       5.915  36.287  11.285  1.00  31.80      1DIK 371
ATOM    280  O    PRO    42       5.950  35.062  11.241  1.00  34.31      1DIK 372
ATOM    281  CB   PRO    42       4.056  37.109  12.791  1.00  28.85      1DIK 373
ATOM    282  CG   PRO    42       3.852  38.432  13.454  1.00  32.81      1DIK 374
ATOM    283  CD   PRO    42       4.863  39.312  12.766  1.00  31.32      1DIK 375
ATOM    284  N    GLU    43       6.160  37.047  10.226  1.00  34.83      1DIK 376
ATOM    285  CA   GLU    43       6.467  36.483   8.917  1.00  36.61      1DIK 377
ATOM    286  C    GLU    43       7.765  35.703   8.835  1.00  35.76      1DIK 378
ATOM    287  O    GLU    43       8.757  36.046   9.480  1.00  37.48      1DIK 379
ATOM    288  CB   GLU    43       6.516  37.586   7.867  1.00  45.46      1DIK 380
ATOM    289  CG   GLU    43       5.236  38.394   7.734  1.00  61.52      1DIK 381
ATOM    290  CD   GLU    43       5.488  39.889   7.891  1.00  71.53      1DIK 382
ATOM    291  OE1  GLU    43       6.553  40.371   7.420  1.00  76.20      1DIK 383
ATOM    292  OE2  GLU    43       4.624  40.581   8.487  1.00  75.49      1DIK 384
ATOM    293  N    VAL    44       7.739  34.654   8.020  1.00  35.15      1DIK 385
ATOM    294  CA   VAL    44       8.900  33.806   7.785  1.00  34.87      1DIK 386
ATOM    295  C    VAL    44       9.900  34.708   7.060  1.00  36.04      1DIK 387
ATOM    296  O    VAL    44       9.570  35.289   6.031  1.00  37.59      1DIK 388
ATOM    297  CB   VAL    44       8.529  32.582   6.883  1.00  33.01      1DIK 389
ATOM    298  CG1  VAL    44       9.757  31.698   6.657  1.00  28.63      1DIK 390
ATOM    299  CG2  VAL    44       7.398  31.773   7.522  1.00  26.10      1DIK 391
ATOM    300  N    PRO    45      11.131  34.837   7.590  1.00  38.73      1DIK 392
ATOM    301  CA   PRO    45      12.171  35.680   6.996  1.00  40.95      1DIK 393
ATOM    302  C    PRO    45      12.492  35.362   5.558  1.00  44.42      1DIK 394
ATOM    303  O    PRO    45      12.492  34.196   5.149  1.00  44.24      1DIK 395
ATOM    304  CB   PRO    45      13.382  35.431   7.893  1.00  39.65      1DIK 396
ATOM    305  CG   PRO    45      12.775  35.101   9.201  1.00  40.04      1DIK 397
ATOM    306  CD   PRO    45      11.645  34.183   8.806  1.00  40.88      1DIK 398
ATOM    307  N    ALA    46      12.769  36.418   4.798  1.00  48.71      1DIK 399
ATOM    308  CA   ALA    46      13.127  36.292   3.396  1.00  50.25      1DIK 400
ATOM    309  C    ALA    46      14.456  35.555   3.435  1.00  49.80      1DIK 401
ATOM    310  O    ALA    46      15.326  35.906   4.229  1.00  49.90      1DIK 402
ATOM    311  CB   ALA    46      13.304  37.677   2.777  1.00  50.74      1DIK 403
ATOM    312  N    GLY    47      14.613  34.533   2.600  1.00  47.13      1DIK 404
ATOM    313  CA   GLY    47      15.862  33.789   2.596  1.00  41.93      1DIK 405
ATOM    314  C    GLY    47      15.863  32.579   3.520  1.00  39.94      1DIK 406
ATOM    315  O    GLY    47      16.893  31.906   3.681  1.00  36.72      1DIK 407
ATOM    316  N    CYS    48      14.720  32.300   4.141  1.00  36.56      1DIK 408
ATOM    317  CA   CYS    48      14.609  31.139   5.012  1.00  34.94      1DIK 409
ATOM    318  C    CYS    48      15.549  30.237   4.434  1.00  34.24      1DIK 410
```

FIG. 8-6

```
ATOM  319  O    CYS  48    12.669  30.684   3.693  1.00  33.85     1DIK 411
ATOM  320  CB   CYS  48    14.232  31.528   6.435  1.00  29.09     1DIK 412
ATOM  321  SG   CYS  48    15.506  32.511   7.263  1.00  30.08     1DIK 413
ATOM  322  N    ARG  49    13.643  28.962   4.775  1.00  32.71     1DIK 414
ATOM  323  CA   ARG  49    12.707  27.965   4.293  1.00  31.47     1DIK 415
ATOM  324  C    ARG  49    12.307  27.093   5.496  1.00  29.98     1DIK 416
ATOM  325  O    ARG  49    13.181  26.547   6.196  1.00  24.89     1DIK 417
ATOM  326  CB   ARG  49    13.424  27.153   3.219  1.00  34.59     1DIK 418
ATOM  327  CG   ARG  49    12.615  26.104   2.516  1.00  45.38     1DIK 419
ATOM  328  CD   ARG  49    13.520  25.363   1.547  1.00  50.77     1DIK 420
ATOM  329  NE   ARG  49    14.760  24.899   2.185  1.00  53.82     1DIK 421
ATOM  330  CZ   ARG  49    15.024  23.626   2.479  1.00  54.48     1DIK 422
ATOM  331  NH1  ARG  49    14.132  22.680   2.199  1.00  54.38     1DIK 223
ATOM  332  NH2  ARG  49    16.178  23.297   3.054  1.00  53.78     1DIK 424
ATOM  333  N    VAL  50    11.001  26.975   5.747  1.00  26.52     1DIK 425
ATOM  334  CA   VAL  50    10.510  26.167   6.865  1.00  23.44     1DIK 426
ATOM  335  C    VAL  50    10.718  24.689   6.555  1.00  22.87     1DIK 427
ATOM  336  O    VAL  50    10.383  24.223   5.472  1.00  24.36     1DIK 428
ATOM  337  CB   VAL  50     9.012  26.441   7.157  1.00  22.39     1DIK 429
ATOM  338  CG1  VAL  50     8.518  25.564   8.318  1.00  22.32     1DIK 430
ATOM  339  CG2  VAL  50     8.817  27.903   7.506  1.00  18.72     1DIK 431
ATOM  340  N    THR  51    11.278  23.958   7.510  1.00  23.31     1DIK 432
ATOM  341  CA   THR  51    11.533  22.536   7.341  1.00  23.80     1DIK 433
ATOM  342  C    THR  51    10.764  21.649   8.332  1.00  25.07     1DIK 434
ATOM  343  O    THR  51    10.821  20.422   8.242  1.00  25.40     1DIK 435
ATOM  344  CB   THR  51    13.042  22.240   7.471  1.00  26.51     1DIK 436
ATOM  345  OG1  THR  51    13.516  22.691   8.745  1.00  27.16     1DIK 437
ATOM  346  OG2  THR  51    13.823  22.954   6.378  1.00  26.68     1DIK 438
ATOM  347  N    PHE  52    10.052  22.267   9.274  1.00  23.82     1DIK 439
ATOM  348  CA   PHE  52     9.280  21.543  10.285  1.00  18.63     1DIK 440
ATOM  349  C    PHE  52     8.264  22.527  10.821  1.00  19.14     1DIK 441
ATOM  350  O    PHE  52     8.559  23.710  10.993  1.00  19.73     1DIK 442
ATOM  351  CB   PHE  52    10.211  21.081  11.425  1.00  17.98     1DIK 443
ATOM  352  CG   PHE  52     9.497  20.552  12.661  1.00  19.23     1DIK 444
ATOM  353  CD1  PHE  52     9.006  21.424  13.636  1.00  18.19     1DIK 445
ATOM  354  CD2  PHE  52     9.328  19.185  12.854  1.00  18.71     1DIK 446
ATOM  355  CE1  PHE  52     8.359  20.941  14.783  1.00  15.91     1DIK 447
ATOM  356  CE2  PHE  52     8.682  18.690  14.001  1.00  20.50     1DIK 448
ATOM  357  CZ   PHE  52     8.198  19.576  14.964  1.00  16.11     1DIK 449
ATOM  358  N    ALA  53     7.061  22.053  11.072  1.00  16.93     1DIK 450
ATOM  359  CA   ALA  53     6.045  22.910  11.647  1.00  19.01     1DIK 451
ATOM  360  C    ALA  53     5.112  22.048  12.468  1.00  19.84     1DIK 452
ATOM  361  O    ALA  53     4.647  21.002  12.011  1.00  21.85     1DIK 453
ATOM  362  CB   ALA  53     5.265  23.658  10.563  1.00  17.27     1DIK 454
ATOM  363  N    GLN  54     4.866  22.479  13.696  1.00  19.97     1DIK 455
ATOM  364  CA   GLN  54     3.924  21.801  14.570  1.00  16.77     1DIK 456
ATOM  365  C    GLN  54     2.963  22.820  15.172  1.00  13.22     1DIK 457
ATOM  366  O    GLN  54     3.370  23.901  15.592  1.00  15.19     1DIK 458
ATOM  367  CB   GLN  54     4.619  21.072  15.711  1.00  18.35     1DIK 459
ATOM  368  CG   GLN  54     3.595  20.527  16.697  1.00  24.84     1DIK 460
ATOM  369  CD   GLN  54     4.138  19.486  17.607  1.00  27.27     1DIK 461
ATOM  370  OE1  GLN  54     4.891  18.614  17.195  1.00  28.71     1DIK 462
ATOM  371  NE2  GLN  54     3.758  19.561  18.863  1.00  33.46     1DIK 463
ATOM  372  N    VAL  55     1.686  22.486  15.206  1.00  13.93     1DIK 464
ATOM  373  CA   VAL  55     0.721  23.372  15.822  1.00  14.13     1DIK 465
ATOM  374  C    VAL  55     0.094  22.604  16.990  1.00  14.94     1DIK 466
ATOM  375  O    VAL  55    -0.192  21.404  16.878  1.00  13.02     1DIK 467
ATOM  376  CB   VAL  55    -0.377  23.842  14.812  1.00  14.68     1DIK 468
ATOM  377  CG1  VAL  55    -1.062  22.645  14.155  1.00   8.55     1DIK 469
ATOM  378  CG2  VAL  55    -0.407  24.739  15.521  1.00  15.11     1DIK 470
ATOM  379  N    LEU  56    -0.076  23.292  18.111  1.00  11.84     1DIK 471
ATOM  380  CA   LEU  56    -0.719  22.731  19.278  1.00  11.96     1DIK 472
ATOM  381  C    LEU  56    -1.896  23.694  19.426  1.00  14.67     1DIK 473
ATOM  382  O    LEU  56    -1.721  24.903  19.647  1.00  13.79     1DIK 474
ATOM  383  CB   LEU  56     0.197  22.771  20.503  1.00  17.28     1DIK 475
ATOM  384  CG   LEU  56    -0.513  22.538  21.842  1.00  17.00     1DIK 476
```

FIG. 8-7

```
ATOM   385  CD1 LEU  56    -1.065  21.122  21.949  1.00 13.43      1DIK 477
ATOM   386  CD2 LEU  56     0.472  22.817  22.938  1.00 17.28      1DIK 478
ATOM   387  N   SER  57    -3.095  23.162  19.277  1.00 16.89      1DIK 479
ATOM   388  CA  SER  57    -4.289  23.976  19.329  1.00 16.37      1DIK 480
ATOM   389  C   SER  57    -5.260  23.544  20.411  1.00 16.34      1DIK 481
ATOM   390  O   SER  57    -5.341  22.363  20.760  1.00 18.09      1DIK 482
ATOM   391  CB  SER  57    -4.984  23.906  17.960  1.00 15.08      1DIK 483
ATOM   392  OG  SER  57    -6.256  24.527  17.966  1.00 15.23      1DIK 484
ATOM   393  N   ARG  58    -5.986  24.514  20.946  1.00 14.89      1DIK 485
ATOM   394  CA  ARG  58    -7.015  24.257  21.934  1.00 16.34      1DIK 486
ATOM   395  C   ARG  58    -8.299  24.104  21.100  1.00 20.75      1DIK 487
ATOM   396  O   ARG  58    -8.352  24.546  19.940  1.00 20.55      1DIK 488
ATOM   397  CB  ARG  58    -7.159  25.457  22.874  1.00 14.15      1DIK 489
ATOM   398  CG  ARG  58    -8.315  25.320  23.835  1.00 13.80      1DIK 490
ATOM   399  CD  ARG  58    -8.411  26.468  24.791  1.00 15.28      1DIK 491
ATOM   400  NE  ARG  58    -9.551  26.299  25.692  1.00 16.96      1DIK 492
ATOM   401  CZ  ARG  58   -10.218  27.306  26.253  1.00 17.74      1DIK 493
ATOM   402  NH1 ARG  58    -9.863  28.564  26.021  1.00 19.32      1DIK 494
ATOM   403  NH2 ARG  58   -11.239  27.055  27.051  1.00 14.92      1DIK 495
ATOM   404  N   HIS  59    -9.326  23.478  21.673  1.00 22.89      1DIK 496
ATOM   405  CA  HIS  59   -10.620  23.324  20.993  1.00 21.80      1DIK 497
ATOM   406  C   HIS  59   -11.286  24.703  20.795  1.00 21.30      1DIK 498
ATOM   407  O   HIS  59   -10.860  25.693  21.403  1.00 20.60      1DIK 499
ATOM   408  CB  HIS  59   -11.537  22.407  21.809  1.00 20.25      1DIK 500
ATOM   409  CG  HIS  59   -11.767  22.867  23.218  1.00 21.97      1DIK 501
ATOM   410  ND1 HIS  59   -12.523  23.979  23.527  1.00 21.32      1DIK 502
ATOM   411  CD2 HIS  59   -11.350  22.356  24.400  1.00 18.14      1DIK 503
ATOM   412  CE1 HIS  59   -12.564  24.132  24.838  1.00 18.77      1DIK 504
ATOM   413  NE2 HIS  59   -11.860  23.161  25.390  1.00 19.93      1DIK 505
ATOM   414  N   GLY  60   -12.318  24.782  19.957  1.00 20.66      1DIK 506
ATOM   415  CA  GLY  60   -12.976  26.063  19.736  1.00 20.29      1DIK 507
ATOM   416  C   GLY  60   -13.950  26.442  20.847  1.00 21.51      1DIK 508
ATOM   417  O   GLY  60   -14.042  25.737  21.856  1.00 21.15      1DIK 509
ATOM   418  N   ALA  61   -14.669  27.549  20.659  1.00 20.16      1DIK 510
ATOM   419  CA  ALA  61   -15.664  28.047  21.618  1.00 20.00      1DIK 511
ATOM   420  C   ALA  61   -16.735  26.996  21.888  1.00 20.35      1DIK 512
ATOM   421  O   ALA  61   -17.247  26.366  20.954  1.00 21.69      1DIK 513
ATOM   422  CB  ALA  61   -16.326  29.320  21.079  1.00 15.53      1DIK 514
ATOM   423  N   ARG  62   -17.077  26.823  23.161  1.00 19.64      1DIK 515
ATOM   424  CA  ARG  62   -18.070  25.832  23.581  1.00 19.57      1DIK 516
ATOM   425  C   ARG  62   -19.162  26.420  24.482  1.00 21.60      1DIK 517
ATOM   426  O   ARG  62   -19.079  27.574  24.932  1.00 18.58      1DIK 518
ATOM   427  CB  ARG  62   -17.378  24.703  24.346  1.00 15.11      1DIK 519
ATOM   428  CG  ARG  62   -16.505  25.211  25.486  1.00 17.39      1DIK 520
ATOM   429  CD  ARG  62   -16.371  24.195  26.609  1.00 22.59      1DIK 521
ATOM   430  NE  ARG  62   -15.570  24.726  27.711  1.00 23.06      1DIK 522
ATOM   431  CZ  ARG  62   -16.067  25.234  28.839  1.00 25.28      1DIK 523
ATOM   432  NH1 ARG  62   -17.379  25.272  29.052  1.00 28.41      1DIK 524
ATOM   433  NH2 ARG  62   -15.244  25.704  29.766  1.00 27.40      1DIK 525
ATOM   434  N   TYR  63   -20.193  25.619  24.726  1.00 23.53      1DIK 526
ATOM   435  CA  TYR  63   -21.280  26.004  25.615  1.00 25.54      1DIK 527
ATOM   436  C   TYR  63   -20.729  25.786  27.033  1.00 28.59      1DIK 528
ATOM   437  O   TYR  63   -19.646  25.206  27.200  1.00 28.67      1DIK 529
ATOM   438  CB  TYR  63   -22.481  25.082  25.394  1.00 24.63      1DIK 530
ATOM   439  CG  TYR  63   -23.192  25.300  24.082  1.00 29.77      1DIK 531
ATOM   440  CD1 TYR  63   -23.806  26.529  23.795  1.00 29.27      1DIK 532
ATOM   441  CD2 TYR  63   -23.237  24.290  23.116  1.00 27.48      1DIK 533
ATOM   442  CE1 TYR  63   -24.444  26.748  22.576  1.00 31.57      1DIK 534
ATOM   443  CE2 TYR  63   -23.867  24.495  21.895  1.00 26.46      1DIK 535
ATOM   444  CZ  TYR  63   -24.468  25.727  21.626  1.00 34.26      1DIK 536
ATOM   445  OH  TYR  63   -25.067  25.950  20.398  1.00 35.58      1DIK 537
ATOM   446  N   PRO  64   -21.444  26.254  28.076  1.00 31.03      1DIK 538
ATOM   447  CA  PRO  64   -20.879  26.003  29.407  1.00 31.84      1DIK 539
ATOM   448  C   PRO  64   -20.849  24.482  29.625  1.00 32.43      1DIK 540
ATOM   449  O   PRO  64   -21.547  23.728  28.932  1.00 30.67      1DIK 541
ATOM   450  CB  PRO  64   -21.891  26.670  30.342  1.00 27.12      1DIK 542
```

FIG. 8-8

```
ATOM   451  CG  PRO  64   -22.524  27.706  29.487  1.00  30.89    1DIK 543
ATOM   452  CD  PRO  64   -22.706  27.004  28.181  1.00  27.90    1DIK 544
ATOM   453  N   THR  65   -20.042  24.011  30.564  1.00  35.27    1DIK 545
ATOM   454  CA  THR  65   -20.038  22.579  30.830  1.00  37.08    1DIK 546
ATOM   455  C   THR  65   -21.375  22.333  31.507  1.00  38.68    1DIK 547
ATOM   456  O   THR  65   -21.897  23.224  32.185  1.00  35.35    1DIK 548
ATOM   457  CB  THR  65   -18.897  22.170  31.774  1.00  35.91    1DIK 549
ATOM   458  OG1 THR  65   -18.997  22.906  32.999  1.00  40.63    1DIK 550
ATOM   459  CG2 THR  65   -17.544  22.438  31.116  1.00  35.54    1DIK 551
ATOM   460  N   ASP  66   -21.933  21.141  31.329  1.00  44.49    1DIK 552
ATOM   461  CA  ASP  66   -23.222  20.806  31.935  1.00  48.12    1DIK 553
ATOM   462  C   ASP  66   -23.305  21.205  33.418  1.00  48.96    1DIK 554
ATOM   463  O   ASP  66   -24.299  21.789  33.858  1.00  48.33    1DIK 555
ATOM   464  CB  ASP  66   -23.513  19.309  31.782  1.00  50.94    1DIK 556
ATOM   465  CG  ASP  66   -24.974  18.977  32.030  1.00  54.72    1DIK 557
ATOM   466  OD1 ASP  66   -25.838  19.495  31.280  1.00  55.38    1DIK 558
ATOM   467  OD2 ASP  66   -25.255  18.206  32.977  1.00  55.13    1DIK 559
ATOM   468  N   SER  67   -22.262  20.895  34.180  1.00  47.71    1DIK 560
ATOM   469  CA  SER  67   -22.233  21.247  35.587  1.00  46.65    1DIK 561
ATOM   470  C   SER  67   -22.525  22.751  35.796  1.00  45.82    1DIK 562
ATOM   471  O   SER  67   -23.477  23.102  36.501  1.00  47.90    1DIK 563
ATOM   472  CB  SER  67   -20.875  20.861  36.172  1.00  45.81    1DIK 564
ATOM   473  OG  SER  67   -20.769  21.285  37.516  1.00  51.18    1DIK 565
ATOM   474  N   LYS  68   -21.727  23.630  35.178  1.00  43.55    1DIK 566
ATOM   475  CA  LYS  68   -21.896  25.092  35.312  1.00  39.40    1DIK 567
ATOM   476  C   LYS  68   -23.201  25.626  34.753  1.00  37.75    1DIK 568
ATOM   477  O   LYS  68   -23.760  26.578  35.301  1.00  36.03    1DIK 569
ATOM   478  CB  LYS  68   -20.753  25.837  34.638  1.00  38.35    1DIK 570
ATOM   479  CG  LYS  68   -19.448  25.727  35.356  1.00  38.37    1DIK 571
ATOM   480  CD  LYS  68   -19.273  26.838  36.351  1.00  39.44    1DIK 572
ATOM   481  CE  LYS  68   -17.830  26.847  36.833  1.00  44.75    1DIK 573
ATOM   482  NZ  LYS  68   -17.376  28.222  37.198  1.00  52.53    1DIK 574
ATOM   483  N   GLY  69   -23.675  25.022  33.664  1.00  35.27    1DIK 575
ATOM   484  CA  GLY  69   -24.928  25.439  33.058  1.00  38.22    1DIK 576
ATOM   485  C   GLY  69   -26.073  25.358  34.054  1.00  41.32    1DIK 577
ATOM   486  O   GLY  69   -26.947  26.228  34.057  1.00  41.17    1DIK 578
ATOM   487  N   LYS  70   -26.059  24.313  34.891  1.00  42.89    1DIK 579
ATOM   488  CA  LYS  70   -27.071  24.092  35.934  1.00  44.02    1DIK 580
ATOM   489  C   LYS  70   -27.075  25.317  36.840  1.00  41.82    1DIK 581
ATOM   490  O   LYS  70   -28.110  25.959  37.043  1.00  42.10    1DIK 582
ATOM   491  CB  LYS  70   -26.717  22.892  36.835  1.00  49.51    1DIK 583
ATOM   492  CG  LYS  70   -26.624  21.513  36.195  1.00  53.72    1DIK 584
ATOM   493  CD  LYS  70   -27.976  20.920  35.867  1.00  56.10    1DIK 585
ATOM   494  CE  LYS  70   -27.822  19.444  35.549  1.00  56.46    1DIK 586
ATOM   495  NZ  LYS  70   -28.950  18.940  34.717  1.00  58.23    1DIK 587
ATOM   496  N   LYS  71   -25.901  25.625  37.382  1.00  34.23    1DIK 588
ATOM   497  CA  LYS  71   -25.735  26.752  38.278  1.00  32.70    1DIK 589
ATOM   498  C   LYS  71   -26.157  28.070  37.644  1.00  32.77    1DIK 590
ATOM   499  O   LYS  71   -26.839  28.867  38.283  1.00  34.19    1DIK 591
ATOM   500  CB  LYS  71   -24.294  26.814  38.743  1.00  34.32    1DIK 592
ATOM   501  CG  LYS  71   -23.848  25.549  39.465  1.00  38.15    1DIK 593
ATOM   502  CD  LYS  71   -22.365  25.606  39.758  1.00  42.92    1DIK 594
ATOM   503  CE  LYS  71   -21.904  24.450  40.639  1.00  47.95    1DIK 595
ATOM   504  NZ  LYS  71   -20.408  24.463  40.789  1.00  52.26    1DIK 596
ATOM   505  N   TYR  72   -25.764  28.298  36.393  1.00  31.69    1DIK 597
ATOM   506  CA  TYR  72   -26.128  29.526  35.676  1.00  31.22    1DIK 598
ATOM   507  C   TYR  72   -27.642  29.636  35.580  1.00  32.50    1DIK 599
ATOM   508  O   TYR  72   -28.232  30.663  35.916  1.00  31.20    1DIK 600
ATOM   509  CB  TYR  72   -25.550  29.524  34.254  1.00  28.26    1DIK 601
ATOM   510  CG  TYR  72   -24.045  29.680  34.164  1.00  24.30    1DIK 602
ATOM   511  CD1 TYR  72   -23.278  30.037  35.282  1.00  21.92    1DIK 603
ATOM   512  CD2 TYR  72   -23.383  29.475  32.951  1.00  26.92    1DIK 604
ATOM   513  CE1 TYR  72   -21.894  30.186  35.192  1.00  21.95    1DIK 605
ATOM   514  CE2 TYR  72   -21.999  29.623  32.850  1.00  25.41    1DIK 606
ATOM   515  CZ  TYR  72   -21.265  29.977  33.971  1.00  26.50    1DIK 607
ATOM   516  OH  TYR  72   -19.904  30.124  33.860  1.00  31.12    1DIK 608
```

FIG. 8-9

```
ATOM  517  N    SER  73   -28.262  28.562  35.114  1.00  34.91      1DIK 609
ATOM  518  CA   SER  73   -29.705  28.498  34.965  1.00  37.19      1DIK 610
ATOM  519  C    SER  73   -30.430  28.745  36.286  1.00  36.76      1DIK 611
ATOM  520  O    SER  73   -31.337  29.576  36.367  1.00  39.80      1DIK 612
ATOM  521  CB   SER  73   -30.100  27.133  34.421  1.00  37.82      1DIK 613
ATOM  522  OG   SER  73   -31.450  27.151  34.001  1.00  48.85      1DIK 614
ATOM  523  N    ALA  74   -30.027  28.017  37.321  1.00  36.25      1DIK 615
ATOM  524  CA   ALA  74   -30.627  28.143  38.645  1.00  32.75      1DIK 616
ATOM  525  C    ALA  74   -30.544  29.585  39.162  1.00  33.94      1DIK 617
ATOM  526  O    ALA  74   -31.544  30.156  39.607  1.00  37.43      1DIK 618
ATOM  527  CB   ALA  74   -29.929  27.196  39.612  1.00  27.83      1DIK 619
ATOM  528  N    LEU  75   -29.352  30.169  39.094  1.00  31.82      1DIK 620
ATOM  529  CA   LEU  75   -29.130  31.529  39.552  1.00  30.28      1DIK 621
ATOM  530  C    LEU  75   -30.043  32.526  38.855  1.00  32.18      1DIK 622
ATOM  531  O    LEU  75   -30.553  33.460  39.483  1.00  33.24      1DIK 623
ATOM  532  CB   LEU  75   -27.669  31.929  39.343  1.00  27.09      1DIK 624
ATOM  533  CG   LEU  75   -27.340  33.380  39.705  1.00  31.49      1DIK 625
ATOM  534  CD1  LEU  75   -27.680  33.616  41.182  1.00  32.22      1DIK 626
ATOM  535  CD2  LEU  75   -25.871  33.687  39.422  1.00  28.98      1DIK 627
ATOM  536  N    ILE  76   -30.253  32.334  37.559  1.00  34.42      1DIK 628
ATOM  537  CA   ILE  76   -31.107  33.235  36.800  1.00  35.51      1DIK 629
ATOM  538  C    ILE  76   -32.581  33.100  37.187  1.00  38.20      1DIK 630
ATOM  539  O    ILE  76   -33.287  34.104  37.290  1.00  37.73      1DIK 631
ATOM  540  CB   ILE  76   -30.897  33.040  35.271  1.00  35.44      1DIK 632
ATOM  541  CG1  ILE  76   -29.543  33.649  34.872  1.00  32.79      1DIK 633
ATOM  542  CG2  ILE  76   -32.051  33.665  34.467  1.00  30.04      1DIK 634
ATOM  543  CD1  ILE  76   -29.180  33.468  33.407  1.00  32.29      1DIK 635
ATOM  544  N    GLU  77   -33.050  31.876  37.409  1.00  41.02      1DIK 636
ATOM  545  CA   GLU  77   -34.440  31.683  37.801  1.00  45.17      1DIK 637
ATOM  546  C    GLU  77   -34.630  32.291  39.166  1.00  45.15      1DIK 638
ATOM  547  O    GLU  77   -35.655  32.926  39.434  1.00  46.76      1DIK 639
ATOM  548  CB   GLU  77   -34.800  30.209  37.861  1.00  51.95      1DIK 640
ATOM  549  CG   GLU  77   -34.891  29.564  36.499  1.00  66.31      1DIK 641
ATOM  550  CD   GLU  77   -35.578  28.203  36.531  1.00  74.99      1DIK 642
ATOM  551  OE1  GLU  77   -35.736  27.633  37.642  1.00  78.28      1DIK 643
ATOM  552  OE2  GLU  77   -35.960  27.702  35.443  1.00  79.43      1DIK 644
ATOM  553  N    GLU  78   -33.631  32.098  40.025  1.00  43.62      1DIK 645
ATOM  554  CA   GLU  78   -33.667  32.631  41.378  1.00  41.02      1DIK 646
ATOM  555  C    GLU  78   -33.758  34.155  41.364  1.00  38.09      1DIK 647
ATOM  556  O    GLU  78   -34.518  34.733  42.134  1.00  37.93      1DIK 648
ATOM  557  CB   GLU  78   -32.445  32.185  42.175  1.00  41.48      1DIK 649
ATOM  558  CG   GLU  78   -32.538  32.616  43.621  1.00  49.04      1DIK 650
ATOM  559  CD   GLU  78   -31.261  32.413  44.414  1.00  53.16      1DIK 651
ATOM  560  OE1  GLU  78   -30.551  31.404  44.174  1.00  56.49      1DIK 652
ATOM  561  OE2  GLU  78   -30.977  33.272  45.283  1.00  50.49      1DIK 653
ATOM  562  N    ILE  79   -32.989  34.810  40.501  1.00  36.46      1DIK 654
ATOM  563  CA   ILE  79   -33.059  36.265  40.400  1.00  37.33      1DIK 655
ATOM  564  C    ILE  79   -34.446  36.672  39.897  1.00  41.12      1DIK 656
ATOM  565  O    ILE  79   -35.034  37.648  40.374  1.00  43.28      1DIK 657
ATOM  566  CB   ILE  79   -32.003  36.829  39.418  1.00  36.22      1DIK 658
ATOM  567  CG1  ILE  79   -30.606  36.694  40.031  1.00  32.53      1DIK 659
ATOM  568  CG2  ILE  79   -32.341  38.300  39.057  1.00  30.60      1DIK 660
ATOM  569  CD1  ILE  79   -29.481  37.029  39.088  1.00  28.25      1DIK 661
ATOM  570  N    GLN  80   -34.965  35.918  38.934  1.00  41.53      1DIK 662
ATOM  571  CA   GLN  80   -36.276  36.201  38.375  1.00  43.98      1DIK 663
ATOM  572  C    GLN  80   -37.399  36.074  39.392  1.00  48.10      1DIK 664
ATOM  573  O    GLN  80   -38.450  36.687  39.228  1.00  51.13      1DIK 665
ATOM  574  CB   GLN  80   -36.549  35.290  37.186  1.00  40.14      1DIK 666
ATOM  575  CG   GLN  80   -35.828  35.733  35.933  1.00  41.38      1DIK 667
ATOM  576  CD   GLN  80   -35.983  34.751  34.792  1.00  42.01      1DIK 668
ATOM  577  OE1  GLN  80   -36.303  33.583  35.000  1.00  43.95      1DIK 669
ATOM  578  NE2  GLN  80   -35.753  35.220  33.577  1.00  40.77      1DIK 670
ATOM  579  N    GLN  81   -37.186  35.281  40.437  1.00  51.52      1DIK 671
ATOM  580  CA   GLN  81   -38.205  35.105  41.468  1.00  54.70      1DIK 672
ATOM  581  C    GLN  81   -38.099  36.109  42.611  1.00  54.45      1DIK 673
ATOM  582  O    GLN  81   -39.089  36.717  43.004  1.00  57.66      1DIK 674
```

FIG. 8-10

```
ATOM    583  CB  GLN    81     -38.139  33.699  42.050  1.00  58.18      1DIK 675
ATOM    584  CG  GLN    81     -38.560  32.607  41.093  1.00  70.29      1DIK 676
ATOM    585  CD  GLN    81     -38.505  31.233  41.746  1.00  78.03      1DIK 677
ATOM    586  OE1 GLN    81     -39.099  31.014  42.809  1.00  80.87      1DIK 678
ATOM    587  NE2 GLN    81     -37.790  30.300  41.116  1.00  80.03      1DIK 679
ATOM    588  N   ASN    82     -36.896  36.280  43.138  1.00  52.58      1DIK 680
ATOM    589  CA  ASN    82     -36.668  37.179  44.263  1.00  52.84      1DIK 681
ATOM    590  C   ASN    82     -36.717  38.688  44.013  1.00  53.31      1DIK 682
ATOM    591  O   ASN    82     -37.110  39.445  44.905  1.00  53.72      1DIK 683
ATOM    592  CB  ASN    82     -35.336  36.828  44.944  1.00  51.31      1DIK 684
ATOM    593  CG  ASN    82     -35.320  35.418  45.520  1.00  50.40      1DIK 685
ATOM    594  OD1 ASN    82     -36.250  34.629  45.312  1.00  46.50      1DIK 686
ATOM    595  ND2 ASN    82     -34.257  35.092  46.246  1.00  48.14      1DIK 687
ATOM    596  N   ALA    83     -36.316  39.133  42.823  1.00  55.26      1DIK 688
ATOM    597  CA  ALA    83     -36.300  40.566  42.518  1.00  54.90      1DIK 689
ATOM    598  C   ALA    83     -37.693  41.174  42.326  1.00  56.32      1DIK 690
ATOM    599  O   ALA    83     -38.545  40.619  41.617  1.00  52.96      1DIK 691
ATOM    600  CB  ALA    83     -35.417  40.846  41.296  1.00  51.72      1DIK 692
ATOM    601  N   THR    84     -37.905  42.320  42.974  1.00  58.60      1DIK 693
ATOM    602  CA  THR    84     -39.166  43.048  42.904  1.00  59.70      1DIK 694
ATOM    603  C   THR    84     -39.170  44.025  41.730  1.00  60.59      1DIK 695
ATOM    604  O   THR    84     -40.212  44.256  41.116  1.00  63.43      1DIK 696
ATOM    605  CB  THR    84     -39.452  43.835  44.223  1.00  61.01      1DIK 697
ATOM    606  OG1 THR    84     -38.308  44.638  44.574  1.00  61.94      1DIK 698
ATOM    607  CG2 THR    84     -39.786  42.871  45.375  1.00  57.54      1DIK 699
ATOM    608  N   THR    85     -38.011  44.595  41.410  1.00  60.26      1DIK 700
ATOM    609  CA  THR    85     -37.923  45.550  40.309  1.00  61.94      1DIK 701
ATOM    610  C   THR    85     -36.844  45.254  39.271  1.00  60.00      1DIK 702
ATOM    611  O   THR    85     -35.710  44.923  39.608  1.00  58.14      1DIK 703
ATOM    612  CB  THR    85     -37.714  46.973  40.844  1.00  64.54      1DIK 704
ATOM    613  OG1 THR    85     -36.901  46.916  42.027  1.00  68.74      1DIK 705
ATOM    614  CG2 THR    85     -39.062  47.627  41.167  1.00  64.69      1DIK 706
ATOM    615  N   PHE    86     -37.217  45.380  38.003  1.00  59.68      1DIK 707
ATOM    616  CA  PHE    86     -36.301  45.143  36.895  1.00  59.09      1DIK 708
ATOM    617  C   PHE    86     -36.308  46.366  35.988  1.00  58.32      1DIK 709
ATOM    618  O   PHE    86     -36.829  46.298  34.880  1.00  58.58      1DIK 710
ATOM    619  CB  PHE    86     -36.752  43.940  36.055  1.00  59.17      1DIK 711
ATOM    620  CG  PHE    86     -36.747  42.633  36.787  1.00  60.12      1DIK 712
ATOM    621  CD1 PHE    86     -35.566  41.917  36.952  1.00  60.09      1DIK 713
ATOM    622  CD2 PHE    86     -37.928  42.103  37.294  1.00  58.71      1DIK 714
ATOM    623  CE1 PHE    86     -35.564  40.685  37.614  1.00  62.46      1DIK 715
ATOM    624  CE2 PHE    86     -37.939  40.873  37.957  1.00  59.49      1DIK 716
ATOM    625  CZ  PHE    86     -36.756  40.162  38.117  1.00  59.88      1DIK 717
ATOM    626  N   ASP    87     -35.743  47.484  36.432  1.00  59.28      1DIK 718
ATOM    627  CA  ASP    87     -35.745  48.672  35.576  1.00  61.03      1DIK 719
ATOM    628  C   ASP    87     -34.390  49.050  34.977  1.00  58.67      1DIK 720
ATOM    629  O   ASP    87     -33.331  48.696  35.503  1.00  56.33      1DIK 721
ATOM    630  CB  ASP    87     -36.376  49.882  36.294  1.00  67.39      1DIK 722
ATOM    631  CG  ASP    87     -35.731  50.181  37.634  1.00  74.12      1DIK 723
ATOM    632  OD1 ASP    87     -34.542  50.581  37.654  1.00  77.08      1DIK 724
ATOM    633  OD2 ASP    87     -36.422  50.017  38.670  1.00  76.76      1DIK 725
ATOM    634  N   GLY    88     -34.438  49.775  33.864  1.00  56.11      1DIK 726
ATOM    635  CA  GLY    88     -33.223  50.193  33.195  1.00  52.64      1DIK 727
ATOM    636  C   GLY    88     -32.521  49.004  32.565  1.00  50.66      1DIK 728
ATOM    637  O   GLY    88     -33.161  48.140  31.950  1.00  48.22      1DIK 729
ATOM    638  N   LYS    89     -31.202  48.957  32.734  1.00  47.80      1DIK 730
ATOM    639  CA  LYS    89     -30.376  47.885  32.188  1.00  45.18      1DIK 731
ATOM    640  C   LYS    89     -30.681  46.482  32.744  1.00  44.09      1DIK 732
ATOM    641  O   LYS    89     -30.087  45.504  32.301  1.00  46.90      1DIK 733
ATOM    642  CB  LYS    89     -28.898  48.222  32.390  1.00  42.58      1DIK 734
ATOM    643  CG  LYS    89     -28.530  48.500  33.828  1.00  47.71      1DIK 735
ATOM    644  CD  LYS    89     -27.068  48.905  33.973  1.00  54.98      1DIK 736
ATOM    645  CE  LYS    89     -26.737  49.253  35.426  1.00  56.55      1DIK 737
ATOM    646  NZ  LYS    89     -25.293  49.611  35.610  1.00  61.03      1DIK 738
ATOM    647  N   TYR    90     -31.594  46.382  33.705  1.00  38.46      1DIK 739
ATOM    648  CA  TYR    90     -31.959  45.095  34.277  1.00  35.36      1DIK 740
```

FIG. 8-11

```
ATOM  649 C   TYR 90  -33.269 44.568 33.699 1.00 38.19      1DIK 741
ATOM  650 O   TYR 90  -33.709 43.469 34.042 1.00 36.65      1DIK 742
ATOM  651 CB  TYR 90  -32.122 45.220 35.781 1.00 32.46      1DIK 743
ATOM  652 CG  TYR 90  -30.873 45.633 36.506 1.00 31.81      1DIK 744
ATOM  653 CD1 TYR 90  -29.901 44.693 36.851 1.00 32.85      1DIK 745
ATOM  654 CD2 TYR 90  -30.668 46.959 36.866 1.00 32.53      1DIK 746
ATOM  655 CE1 TYR 90  -28.754 45.066 37.539 1.00 29.82      1DIK 747
ATOM  656 CE2 TYR 90  -29.528 47.351 37.553 1.00 32.39      1DIK 748
ATOM  657 CZ  TYR 90  -28.574 46.400 37.887 1.00 34.71      1DIK 749
ATOM  658 OH  TYR 90  -27.446 46.792 38.565 1.00 31.33      1DIK 750
ATOM  659 N   ALA 91  -33.891 45.351 32.820 1.00 41.63      1DIK 751
ATOM  660 CA  ALA 91  -35.168 44.978 32.218 1.00 40.63      1DIK 752
ATOM  661 C   ALA 91  -35.159 43.631 31.510 1.00 40.55      1DIK 753
ATOM  662 O   ALA 91  -36.105 42.858 31.641 1.00 41.26      1DIK 754
ATOM  663 CB  ALA 91  -35.632 46.069 31.262 1.00 40.02      1DIK 755
ATOM  664 N   PHE 92  -34.097 43.340 30.763 1.00 41.42      1DIK 756
ATOM  665 CA  PHE 92  -34.010 42.069 30.036 1.00 39.95      1DIK 757
ATOM  666 C   PHE 92  -34.164 40.849 30.938 1.00 38.42      1DIK 758
ATOM  667 O   PHE 92  -34.726 39.836 30.526 1.00 36.46      1DIK 759
ATOM  668 CB  PHE 92  -32.677 41.972 29.287 1.00 38.12      1DIK 760
ATOM  669 CG  PHE 92  -31.499 41.624 30.163 1.00 36.18      1DIK 761
ATOM  670 CD1 PHE 92  -30.861 42.606 30.919 1.00 32.76      1DIK 762
ATOM  671 CD2 PHE 92  -31.018 40.314 30.215 1.00 34.57      1DIK 763
ATOM  672 CE1 PHE 92  -29.760 42.297 31.713 1.00 34.09      1DIK 764
ATOM  673 CE2 PHE 92  -29.917 39.991 31.006 1.00 33.52      1DIK 765
ATOM  674 CZ  PHE 92  -29.284 40.988 31.759 1.00 34.32      1DIK 766
ATOM  675 N   LEU 93  -33.657 40.961 32.164 1.00 39.65      1DIK 767
ATOM  676 CA  LEU 93  -33.707 39.877 33.143 1.00 42.68      1DIK 768
ATOM  677 C   LEU 93  -35.097 39.376 33.504 1.00 46.01      1DIK 769
ATOM  678 O   LEU 93  -35.271 38.199 33.839 1.00 46.08      1DIK 770
ATOM  679 CB  LEU 93  -32.981 40.284 34.428 1.00 39.70      1DIK 771
ATOM  680 CG  LEU 93  -31.479 39.991 34.430 1.00 38.98      1DIK 772
ATOM  681 CD1 LEU 93  -30.805 40.641 35.632 1.00 37.62      1DIK 773
ATOM  682 CD2 LEU 93  -31.258 38.480 34.419 1.00 35.20      1DIK 774
ATOM  683 N   LYS 94  -36.085 40.257 33.437 1.00 50.11      1DIK 775
ATOM  684 CA  LYS 94  -37.445 39.874 33.780 1.00 54.55      1DIK 776
ATOM  685 C   LYS 94  -37.938 38.709 32.915 1.00 54.53      1DIK 777
ATOM  686 O   LYS 94  -38.651 37.831 33.402 1.00 56.72      1DIK 778
ATOM  687 CB  LYS 94  -38.380 41.087 33.663 1.00 59.55      1DIK 779
ATOM  688 CG  LYS 94  -39.736 40.899 34.322 1.00 66.52      1DIK 780
ATOM  689 CD  LYS 94  -40.436 42.236 34.556 1.00 71.87      1DIK 781
ATOM  690 CE  LYS 94  -41.818 42.031 35.189 1.00 75.09      1DIK 782
ATOM  691 NZ  LYS 94  -42.493 43.320 35.533 1.00 75.30      1DIK 783
ATOM  692 N   THR 95  -37.549 38.687 31.643 1.00 52.52      1DIK 784
ATOM  693 CA  THR 95  -37.991 37.622 30.748 1.00 50.56      1DIK 785
ATOM  694 C   THR 95  -36.902 36.850 30.009 1.00 49.46      1DIK 786
ATOM  695 O   THR 95  -37.177 36.258 28.960 1.00 48.63      1DIK 787
ATOM  696 CB  THR 95  -38.962 38.168 29.700 1.00 52.17      1DIK 788
ATOM  697 OG1 THR 95  -38.366 39.295 29.039 1.00 48.18      1DIK 789
ATOM  698 CG2 THR 95  -40.272 38.574 30.357 1.00 54.41      1DIK 790
ATOM  699 N   TYR 96  -35.676 36.855 30.531 1.00 47.27      1DIK 791
ATOM  700 CA  TYR 96  -34.582 36.119 29.894 1.00 44.27      1DIK 792
ATOM  701 C   TYR 96  -34.863 34.613 29.997 1.00 44.70      1DIK 793
ATOM  702 O   TYR 96  -35.227 34.107 31.060 1.00 43.58      1DIK 794
ATOM  703 CB  TYR 96  -33.236 36.456 30.550 1.00 37.81      1DIK 795
ATOM  704 CG  TYR 96  -32.071 35.699 29.957 1.00 34.72      1DIK 796
ATOM  705 CD1 TYR 96  -31.362 36.208 28.866 1.00 38.16      1DIK 797
ATOM  706 CD2 TYR 96  -31.683 34.465 30.474 1.00 35.36      1DIK 798
ATOM  707 CE1 TYR 96  -30.290 35.499 28.302 1.00 37.21      1DIK 799
ATOM  708 CE2 TYR 96  -30.620 33.747 29.923 1.00 37.79      1DIK 800
ATOM  709 CZ  TYR 96  -29.929 34.269 28.839 1.00 39.34      1DIK 801
ATOM  710 OH  TYR 96  -28.882 33.557 28.303 1.00 37.35      1DIK 802
ATOM  711 N   ASN 97  -34.694 33.903 28.888 1.00 43.16      1DIK 803
ATOM  712 CA  ASN 97  -34.937 32.471 28.859 1.00 45.14      1DIK 804
ATOM  713 C   ASN 97  -33.617 31.744 28.554 1.00 45.53      1DIK 805
ATOM  714 O   ASN 97  -33.097 31.838 27.436 1.00 46.50      1DIK 806
```

FIG. 8-12

```
ATOM  715  CB   ASN   97   -35.988  32.167  27.788  1.00  50.43    1DIK 807
ATOM  716  CG   ASN   97   -36.536  30.758  27.895  1.00  58.07    1DIK 808
ATOM  717  OD1  ASN   97   -36.630  30.191  28.991  1.00  62.08    1DIK 809
ATOM  718  ND2  ASN   97   -36.905  30.179  26.755  1.00  59.47    1DIK 810
ATOM  719  N    TYR   98   -33.079  31.035  29.550  1.00  42.20    1DIK 811
ATOM  720  CA   TYR   98   -31.814  30.308  29.413  1.00  39.67    1DIK 812
ATOM  721  C    TYR   98   -31.937  29.149  28.430  1.00  39.43    1DIK 813
ATOM  722  O    TYR   98   -32.589  28.156  28.719  1.00  42.93    1DIK 814
ATOM  723  CB   TYR   98   -31.357  29.772  30.775  1.00  35.56    1DIK 815
ATOM  724  CG   TYR   98   -29.955  29.201  30.763  1.00  34.67    1DIK 816
ATOM  725  CD1  TYR   98   -29.720  27.862  30.440  1.00  33.36    1DIK 817
ATOM  726  CD2  TYR   98   -28.857  30.004  31.067  1.00  30.84    1DIK 818
ATOM  727  CE1  TYR   98   -28.421  27.343  30.421  1.00  33.02    1DIK 819
ATOM  728  CE2  TYR   98   -27.564  29.496  31.053  1.00  31.68    1DIK 820
ATOM  729  CZ   TYR   98   -27.351  28.167  30.731  1.00  32.17    1DIK 821
ATOM  730  OH   TYR   98   -26.071  27.673  30.742  1.00  31.22    1DIK 822
ATOM  731  N    SER   99   -31.304  29.267  27.272  1.00  41.23    1DIK 823
ATOM  732  CA   SER   99   -31.395  28.211  26.277  1.00  42.13    1DIK 824
ATOM  733  C    SER   99   -30.043  27.782  25.699  1.00  41.05    1DIK 825
ATOM  734  O    SER   99   -29.972  27.293  24.572  1.00  39.39    1DIK 826
ATOM  735  CB   SER   99   -32.340  28.645  25.148  1.00  43.93    1DIK 827
ATOM  736  OG   SER   99   -31.869  29.828  24.518  1.00  44.91    1DIK 828
ATOM  737  N    LEU  100   -28.970  27.964  26.464  1.00  38.89    1DIK 829
ATOM  738  CA   LEU  100   -27.647  27.561  25.999  1.00  36.71    1DIK 830
ATOM  739  C    LEU  100   -27.555  26.038  26.067  1.00  35.82    1DIK 831
ATOM  740  O    LEU  100   -28.181  25.425  26.932  1.00  37.24    1DIK 832
ATOM  741  CB   LEU  100   -26.548  28.175  26.878  1.00  33.03    1DIK 833
ATOM  742  CG   LEU  100   -26.381  29.694  26.799  1.00  33.85    1DIK 834
ATOM  743  CD1  LEU  100   -25.272  30.149  27.725  1.00  30.27    1DIK 835
ATOM  744  CD2  LEU  100   -26.063  30.090  25.375  1.00  33.01    1DIK 836
ATOM  745  N    GLY  101   -26.789  25.437  25.153  1.00  34.71    1DIK 837
ATOM  746  CA   GLY  101   -26.585  23.999  25.169  1.00  29.13    1DIK 838
ATOM  747  C    GLY  101   -25.572  23.673  26.270  1.00  31.41    1DIK 839
ATOM  748  O    GLY  101   -25.410  24.443  27.227  1.00  28.98    1DIK 840
ATOM  749  N    ALA  102   -24.875  22.547  26.163  1.00  30.11    1DIK 841
ATOM  750  CA   ALA  102   -23.892  22.208  27.180  1.00  29.75    1DIK 842
ATOM  751  C    ALA  102   -22.745  21.409  26.581  1.00  29.60    1DIK 843
ATOM  752  O    ALA  102   -22.943  20.675  25.622  1.00  32.26    1DIK 844
ATOM  753  CB   ALA  102   -24.556  21.423  28.318  1.00  26.45    1DIK 845
ATOM  754  N    ASP  103   -21.553  21.578  27.148  1.00  29.83    1DIK 846
ATOM  755  CA   ASP  103   -20.329  20.868  26.756  1.00  31.04    1DIK 847
ATOM  756  C    ASP  103   -19.817  20.909  25.318  1.00  29.41    1DIK 848
ATOM  757  O    ASP  103   -18.603  20.919  25.093  1.00  26.94    1DIK 849
ATOM  758  CB   ASP  103   -20.425  19.391  27.175  1.00  32.82    1DIK 850
ATOM  759  CG   ASP  103   -20.685  19.213  28.665  1.00  37.87    1DIK 851
ATOM  760  OD1  ASP  103   -19.906  19.738  29.490  1.00  39.37    1DIK 852
ATOM  761  OD2  ASP  103   -21.677  18.540  29.013  1.00  39.81    1DIK 853
ATOM  762  N    ASP  104   -20.723  20.924  24.351  1.00  28.43    1DIK 854
ATOM  763  CA   ASP  104   -20.356  20.891  22.954  1.00  29.73    1DIK 855
ATOM  764  C    ASP  104   -19.720  22.127  22.382  1.00  30.60    1DIK 856
ATOM  765  O    ASP  104   -19.830  23.226  22.925  1.00  32.58    1DIK 857
ATOM  766  CB   ASP  104   -21.581  20.573  22.096  1.00  37.28    1DIK 858
ATOM  767  CG   ASP  104   -22.117  19.176  22.321  1.00  43.64    1DIK 859
ATOM  768  OD1  ASP  104   -21.308  18.243  22.545  1.00  45.93    1DIK 860
ATOM  769  OD2  ASP  104   -23.358  19.019  22.268  1.00  49.65    1DIK 861
ATOM  770  N    LEU  105   -19.053  21.915  21.257  1.00  27.70    1DIK 862
ATOM  771  CA   LEU  105   -18.432  22.973  20.491  1.00  27.87    1DIK 863
ATOM  772  C    LEU  105   -19.642  23.744  19.933  1.00  29.06    1DIK 864
ATOM  773  O    LEU  105   -20.626  23.116  19.531  1.00  27.73    1DIK 865
ATOM  774  CB   LEU  105   -17.668  22.327  19.334  1.00  27.40    1DIK 866
ATOM  775  CG   LEU  105   -16.474  23.040  18.736  1.00  27.83    1DIK 867
ATOM  776  CD1  LEU  105   -15.518  23.368  19.855  1.00  33.80    1DIK 868
ATOM  777  CD2  LEU  105   -15.790  22.162  17.716  1.00  27.39    1DIK 869
ATOM  778  N    THR  106   -19.599  25.075  19.917  1.00  28.75    1DIK 870
ATOM  779  CA   THR  106   -20.714  25.848  19.358  1.00  28.71    1DIK 871
ATOM  780  C    THR  106   -20.462  26.060  17.858  1.00  31.52    1DIK 872
```

FIG. 8-13

```
ATOM    781  O   THR   106     -19.338  25.863  17.369  1.00  32.15      1DIK 873
ATOM    782  CB  THR   106     -20.849  27.256  20.001  1.00  29.41      1DIK 874
ATOM    783  OG1 THR   106     -19.691  28.044  19.698  1.00  28.94      1DIK 875
ATOM    784  CG2 THR   106     -21.034  27.164  21.496  1.00  27.82      1DIK 876
ATOM    785  N   PRO   107     -21.503  26.448  17.098  1.00  30.71      1DIK 877
ATOM    786  CA  PRO   107     -21.312  26.680  15.658  1.00  28.88      1DIK 878
ATOM    787  C   PRO   107     -20.169  27.693  15.406  1.00  27.50      1DIK 879
ATOM    788  O   PRO   107     -19.381  27.531  14.464  1.00  30.80      1DIK 880
ATOM    789  CB  PRO   107     -22.679  27.203  15.218  1.00  25.78      1DIK 881
ATOM    790  CG  PRO   107     -23.610  26.495  16.163  1.00  27.66      1DIK 882
ATOM    791  CD  PRO   107     -22.910  26.662  17.481  1.00  28.45      1DIK 883
ATOM    792  N   PHE   108     -20.082  28.727  16.245  1.00  23.11      1DIK 884
ATOM    793  CA  PHE   108     -19.015  29.729  16.151  1.00  22.62      1DIK 885
ATOM    794  C   PHE   108     -17.644  29.059  16.383  1.00  25.28      1DIK 886
ATOM    795  O   PHE   108     -16.657  29.356  15.670  1.00  25.00      1DIK 887
ATOM    796  CB  PHE   108     -19.226  30.837  17.195  1.00  20.26      1DIK 888
ATOM    797  CG  PHE   108     -18.063  31.794  17.312  1.00  25.13      1DIK 889
ATOM    798  CD1 PHE   108     -17.819  32.743  16.325  1.00  24.81      1DIK 890
ATOM    799  CD2 PHE   108     -17.196  31.737  18.410  1.00  28.22      1DIK 891
ATOM    800  CE1 PHE   108     -16.726  33.617  16.430  1.00  26.50      1DIK 892
ATOM    801  CE2 PHE   108     -16.101  32.609  18.521  1.00  25.64      1DIK 893
ATOM    802  CZ  PHE   108     -15.868  33.546  17.531  1.00  22.77      1DIK 894
ATOM    803  N   GLY   109     -17.597  28.164  17.380  1.00  21.53      1DIK 895
ATOM    804  CA  GLY   109     -16.383  27.428  17.704  1.00  21.31      1DIK 896
ATOM    805  C   GLY   109     -15.917  26.535  16.562  1.00  22.06      1DIK 897
ATOM    806  O   GLY   109     -14.713  26.384  16.338  1.00  22.23      1DIK 898
ATOM    807  N   GLU   110     -16.869  25.941  15.842  1.00  20.87      1DIK 899
ATOM    808  CA  GLU   110     -16.565  25.108  14.687  1.00  18.70      1DIK 900
ATOM    809  C   GLU   110     -15.908  25.975  13.623  1.00  19.56      1DIK 901
ATOM    810  O   GLU   110     -14.895  25.590  13.019  1.00  20.43      1DIK 902
ATOM    811  CB  GLU   110     -17.843  24.513  14.123  1.00  19.80      1DIK 903
ATOM    812  CG  GLU   110     -18.563  23.605  15.104  1.00  22.70      1DIK 904
ATOM    813  CD  GLU   110     -19.803  22.983  14.520  1.00  23.25      1DIK 905
ATOM    814  OE1 GLU   110     -20.346  23.513  13.524  1.00  27.96      1DIK 906
ATOM    815  OE2 GLU   110     -20.237  21.955  15.063  1.00  26.17      1DIK 907
ATOM    816  N   GLN   111     -16.489  27.153  13.402  1.00  18.95      1DIK 908
ATOM    817  CA  GLN   111     -15.963  28.094  12.427  1.00  20.74      1DIK 909
ATOM    818  C   GLN   111     -14.541  28.523  12.791  1.00  21.64      1DIK 910
ATOM    819  O   GLN   111     -13.679  28.651  11.908  1.00  21.26      1DIK 911
ATOM    820  CB  GLN   111     -16.868  29.321  12.319  1.00  26.01      1DIK 912
ATOM    821  CG  GLN   111     -16.527  30.222  11.144  1.00  32.20      1DIK 913
ATOM    822  CD  GLN   111     -16.503  29.455   9.825  1.00  37.67      1DIK 914
ATOM    823  OE1 GLN   111     -17.440  28.718   9.511  1.00  42.78      1DIK 915
ATOM    824  NE2 GLN   111     -15.432  29.620   9.051  1.00  34.61      1DIK 916
ATOM    825  N   GLU   112     -14.292  28.743  14.084  1.00  20.80      1DIK 917
ATOM    826  CA  GLU   112     -12.960  29.137  14.550  1.00  19.26      1DIK 918
ATOM    827  C   GLU   112     -11.875  28.135  14.133  1.00  19.50      1DIK 919
ATOM    828  O   GLU   112     -10.777  28.537  13.705  1.00  14.92      1DIK 920
ATOM    829  CB  GLU   112     -12.923  29.262  16.075  1.00  19.60      1DIK 921
ATOM    830  CG  GLU   112     -13.535  30.522  16.669  1.00  19.22      1DIK 922
ATOM    831  CD  GLU   112     -13.276  30.607  18.157  1.00  19.02      1DIK 923
ATOM    832  OE1 GLU   112     -13.712  29.691  18.878  1.00  19.03      1DIK 924
ATOM    833  OE2 GLU   112     -12.636  31.576  18.611  1.00  19.54      1DIK 925
ATOM    834  N   LEU   113     -12.177  26.841  14.262  1.00  15.87      1DIK 926
ATOM    835  CA  LEU   113     -11.213  25.803  13.908  1.00  18.95      1DIK 927
ATOM    836  C   LEU   113     -11.023  25.666  12.398  1.00  19.66      1DIK 928
ATOM    837  O   LEU   113      -9.907  25.411  11.929  1.00  19.09      1DIK 929
ATOM    838  CB  LEU   113     -11.592  24.471  14.559  1.00  19.94      1DIK 930
ATOM    839  CG  LEU   113     -11.016  24.283  15.966  1.00  19.61      1DIK 931
ATOM    840  CD1 LEU   113      -9.550  23.910  15.842  1.00  17.82      1DIK 932
ATOM    841  CD2 LEU   113     -11.190  25.552  16.819  1.00  15.58      1DIK 933
ATOM    842  N   VAL   114     -12.104  25.840  11.641  1.00  20.06      1DIK 934
ATOM    843  CA  VAL   114     -12.020  25.801  10.183  1.00  18.34      1DIK 935
ATOM    844  C   VAL   114     -11.039  26.916   9.779  1.00  19.73      1DIK 936
ATOM    845  O   VAL   114     -10.108  26.692   9.003  1.00  20.73      1DIK 937
ATOM    846  CB  VAL   114     -13.411  26.071   9.526  1.00  21.09      1DIK 938
```

FIG. 8-14

```
ATOM    847  CG1 VAL   114     -13.246  26.333   8.048  1.00 11.01      1DIK 939
ATOM    848  CG2 VAL   114     -14.361  24.877   9.747  1.00 14.20      1DIK 940
ATOM    849  N   ASN   115     -11.245  28.115  10.322  1.00 19.62      1DIK 941
ATOM    850  CA  ASN   115     -10.371  29.255  10.031  1.00 19.27      1DIK 942
ATOM    851  C   ASN   115      -8.909  28.985  10.398  1.00 20.48      1DIK 943
ATOM    852  O   ASN   115      -7.993  29.371   9.673  1.00 19.85      1DIK 944
ATOM    853  CB  ASN   115     -10.844  30.494  10.776  1.00 19.96      1DIK 945
ATOM    854  CG  ASN   115     -12.094  31.109  10.175  1.00 21.18      1DIK 946
ATOM    855  OD1 ASN   115     -12.671  30.593   9.226  1.00 22.64      1DIK 947
ATOM    856  ND2 ASN   115     -12.516  32.227  10.733  1.00 19.58      1DIK 948
ATOM    857  N   SER   116      -8.699  28.327  11.532  1.00 22.03      1DIK 949
ATOM    858  CA  SER   116      -7.358  27.966  12.004  1.00 20.45      1DIK 950
ATOM    859  C   SER   116      -6.696  26.987  11.000  1.00 20.54      1DIK 951
ATOM    860  O   SER   116      -5.489  27.078  10.725  1.00 19.21      1DIK 952
ATOM    861  CB  SER   116      -7.465  27.330  13.407  1.00 20.16      1DIK 953
ATOM    862  OG  SER   116      -6.199  27.086  13.987  1.00 15.09      1DIK 954
ATOM    863  N   GLY   117      -7.484  26.059  10.458  1.00 17.37      1DIK 955
ATOM    864  CA  GLY   117      -6.963  25.112   9.485  1.00 18.31      1DIK 956
ATOM    865  C   GLY   117      -6.507  25.807   8.209  1.00 19.33      1DIK 957
ATOM    866  O   GLY   117      -5.468  25.455   7.647  1.00 22.20      1DIK 958
ATOM    867  N   ILE   118      -7.294  26.784   7.759  1.00 18.87      1DIK 959
ATOM    868  CA  ILE   118      -6.998  27.585   6.567  1.00 19.05      1DIK 960
ATOM    869  C   ILE   118      -5.690  28.347   6.739  1.00 19.38      1DIK 961
ATOM    870  O   ILE   118      -4.831  28.365   5.848  1.00 20.03      1DIK 962
ATOM    871  CB  ILE   118      -8.105  28.640   6.316  1.00 18.22      1DIK 963
ATOM    872  CG1 ILE   118      -9.392  27.959   5.860  1.00 16.45      1DIK 964
ATOM    873  CG2 ILE   118      -7.627  29.688   5.310  1.00 13.65      1DIK 965
ATOM    874  CD1 ILE   118     -10.549  28.901   5.792  1.00 12.46      1DIK 966
ATOM    875  N   LYS   119      -5.555  28.979   7.900  1.00 21.72      1DIK 967
ATOM    876  CA  LYS   119      -4.381  29.775   8.225  1.00 21.99      1DIK 968
ATOM    877  C   LYS   119      -3.095  28.955   8.340  1.00 22.12      1DIK 969
ATOM    878  O   LYS   119      -2.034  29.404   7.881  1.00 22.21      1DIK 970
ATOM    879  CB  LYS   119      -4.636  30.574   9.503  1.00 22.43      1DIK 971
ATOM    880  CG  LYS   119      -3.536  31.557   9.789  1.00 27.62      1DIK 972
ATOM    881  CD  LYS   119      -4.020  32.690  10.649  1.00 29.86      1DIK 973
ATOM    882  CE  LYS   119      -2.986  33.798  10.646  1.00 29.14      1DIK 974
ATOM    883  NZ  LYS   119      -3.311  34.827  11.667  1.00 30.24      1DIK 975
ATOM    884  N   PHE   120      -3.191  27.765   8.942  1.00 19.44      1DIK 976
ATOM    885  CA  PHE   120      -2.034  26.879   9.084  1.00 20.52      1DIK 977
ATOM    886  C   PHE   120      -1.561  26.429   7.694  1.00 22.99      1DIK 978
ATOM    887  O   PHE   120      -0.355  26.404   7.415  1.00 21.56      1DIK 979
ATOM    888  CB  PHE   120      -2.381  25.647   9.927  1.00 18.62      1DIK 980
ATOM    889  CG  PHE   120      -1.208  24.727  10.163  1.00 25.65      1DIK 981
ATOM    890  CD1 PHE   120      -0.192  25.083  11.059  1.00 23.32      1DIK 982
ATOM    891  CD2 PHE   120      -1.114  23.504   9.493  1.00 25.43      1DIK 983
ATOM    892  CE1 PHE   120       0.894  24.243  11.284  1.00 18.73      1DIK 984
ATOM    893  CE2 PHE   120      -0.025  22.651   9.712  1.00 22.55      1DIK 985
ATOM    894  CZ  PHE   120       0.981  23.021  10.610  1.00 20.53      1DIK 986
ATOM    895  N   TYR   121      -2.515  26.074   6.830  1.00 20.17      1DIK 987
ATOM    896  CA  TYR   121      -2.179  25.656   5.482  1.00 19.95      1DIK 988
ATOM    897  C   TYR   121      -1.450  26.766   4.718  1.00 21.59      1DIK 989
ATOM    898  O   TYR   121      -0.402  26.528   4.112  1.00 19.41      1DIK 990
ATOM    899  CB  TYR   121      -3.427  25.271   4.668  1.00 19.72      1DIK 991
ATOM    900  CG  TYR   121      -3.029  24.865   3.265  1.00 20.01      1DIK 992
ATOM    901  CD1 TYR   121      -2.859  25.819   2.240  1.00 18.79      1DIK 993
ATOM    902  CD2 TYR   121      -2.721  23.537   2.983  1.00 20.66      1DIK 994
ATOM    903  CE1 TYR   121      -2.381  25.445   0.976  1.00 19.33      1DIK 995
ATOM    904  CE2 TYR   121      -2.246  23.152   1.730  1.00 23.50      1DIK 996
ATOM    905  CZ  TYR   121      -2.074  24.097   0.737  1.00 23.64      1DIK 997
ATOM    906  OH  TYR   121      -1.593  23.670  -0.472  1.00 22.79      1DIK 998
ATOM    907  N   GLN   122      -2.021  27.969   4.734  1.00 23.17      1DIK 999
ATOM    908  CA  GLN   122      -1.447  29.104   4.022  1.00 22.67      1DIK1000
ATOM    909  C   GLN   122      -0.085  29.549   4.527  1.00 22.41      1DIK1001
ATOM    910  O   GLN   122       0.799  29.860   3.735  1.00 25.99      1DIK1002
ATOM    911  CB  GLN   122      -2.387  30.296   4.071  1.00 26.42      1DIK1103
ATOM    912  CG  GLN   122      -3.691  30.133   3.323  1.00 27.92      1DIK1004
```

FIG. 8-15

```
ATOM    913  CD   GLN  122   -4.623  31.333   3.531  1.00  34.41      1DIK1005
ATOM    914  OE1  GLN  122   -4.531  32.066   4.537  1.00  33.16      1DIK1006
ATOM    915  NE2  GLN  122   -5.528  31.538   2.582  1.00  36.14      1DIK1007
ATOM    916  N    ARG  123    0.089  29.586   5.841  1.00  22.55      1DIK1008
ATOM    917  CA   ARG  123    1.359  30.011   6.416  1.00  21.19      1DIK1009
ATOM    918  C    ARG  123    2.541  29.106   6.012  1.00  23.05      1DIK1010
ATOM    919  O    ARG  123    3.652  29.582   5.785  1.00  23.96      1DIK1011
ATOM    920  CB   ARG  123    1.225  30.083   7.947  1.00  20.65      1DIK1012
ATOM    921  CG   ARG  123    2.485  30.519   8.653  1.00  19.56      1DIK1013
ATOM    922  CD   ARG  123    2.297  30.672  10.146  1.00  21.87      1DIK1014
ATOM    923  NE   ARG  123    3.580  30.973  10.789  1.00  24.63      1DIK1015
ATOM    924  CZ   ARG  123    4.173  32.174  10.802  1.00  28.06      1DIK1016
ATOM    925  NH1  ARG  123    3.605  33.236  10.232  1.00  18.64      1DIK1017
ATOM    926  NH2  ARG  123    5.349  32.319  11.402  1.00  24.13      1DIK1018
ATOM    927  N    TYR  124    2.298  27.803   5.915  1.00  24.21      1DIK1019
ATOM    928  CA   TYR  124    3.346  26.852   5.572  1.00  24.48      1DIK1020
ATOM    929  C    TYR  124    3.125  26.182   4.222  1.00  26.16      1DIK1021
ATOM    930  O    TYR  124    3.486  25.016   4.049  1.00  24.40      1DIK1022
ATOM    931  CB   TYR  124    3.444  25.790   6.679  1.00  22.35      1DIK1023
ATOM    932  CG   TYR  124    3.696  26.398   8.040  1.00  24.40      1DIK1024
ATOM    933  CD1  TYR  124    4.946  26.923   8.360  1.00  20.62      1DIK1025
ATOM    934  CD2  TYR  124    2.677  26.484   8.998  1.00  25.42      1DIK1026
ATOM    935  CE1  TYR  124    5.186  27.515   9.579  1.00  20.04      1DIK1027
ATOM    936  CE2  TYR  124    2.907  27.082  10.236  1.00  22.59      1DIK1028
ATOM    937  CZ   TYR  124    4.176  27.600  10.521  1.00  22.79      1DIK1029
ATOM    938  OH   TYR  124    4.450  28.205  11.737  1.00  16.28      1DIK1030
ATOM    939  N    GLU  125    2.548  26.921   3.273  1.00  27.83      1DIK1031
ATOM    940  CA   GLU  125    2.242  26.406   1.931  1.00  31.93      1DIK1032
ATOM    941  C    GLU  125    3.321  25.534   1.276  1.00  31.07      1DIK1033
ATOM    942  O    GLU  125    3.008  24.504   0.680  1.00  31.87      1DIK1034
ATOM    943  CB   GLU  125    1.875  27.566   0.985  1.00  35.88      1DIK1035
ATOM    944  CG   GLU  125    1.226  27.149  -0.360  1.00  46.46      1DIK1036
ATOM    945  CD   GLU  125    2.239  26.814  -1.475  1.00  54.36      1DIK1037
ATOM    946  OE1  GLU  125    3.343  27.412  -1.491  1.00  58.38      1DIK1038
ATOM    947  OE2  GLU  125    1.937  25.955  -2.343  1.00  54.70      1DIK1039
ATOM    948  N    SER  126    4.583  25.929   1.383  1.00  28.00      1DIK1040
ATOM    949  CA   SER  126    5.651  25.161   0.755  1.00  31.00      1DIK1041
ATOM    950  C    SER  126    5.733  23.711   1.249  1.00  31.74      1DIK1042
ATOM    951  O    SER  126    6.217  22.831   0.525  1.00  32.26      1DIK1043
ATOM    952  CB   SER  126    6.992  25.881   0.936  1.00  33.57      1DIK1044
ATOM    953  OG   SER  126    7.256  26.134   2.308  1.00  41.28      1DIK1045
ATOM    954  N    LEU  127    5.262  23.476   2.477  1.00  28.17      1DIK1046
ATOM    955  CA   LEU  127    5.246  22.148   3.087  1.00  23.13      1DIK1047
ATOM    956  C    LEU  127    3.879  21.466   2.981  1.00  22.92      1DIK1048
ATOM    957  O    LEU  127    3.781  20.304   2.584  1.00  24.92      1DIK1049
ATOM    958  CB   LEU  127    5.601  22.236   4.569  1.00  21.37      1DIK1050
ATOM    959  CG   LEU  127    7.017  22.618   4.969  1.00  24.27      1DIK1051
ATOM    960  CD1  LEU  127    7.125  22.582   6.485  1.00  17.41      1DIK1052
ATOM    961  CD2  LEU  127    8.006  21.652   4.316  1.00  20.13      1DIK1053
ATOM    962  N    THR  128    2.833  22.198   3.352  1.00  22.22      1DIK1054
ATOM    963  CA   THR  128    1.461  21.701   3.357  1.00  21.36      1DIK1055
ATOM    964  C    THR  128    0.935  21.259   1.989  1.00  25.64      1DIK1056
ATOM    965  O    THR  128    0.016  20.429   1.907  1.00  26.78      1DIK1057
ATOM    966  CB   THR  128    0.502  22.765   3.941  1.00  18.91      1DIK1058
ATOM    967  OG1  THR  128    0.687  24.008   3.248  1.00  16.25      1DIK1059
ATOM    968  CG2  THR  128    0.771  22.971   5.413  1.00   8.45      1DIK1060
ATOM    969  N    ARG  129    1.510  21.803   0.917  1.00  27.58      1DIK1061
ATOM    970  CA   ARG  129    1.070  21.436  -0.423  1.00  27.49      1DIK1062
ATOM    971  C    ARG  129    1.303  19.975  -0.790  1.00  24.39      1DIK1063
ATOM    972  O    ARG  129    0.612  19.448  -1.652  1.00  25.81      1DIK1064
ATOM    973  CB   ARG  129    1.673  22.351  -1.484  1.00  28.84      1DIK1065
ATOM    974  CG   ARG  129    3.139  22.218  -1.685  1.00  31.94      1DIK1066
ATOM    975  CD   ARG  129    3.536  23.072  -2.860  1.00  46.51      1DIK1067
ATOM    976  NE   ARG  129    4.899  22.774  -3.270  1.00  59.18      1DIK1068
ATOM    977  CZ   ARG  129    5.879  23.669  -3.295  1.00  67.18      1DIK1069
ATOM    978  NH1  ARG  129    5.643  24.936  -2.948  1.00  66.97      1DIK1070
```

FIG. 8-16

```
ATOM    979  NH2 ARG 129     7.098  23.294  -3.672  1.00 69.63      1DIK1071
ATOM    980  N   ASN 130     2.266  19.306  -0.166  1.00 26.81      1DIK1072
ATOM    981  CA  ASN 130     2.456  17.883  -0.470  1.00 29.49      1DIK1073
ATOM    982  C   ASN 130     2.819  16.977   0.691  1.00 25.25      1DIK1074
ATOM    983  O   ASN 130     3.369  15.904   0.489  1.00 22.37      1DIK1075
ATOM    984  CB  ASN 130     3.407  17.643  -1.657  1.00 33.67      1DIK1076
ATOM    985  CG  ASN 130     4.679  18.415  -1.550  1.00 35.85      1DIK1077
ATOM    986  OD1 ASN 130     5.242  18.561  -0.472  1.00 41.17      1DIK1078
ATOM    987  ND2 ASN 130     5.148  18.926  -2.678  1.00 36.92      1DIK1079
ATOM    988  N   ILE 131     2.499  17.409   1.905  1.00 23.74      1DIK1080
ATOM    989  CA  ILE 131     2.729  16.600   3.087  1.00 22.76      1DIK1081
ATOM    990  C   ILE 131     1.405  16.555   3.857  1.00 22.22      1DIK1082
ATOM    991  O   ILE 131     0.706  17.568   3.994  1.00 20.81      1DIK1083
ATOM    992  CB  ILE 131     3.864  17.171   3.974  1.00 25.01      1DIK1084
ATOM    993  CG1 ILE 131     5.196  17.051   3.237  1.00 22.26      1DIK1085
ATOM    994  CG2 ILE 131     3.966  16.383   5.296  1.00 25.81      1DIK1086
ATOM    995  CD1 ILE 131     6.264  18.012   3.705  1.00 19.55      1DIK1087
ATOM    996  N   VAL 132     1.052  15.368   4.336  1.00 21.56      1DIK1088
ATOM    997  CA  VAL 132    -0.173  15.184   5.113  1.00 21.17      1DIK1089
ATOM    998  C   VAL 132     0.285  15.221   6.575  1.00 20.81      1DIK1090
ATOM    999  O   VAL 132     1.137  14.422   6.979  1.00 20.82      1DIK1091
ATOM   1000  CB  VAL 132    -0.841  13.807   4.803  1.00 18.52      1DIK1092
ATOM   1001  CG1 VAL 132    -2.123  13.651   5.597  1.00 14.56      1DIK1093
ATOM   1002  CG2 VAL 132    -1.126  13.686   3.320  1.00 13.43      1DIK1094
ATOM   1003  N   PRO 133    -0.260  16.151   7.383  1.00 20.75      1DIK1095
ATOM   1004  CA  PRO 133     0.116  16.273   8.798  1.00 17.17      1DIK1096
ATOM   1005  C   PRO 133    -0.288  15.036   9.585  1.00 20.37      1DIK1097
ATOM   1006  O   PRO 133    -1.268  14.364   9.229  1.00 19.54      1DIK1098
ATOM   1007  CB  PRO 133    -0.684  17.488   9.277  1.00 17.52      1DIK1099
ATOM   1008  CG  PRO 133    -1.029  18.231   8.029  1.00 19.74      1DIK1100
ATOM   1009  CD  PRO 133    -1.278  17.151   7.020  1.00 21.29      1DIK1101
ATOM   1010  N   PHE 134     0.467  14.721  10.641  1.00 20.95      1DIK1102
ATOM   1011  CA  PHE 134     0.131  13.596  11.514  1.00 18.61      1DIK1103
ATOM   1012  C   PHE 134    -0.583  14.285  12.677  1.00 17.69      1DIK1104
ATOM   1013  O   PHE 134    -0.016  15.175  13.310  1.00 17.93      1DIK1105
ATOM   1014  CB  PHE 134     1.368  12.847  12.003  1.00 17.50      1DIK1106
ATOM   1015  CG  PHE 134     1.040  11.715  12.941  1.00 17.28      1DIK1107
ATOM   1016  CD1 PHE 134     0.616  10.478  12.443  1.00 11.84      1DIK1108
ATOM   1017  CD2 PHE 134     1.133  11.888  14.324  1.00 13.50      1DIK1109
ATOM   1018  CE1 PHE 134     0.285   9.423  13.310  1.00 11.64      1DIK1110
ATOM   1019  CE2 PHE 134     0.804  10.837  15.203  1.00 12.13      1DIK1111
ATOM   1020  CZ  PHE 134     0.379   9.607  14.693  1.00 15.07      1DIK1112
ATOM   1021  N   ILE 135    -1.816  13.863  12.949  1.00 15.82      1DIK1113
ATOM   1022  CA  ILE 135    -2.670  14.495  13.953  1.00 13.71      1DIK1114
ATOM   1023  C   ILE 135    -3.088  13.644  15.156  1.00 14.35      1DIK1115
ATOM   1024  O   ILE 135    -3.425  12.461  15.015  1.00 16.80      1DIK1116
ATOM   1025  CB  ILE 135    -3.952  15.018  13.243  1.00 11.04      1DIK1117
ATOM   1026  CG1 ILE 135    -3.568  15.994  12.134  1.00  9.94      1DIK1118
ATOM   1027  CG2 ILE 135    -4.906  15.690  14.222  1.00 15.43      1DIK1119
ATOM   1028  CD1 ILE 135    -4.731  16.360  11.245  1.00 11.33      1DIK1120
ATOM   1029  N   ARG 136    -3.074  14.259  16.335  1.00 13.24      1DIK1121
ATOM   1030  CA  ARG 136    -3.480  13.593  17.571  1.00 15.19      1DIK1122
ATOM   1031  C   ARG 136    -4.451  14.511  18.296  1.00 16.07      1DIK1123
ATOM   1032  O   ARG 136    -4.355  15.734  18.190  1.00 16.44      1DIK1124
ATOM   1033  CB  ARG 136    -2.289  13.322  18.487  1.00 13.97      1DIK1125
ATOM   1034  CG  ARG 136    -1.203  12.434  17.905  1.00 12.99      1DIK1126
ATOM   1035  CD  ARG 136    -0.176  12.079  18.973  1.00 14.14      1DIK1127
ATOM   1036  NE  ARG 136     0.441  13.277  19.540  1.00 22.30      1DIK1128
ATOM   1037  CZ  ARG 136     1.335  13.288  20.525  1.00 20.79      1DIK1129
ATOM   1038  NH1 ARG 136     1.743  12.150  21.081  1.00 17.01      1DIK1130
ATOM   1039  NH2 ARG 136     1.819  14.450  20.951  1.00 17.84      1DIK1131
ATOM   1040  N   SER 137    -5.378  13.918  19.035  1.00 16.59      1DIK1132
ATOM   1041  CA  SER 137    -6.381  14.663  19.789  1.00 14.27      1DIK1133
ATOM   1042  C   SER 137    -6.624  13.982  21.147  1.00 17.11      1DIK1134
ATOM   1043  O   SER 137    -6.549  12.754  21.272  1.00 16.51      1DIK1135
ATOM   1044  CB  SER 137    -7.682  14.703  18.966  1.00 13.24      1DIK1136
```

FIG. 8-17

```
ATOM   1045  OG  SER 137   -8.804 15.178 19.690 1.00 13.55     1DIK1137
ATOM   1046  N   SER 138   -6.898 14.782 22.169 1.00 18.79     1DIK1138
ATOM   1047  CA  SER 138   -7.212 14.246 23.486 1.00 18.47     1DIK1139
ATOM   1048  C   SER 138   -8.651 13.714 23.338 1.00 20.67     1DIK1140
ATOM   1049  O   SER 138   -9.436 14.261 22.557 1.00 21.12     1DIK1141
ATOM   1050  CB  SER 138   -7.123 15.360 24.526 1.00 19.25     1DIK1142
ATOM   1051  OG  SER 138   -7.161 14.832 25.831 1.00 19.54     1DIK1143
ATOM   1052  N   GLY 139   -9.005 12.660 24.070 1.00 24.07     1DIK1144
ATOM   1053  CA  GLY 139  -10.326 12.064 23.923 1.00 23.86     1DIK1145
ATOM   1054  C   GLY 139  -11.511 12.774 24.550 1.00 26.14     1DIK1146
ATOM   1055  O   GLY 139  -12.114 12.261 25.491 1.00 33.68     1DIK1147
ATOM   1056  N   SER 140  -11.853 13.946 24.046 1.00 23.95     1DIK1148
ATOM   1057  CA  SER 140  -12.976 14.715 24.553 1.00 18.34     1DIK1149
ATOM   1058  C   SER 140  -13.709 15.148 23.296 1.00 21.76     1DIK1150
ATOM   1059  O   SER 140  -13.084 15.655 22.356 1.00 22.25     1DIK1151
ATOM   1060  CB  SER 140  -12.479 15.925 25.319 1.00 17.99     1DIK1152
ATOM   1061  OG  SER 140  -13.543 16.819 25.617 1.00 22.47     1DIK1153
ATOM   1062  N   SER 141  -15.024 14.959 23.274 1.00 19.07     1DIK1154
ATOM   1063  CA  SER 141  -15.825 15.278 22.097 1.00 21.60     1DIK1155
ATOM   1064  C   SER 141  -15.592 16.644 21.496 1.00 22.01     1DIK1156
ATOM   1065  O   SER 141  -15.468 16.764 20.275 1.00 23.16     1DIK1157
ATOM   1066  CB  SER 141  -17.303 15.111 22.399 1.00 23.43     1DIK1158
ATOM   1067  OG  SER 141  -17.480 14.054 23.319 1.00 40.45     1DIK1159
ATOM   1068  N   ARG 142  -15.526 17.675 22.335 1.00 19.81     1DIK1160
ATOM   1069  CA  ARG 142  -15.325 19.010 21.809 1.00 18.48     1DIK1161
ATOM   1070  C   ARG 142  -13.951 19.187 21.180 1.00 18.52     1DIK1162
ATOM   1071  O   ARG 142  -13.779 19.999 20.264 1.00 17.81     1DIK1163
ATOM   1072  CB  ARG 142  -15.580 20.072 22.885 1.00 17.69     1DIK1164
ATOM   1073  CG  ARG 142  -14.661 20.050 24.069 1.00 20.10     1DIK1165
ATOM   1074  CD  ARG 142  -14.952 21.269 24.913 1.00 23.72     1DIK1166
ATOM   1075  NE  ARG 142  -14.441 21.157 26.280 1.00 27.97     1DIK1167
ATOM   1076  CZ  ARG 142  -15.100 20.586 27.292 1.00 28.86     1DIK1168
ATOM   1077  NH1 ARG 142  -16.301 20.053 27.106 1.00 28.91     1DIK1169
ATOM   1078  NH2 ARG 142  -14.552 20.543 28.499 1.00 29.64     1DIK1170
ATOM   1079  N   VAL 143  -12.973 18.424 21.662 1.00 18.71     1DIK1171
ATOM   1080  CA  VAL 143  -11.620 18.516 21.137 1.00 16.09     1DIK1172
ATOM   1081  C   VAL 143  -11.561 17.777 19.799 1.00 19.00     1DIK1173
ATOM   1082  O   VAL 143  -11.031 18.303 18.802 1.00 19.96     1DIK1174
ATOM   1083  CB  VAL 143  -10.604 17.962 22.152 1.00 14.17     1DIK1175
ATOM   1084  CG1 VAL 143   -9.179 18.106 21.630 1.00 13.33     1DIK1176
ATOM   1085  CG2 VAL 143  -10.746 18.717 23.450 1.00 11.92     1DIK1177
ATOM   1086  N   ILE 144  -12.132 16.576 19.778 1.00 17.56     1DIK1178
ATOM   1087  CA  ILE 144  -12.177 15.752 18.582 1.00 17.36     1DIK1179
ATOM   1088  C   ILE 144  -12.882 16.490 17.431 1.00 19.27     1DIK1180
ATOM   1089  O   ILE 144  -12.400 16.492 16.281 1.00 20.66     1DIK1181
ATOM   1090  CB  ILE 144  -12.874 14.422 18.911 1.00 21.52     1DIK1182
ATOM   1091  CG1 ILE 144  -11.943 13.584 19.789 1.00 21.60     1DIK1183
ATOM   1092  CG2 ILE 144  -13.274 13.677 17.637 1.00 18.16     1DIK1184
ATOM   1093  CD1 ILE 144  -12.628 12.446 20.491 1.00 28.65     1DIK1185
ATOM   1094  N   ALA 145  -14.013 17.123 17.742 1.00 17.39     1DIK1186
ATOM   1095  CA  ALA 145  -14.780 17.889 16.752 1.00 15.97     1DIK1187
ATOM   1096  C   ALA 145  -13.951 19.066 16.243 1.00 18.18     1DIK1188
ATOM   1097  O   ALA 145  -14.049 19.436 15.073 1.00 20.54     1DIK1189
ATOM   1098  CB  ALA 145  -16.080 18.397 17.362 1.00 11.92     1DIK1190
ATOM   1099  N   SER 146  -13.141 19.654 17.125 1.00 17.49     1DIK1191
ATOM   1110  CA  SER 146  -12.273 20.768 16.759 1.00 18.53     1DIK1192
ATOM   1101  C   SER 146  -11.188 20.288 15.788 1.00 17.95     1DIK1193
ATOM   1102  O   SER 146  -10.843 20.988 14.823 1.00 15.32     1DIK1194
ATOM   1103  CB  SER 146  -11.648 21.379 18.015 1.00 20.60     1DIK1195
ATOM   1104  OG  SER 146  -12.654 21.966 18.836 1.00 18.35     1DIK1196
ATOM   1105  N   GLY 147  -10.668 19.088 16.047 1.00 17.16     1DIK1197
ATOM   1106  CA  GLY 147   -9.658 18.498 15.182 1.00 15.76     1DIK1198
ATOM   1107  C   GLY 147  -10.229 18.313 13.782 1.00 18.06     1DIK1199
ATOM   1108  O   GLY 147   -9.582 18.643 12.786 1.00 17.79     1DIK1200
ATOM   1109  N   LYS 148  -11.450 17.790 13.702 1.00 17.79     1DIK1201
ATOM   1110  CA  LYS 148  -12.123 17.585 12.422 1.00 16.21     1DIK1202
```

FIG. 8-18

```
ATOM   1111  C    LYS  148   -12.423  18.870  11.651  1.00  17.80      1DIK1203
ATOM   1112  O    LYS  148   -12.351  18.871  10.414  1.00  16.69      1DIK1204
ATOM   1113  CB   LYS  148   -13.422  16.821  12.631  1.00  20.50      1DIK1205
ATOM   1114  CG   LYS  148   -13.219  15.389  13.023  1.00  22.63      1DIK1206
ATOM   1115  CD   LYS  148   -14.539  14.722  13.227  1.00  27.17      1DIK1207
ATOM   1116  CE   LYS  148   -14.342  13.245  13.427  1.00  34.56      1DIK1208
ATOM   1117  NZ   LYS  148   -15.652  12.546  13.477  1.00  43.70      1DIK1209
ATOM   1118  N    LYS  149   -12.765  19.956  12.355  1.00  16.53      1DIK1210
ATOM   1119  CA   LYS  149   -13.049  21.221  11.680  1.00  19.05      1DIK1211
ATOM   1120  C    LYS  149   -11.756  21.821  11.132  1.00  19.26      1DIK1212
ATOM   1121  O    LYS  149   -11.747  22.412  10.050  1.00  19.18      1DIK1213
ATOM   1122  CB   LYS  149   -13.725  22.234  12.608  1.00  19.43      1DIK1214
ATOM   1123  CG   LYS  149   -15.018  21.775  13.196  1.00  25.49      1DIK1215
ATOM   1124  CD   LYS  149   -15.954  21.157  12.163  1.00  24.15      1DIK1216
ATOM   1125  CE   LYS  149   -16.677  22.178  11.350  1.00  24.54      1DIK1217
ATOM   1126  NZ   LYS  149   -17.717  21.492  10.530  1.00  23.29      1DIK1218
ATOM   1127  N    PHE  150   -10.672  21.677  11.885  1.00  17.03      1DIK1219
ATOM   1128  CA   PHE  150    -9.368  22.178  11.462  1.00  17.33      1DIK1220
ATOM   1129  C    PHE  150    -8.992  21.469  10.163  1.00  18.46      1DIK1221
ATOM   1130  O    PHE  150    -8.540  22.104   9.222  1.00  20.65      1DIK1222
ATOM   1131  CB   PHE  150    -8.321  21.892  12.555  1.00  17.32      1DIK1223
ATOM   1132  CG   PHE  150    -6.916  22.282  12.185  1.00  17.15      1DIK1224
ATOM   1133  CD1  PHE  150    -6.110  21.428  11.433  1.00  15.76      1DIK1225
ATOM   1134  CD2  PHE  150    -6.387  23.491  12.601  1.00  16.86      1DIK1226
ATOM   1135  CE1  PHE  150    -4.803  21.769  11.102  1.00  13.21      1DIK1227
ATOM   1136  CE2  PHE  150    -5.075  23.841  12.274  1.00  18.79      1DIK1228
ATOM   1137  CZ   PHE  150    -4.283  22.973  11.521  1.00  18.15      1DIK1229
ATOM   1138  N    ILE  151    -9.186  20.151  10.123  1.00  18.70      1DIK1230
ATOM   1139  CA   ILE  151    -8.887  19.337   8.949  1.00  16.84      1DIK1231
ATOM   1140  C    ILE  151    -9.700  19.829   7.751  1.00  21.25      1DIK1232
ATOM   1141  O    ILE  151    -9.212  19.895   6.621  1.00  22.35      1DIK1233
ATOM   1142  CB   ILE  151    -9.205  17.858   9.229  1.00  19.09      1DIK1234
ATOM   1143  CG1  ILE  151    -8.109  17.255  10.109  1.00  15.35      1DIK1235
ATOM   1144  CG2  ILE  151    -9.324  17.067   7.938  1.00  15.46      1DIK1236
ATOM   1145  CD1  ILE  151    -8.418  15.850  10.569  1.00  15.29      1DIK1237
ATOM   1146  N    GLU  152   -10.948  20.181   8.001  1.00  22.78      1DIK1238
ATOM   1147  CA   GLU  152   -11.821  20.692   6.954  1.00  22.06      1DIK1239
ATOM   1148  C    GLU  152   -11.208  21.958   6.339  1.00  22.51      1DIK1240
ATOM   1149  O    GLU  152   -11.019  22.033   5.125  1.00  27.84      1DIK1241
ATOM   1150  CB   GLU  152   -13.186  20.998   7.560  1.00  23.89      1DIK1242
ATOM   1151  CG   GLU  152   -14.321  21.169   6.578  1.00  27.41      1DIK1243
ATOM   1152  CD   GLU  152   -15.650  21.403   7.293  1.00  27.55      1DIK1244
ATOM   1153  OE1  GLU  152   -15.975  20.635   8.241  1.00  21.35      1DIK1245
ATOM   1154  OE2  GLU  152   -16.357  22.358   6.897  1.00  28.87      1DIK1246
ATOM   1155  N    GLY  153   -10.892  22.943   7.176  1.00  20.57      1DIK1247
ATOM   1156  CA   GLY  153   -10.305  24.177   6.693  1.00  19.76      1DIK1248
ATOM   1157  C    GLY  153    -8.990  23.965   5.955  1.00  23.46      1DIK1249
ATOM   1158  O    GLY  153    -8.773  24.528   4.886  1.00  25.73      1DIK1250
ATOM   1159  N    PHE  154    -8.114  23.145   6.528  1.00  22.50      1DIK1251
ATOM   1160  CA   PHE  154    -6.803  22.835   5.958  1.00  18.12      1DIK1252
ATOM   1161  C    PHE  154    -6.921  22.181   4.570  1.00  21.03      1DIK1253
ATOM   1162  O    PHE  154    -6.275  22.606   3.595  1.00  16.52      1DIK1254
ATOM   1163  CB   PHE  154    -6.048  21.909   6.937  1.00  16.95      1DIK1255
ATOM   1164  CG   PHE  154    -4.730  21.407   6.422  1.00  14.32      1DIK1256
ATOM   1165  CD1  PHE  154    -4.666  20.253   5.635  1.00  13.33      1DIK1257
ATOM   1166  CD2  PHE  154    -3.548  22.093   6.713  1.00  14.60      1DIK1258
ATOM   1167  CE1  PHE  154    -3.432  19.781   5.134  1.00  13.26      1DIK1259
ATOM   1168  CE2  PHE  154    -2.308  21.639   6.224  1.00  15.41      1DIK1260
ATOM   1169  CZ   PHE  154    -2.250  20.483   5.432  1.00  15.03      1DIK1261
ATOM   1170  N    GLN  155    -7.757  21.152   4.479  1.00  20.29      1DIK1262
ATOM   1171  CA   GLN  155    -7.921  20.441   3.231  1.00  21.66      1DIK1263
ATOM   1172  C    GLN  155    -8.626  21.290   2.170  1.00  25.36      1DIK1264
ATOM   1173  O    GLN  155    -8.255  21.256   0.983  1.00  26.48      1DIK1265
ATOM   1174  CB   GLN  155    -8.653  19.118   3.475  1.00  21.80      1DIK1266
ATOM   1175  CG   GLN  155    -8.471  18.085   2.369  1.00  27.70      1DIK1267
ATOM   1176  CD   GLN  155    -7.001  17.785   2.056  1.00  32.63      1DIK1268
```

FIG. 8-19

```
ATOM   1177  OE1 GLN 155      -6.105  18.052   2.859  1.00 34.93           1DIK1269
ATOM   1178  NE2 GLN 155      -6.753  17.229   0.883  1.00 32.41           1DIK1270
ATOM   1179  N   SER 156      -9.628  22.059   2.581  1.00 22.38           1DIK1271
ATOM   1180  CA  SER 156     -10.355  22.911   1.632  1.00 27.24           1DIK1272
ATOM   1181  C   SER 156      -9.474  23.925   0.912  1.00 26.37           1DIK1273
ATOM   1182  O   SER 156      -9.733  24.273  -0.246  1.00 26.94           1DIK1274
ATOM   1183  CB  SER 156     -11.477  23.644   2.347  1.00 25.77           1DIK1275
ATOM   1184  OG  SER 156     -12.392  22.686   2.834  1.00 38.06           1DIK1276
ATOM   1185  N   THR 157      -8.442  24.400   1.610  1.00 25.19           1DIK1277
ATOM   1186  CA  THR 157      -7.499  25.365   1.062  1.00 22.52           1DIK1278
ATOM   1187  C   THR 157      -6.535  24.632   0.123  1.00 24.65           1DIK1279
ATOM   1188  O   THR 157      -6.147  25.163  -0.928  1.00 23.24           1DIK1280
ATOM   1189  CB  THR 157      -6.702  26.040   2.189  1.00 21.15           1DIK1281
ATOM   1190  OG1 THR 157      -7.599  26.414   3.238  1.00 24.29           1DIK1282
ATOM   1191  CG2 THR 157      -6.012  27.292   1.679  1.00 16.11           1DIK1283
ATOM   1192  N   LYS 158      -6.161  23.411   0.509  1.00 21.14           1DIK1284
ATOM   1193  CA  LYS 158      -5.254  22.599  -0.279  1.00 22.69           1DIK1285
ATOM   1194  C   LYS 158      -5.848  22.241  -1.656  1.00 22.91           1DIK1286
ATOM   1195  O   LYS 158      -5.131  22.216  -2.655  1.00 20.40           1DIK1287
ATOM   1196  CB  LYS 158      -4.890  21.335   0.495  1.00 20.54           1DIK1288
ATOM   1197  CG  LYS 158      -3.806  20.504  -0.174  1.00 20.74           1DIK1289
ATOM   1198  CD  LYS 158      -3.200  19.556   0.829  1.00 24.06           1DIK1290
ATOM   1199  CE  LYS 158      -2.215  18.618   0.187  1.00 20.01           1DIK1291
ATOM   1200  NZ  LYS 158      -1.529  17.800   1.220  1.00 21.14           1DIK1292
ATOM   1201  N   LEU 159      -7.151  21.972  -1.703  1.00 22.71           1DIK1293
ATOM   1202  CA  LEU 159      -7.819  21.638  -2.959  1.00 24.27           1DIK1294
ATOM   1203  C   LEU 159      -7.784  22.786  -3.940  1.00 26.47           1DIK1295
ATOM   1204  O   LEU 159      -7.781  22.558  -5.144  1.00 29.65           1DIK1296
ATOM   1205  CB  LEU 159      -9.286  21.297  -2.743  1.00 21.63           1DIK1297
ATOM   1206  CG  LEU 159      -9.611  20.081  -1.913  1.00 25.68           1DIK1298
ATOM   1207  CD1 LEU 159     -11.110  20.032  -1.750  1.00 29.97           1DIK1299
ATOM   1208  CD2 LEU 159      -9.069  18.832  -2.571  1.00 25.43           1DIK1300
ATOM   1209  N   LYS 160      -7.781  24.015  -3.428  1.00 27.67           1DIK1301
ATOM   1210  CA  LYS 160      -7.759  25.196  -4.281  1.00 27.18           1DIK1302
ATOM   1211  C   LYS 160      -6.343  25.615  -4.632  1.00 27.06           1DIK1303
ATOM   1212  O   LYS 160      -6.161  26.651  -5.268  1.00 31.28           1DIK1304
ATOM   1213  CB  LYS 160      -8.426  26.383  -3.592  1.00 29.62           1DIK1305
ATOM   1214  CG  LYS 160      -9.827  26.183  -3.080  1.00 31.58           1DIK1306
ATOM   1215  CD  LYS 160     -10.152  27.402  -2.228  1.00 41.75           1DIK1307
ATOM   1216  CE  LYS 160     -11.463  27.266  -1.482  1.00 49.39           1DIK1308
ATOM   1217  NZ  LYS 160     -11.817  28.556  -0.806  1.00 51.98           1DIK1309
ATOM   1218  N   ASP 161      -5.343  24.840  -4.223  1.00 25.13           1DIK1310
ATOM   1219  CA  ASP 161      -3.954  25.193  -4.506  1.00 27.83           1DIK1311
ATOM   1220  C   ASP 161      -3.416  24.467  -5.758  1.00 30.73           1DIK1312
ATOM   1221  O   ASP 161      -3.237  23.250  -5.753  1.00 29.13           1DIK1313
ATOM   1222  CB  ASP 161      -3.082  24.897  -3.276  1.00 27.42           1DIK1314
ATOM   1223  CG  ASP 161      -1.642  25.368  -3.442  1.00 30.76           1DIK1315
ATOM   1224  OD1 ASP 161      -1.314  25.998  -4.468  1.00 38.67           1DIK1316
ATOM   1225  OD2 ASP 161      -0.819  25.114  -2.542  1.00 29.87           1DIK1317
ATOM   1226  N   PRO 162      -3.134  25.222  -6.842  1.00 33.61           1DIK1318
ATOM   1227  CA  PRO 162      -2.622  24.685  -8.110  1.00 33.28           1DIK1319
ATOM   1228  C   PRO 162      -1.352  23.853  -7.960  1.00 33.91           1DIK1320
ATOM   1229  O   PRO 162      -1.148  22.886  -8.684  1.00 34.55           1DIK1321
ATOM   1230  CB  PRO 162      -2.354  25.947  -8.932  1.00 33.55           1DIK1322
ATOM   1231  CG  PRO 162      -3.370  26.919  -8.413  1.00 33.99           1DIK1323
ATOM   1232  CD  PRO 162      -3.274  26.690  -6.927  1.00 34.27           1DIK1324
ATOM   1233  N   ARG 163      -0.502  24.231  -7.017  1.00 36.00           1DIK1325
ATOM   1234  CA  ARG 163       0.758  23.529  -6.799  1.00 36.01           1DIK1326
ATOM   1235  C   ARG 163       0.664  22.345  -5.833  1.00 34.24           1DIK1327
ATOM   1236  O   ARG 163       1.669  21.693  -5.548  1.00 31.55           1DIK1328
ATOM   1237  CB  ARG 163       1.802  24.525  -6.310  1.00 42.55           1DIK1329
ATOM   1238  CG  ARG 163       1.929  25.753  -7.205  1.00 53.77           1DIK1330
ATOM   1239  CD  ARG 163       3.014  26.683  -6.704  1.00 63.94           1DIK1331
ATOM   1240  NE  ARG 163       4.304  25.997  -6.634  1.00 74.87           1DIK1332
ATOM   1241  CZ  ARG 163       5.337  26.386  -5.886  1.00 79.93           1DIK1333
ATOM   1242  NH1 ARG 163       5.258  27.468  -5.123  1.00 82.39           1DIK1334
```

FIG. 8-20

```
ATOM   1243  NH2  ARG  163    6.464  25.685  -5.902  1.00  84.40    1DIK1335
ATOM   1244  N    ALA  164   -0.539  22.072  -5.331  1.00  33.77    1DIK1336
ATOM   1245  CA   ALA  164   -0.762  20.962  -4.407  1.00  34.08    1DIK1337
ATOM   1246  C    ALA  164   -0.656  19.630  -5.149  1.00  35.29    1DIK1338
ATOM   1247  O    ALA  164   -0.984  19.540  -6.325  1.00  36.67    1DIK1339
ATOM   1248  CB   ALA  164   -2.130  21.087  -3.744  1.00  33.17    1DIK1340
ATOM   1249  N    GLN  165   -0.197  18.593  -4.460  1.00  38.92    1DIK1341
ATOM   1250  CA   GLN  165   -0.035  17.283  -5.076  1.00  38.56    1DIK1342
ATOM   1251  C    GLN  165   -1.336  16.530  -5.281  1.00  35.34    1DIK1343
ATOM   1252  O    GLN  165   -2.031  16.207  -4.319  1.00  38.47    1DIK1344
ATOM   1253  CB   GLN  165    0.895  16.422  -4.248  1.00  42.23    1DIK1345
ATOM   1254  CG   GLN  165    1.155  15.104  -4.907  1.00  52.03    1DIK1346
ATOM   1255  CD   GLN  165    2.472  14.565  -4.502  1.00  57.76    1DIK1347
ATOM   1256  OE1  GLN  165    3.461  14.718  -5.224  1.00  62.19    1DIK1348
ATOM   1257  NE2  GLN  165    2.516  13.932  -3.332  1.00  58.19    1DIK1349
ATOM   1258  N    PRO  166   -1.664  16.207  -6.542  1.00  33.99    1DIK1350
ATOM   1259  CA   PRO  166   -2.902  15.485  -6.886  1.00  31.51    1DIK1351
ATOM   1260  C    PRO  166   -3.006  14.057  -6.326  1.00  28.15    1DIK1352
ATOM   1261  O    PRO  166   -2.010  13.348  -6.240  1.00  30.43    1DIK1353
ATOM   1262  CB   PRO  166   -2.889  15.502  -8.420  1.00  28.29    1DIK1354
ATOM   1263  CG   PRO  166   -1.405  15.492  -8.737  1.00  29.54    1DIK1355
ATOM   1264  CD   PRO  166   -0.854  16.486  -7.747  1.00  28.70    1DIK1356
ATOM   1265  N    GLY  167   -4.215  13.656  -5.940  1.00  24.69    1DIK1357
ATOM   1266  CA   GLY  167   -4.453  12.313  -5.437  1.00  21.00    1DIK1358
ATOM   1267  C    GLY  167   -3.990  11.986  -4.032  1.00  25.28    1DIK1359
ATOM   1268  O    GLY  167   -4.190  10.867  -3.550  1.00  27.36    1DIK1360
ATOM   1269  N    GLN  168   -3.372  12.951  -3.367  1.00  24.69    1DIK1361
ATOM   1270  CA   GLN  168   -2.882  12.759  -2.010  1.00  24.46    1DIK1362
ATOM   1271  C    GLN  168   -4.065  12.534  -1.062  1.00  24.95    1DIK1363
ATOM   1272  O    GLN  168   -5.177  13.035  -1.295  1.00  24.47    1DIK1364
ATOM   1273  CB   GLN  168   -2.081  13.987  -1.596  1.00  26.68    1DIK1365
ATOM   1274  CG   GLN  168   -1.155  13.744  -0.439  1.00  30.05    1DIK1366
ATOM   1275  CD   GLN  168   -0.012  14.736  -0.405  1.00  33.87    1DIK1367
ATOM   1276  OE1  GLN  168   -0.185  15.937  -0.685  1.00  29.61    1DIK1368
ATOM   1277  NE2  GLN  168    1.176  14.239  -0.064  1.00  30.19    1DIK1369
ATOM   1278  N    SER  169   -3.853  11.781   0.005  1.00  23.60    1DIK1370
ATOM   1279  CA   SER  169   -4.958  11.530   0.916  1.00  26.25    1DIK1371
ATOM   1280  C    SER  169   -5.214  12.673   1.896  1.00  25.94    1DIK1372
ATOM   1281  O    SER  169   -4.342  13.503   2.146  1.00  29.04    1DIK1373
ATOM   1282  CB   SER  169   -4.737  10.205   1.652  1.00  26.64    1DIK1374
ATOM   1283  OG   SER  169   -3.432  10.135   2.184  1.00  35.33    1DIK1375
ATOM   1284  N    SER  170   -6.418  12.724   2.444  1.00  25.08    1DIK1376
ATOM   1285  CA   SER  170   -6.756  13.759   3.414  1.00  23.05    1DIK1377
ATOM   1286  C    SER  170   -6.169  13.440   4.791  1.00  21.06    1DIK1378
ATOM   1287  O    SER  170   -5.867  12.280   5.101  1.00  19.23    1DIK1379
ATOM   1288  CB   SER  170   -8.273  13.838   3.586  1.00  20.90    1DIK1380
ATOM   1289  OG   SER  170   -8.909  14.154   2.380  1.00  31.58    1DIK1381
ATOM   1290  N    PRO  171   -5.993  14.463   5.637  1.00  20.40    1DIK1382
ATOM   1291  CA   PRO  171   -5.461  14.175   6.967  1.00  19.96    1DIK1383
ATOM   1292  C    PRO  171   -6.650  13.566   7.727  1.00  20.25    1DIK1384
ATOM   1293  O    PRO  171   -7.788  13.548   7.228  1.00  16.51    1DIK1385
ATOM   1294  CB   PRO  171   -5.147  15.566   7.531  1.00  22.09    1DIK1386
ATOM   1295  CG   PRO  171   -5.169  16.491   6.329  1.00  21.91    1DIK1387
ATOM   1296  CD   PRO  171   -6.236  15.905   5.471  1.00  22.51    1DIK1388
ATOM   1297  N    LYS  172   -6.397  13.076   8.931  1.00  20.67    1DIK1389
ATOM   1298  CA   LYS  172   -7.458  12.515   9.764  1.00  20.50    1DIK1390
ATOM   1299  C    LYS  172   -6.873  12.446  11.164  1.00  19.29    1DIK1391
ATOM   1300  O    LYS  172   -5.686  12.709  11.362  1.00  19.22    1DIK1392
ATOM   1301  CB   LYS  172   -7.867  11.114   9.286  1.00  18.29    1DIK1393
ATOM   1302  CG   LYS  172   -6.703  10.172   9.177  1.00  18.63    1DIK1394
ATOM   1303  CD   LYS  172   -7.122   8.761   9.350  1.00  23.30    1DIK1395
ATOM   1304  CE   LYS  172   -5.885   7.903   9.304  1.00  30.02    1DIK1396
ATOM   1305  NZ   LYS  172   -6.233   6.492   9.627  1.00  44.40    1DIK1397
ATOM   1306  N    ILE  173   -7.698  12.100  12.136  1.00  16.98    1DIK1398
ATOM   1307  CA   ILE  173   -7.218  11.998  13.493  1.00  19.06    1DIK1399
ATOM   1308  C    ILE  173   -6.583  10.614  13.635  1.00  22.40    1DIK1400
```

FIG. 8-21

```
ATOM   1309  O    ILE   173      -7.266   9.593  13.768  1.00 21.26      1DIK1401
ATOM   1310  CB   ILE   173      -8.371  12.274  14.475  1.00 19.92      1DIK1402
ATOM   1311  CG1  ILE   173      -8.868  13.715  14.232  1.00 18.99      1DIK1403
ATOM   1312  CG2  ILE   173      -7.902  12.109  15.921  1.00 20.59      1DIK1404
ATOM   1313  CD1  ILE   173     -10.087  14.103  14.987  1.00 16.15      1DIK1405
ATOM   1314  N    ASP   174      -5.256  10.599  13.588  1.00 19.22      1DIK1406
ATOM   1315  CA   ASP   174      -4.504   9.366  13.667  1.00 18.78      1DIK1407
ATOM   1316  C    ASP   174      -4.495   8.689  15.021  1.00 20.21      1DIK1408
ATOM   1317  O    ASP   174      -4.507   7.463  15.087  1.00 23.44      1DIK1409
ATOM   1318  CB   ASP   174      -3.074   9.606  13.213  1.00 16.70      1DIK1410
ATOM   1319  CG   ASP   174      -3.001  10.130  11.793  1.00 21.97      1DIK1411
ATOM   1320  OD1  ASP   174      -3.185   9.320  10.853  1.00 28.66      1DIK1412
ATOM   1321  OD2  ASP   174      -2.763  11.348  11.618  1.00 15.14      1DIK1413
ATOM   1322  N    VAL   175      -4.464   9.470  16.099  1.00 19.64      1DIK1414
ATOM   1323  CA   VAL   175      -4.453   8.903  17.449  1.00 15.74      1DIK1415
ATOM   1324  C    VAL   175      -5.381   9.700  18.364  1.00 19.16      1DIK1416
ATOM   1325  O    VAL   175      -5.346  10.942  18.361  1.00 22.21      1DIK1417
ATOM   1326  CB   VAL   175      -3.016   8.940  18.088  1.00 15.96      1DIK1418
ATOM   1327  CG1  VAL   175      -3.013   8.205  19.427  1.00 11.79      1DIK1419
ATOM   1328  CG2  VAL   175      -1.967   8.323  17.154  1.00 15.25      1DIK1420
ATOM   1329  N    VAL   176      -6.220   9.009  19.135  1.00 16.60      1DIK1421
ATOM   1330  CA   VAL   176      -7.078   9.696  20.099  1.00 18.96      1DIK1422
ATOM   1331  C    VAL   176      -6.630   9.238  21.484  1.00 18.63      1DIK1423
ATOM   1332  O    VAL   176      -6.837   8.084  21.849  1.00 19.14      1DIK1424
ATOM   1333  CB   VAL   176      -8.585   9.390  19.923  1.00 19.70      1DIK1425
ATOM   1334  CG1  VAL   176      -9.382  10.058  21.050  1.00 18.39      1DIK1426
ATOM   1335  CG2  VAL   176      -9.071   9.919  18.580  1.00 17.14      1DIK1427
ATOM   1336  N    ILE   177      -6.017  10.135  22.249  1.00 16.49      1DIK1428
ATOM   1337  CA   ILE   177      -5.528   9.790  23.578  1.00 18.84      1DIK1429
ATOM   1338  C    ILE   177      -6.626   9.871  24.646  1.00 22.64      1DIK1430
ATOM   1339  O    ILE   177      -7.233  10.926  24.877  1.00 21.84      1DIK1431
ATOM   1340  CB   ILE   177      -4.331  10.669  23.959  1.00 17.93      1DIK1432
ATOM   1341  CG1  ILE   177      -3.258  10.548  22.876  1.00 21.31      1DIK1433
ATOM   1342  CG2  ILE   177      -3.747  10.209  25.293  1.00 13.33      1DIK1434
ATOM   1343  CD1  ILE   177      -2.129  11.530  23.031  1.00 24.99      1DIK1435
ATOM   1344  N    SER   178      -6.879   8.740  25.293  1.00 22.92      1DIK1436
ATOM   1345  CA   SER   178      -7.913   8.664  26.308  1.00 22.43      1DIK1437
ATOM   1346  C    SER   178      -7.692   9.620  27.469  1.00 23.70      1DIK1438
ATOM   1347  O    SER   178      -6.562   9.880  27.896  1.00 19.07      1DIK1439
ATOM   1348  CB   SER   178      -8.019   7.234  26.832  1.00 24.76      1DIK1440
ATOM   1349  OG   SER   178      -8.931   7.149  27.918  1.00 26.50      1DIK1441
ATOM   1350  N    GLU   179      -8.802  10.138  27.975  1.00 23.30      1DIK1442
ATOM   1351  CA   GLU   179      -8.763  11.032  29.109  1.00 24.10      1DIK1443
ATOM   1352  C    GLU   179      -9.145  10.299  30.390  1.00 26.08      1DIK1444
ATOM   1353  O    GLU   179      -9.372  10.930  31.424  1.00 28.11      1DIK1445
ATOM   1354  CB   GLU   179      -9.683  12.219  28.875  1.00 20.32      1DIK1446
ATOM   1355  CG   GLU   179      -9.046  13.277  28.013  1.00 19.78      1DIK1447
ATOM   1356  CD   GLU   179      -9.975  14.413  27.679  1.00 21.33      1DIK1448
ATOM   1357  OE1  GLU   179     -11.081  14.507  28.248  1.00 28.21      1DIK1449
ATOM   1358  OE2  GLU   179      -9.595  15.224  26.832  1.00 24.31      1DIK1450
ATOM   1359  N    ALA   180      -9.220   8.970  30.326  1.00 27.12      1DIK1451
ATOM   1360  CA   ALA   180      -9.554   8.166  31.501  1.00 28.40      1DIK1452
ATOM   1361  C    ALA   180      -8.508   8.476  32.578  1.00 29.95      1DIK1453
ATOM   1362  O    ALA   180      -7.325   8.664  32.271  1.00 28.75      1DIK1454
ATOM   1363  CB   ALA   180      -9.542   6.694  31.151  1.00 22.95      1DIK1455
ATOM   1364  N    SER   181      -8.944   8.525  33.831  1.00 31.85      1DIK1456
ATOM   1365  CA   SER   181      -8.049   8.866  34.939  1.00 35.04      1DIK1457
ATOM   1366  C    SER   181      -6.762   8.047  35.009  1.00 31.72      1DIK1458
ATOM   1367  O    SER   181      -5.755   8.525  35.525  1.00 33.94      1DIK1459
ATOM   1368  CB   SER   181      -8.806   8.770  36.260  1.00 36.11      1DIK1460
ATOM   1369  OG   SER   181      -9.377   7.479  36.373  1.00 46.40      1DIK1461
ATOM   1370  N    SER   182      -6.798   6.821  34.500  1.00 27.14      1DIK1462
ATOM   1371  CA   SER   182      -5.615   5.963  34.488  1.00 29.83      1DIK1463
ATOM   1372  C    SER   182      -4.792   6.051  33.181  1.00 30.65      1DIK1464
ATOM   1373  O    SER   182      -3.808   5.329  33.013  1.00 35.32      1DIK1465
ATOM   1374  CB   SER   182      -6.023   4.496  34.726  1.00 32.11      1DIK1466
```

FIG. 8-22

```
ATOM   1375  OG  SER   182    -6.967    4.032   33.757  1.00 33.33      1DIK1467
ATOM   1376  N   SER   183    -5.187    6.924   32.261  1.00 26.39      1DIK1468
ATOM   1377  CA  SER   183    -4.499    7.049   30.986  1.00 21.35      1DIK1469
ATOM   1378  C   SER   183    -3.268    7.953   30.986  1.00 18.80      1DIK1470
ATOM   1379  O   SER   183    -3.263    9.002   31.621  1.00 18.57      1DIK1471
ATOM   1380  CB  SER   183    -5.499    7.547   29.952  1.00 23.15      1DIK1472
ATOM   1381  OG  SER   183    -4.884    7.739   28.702  1.00 22.70      1DIK1473
ATOM   1382  N   ASN   184    -2.216    7.545   30.281  1.00 21.24      1DIK1474
ATOM   1383  CA  ASN   184    -1.012    8.383   30.160  1.00 22.85      1DIK1475
ATOM   1384  C   ASN   184    -1.287    9.264   28.942  1.00 22.55      1DIK1476
ATOM   1385  O   ASN   184    -1.275    8.786   27.805  1.00 21.64      1DIK1477
ATOM   1386  CB  ASN   184     0.233    7.542   29.918  1.00 25.23      1DIK1478
ATOM   1387  CG  ASN   184     0.476    6.547   31.027  1.00 29.76      1DIK1479
ATOM   1388  OD1 ASN   184     0.631    6.927   32.186  1.00 25.74      1DIK1480
ATOM   1389  ND2 ASN   184     0.505    5.259   30.680  1.00 31.61      1DIK1481
ATOM   1390  N   ASN   185    -1.536   10.546   29.197  1.00 20.70      1DIK1482
ATOM   1391  CA  ASN   185    -1.903   11.526   28.177  1.00 18.51      1DIK1483
ATOM   1392  C   ASN   185    -1.015   12.775   28.289  1.00 18.05      1DIK1484
ATOM   1393  O   ASN   185    -1.179   13.567   29.209  1.00 19.30      1DIK1485
ATOM   1394  CB  ASN   185    -3.386   11.879   28.421  1.00 17.92      1DIK1486
ATOM   1395  CG  ASN   185    -3.990   12.809   27.376  1.00 20.11      1DIK1487
ATOM   1396  OD1 ASN   185    -5.199   12.965   27.331  1.00 25.61      1DIK1488
ATOM   1397  ND2 ASN   185    -3.174   13.421   26.543  1.00 23.70      1DIK1489
ATOM   1398  N   THR   186    -0.089   12.962   27.350  1.00 18.02      1DIK1490
ATOM   1399  CA  THR   186     0.809   14.116   27.383  1.00 19.61      1DIK1491
ATOM   1400  C   THR   186     0.117   15.452   27.104  1.00 23.05      1DIK1492
ATOM   1401  O   THR   186     0.619   16.513   27.477  1.00 24.23      1DIK1493
ATOM   1402  CB  THR   186     1.959   13.971   26.367  1.00 20.27      1DIK1494
ATOM   1403  OG1 THR   186     1.410   13.772   25.062  1.00 19.57      1DIK1495
ATOM   1404  CG2 THR   186     2.871   12.815   26.731  1.00 15.78      1DIK1496
ATOM   1405  N   LEU   187    -1.030   15.398   26.443  1.00 22.21      1DIK1497
ATOM   1406  CA  LEU   187    -1.772   16.597   26.092  1.00 21.72      1DIK1498
ATOM   1407  C   LEU   187    -2.549   17.208   27.259  1.00 23.64      1DIK1499
ATOM   1408  O   LEU   187    -2.797   18.410   27.282  1.00 22.02      1DIK1500
ATOM   1409  CB  LEU   187    -2.716   16.276   24.933  1.00 23.09      1DIK1501
ATOM   1410  CG  LEU   187    -2.063   15.798   23.623  1.00 23.80      1DIK1502
ATOM   1411  CD1 LEU   187    -3.140   15.295   22.673  1.00 19.98      1DIK1503
ATOM   1412  CD2 LEU   187    -1.262   16.926   22.984  1.00 19.12      1DIK1504
ATOM   1413  N   ASP   188    -2.934   16.376   28.218  1.00 24.87      1DIK1505
ATOM   1414  CA  ASP   188    -3.684   16.815   29.399  1.00 28.75      1DIK1506
ATOM   1415  C   ASP   188    -3.540   15.688   30.424  1.00 27.51      1DIK1507
ATOM   1416  O   ASP   188    -4.431   14.851   30.584  1.00 30.17      1DIK1508
ATOM   1417  CB  ASP   188    -5.165   17.042   29.041  1.00 34.58      1DIK1509
ATOM   1418  CG  ASP   188    -5.958   17.724   30.171  1.00 41.42      1DIK1510
ATOM   1419  OD1 ASP   188    -5.474   18.727   30.765  1.00 42.84      1DIK1511
ATOM   1420  OD2 ASP   188    -7.079   17.246   30.461  1.00 42.36      1DIK1512
ATOM   1421  N   PRO   189    -2.398   15.653   31.129  1.00 26.10      1DIK1513
ATOM   1422  CA  PRO   189    -2.107   14.622   32.137  1.00 25.17      1DIK1514
ATOM   1423  C   PRO   189    -3.063   14.609   33.322  1.00 26.14      1DIK1515
ATOM   1424  O   PRO   189    -3.442   15.671   33.825  1.00 27.85      1DIK1516
ATOM   1425  CB  PRO   189    -0.677   14.959   32.579  1.00 21.04      1DIK1517
ATOM   1426  CG  PRO   189    -0.113   15.765   31.425  1.00 21.36      1DIK1518
ATOM   1427  CD  PRO   189    -1.286   16.615   31.026  1.00 22.23      1DIK1519
ATOM   1428  N   GLY   190    -3.442   13.413   33.766  1.00 24.92      1DIK1520
ATOM   1429  CA  GLY   190    -4.325   13.296   34.910  1.00 24.73      1DIK1521
ATOM   1430  C   GLY   190    -3.783   12.314   35.934  1.00 29.33      1DIK1522
ATOM   1431  O   GLY   190    -4.457   12.016   36.917  1.00 32.88      1DIK1523
ATOM   1432  N   THR   191    -2.563   11.824   35.722  1.00 26.97      1DIK1524
ATOM   1433  CA  THR   191    -1.964   10.826   36.603  1.00 26.69      1DIK1525
ATOM   1434  C   THR   191    -1.040   11.316   37.725  1.00 30.17      1DIK1526
ATOM   1435  O   THR   191    -0.535   10.507   38.518  1.00 32.24      1DIK1527
ATOM   1436  CB  THR   191    -1.202    9.781   35.776  1.00 25.25      1DIK1528
ATOM   1437  OG1 THR   191    -0.258   10.449   34.927  1.00 25.22      1DIK1529
ATOM   1438  CG2 THR   191    -2.170    8.967   34.918  1.00 24.37      1DIK1530
ATOM   1439  N   CYS   192    -0.805   12.621   37.800  1.00 29.82      1DIK1531
ATOM   1440  CA  CYS   192     0.055   13.164   38.847  1.00 29.63      1DIK1532
```

FIG. 8-23

```
ATOM   1441  C    CYS  192   -0.783  13.395  40.101  1.00  29.84      1DIK1533
ATOM   1442  O    CYS  192   -1.282  14.507  40.330  1.00  26.80      1DIK1534
ATOM   1443  CB   CYS  192    0.699  14.466  38.387  1.00  28.28      1DIK1535
ATOM   1444  SG   CYS  192    1.766  15.227  39.646  1.00  30.95      1DIK1536
ATOM   1445  N    THR  193   -0.924  12.333  40.900  1.00  31.00      1DIK1537
ATOM   1446  CA   THR  193   -1.719  12.331  42.134  1.00  30.54      1DIK1538
ATOM   1447  C    THR  193   -1.679  13.595  42.998  1.00  28.74      1DIK1539
ATOM   1448  O    THR  193   -2.718  14.231  43.213  1.00  26.01      1DIK1540
ATOM   1449  CB   THR  193   -1.371  11.117  43.018  1.00  34.12      1DIK1541
ATOM   1450  OG1  THR  193   -1.408   9.919  42.231  1.00  39.67      1DIK1542
ATOM   1451  CG2  THR  193   -2.386  10.976  44.130  1.00  35.19      1DIK1543
ATOM   1452  N    VAL  194   -0.503  13.969  43.489  1.00  27.22      1DIK1544
ATOM   1453  CA   VAL  194   -0.415  15.157  44.323  1.00  30.44      1DIK1545
ATOM   1454  C    VAL  194   -0.953  16.406  43.614  1.00  33.87      1DIK1546
ATOM   1455  O    VAL  194   -1.705  17.178  44.211  1.00  37.21      1DIK1547
ATOM   1456  CB   VAL  194    1.022  15.387  44.829  1.00  31.50      1DIK1548
ATOM   1457  CG1  VAL  194    1.175  16.793  45.390  1.00  27.45      1DIK1549
ATOM   1458  CG2  VAL  194    1.339  14.382  45.914  1.00  26.96      1DIK1550
ATOM   1459  N    PHE  195   -0.587  16.600  42.349  1.00  33.70      1DIK1551
ATOM   1460  CA   PHE  195   -1.049  17.768  41.598  1.00  32.23      1DIK1552
ATOM   1461  C    PHE  195   -2.575  17.802  41.485  1.00  33.46      1DIK1553
ATOM   1462  O    PHE  195   -3.195  18.853  41.665  1.00  34.15      1DIK1554
ATOM   1463  CB   PHE  195   -0.429  17.803  40.192  1.00  28.54      1DIK1555
ATOM   1464  CG   PHE  195   -0.987  18.890  39.311  1.00  24.30      1DIK1556
ATOM   1465  CD1  PHE  195   -0.563  20.207  39.457  1.00  21.84      1DIK1557
ATOM   1466  CD2  PHE  195   -1.952  18.595  38.344  1.00  22.84      1DIK1558
ATOM   1467  CE1  PHE  195   -1.087  21.237  38.650  1.00  28.26      1DIK1559
ATOM   1468  CE2  PHE  195   -2.486  19.610  37.529  1.00  26.40      1DIK1560
ATOM   1469  CZ   PHE  195   -2.051  20.940  37.684  1.00  23.76      1DIK1561
ATOM   1470  N    GLU  196   -3.174  16.656  41.188  1.00  33.59      1DIK1562
ATOM   1471  CA   GLU  196   -4.618  16.574  41.048  1.00  34.08      1DIK1563
ATOM   1472  C    GLU  196   -5.357  16.966  42.328  1.00  35.44      1DIK1564
ATOM   1473  O    GLU  196   -6.497  17.411  42.266  1.00  35.61      1DIK1565
ATOM   1474  CB   GLU  196   -5.026  15.165  40.602  1.00  34.98      1DIK1566
ATOM   1475  CG   GLU  196   -4.509  14.774  39.211  1.00  37.27      1DIK1567
ATOM   1476  CD   GLU  196   -5.098  15.638  38.094  1.00  40.35      1DIK1568
ATOM   1477  OE1  GLU  196   -6.338  15.806  38.053  1.00  45.20      1DIK1569
ATOM   1478  OE2  GLU  196   -4.332  16.154  37.256  1.00  33.72      1DIK1570
ATOM   1479  N    ASP  197   -4.715  16.807  43.483  1.00  38.29      1DIK1571
ATOM   1480  CA   ASP  197   -5.352  17.160  44.758  1.00  40.02      1DIK1572
ATOM   1481  C    ASP  197   -5.141  18.621  45.173  1.00  38.28      1DIK1573
ATOM   1482  O    ASP  197   -5.770  19.093  46.110  1.00  38.49      1DIK1574
ATOM   1483  CB   ASP  197   -4.862  16.234  45.887  1.00  43.17      1DIK1575
ATOM   1484  CG   ASP  197   -5.402  14.805  45.766  1.00  48.76      1DIK1576
ATOM   1485  OD1  ASP  197   -6.582  14.630  45.373  1.00  50.32      1DIK1577
ATOM   1486  OD2  ASP  197   -4.640  13.853  46.069  1.00  49.19      1DIK1578
ATOM   1487  N    SER  198   -4.261  19.327  44.470  1.00  38.44      1DIK1579
ATOM   1488  CA   SER  198   -3.928  20.724  44.763  1.00  38.19      1DIK1580
ATOM   1489  C    SER  198   -5.131  21.675  44.824  1.00  39.35      1DIK1581
ATOM   1490  O    SER  198   -6.001  21.639  43.952  1.00  38.20      1DIK1582
ATOM   1491  CB   SER  198   -2.929  21.231  43.713  1.00  34.00      1DIK1583
ATOM   1492  OG   SER  198   -2.404  22.508  44.049  1.00  37.33      1DIK1584
ATOM   1493  N    GLU  199   -5.175  22.530  45.848  1.00  40.37      1DIK1585
ATOM   1494  CA   GLU  199   -6.262  23.505  45.981  1.00  42.79      1DIK1586
ATOM   1495  C    GLU  199   -5.735  24.932  45.904  1.00  41.90      1DIK1587
ATOM   1496  O    GLU  199   -6.453  25.886  46.228  1.00  41.14      1DIK1588
ATOM   1497  CB   GLU  199   -7.010  23.322  47.295  1.00  47.81      1DIK1589
ATOM   1498  CG   GLU  199   -7.935  22.127  47.334  1.00  56.13      1DIK1590
ATOM   1499  CD   GLU  199   -8.400  21.817  48.752  1.00  62.12      1DIK1591
ATOM   1500  OE1  GLU  199   -7.533  21.713  49.663  1.00  60.51      1DIK1592
ATOM   1501  OE2  GLU  199   -9.631  21.680  48.952  1.00  64.72      1DIK1593
ATOM   1502  N    LEU  200   -4.485  25.079  45.465  1.00  39.80      1DIK1594
ATOM   1503  CA   LEU  200   -3.861  26.391  45.356  1.00  38.33      1DIK1595
ATOM   1504  C    LEU  200   -4.700  27.405  44.565  1.00  40.30      1DIK1596
ATOM   1505  O    LEU  200   -4.924  28.526  45.027  1.00  41.57      1DIK1597
ATOM   1506  CB   LEU  200   -2.469  26.260  44.740  1.00  34.44      1DIK1598
```

FIG. 8-24

```
ATOM  1507  CG   LEU  200   -1.659  27.564  44.728  1.00  38.04  1DIK1599
ATOM  1508  CD1  LEU  200   -1.503  28.104  46.144  1.00  29.88  1DIK1600
ATOM  1509  CD2  LEU  200   -0.297  27.334  44.087  1.00  36.27  1DIK1601
ATOM  1510  N    ALA  201   -5.170  27.012  43.384  1.00  39.72  1DIK1602
ATOM  1511  CA   ALA  201   -5.974  27.901  42.549  1.00  38.07  1DIK1603
ATOM  1512  C    ALA  201   -7.230  28.400  43.247  1.00  39.57  1DIK1604
ATOM  1513  O    ALA  201   -7.623  29.541  43.048  1.00  41.56  1DIK1605
ATOM  1514  CB   ALA  201   -6.354  27.211  41.249  1.00  33.45  1DIK1606
ATOM  1515  N    ASP  202   -7.863  27.557  44.060  1.00  42.79  1DIK1607
ATOM  1516  CA   ASP  202   -9.089  27.949  44.767  1.00  46.09  1DIK1608
ATOM  1517  C    ASP  202   -8.812  29.026  45.804  1.00  46.30  1DIK1609
ATOM  1518  O    ASP  202   -9.596  29.968  45.962  1.00  48.14  1DIK1610
ATOM  1519  CB   ASP  202   -9.719  26.748  45.461  1.00  52.71  1DIK1611
ATOM  1520  CG   ASP  202  -10.027  25.624  44.503  1.00  62.26  1DIK1612
ATOM  1521  OD1  ASP  202  -10.673  25.892  43.457  1.00  62.64  1DIK1613
ATOM  1522  OD2  ASP  202   -9.617  24.476  44.804  1.00  68.25  1DIK1614
ATOM  1523  N    THR  203   -7.693  28.875  46.507  1.00  42.43  1DIK1615
ATOM  1524  CA   THR  203   -7.283  29.828  47.524  1.00  40.28  1DIK1616
ATOM  1525  C    THR  203   -7.020  31.183  46.875  1.00  38.82  1DIK1617
ATOM  1526  O    THR  203   -7.475  32.212  47.370  1.00  40.38  1DIK1618
ATOM  1527  CB   THR  203   -6.010  29.334  48.243  1.00  41.33  1DIK1619
ATOM  1528  OG1  THR  203   -6.318  28.139  48.976  1.00  42.61  1DIK1620
ATOM  1529  CG2  THR  203   -5.469  30.397  49.192  1.00  37.55  1DIK1621
ATOM  1530  N    VAL  204   -6.291  31.170  45.762  1.00  37.98  1DIK1622
ATOM  1531  CA   VAL  204   -5.953  32.386  45.021  1.00  36.13  1DIK1623
ATOM  1532  C    VAL  204   -7.209  33.048  44.454  1.00  34.77  1DIK1624
ATOM  1533  O    VAL  204   -7.372  34.265  44.544  1.00  35.20  1DIK1625
ATOM  1534  CB   VAL  204   -4.939  32.070  43.888  1.00  36.51  1DIK1626
ATOM  1535  CG1  VAL  204   -4.675  33.291  43.036  1.00  33.64  1DIK1627
ATOM  1536  CG2  VAL  204   -3.638  31.577  44.496  1.00  30.96  1DIK1628
ATOM  1537  N    GLU  205   -8.101  32.248  43.885  1.00  34.36  1DIK1629
ATOM  1538  CA   GLU  205   -9.343  32.778  43.331  1.00  36.22  1DIK1630
ATOM  1539  C    GLU  205  -10.125  33.501  44.414  1.00  36.92  1DIK1631
ATOM  1540  O    GLU  205  -10.662  34.580  44.182  1.00  40.62  1DIK1632
ATOM  1541  CB   GLU  205  -10.201  31.655  42.750  1.00  33.02  1DIK1633
ATOM  1542  CG   GLU  205  -11.607  32.094  42.365  1.00  39.52  1DIK1634
ATOM  1543  CD   GLU  205  -12.312  31.094  41.454  1.00  46.03  1DIK1635
ATOM  1544  OE1  GLU  205  -12.076  29.875  41.597  1.00  48.84  1DIK1636
ATOM  1545  OE2  GLU  205  -13.105  31.526  40.585  1.00  53.38  1DIK1637
ATOM  1546  N    ALA  206  -10.179  32.897  45.597  1.00  39.03  1DIK1638
ATOM  1547  CA   ALA  206  -10.898  33.464  46.731  1.00  37.04  1DIK1639
ATOM  1548  C    ALA  206  -10.262  34.787  47.160  1.00  36.03  1DIK1640
ATOM  1549  O    ALA  206  -10.954  35.803  47.316  1.00  32.23  1DIK1641
ATOM  1550  CB   ALA  206  -10.909  32.472  47.891  1.00  32.31  1DIK1642
ATOM  1551  N    ASN  207   -8.946  34.774  47.335  1.00  35.44  1DIK1643
ATOM  1552  CA   ASN  207   -8.231  35.971  47.754  1.00  40.04  1DIK1644
ATOM  1553  C    ASN  207   -8.484  37.150  46.836  1.00  39.71  1DIK1645
ATOM  1554  O    ASN  207   -8.838  38.235  47.307  1.00  42.35  1DIK1646
ATOM  1555  CB   ASN  207   -6.716  35.722  47.841  1.00  43.98  1DIK1647
ATOM  1556  CG   ASN  207   -6.331  34.791  48.992  1.00  48.43  1DIK1648
ATOM  1557  OD1  ASN  207   -7.115  34.557  49.922  1.00  46.90  1DIK1649
ATOM  1558  ND2  ASN  207   -5.111  34.252  48.930  1.00  50.65  1DIK1650
ATOM  1559  N    PHE  208   -8.318  36.946  45.531  1.00  37.95  1DIK1651
ATOM  1560  CA   PHE  208   -8.499  38.044  44.591  1.00  34.08  1DIK1652
ATOM  1561  C    PHE  208   -9.925  38.528  44.400  1.00  32.61  1DIK1653
ATOM  1562  O    PHE  208  -10.156  39.739  44.401  1.00  32.67  1DIK1654
ATOM  1563  CB   PHE  208   -7.878  37.726  43.229  1.00  32.46  1DIK1655
ATOM  1564  CG   PHE  208   -7.841  38.915  42.287  1.00  32.48  1DIK1656
ATOM  1565  CD1  PHE  208   -6.951  39.966  42.506  1.00  30.74  1DIK1657
ATOM  1566  CD2  PHE  208   -8.713  38.991  41.193  1.00  28.48  1DIK1658
ATOM  1567  CE1  PHE  208   -6.929  41.081  41.650  1.00  29.80  1DIK1659
ATOM  1568  CE2  PHE  208   -8.700  40.090  40.339  1.00  26.94  1DIK1660
ATOM  1569  CZ   PHE  208   -7.805  41.140  40.568  1.00  30.80  1DIK1661
ATOM  1570  N    THR  209  -10.887  37.620  44.238  1.00  31.39  1DIK1662
ATOM  1571  CA   THR  209  -12.259  38.074  44.026  1.00  33.60  1DIK1663
ATOM  1572  C    THR  209  -12.678  38.987  45.171  1.00  34.71  1DIK1664
```

FIG. 8-25

```
ATOM   1573  O    THR  209     -13.415  39.954  44.963  1.00 36.94      1DIK 1665
ATOM   1574  CB   THR  209     -13.280  36.904  43.844  1.00 32.70      1DIK 1666
ATOM   1575  OG1  THR  209     -13.295  36.072  45.004  1.00 36.54      1DIK 1667
ATOM   1576  CG2  THR  209     -12.919  36.057  42.631  1.00 31.98      1DIK 1668
ATOM   1577  N    ALA  210     -12.193  38.693  46.376  1.00 37.10      1DIK 1669
ATOM   1578  CA   ALA  210     -12.504  39.505  47.557  1.00 37.69      1DIK 1670
ATOM   1579  C    ALA  210     -12.126  40.977  47.342  1.00 39.15      1DIK 1671
ATOM   1580  O    ALA  210     -12.801  41.876  47.849  1.00 42.92      1DIK 1672
ATOM   1581  CB   ALA  210     -11.781  38.954  48.770  1.00 31.71      1DIK 1673
ATOM   1582  N    THR  211     -11.067  41.222  46.576  1.00 36.88      1DIK 1674
ATOM   1583  CA   THR  211     -10.610  42.581  46.310  1.00 36.47      1DIK 1675
ATOM   1584  C    THR  211     -11.462  43.431  45.341  1.00 35.57      1DIK 1676
ATOM   1585  O    THR  211     -11.188  44.629  45.192  1.00 37.01      1DIK 1677
ATOM   1586  CB   THR  211      -9.170  42.583  45.769  1.00 37.77      1DIK 1678
ATOM   1587  OG1  THR  211      -9.190  42.206  44.388  1.00 40.97      1DIK 1679
ATOM   1588  CG2  THR  211      -8.297  41.590  46.537  1.00 35.34      1DIK 1680
ATOM   1589  N    PHE  212     -12.473  42.858  44.683  1.00 29.14      1DIK 1681
ATOM   1590  CA   PHE  212     -13.280  43.659  43.749  1.00 24.90      1DIK 1682
ATOM   1591  C    PHE  212     -14.736  43.224  43.559  1.00 27.12      1DIK 1683
ATOM   1592  O    PHE  212     -15.577  44.041  43.190  1.00 31.27      1DIK 1684
ATOM   1593  CB   PHE  212     -12.583  43.755  42.371  1.00 25.16      1DIK 1685
ATOM   1594  CG   PHE  212     -12.772  42.534  41.491  1.00 26.99      1DIK 1686
ATOM   1595  CD1  PHE  212     -12.017  41.382  41.689  1.00 24.61      1DIK 1687
ATOM   1596  CD2  PHE  212     -13.724  42.538  40.469  1.00 29.36      1DIK 1688
ATOM   1597  CE1  PHE  212     -12.213  40.252  40.883  1.00 26.98      1DIK 1689
ATOM   1598  CE2  PHE  212     -13.926  41.417  39.661  1.00 23.41      1DIK 1690
ATOM   1599  CZ   PHE  212     -13.170  40.273  39.869  1.00 24.28      1DIK 1691
ATOM   1600  N    VAL  213     -15.045  41.954  43.798  1.00 26.22      1DIK 1692
ATOM   1601  CA   VAL  213     -16.414  41.458  43.637  1.00 26.85      1DIK 1693
ATOM   1602  C    VAL  213     -17.424  41.996  44.676  1.00 31.61      1DIK 1694
ATOM   1603  O    VAL  213     -18.554  42.341  44.322  1.00 30.84      1DIK 1695
ATOM   1604  CB   VAL  213     -16.449  39.905  43.611  1.00 22.75      1DIK 1696
ATOM   1605  CG1  VAL  213     -17.854  39.405  43.418  1.00 16.76      1DIK 1697
ATOM   1606  CG2  VAL  213     -15.592  39.403  42.489  1.00 20.78      1DIK 1698
ATOM   1607  N    PRO  214     -17.041  42.076  45.966  1.00 33.45      1DIK 1699
ATOM   1608  CA   PRO  214     -17.969  42.585  46.989  1.00 33.40      1DIK 1700
ATOM   1609  C    PRO  214     -18.707  43.889  46.624  1.00 31.74      1DIK 1701
ATOM   1610  O    PRO  214     -19.922  43.978  46.813  1.00 34.40      1DIK 1702
ATOM   1611  CB   PRO  214     -17.067  42.749  48.207  1.00 36.14      1DIK 1703
ATOM   1612  CG   PRO  214     -16.114  41.600  48.040  1.00 37.34      1DIK 1704
ATOM   1613  CD   PRO  214     -15.753  41.702  46.578  1.00 34.24      1DIK 1705
ATOM   1614  N    SER  215     -17.992  44.887  46.103  1.00 29.66      1DIK 1706
ATOM   1615  CA   SER  215     -18.619  46.154  45.698  1.00 31.11      1DIK 1707
ATOM   1616  C    SER  215     -19.661  45.910  44.615  1.00 30.62      1DIK 1708
ATOM   1617  O    SER  215     -20.767  46.451  44.671  1.00 29.20      1DIK 1709
ATOM   1618  CB   SER  215     -17.584  47.123  45.136  1.00 33.71      1DIK 1710
ATOM   1619  OG   SER  215     -16.463  47.219  45.991  1.00 47.07      1DIK 1711
ATOM   1620  N    ILE  216     -19.297  45.093  43.627  1.00 29.96      1DIK 1712
ATOM   1621  CA   ILE  216     -20.199  44.757  42.529  1.00 27.85      1DIK 1713
ATOM   1622  C    ILE  216     -21.446  44.086  43.104  1.00 29.12      1DIK 1714
ATOM   1623  O    ILE  216     -22.578  44.429  42.734  1.00 28.40      1DIK 1715
ATOM   1624  CB   ILE  216     -19.532  43.797  41.512  1.00 24.43      1DIK 1716
ATOM   1625  CG1  ILE  216     -18.194  44.372  41.032  1.00 25.18      1DIK 1717
ATOM   1626  CG2  ILE  216     -20.446  43.596  40.334  1.00 24.08      1DIK 1718
ATOM   1627  CD1  ILE  216     -17.423  43.463  40.073  1.00 19.59      1DIK 1719
ATOM   1628  N    ARG  217     -21.231  43.136  44.016  1.00 32.27      1DIK 1720
ATOM   1629  CA   ARG  217     -22.326  42.415  44.661  1.00 33.05      1DIK 1721
ATOM   1630  C    ARG  217     -23.283  43.390  45.348  1.00 34.41      1DIK 1722
ATOM   1631  O    ARG  217     -24.508  43.263  45.220  1.00 34.77      1DIK 1723
ATOM   1632  CB   ARG  217     -21.798  41.415  45.689  1.00 32.26      1DIK 1724
ATOM   1633  CG   ARG  217     -22.910  40.737  46.468  1.00 28.72      1DIK 1725
ATOM   1634  CD   ARG  217     -22.379  39.772  47.495  1.00 33.69      1DIK 1726
ATOM   1635  NE   ARG  217     -21.418  40.352  48.438  1.00 37.21      1DIK 1727
ATOM   1636  CZ   ARG  217     -21.677  41.336  49.303  1.00 38.84      1DIK 1728
ATOM   1637  NH1  ARG  217     -22.879  41.908  49.355  1.00 34.37      1DIK 1729
ATOM   1638  NH2  ARG  217     -20.713  41.754  50.120  1.00 35.90      1DIK 1730
```

FIG. 8-26

```
ATOM   1639  N   GLN 218     -22.729  44.359  46.073  1.00  32.95      1DIK1731
ATOM   1640  CA  GLN 218     -23.562  45.352  46.749  1.00  36.19      1DIK1732
ATOM   1641  C   GLN 218     -24.392  46.172  45.763  1.00  36.45      1DIK1733
ATOM   1642  O   GLN 218     -25.565  46.450  46.026  1.00  36.62      1DIK1734
ATOM   1643  CB  GLN 218     -22.715  46.275  47.617  1.00  37.01      1DIK1735
ATOM   1644  CG  GLN 218     -22.118  45.574  48.819  1.00  42.03      1DIK1736
ATOM   1645  CD  GLN 218     -21.371  46.519  49.727  1.00  44.82      1DIK1737
ATOM   1646  OE1 GLN 218     -21.019  47.631  49.335  1.00  47.97      1DIK1738
ATOM   1647  NE2 GLN 218     -21.123  46.083  50.955  1.00  49.64      1DIK1739
ATOM   1648  N   ARG 219     -23.799  46.548  44.629  1.00  34.39      1DIK1740
ATOM   1649  CA  ARG 219     -24.529  47.313  43.624  1.00  31.62      1DIK1741
ATOM   1650  C   ARG 219     -25.691  46.487  43.091  1.00  33.49      1DIK1742
ATOM   1651  O   ARG 219     -26.813  46.984  42.982  1.00  34.34      1DIK1743
ATOM   1652  CB  ARG 219     -23.618  47.722  42.470  1.00  29.81      1DIK1744
ATOM   1653  CG  ARG 219     -24.290  48.626  41.446  1.00  27.77      1DIK1745
ATOM   1654  CD  ARG 219     -23.291  49.121  40.410  1.00  28.23      1DIK1746
ATOM   1655  NE  ARG 219     -22.904  48.071  39.462  1.00  27.67      1DIK1747
ATOM   1656  CZ  ARG 219     -21.656  47.650  39.254  1.00  29.17      1DIK1748
ATOM   1657  NH1 ARG 219     -20.638  48.169  39.933  1.00  21.50      1DIK1749
ATOM   1658  NH2 ARG 219     -21.423  46.698  38.360  1.00  32.18      1DIK1750
ATOM   1659  N   LEU 220     -25.437  45.223  42.765  1.00  32.50      1DIK1751
ATOM   1660  CA  LEU 220     -26.504  44.377  42.243  1.00  33.49      1DIK1752
ATOM   1661  C   LEU 220     -27.609  44.104  43.260  1.00  32.41      1DIK1753
ATOM   1662  O   LEU 220     -28.790  44.123  42.901  1.00  29.58      1DIK1754
ATOM   1663  CB  LEU 220     -25.948  43.043  41.727  1.00  34.41      1DIK1755
ATOM   1664  CG  LEU 220     -25.043  43.081  40.494  1.00  36.51      1DIK1756
ATOM   1665  CD1 LEU 220     -24.636  41.657  40.138  1.00  35.97      1DIK1757
ATOM   1666  CD2 LEU 220     -25.758  43.753  39.331  1.00  27.80      1DIK1758
ATOM   1667  N   GLU 221     -27.233  43.848  44.517  1.00  35.98      1DIK1759
ATOM   1668  CA  GLU 221     -28.213  43.560  45.576  1.00  38.20      1DIK1760
ATOM   1669  C   GLU 221     -29.100  44.771  45.795  1.00  39.87      1DIK1761
ATOM   1670  O   GLU 221     -30.302  44.646  46.042  1.00  40.20      1DIK1762
ATOM   1671  CB  GLU 221     -27.519  43.179  46.881  1.00  35.73      1DIK1763
ATOM   1672  CG  GLU 221     -26.800  41.848  46.816  1.00  39.22      1DIK1764
ATOM   1673  CD  GLU 221     -26.340  41.346  48.176  1.00  42.91      1DIK1765
ATOM   1674  OE1 GLU 221     -25.555  42.054  48.861  1.00  43.49      1DIK1766
ATOM   1675  OE2 GLU 221     -26.770  40.234  48.557  1.00  41.59      1DIK1767
ATOM   1676  N   ASN 222     -28.486  45.943  45.689  1.00  41.49      1DIK1768
ATOM   1677  CA  ASN 222     -29.182  47.208  45.841  1.00  45.54      1DIK1769
ATOM   1678  C   ASN 222     -30.139  47.515  44.672  1.00  43.33      1DIK1770
ATOM   1679  O   ASN 222     -31.257  47.971  44.903  1.00  45.33      1DIK1771
ATOM   1680  CB  ASN 222     -28.158  48.329  46.017  1.00  54.00      1DIK1772
ATOM   1681  CG  ASN 222     -28.797  49.701  46.091  1.00  62.65      1DIK1773
ATOM   1682  OD1 ASN 222     -28.256  50.675  45.558  1.00  68.49      1DIK1774
ATOM   1683  ND2 ASN 222     -29.951  49.793  46.752  1.00  66.30      1DIK1775
ATOM   1684  N   ASP 223     -29.715  47.268  43.433  1.00  41.09      1DIK1776
ATOM   1685  CA  ASP 223     -30.562  47.521  42.256  1.00  37.20      1DIK1777
ATOM   1686  C   ASP 223     -31.655  46.482  42.022  1.00  38.11      1DIK1778
ATOM   1687  O   ASP 223     -32.712  46.809  41.482  1.00  39.42      1DIK1779
ATOM   1688  CB  ASP 223     -29.717  47.636  40.990  1.00  35.50      1DIK1780
ATOM   1689  CG  ASP 223     -28.772  48.821  41.017  1.00  38.50      1DIK1781
ATOM   1690  OD1 ASP 223     -28.977  49.753  41.826  1.00  40.58      1DIK1782
ATOM   1691  OD2 ASP 223     -27.811  48.827  40.220  1.00  41.14      1DIK1783
ATOM   1692  N   LEU 224     -31.412  45.231  42.405  1.00  40.35      1DIK1784
ATOM   1693  CA  LEU 224     -32.427  44.188  42.232  1.00  45.31      1DIK1785
ATOM   1694  C   LEU 224     -32.971  43.798  43.604  1.00  49.10      1DIK1786
ATOM   1695  O   LEU 224     -32.732  42.685  44.077  1.00  52.62      1DIK1787
ATOM   1696  CB  LEU 224     -31.835  42.956  41.543  1.00  42.30      1DIK1788
ATOM   1697  CG  LEU 224     -31.389  43.069  40.086  1.00  40.02      1DIK1789
ATOM   1698  CD1 LEU 224     -30.443  41.925  39.770  1.00  37.89      1DIK1790
ATOM   1699  CD2 LEU 224     -32.594  43.046  39.173  1.00  37.37      1DIK1791
ATOM   1700  N   SER 225     -33.701  44.721  44.232  1.00  50.58      1DIK1792
ATOM   1701  CA  SER 225     -34.283  44.522  45.564  1.00  49.16      1DIK1793
ATOM   1702  C   SER 225     -34.977  43.185  45.737  1.00  45.74      1DIK1794
ATOM   1703  O   SER 225     -35.844  42.816  44.944  1.00  45.28      1DIK1795
ATOM   1704  CB  SER 225     -35.280  45.639  45.880  1.00  51.40      1DIK1796
```

FIG. 8-27

| | | | | | | | | | |
|---|---|---|---|---|---|---|---|---|---|
| ATOM | 1705 | OG | SER | 225 | -34.660 | 46.909 | 45.793 | 1.00 58.48 | 1DIK1797 |
| ATOM | 1706 | N | GLY | 226 | -34.591 | 42.465 | 46.781 | 1.00 42.17 | 1DIK1798 |
| ATOM | 1707 | CA | GLY | 226 | -35.196 | 41.173 | 47.040 | 1.00 43.89 | 1DIK1799 |
| ATOM | 1708 | C | GLY | 226 | -34.226 | 40.060 | 46.731 | 1.00 44.37 | 1DIK1800 |
| ATOM | 1709 | O | GLY | 226 | -34.461 | 38.900 | 47.051 | 1.00 47.89 | 1DIK1801 |
| ATOM | 1710 | N | VAL | 227 | -33.119 | 40.422 | 46.108 | 1.00 42.94 | 1DIK1802 |
| ATOM | 1711 | CA | VAL | 227 | -32.108 | 39.465 | 45.727 | 1.00 43.07 | 1DIK1803 |
| ATOM | 1712 | C | VAL | 227 | -30.903 | 39.493 | 46.670 | 1.00 41.79 | 1DIK1804 |
| ATOM | 1713 | O | VAL | 227 | -30.485 | 40.560 | 47.135 | 1.00 41.57 | 1DIK1805 |
| ATOM | 1714 | CB | VAL | 227 | -31.676 | 39.750 | 44.252 | 1.00 45.33 | 1DIK1806 |
| ATOM | 1715 | CG1 | VAL | 227 | -30.316 | 39.167 | 43.947 | 1.00 44.28 | 1DIK1807 |
| ATOM | 1716 | CG2 | VAL | 227 | -32.721 | 39.189 | 43.297 | 1.00 44.62 | 1DIK1808 |
| ATOM | 1717 | N | THR | 228 | -30.371 | 38.307 | 46.963 | 1.00 40.83 | 1DIK1809 |
| ATOM | 1718 | CA | THR | 228 | -29.166 | 38.159 | 47.785 | 1.00 39.67 | 1DIK1810 |
| ATOM | 1719 | C | THR | 228 | -28.234 | 37.336 | 46.893 | 1.00 37.22 | 1DIK1811 |
| ATOM | 1720 | O | THR | 228 | -28.679 | 36.394 | 46.235 | 1.00 33.46 | 1DIK1812 |
| ATOM | 1721 | CB | THR | 228 | -29.412 | 37.398 | 49.124 | 1.00 41.63 | 1DIK1813 |
| ATOM | 1722 | OG1 | THR | 228 | -29.990 | 36.116 | 48.867 | 1.00 44.83 | 1DIK1814 |
| ATOM | 1723 | CG2 | THR | 228 | -30.339 | 38.177 | 50.021 | 1.00 43.36 | 1DIK1845 |
| ATOM | 1724 | N | LEU | 229 | -26.957 | 37.689 | 46.862 | 1.00 36.42 | 1DIK1816 |
| ATOM | 1725 | CA | LEU | 229 | -25.991 | 36.988 | 46.022 | 1.00 35.85 | 1DIK1817 |
| ATOM | 1726 | C | LEU | 229 | -24.689 | 36.735 | 46.771 | 1.00 36.00 | 1DIK1818 |
| ATOM | 1727 | O | LEU | 229 | -24.302 | 37.520 | 47.630 | 1.00 37.29 | 1DIK1819 |
| ATOM | 1728 | CB | LEU | 229 | -25.664 | 37.848 | 44.799 | 1.00 35.69 | 1DIK1820 |
| ATOM | 1729 | CG | LEU | 229 | -26.790 | 38.240 | 43.850 | 1.00 31.77 | 1DIK1821 |
| ATOM | 1730 | CD1 | LEU | 229 | -26.254 | 39.233 | 42.860 | 1.00 32.31 | 1DIK1822 |
| ATOM | 1731 | CD2 | LEU | 229 | -27.334 | 37.014 | 43.143 | 1.00 31.68 | 1DIK1823 |
| ATOM | 1732 | N | THR | 230 | -24.011 | 35.643 | 46.447 | 1.00 33.91 | 1DIK1824 |
| ATOM | 1733 | CA | THR | 230 | -22.729 | 35.359 | 47.072 | 1.00 34.10 | 1DIK1825 |
| ATOM | 1734 | C | THR | 230 | -21.743 | 35.959 | 46.083 | 1.00 34.69 | 1DIK1826 |
| ATOM | 1735 | O | THR | 230 | -22.119 | 36.265 | 44.944 | 1.00 32.68 | 1DIK1827 |
| ATOM | 1736 | CB | THR | 230 | -22.466 | 33.838 | 47.178 | 1.00 34.26 | 1DIK1828 |
| ATOM | 1737 | OG1 | THR | 230 | -22.463 | 33.260 | 45.870 | 1.00 30.93 | 1DIK1829 |
| ATOM | 1738 | CG2 | THR | 230 | -23.552 | 33.151 | 47.997 | 1.00 31.47 | 1DIK1830 |
| ATOM | 1739 | N | ASP | 231 | -20.493 | 36.131 | 46.494 | 1.00 37.66 | 1DIK1831 |
| ATOM | 1740 | CA | ASP | 231 | -19.478 | 36.674 | 45.592 | 1.00 39.60 | 1DIK1832 |
| ATOM | 1741 | C | ASP | 231 | -19.312 | 35.794 | 44.344 | 1.00 40.76 | 1DIK1833 |
| ATOM | 1742 | O | ASP | 231 | -19.186 | 36.303 | 43.227 | 1.00 43.31 | 1DIK1834 |
| ATOM | 1743 | CB | ASP | 231 | -18.138 | 36.827 | 46.313 | 1.00 39.61 | 1DIK1835 |
| ATOM | 1744 | CG | ASP | 231 | -18.147 | 37.956 | 47.321 | 1.00 44.99 | 1DIK1836 |
| ATOM | 1745 | OD1 | ASP | 231 | -19.042 | 38.825 | 47.233 | 1.00 45.50 | 1DIK1837 |
| ATOM | 1746 | OD2 | ASP | 231 | -17.254 | 37.976 | 48.202 | 1.00 49.54 | 1DIK1838 |
| ATOM | 1747 | N | THR | 232 | -19.324 | 34.479 | 44.544 | 1.00 38.28 | 1DIK1839 |
| ATOM | 1748 | CA | THR | 232 | -19.188 | 33.520 | 43.458 | 1.00 34.10 | 1DIK1840 |
| ATOM | 1749 | C | THR | 232 | -20.280 | 33.679 | 42.416 | 1.00 32.21 | 1DIK1841 |
| ATOM | 1750 | O | THR | 232 | -19.994 | 33.663 | 41.222 | 1.00 34.55 | 1DIK1842 |
| ATOM | 1751 | CB | THR | 232 | -19.210 | 32.075 | 44.010 | 1.00 34.37 | 1DIK1843 |
| ATOM | 1752 | OG1 | THR | 232 | -18.074 | 31.896 | 44.856 | 1.00 35.55 | 1DIK1844 |
| ATOM | 1753 | CG2 | THR | 232 | -19.163 | 31.037 | 42.894 | 1.00 26.21 | 1DIK1845 |
| ATOM | 1754 | N | GLU | 233 | -21.525 | 33.835 | 42.856 | 1.00 28.27 | 1DIK1846 |
| ATOM | 1755 | CA | GLU | 233 | -22.637 | 33.978 | 41.919 | 1.00 29.61 | 1DIK1847 |
| ATOM | 1756 | C | GLU | 233 | -22.500 | 35.196 | 41.016 | 1.00 27.81 | 1DIK1848 |
| ATOM | 1757 | O | GLU | 233 | -22.923 | 35.162 | 39.872 | 1.00 30.27 | 1DIK1849 |
| ATOM | 1758 | CB | GLU | 233 | -23.970 | 34.029 | 42.660 | 1.00 32.29 | 1DIK1850 |
| ATOM | 1759 | CG | GLU | 233 | -24.262 | 32.784 | 43.483 | 1.00 38.65 | 1DIK1851 |
| ATOM | 1760 | CD | GLU | 233 | -25.539 | 32.893 | 44.298 | 1.00 41.41 | 1DIK1852 |
| ATOM | 1761 | OE1 | GLU | 233 | -25.716 | 33.897 | 45.041 | 1.00 39.47 | 1DIK1853 |
| ATOM | 1762 | OE2 | GLU | 233 | -26.366 | 31.961 | 44.188 | 1.00 43.44 | 1DIK1854 |
| ATOM | 1763 | N | VAL | 234 | -21.916 | 36.270 | 41.529 | 1.00 26.78 | 1DIK1855 |
| ATOM | 1764 | CA | VAL | 234 | -21.718 | 37.471 | 40.730 | 1.00 27.81 | 1DIK1856 |
| ATOM | 1765 | C | VAL | 234 | -20.779 | 37.131 | 39.555 | 1.00 28.07 | 1DIK1857 |
| ATOM | 1766 | O | VAL | 234 | -21.031 | 37.532 | 38.409 | 1.00 27.61 | 1DIK1858 |
| ATOM | 1767 | CB | VAL | 234 | -21.139 | 38.631 | 41.599 | 1.00 29.25 | 1DIK1859 |
| ATOM | 1768 | CG1 | VAL | 234 | -20.669 | 39.790 | 40.719 | 1.00 26.00 | 1DIK1860 |
| ATOM | 1769 | CG2 | VAL | 234 | -22.202 | 39.114 | 42.574 | 1.00 23.62 | 1DIK1861 |
| ATOM | 1770 | N | THR | 235 | -19.712 | 36.383 | 39.830 | 1.00 25.71 | 1DIK1862 |

FIG. 8-28

```
ATOM  1771 CA   THR 235  -18.784 35.991 38.773 1.00 27.53    1DIK1863
ATOM  1772 C    THR 235  -19.506 35.104 37.728 1.00 28.27    1DIK1864
ATOM  1773 O    THR 235  -19.098 35.065 36.565 1.00 27.05    1DIK1865
ATOM  1774 CB   THR 235  -17.513 35.272 39.329 1.00 26.76    1DIK1866
ATOM  1775 OG1  THR 235  -17.866 33.998 39.876 1.00 28.53    1DIK1867
ATOM  1776 CG2  THR 235  -16.859 36.104 40.416 1.00 27.73    1DIK1868
ATOM  1777 N    TYR 236  -20.575 34.406 38.129 1.00 27.79    1DIK1869
ATOM  1778 CA   TYR 236  -21.339 33.577 37.188 1.00 27.49    1DIK1870
ATOM  1779 C    TYR 236  -22.024 34.490 36.171 1.00 28.77    1DIK1871
ATOM  1780 O    TYR 236  -22.106 34.165 34.980 1.00 30.28    1DIK1872
ATOM  1781 CB   TYR 236  -22.405 32.741 37.908 1.00 28.51    1DIK1873
ATOM  1782 CG   TYR 236  -21.873 31.589 38.735 1.00 31.65    1DIK1874
ATOM  1783 CD1  TYR 236  -20.517 31.243 38.711 1.00 32.72    1DIK1875
ATOM  1784 CD2  TYR 236  -22.733 30.838 39.546 1.00 33.46    1DIK1876
ATOM  1785 CE1  TYR 236  -20.030 30.181 39.471 1.00 33.24    1DIK1877
ATOM  1786 CE2  TYR 236  -22.258 29.768 40.315 1.00 35.17    1DIK1878
ATOM  7187 CZ   TYR 236  -20.904 29.446 40.271 1.00 39.13    1DIK1879
ATOM  1788 OH   TYR 236  -20.422 28.393 41.025 1.00 43.32    1DIK1880
ATOM  1789 N    LEU 237  -22.513 35.632 36.656 1.00 29.13    1DIK1881
ATOM  1790 CA   LEU 237  -23.179 36.634 35.818 1.00 27.63    1DIK1882
ATOM  1791 C    LEU 237  -22.173 37.237 34.842 1.00 27.17    1DIK1883
ATOM  1792 O    LEU 237  -22.506 37.527 33.699 1.00 30.67    1DIK1884
ATOM  1793 CB   LEU 237  -23.813 37.734 36.682 1.00 25.77    1DIK1885
ATOM  1794 CG   LEU 237  -25.081 37.327 37.447 1.00 22.88    1DIK1886
ATOM  1795 CD1  LEU 237  -25.528 38.415 38.421 1.00 24.36    1DIK1887
ATOM  1796 CD2  LEU 237  -26.165 37.036 36.455 1.00 17.71    1DIK1888
ATOM  1797 N    MET 238  -20.940 37.423 35.286 1.00 24.39    1DIK1889
ATOM  1798 CA   MET 238  -19.918 37.948 34.403 1.00 25.37    1DIK1890
ATOM  1799 C    MET 238  -19.575 36.882 33.359 1.00 28.12    1DIK1891
ATOM  1800 O    MET 238  -19.335 37.210 32.195 1.00 31.98    1DIK1892
ATOM  1801 CB   MET 238  -18.684 38.358 35.203 1.00 21.01    1DIK1893
ATOM  1802 CG   MET 238  -18.967 39.504 36.148 1.00 18.56    1DIK1894
ATOM  1803 SD   MET 238  -17.500 40.183 36.915 1.00 26.85    1DIK1895
ATOM  1804 CE   MET 238  -16.964 41.396 35.681 1.00 20.81    1DIK1896
ATOM  1805 N    ASP 239  -19.562 35.608 33.764 1.00 29.27    1DIK1897
ATOM  1806 CA   ASP 239  -19.268 34.497 32.838 1.00 28.12    1DIK1898
ATOM  1807 C    ASP 239  -20.314 34.486 31.727 1.00 26.51    1DIK1899
ATOM  1808 O    ASP 239  -20.003 34.210 30.577 1.00 27.19    1DIK1900
ATOM  1809 CB   ASP 239  -19.340 33.129 33.542 1.00 27.22    1DIK1901
ATOM  1810 CG   ASP 239  -18.144 32.836 34.448 1.00 24.04    1DIK1902
ATOM  1811 OD1  ASP 239  -17.162 33.602 34.461 1.00 22.09    1DIK1903
ATOM  1812 OD2  ASP 239  -18.194 31.807 35.162 1.00 27.85    1DIK1904
ATOM  1813 N    MET 240  -21.557 34.784 32.089 1.00 24.64    1DIK1905
ATOM  1814 CA   MET 240  -22.664 34.800 31.141 1.00 26.17    1DIK1906
ATOM  1815 C    MET 240  -22.509 35.815 30.018 1.00 26.18    1DIK1907
ATOM  1816 O    MET 240  -23.034 35.621 28.924 1.00 25.09    1DIK1908
ATOM  1817 CB   MET 240  -23.984 35.039 31.877 1.00 29.12    1DIK1909
ATOM  1818 CG   MET 240  -24.519 33.809 32.591 1.00 28.59    1DIK1910
ATOM  1819 SD   MET 240  -24.873 32.469 31.404 1.00 34.30    1DIK1911
ATOM  1820 CE   MET 240  -26.354 33.141 30.505 1.00 25.69    1DIK1912
ATOM  1821 N    CYS 241  -21.793 36.899 30.280 1.00 25.30    1DIK1913
ATOM  1822 CA   CYS 241  -21.581 37.910 29.254 1.00 27.89    1DIK1914
ATOM  1823 C    CYS 241  -20.931 37.244 28.032 1.00 25.49    1DIK1915
ATOM  1824 O    CYS 241  -21.348 37.459 26.892 1.00 26.76    1DIK1916
ATOM  1825 CB   CYS 241  -20.710 39.049 29.814 1.00 24.99    1DIK1917
ATOM  1826 SG   CYS 241  -19.856 40.115 28.598 1.00 27.44    1DIK1918
ATOM  1827 N    SER 242  -19.924 36.420 28.291 1.00 25.28    1DIK1919
ATOM  1828 CA   SER 242  -19.197 35.698 27.256 1.00 25.73    1DIK1920
ATOM  1829 C    SER 242  -20.072 34.679 26.507 1.00 26.63    1DIK1921
ATOM  1830 O    SER 242  -20.275 34.786 25.289 1.00 25.57    1DIK1922
ATOM  1831 CB   SER 242  -18.003 34.989 27.897 1.00 27.44    1DIK1923
ATOM  1832 OG   SER 242  -17.294 34.219 26.949 1.00 39.33    1DIK1924
ATOM  1833 N    PHE 243  -20.594 33.697 27.238 1.00 26.85    1DIK1925
ATOM  1834 CA   PHE 243  -21.419 32.642 26.648 1.00 26.10    1DIK1926
ATOM  1835 C    PHE 243  -22.663 33.140 25.941 1.00 27.04    1DIK1927
ATOM  1836 O    PHE 243  -23.021 32.637 24.872 1.00 26.53    1DIK1928
```

FIG. 8-29

```
ATOM   1837  CB   PHE   243     -21.818  31.617  27.714  1.00  25.98      1DIK1929
ATOM   1838  CG   PHE   243     -20.655  30.845  28.277  1.00  26.19      1DIK1930
ATOM   1839  CD1  PHE   243     -20.075  29.805  27.549  1.00  23.12      1DIK1931
ATOM   1840  CD2  PHE   243     -20.129  31.168  29.530  1.00  21.56      1DIK1932
ATOM   1841  CE1  PHE   243     -18.978  29.093  28.066  1.00  25.40      1DIK1933
ATOM   1842  CE2  PHE   243     -19.042  30.469  30.052  1.00  22.05      1DIK1934
ATOM   1843  CZ   PHE   243     -18.461  29.427  29.319  1.00  21.32      1DIK1935
ATOM   1844  N    ASP   244     -23.330  34.126  26.529  1.00  27.71      1DIK1936
ATOM   1845  CA   ASP   244     -24.537  34.643  25.907  1.00  30.62      1DIK1937
ATOM   1846  C    ASP   244     -24.235  35.494  24.666  1.00  32.18      1DIK1938
ATOM   1847  O    ASP   244     -25.120  35.741  23.854  1.00  34.05      1DIK1939
ATOM   1848  CB   ASP   244     -25.379  35.428  26.917  1.00  27.50      1DIK1940
ATOM   1849  CG   ASP   244     -26.785  35.723  26.404  1.00  28.82      1DIK1941
ATOM   1850  OD1  ASP   244     -27.531  34.777  26.077  1.00  24.13      1DIK1942
ATOM   1851  OD2  ASP   244     -27.149  36.910  26.323  1.00  30.15      1DIK1943
ATOM   1852  N    THR   245     -22.996  35.944  24.510  1.00  32.39      1DIK1944
ATOM   1853  CA   THR   245     -22.658  36.740  23.343  1.00  33.50      1DIK1945
ATOM   1854  C    THR   245     -22.282  35.850  22.153  1.00  38.87      1DIK1946
ATOM   1855  O    THR   245     -22.911  35.918  21.091  1.00  37.64      1DIK1947
ATOM   1856  CB   THR   245     -21.511  37.706  23.647  1.00  32.72      1DIK1948
ATOM   1857  OG1  THR   245     -21.940  38.652  24.631  1.00  37.51      1DIK1949
ATOM   1858  CG2  THR   245     -21.084  38.446  22.394  1.00  28.33      1DIK1950
ATOM   1859  N    ILE   246     -21.268  35.008  22.335  1.00  40.95      1DIK1951
ATOM   1860  CA   ILE   246     -20.803  34.140  21.262  1.00  43.89      1DIK1952
ATOM   1861  C    ILE   246     -21.590  32.847  21.034  1.00  48.67      1DIK1953
ATOM   1862  O    ILE   246     -21.151  31.992  20.262  1.00  48.67      1DIK1954
ATOM   1863  CB   ILE   246     -19.279  33.826  21.419  1.00  41.80      1DIK1955
ATOM   1864  CG1  ILE   246     -18.988  33.144  22.757  1.00  37.29      1DIK1956
ATOM   1865  CG2  ILE   246     -18.464  35.125  21.329  1.00  43.70      1DIK1957
ATOM   1866  CD1  ILE   246     -17.508  33.098  23.087  1.00  29.59      1DIK1958
ATOM   1867  N    SER   247     -22.747  32.710  21.688  1.00  56.97      1DIK1959
ATOM   1868  CA   SER   247     -23.601  31.523  21.534  1.00  63.90      1DIK1960
ATOM   1869  C    SER   247     -24.145  31.424  20.107  1.00  70.33      1DIK1961
ATOM   1870  O    SER   247     -24.503  30.328  19.662  1.00  73.70      1DIK1962
ATOM   1871  CB   SER   247     -24.787  31.567  22.499  1.00  67.11      1DIK1963
ATOM   1872  OG   SER   247     -25.783  32.483  22.058  1.00  66.63      1DIK1964
ATOM   1873  N    THR   248     -24.213  32.569  19.411  1.00  74.67      1DIK1965
ATOM   1874  CA   THR   248     -24.683  32.671  18.015  1.00  74.94      1DIK1966
ATOM   1875  C    THR   248     -23.546  33.054  17.049  1.00  76.44      1DIK1967
ATOM   1876  O    THR   248     -23.272  34.241  16.808  1.00  77.32      1DIK1968
ATOM   1877  CB   THR   248     -25.810  33.719  17.893  1.00  74.59      1DIK1969
ATOM   1878  OG1  THR   248     -26.917  33.299  18.699  1.00  74.12      1DIK1970
ATOM   1879  CG2  THR   248     -26.262  33.888  16.427  1.00  72.58      1DIK1971
ATOM   1880  N    THR   253     -23.919  38.646  16.591  1.00  49.08      1DIK1972
ATOM   1881  CA   THR   253     -24.110  39.972  15.999  1.00  51.56      1DIK1973
ATOM   1882  C    THR   253     -24.258  41.028  17.100  1.00  49.54      1DIK1974
ATOM   1883  O    THR   253     -23.757  42.146  16.965  1.00  49.39      1DIK1975
ATOM   1884  CB   THR   253     -25.394  40.051  15.103  1.00  52.26      1DIK1976
ATOM   1885  OG1  THR   253     -25.489  38.881  14.282  1.00  61.78      1DIK1977
ATOM   1886  CG2  THR   253     -25.344  41.284  14.189  1.00  51.28      1DIK1978
ATOM   1887  N    LYS   254     -24.941  40.670  18.185  1.00  46.23      1DIK1979
ATOM   1888  CA   LYS   254     -25.170  41.610  19.275  1.00  45.73      1DIK1980
ATOM   1889  C    LYS   254     -24.562  41.222  20.618  1.00  42.99      1DIK1981
ATOM   1890  O    LYS   254     -24.470  40.044  20.939  1.00  45.43      1DIK1982
ATOM   1891  CB   LYS   254     -26.664  41.864  19.410  1.00  46.12      1DIK1983
ATOM   1892  CG   LYS   254     -27.214  42.520  18.157  1.00  51.91      1DIK1984
ATOM   1893  CD   LYS   254     -28.671  42.840  18.273  1.00  56.51      1DIK1985
ATOM   1894  CE   LYS   254     -29.168  43.456  16.987  1.00  60.44      1DIK1986
ATOM   1895  NZ   LYS   254     -30.576  43.918  17.160  1.00  67.71      1DIK1987
ATOM   1896  N    LEU   255     -24.141  42.226  21.387  1.00  38.90      1DIK1988
ATOM   1897  CA   LEU   255     -23.533  42.022  22.705  1.00  33.29      1DIK1989
ATOM   1898  C    LEU   255     -24.584  41.661  23.751  1.00  32.90      1DIK1990
ATOM   1899  O    LEU   255     -25.637  42.288  23.825  1.00  33.07      1DIK1991
ATOM   1900  CB   LEU   255     -22.797  43.286  23.141  1.00  25.06      1DIK1992
ATOM   1901  CG   LEU   255     -21.856  43.213  24.344  1.00  26.05      1DIK1993
ATOM   1902  CD1  LEU   255     -20.707  42.242  24.095  1.00  21.04      1DIK1994
```

FIG. 8-30

```
ATOM   1903  CD2 LEU  255    -21.326  44.595  24.608  1.00 22.14      1DIK1995
ATOM   1904  N   SER  256    -24.293  40.647  24.558  1.00 32.93      1DIK1996
ATOM   1905  CA  SER  256    -25.212  40.207  25.598  1.00 31.52      1DIK1997
ATOM   1906  C   SER  256    -25.489  41.293  26.643  1.00 32.01      1DIK1998
ATOM   1907  O   SER  256    -24.574  42.013  27.082  1.00 30.64      1DIK1999
ATOM   1908  CB  SER  256    -24.650  38.965  26.306  1.00 30.76      1DIK2000
ATOM   1909  OG  SER  256    -25.446  38.602  27.430  1.00 27.78      1DIK2001
ATOM   1910  N   PRO  257    -26.766  41.432  27.051  1.00 32.46      1DIK2002
ATOM   1911  CA  PRO  257    -27.131  42.434  28.060  1.00 32.73      1DIK2003
ATOM   1912  C   PRO  257    -26.372  42.191  29.379  1.00 31.79      1DIK2004
ATOM   1913  O   PRO  257    -26.136  43.130  30.138  1.00 35.33      1DIK2005
ATOM   1914  CB  PRO  257    -28.644  42.239  28.209  1.00 32.20      1DIK2006
ATOM   1915  CG  PRO  257    -29.053  41.696  26.861  1.00 31.42      1DIK2007
ATOM   1916  CD  PRO  257    -27.960  40.701  26.587  1.00 30.36      1DIK2008
ATOM   1917  N   PHE  258    -25.984  40.941  29.646  1.00 27.64      1DIK2009
ATOM   1918  CA  PHE  258    -25.221  40.617  30.859  1.00 25.04      1DIK2010
ATOM   1919  C   PHE  258    -23.910  41.407  30.928  1.00 24.80      1DIK2011
ATOM   1920  O   PHE  258    -23.389  41.661  32.011  1.00 22.95      1DIK2012
ATOM   1921  CB  PHE  258    -24.877  39.122  30.911  1.00 25.72      1DIK2013
ATOM   1922  CG  PHE  258    -26.033  38.239  31.253  1.00 24.20      1DIK2014
ATOM   1923  CD1 PHE  258    -26.455  38.105  32.569  1.00 23.98      1DIK2015
ATOM   1924  CD2 PHE  258    -26.712  37.544  30.257  1.00 26.82      1DIK2016
ATOM   1925  CE1 PHE  258    -27.543  37.288  32.890  1.00 23.72      1DIK2017
ATOM   1926  CE2 PHE  258    -27.806  36.721  30.565  1.00 24.56      1DIK2018
ATOM   1927  CZ  PHE  258    -28.220  36.594  31.879  1.00 24.85      1DIK2019
ATOM   1928  N   CYS  259    -23.375  41.790  29.772  1.00 24.43      1DIK2020
ATOM   1929  CA  CYS  259    -22.119  42.536  29.731  1.00 27.30      1DIK2021
ATOM   1930  C   CYS  259    -22.323  43.952  30.207  1.00 29.38      1DIK2022
ATOM   1931  O   CYS  259    -21.420  44.565  30.771  1.00 29.68      1DIK2023
ATOM   1932  CB  CYS  259    -21.564  42.591  28.307  1.00 26.45      1DIK2024
ATOM   1933  SG  CYS  259    -21.348  40.968  27.516  1.00 30.19      1DIK2025
ATOM   1934  N   ASP  260    -23.527  44.460  29.975  1.00 31.11      1DIK2026
ATOM   1935  CA  ASP  260    -23.879  45.821  30.326  1.00 33.64      1DIK2027
ATOM   1936  C   ASP  260    -24.002  46.070  31.815  1.00 32.59      1DIK2028
ATOM   1937  O   ASP  260    -24.054  47.212  32.246  1.00 34.03      1DIK2029
ATOM   1938  CB  ASP  060    -25.194  46.201  29.645  1.00 39.78      1DIK2030
ATOM   1939  CG  ASP  260    -25.246  47.667  29.252  1.00 44.26      1DIK2031
ATOM   1940  OD1 ASP  260    -24.190  48.185  28.834  1.00 45.01      1DIK2032
ATOM   1941  OD2 ASP  260    -26.328  48.292  29.362  1.00 42.47      1DIK2033
ATOM   1942  N   LEU  261    -24.051  45.007  32.603  1.00 33.47      1DIK2034
ATOM   1943  CA  LEU  261    -24.200  45.149  34.043  1.00 29.07      1DIK2035
ATOM   1944  C   LEU  261    -22.887  45.446  34.736  1.00 29.71      1DIK2036
ATOM   1945  O   LEU  261    -22.867  45.747  35.929  1.00 33.17      1DIK2037
ATOM   1946  CB  LEU  261    -24.816  43.880  34.629  1.00 28.55      1DIK2038
ATOM   1947  CG  LEU  261    -26.103  43.405  33.947  1.00 27.56      1DIK2039
ATOM   1948  CD1 LEU  261    -26.541  42.089  34.534  1.00 25.79      1DIK2040
ATOM   1949  CD2 LEU  261    -27.197  44.441  34.130  1.00 27.02      1DIK2041
ATOM   1950  N   PHE  262    -21.786  45.376  33.997  1.00 29.05      1DIK2042
ATOM   1951  CA  PHE  262    -20.471  45.607  34.586  1.00 27.80      1DIK2043
ATOM   1952  C   PHE  262    -19.709  46.685  33.837  1.00 29.74      1DIK2044
ATOM   1953  O   PHE  262    -19.869  46.846  32.622  1.00 35.51      1DIK2045
ATOM   1954  CB  PHE  262    -19.685  44.280  34.621  1.00 24.44      1DIK2046
ATOM   1955  CG  PHE  262    -20.478  43.146  35.192  1.00 21.66      1DIK2047
ATOM   1956  CD1 PHE  262    -20.589  42.987  36.572  1.00 18.94      1DIK2048
ATOM   1957  CD2 PHE  262    -21.176  42.277  34.348  1.00 20.22      1DIK2049
ATOM   1958  CE1 PHE  262    -21.396  41.976  37.106  1.00 21.42      1DIK2050
ATOM   1959  CE2 PHE  262    -21.985  41.265  34.865  1.00 19.46      1DIK2051
ATOM   1960  CZ  PHE  262    -22.099  41.112  36.250  1.00 21.48      1DIK2052
ATOM   1961  N   THR  263    -18.881  47.428  34.564  1.00 30.27      1DIK2053
ATOM   1962  CA  THR  263    -18.113  48.502  33.967  1.00 29.94      1DIK2054
ATOM   1963  C   THR  263    -16.811  47.961  33.425  1.00 29.54      1DIK2055
ATOM   1964  O   THR  263    -16.466  46.805  33.671  1.00 31.34      1DIK2056
ATOM   1965  CB  THR  263    -17.860  49.648  34.985  1.00 32.12      1DIK2057
ATOM   1966  OG1 THR  263    -16.998  49.193  36.036  1.00 29.58      1DIK2058
ATOM   1967  CG2 THR  263    -19.183  50.112  35.589  1.00 22.67      1DIK2059
ATOM   1968  N   HIS  264    -16.087  48.802  32.693  1.00 30.02      1DIK2060
```

FIG. 8-31

```
ATOM   1969  CA   HIS  264    -14.829  48.400  32.090  1.00  28.00      1DIK2061
ATOM   1970  C    HIS  264    -13.717  47.984  33.052  1.00  30.02      1DIK2062
ATOM   1971  O    HIS  264    -12.998  47.015  32.774  1.00  31.35      1DIK2063
ATOM   1972  CB   HIS  264    -14.314  49.480  31.143  1.00  27.91      1DIK2064
ATOM   1973  CG   HIS  264    -13.111  49.048  30.370  1.00  34.68      1DIK2065
ATOM   1974  ND1  HIS  264    -13.186  48.157  29.318  1.00  31.27      1DIK2066
ATOM   1975  CD2  HIS  264    -11.795  49.339  30.527  1.00  35.74      1DIK2067
ATOM   1976  CE1  HIS  264    -11.969  47.916  28.863  1.00  37.49      1DIK2068
ATOM   1977  NE2  HIS  264    -11.108  48.620  29.579  1.00  38.67      1DIK2069
ATOM   1978  N    ASP  265    -13.560  48.703  34.167  1.00  31.42      1DIK2070
ATOM   1979  CA   ASP  265    -12.533  48.371  35.172  1.00  29.27      1DIK2071
ATOM   1980  C    ASP  265    -12.831  47.030  35.859  1.00  27.71      1DIK2072
ATOM   1981  O    ASP  265    -11.923  46.352  36.346  1.00  25.15      1DIK2073
ATOM   1982  CB   ASP  265    -12.421  49.481  36.222  1.00  36.26      1DIK2074
ATOM   1983  CG   ASP  265    -13.745  49.764  36.921  1.00  44.48      1DIK2075
ATOM   1984  OD1  ASP  265    -14.671  50.307  36.267  1.00  43.98      1DIK2076
ATOM   1985  OD2  ASP  265    -13.860  49.441  38.128  1.00  49.77      1DIK2077
ATOM   1986  N    GLU  266    -14.108  46.651  35.896  1.00  26.27      1DIK2078
ATOM   1987  CA   GLU  266    -14.502  45.378  36.484  1.00  26.01      1DIK2079
ATOM   1988  C    GLU  266    -14.093  44.272  35.517  1.00  27.04      1DIK2080
ATOM   1989  O    GLU  266    -13.665  43.205  35.956  1.00  28.64      1DIK2081
ATOM   1990  CB   GLU  266    -15.997  45.359  36.785  1.00  24.19      1DIK2082
ATOM   1991  CG   GLU  266    -16.336  46.287  37.939  1.00  24.01      1DIK2083
ATOM   1992  CD   GLU  266    -17.824  46.521  38.139  1.00  28.94      1DIK2084
ATOM   1993  OE1  GLU  266    -18.647  46.091  37.299  1.00  30.18      1DIK2085
ATOM   1994  OE2  GLU  266    -18.175  47.150  39.160  1.00  32.29      1DIK2086
ATOM   1995  N    TRP  267    -14.207  44.521  34.210  1.00  24.96      1DIK2087
ATOM   1996  CA   TRP  267    -13.765  43.535  33.221  1.00  24.91      1DIK2088
ATOM   1997  C    TRP  267    -12.243  43.380  33.306  1.00  24.45      1DIK2089
ATOM   1998  O    TRP  267    -11.723  42.269  33.202  1.00  25.00      1DIK2090
ATOM   1999  CB   TRP  267    -14.210  43.915  31.801  1.00  22.45      1DIK2091
ATOM   2000  CG   TRP  267    -15.684  43.646  31.596  1.00  22.28      1DIK2092
ATOM   2001  CD1  TRP  267    -16.661  44.567  31.355  1.00  20.97      1DIK2093
ATOM   2002  CD2  TRP  267    -16.349  42.370  31.684  1.00  20.83      1DIK2094
ATOM   2003  NE1  TRP  267    -17.889  43.952  31.293  1.00  23.15      1DIK2095
ATOM   2004  CE2  TRP  267    -17.726  42.604  31.493  1.00  23.26      1DIK2096
ATOM   2005  CE3  TRP  267    -15.913  41.055  31.914  1.00  18.67      1DIK2097
ATOM   2006  CZ2  TRP  267    -18.672  41.569  31.529  1.00  22.56      1DIK2098
ATOM   2007  CZ3  TRP  267    -16.849  40.032  31.951  1.00  15.00      1DIK2099
ATOM   2008  CH2  TRP  267    -18.211  40.294  31.761  1.00  18.10      1DIK2100
ATOM   2009  N    ILE  268    -11.526  44.479  33.517  1.00  23.42      1DIK2101
ATOM   2010  CA   ILE  268    -10.073  44.399  33.647  1.00  25.35      1DIK2102
ATOM   2011  C    ILE  268     -9.721  43.461  34.801  1.00  27.88      1DIK2103
ATOM   2012  O    ILE  268     -8.776  42.673  34.714  1.00  28.12      1DIK2104
ATOM   2013  CB   ILE  268     -9.460  45.786  33.889  1.00  27.94      1DIK2105
ATOM   2014  CG1  ILE  268     -9.515  46.575  32.579  1.00  27.22      1DIK2106
ATOM   2015  CG2  ILE  268     -8.031  45.659  34.457  1.00  19.33      1DIK2107
ATOM   2016  CD1  ILE  268     -9.124  48.027  32.704  1.00  36.44      1DIK2108
ATOM   2017  N    ASN  269    -10.495  43.553  35.877  1.00  27.63      1DIK2109
ATOM   2018  CA   ASN  269    -10.290  42.704  37.039  1.00  27.33      1DIK2110
ATOM   2019  C    ASN  269    -10.656  41.259  36.739  1.00  26.62      1DIK2111
ATOM   2020  O    ASN  269     -9.918  40.348  37.108  1.00  27.01      1DIK2112
ATOM   2021  CB   ASN  269    -11.110  43.206  38.226  1.00  32.36      1DIK2113
ATOM   2022  CG   ASN  269    -10.427  44.332  38.966  1.00  32.62      1DIK2114
ATOM   2023  OD1  ASN  269     -9.287  44.208  39.423  1.00  29.54      1DIK2115
ATOM   2024  ND2  ASN  269    -11.120  45.443  39.088  1.00  38.68      1DIK2116
ATOM   2025  N    TYR  270    -11.794  41.052  36.075  1.00  22.76      1DIK2117
ATOM   2026  CA   TYR  270    -12.245  39.708  35.712  1.00  22.97      1DIK2118
ATOM   2027  C    TYR  270    -11.168  39.013  34.866  1.00  25.78      1DIK2119
ATOM   2028  O    TYR  270    -10.788  37.868  35.135  1.00  27.56      1DIK2120
ATOM   2029  CB   TYR  270    -13.559  39.800  34.934  1.00  22.99      1DIK2121
ATOM   2030  CG   TYR  270    -14.101  38.485  34.386  1.00  25.74      1DIK2122
ATOM   2031  CD1  TYR  270    -14.989  37.699  35.134  1.00  26.53      1DIK2123
ATOM   2032  CD2  TYR  270    -13.761  38.050  33.099  1.00  23.95      1DIK2124
ATOM   2033  CE1  TYR  270    -15.528  36.511  34.607  1.00  23.23      1DIK2125
ATOM   2034  CE2  TYR  270    -14.288  36.878  32.570  1.00  23.85      1DIK2126
```

FIG. 8-32

```
ATOM   2035  CZ   TYR  270   -15.173  36.113  33.327  1.00  25.13      1DIK2127
ATOM   2036  OH   TYR  270   -15.705  34.964  32.790  1.00  23.62      1DIK2128
ATOM   2037  N    ASP  271   -10.678  39.714  33.847  1.00  23.05      1DIK2129
ATOM   2038  CA   ASP  271    -9.651  39.186  32.975  1.00  21.40      1DIK2130
ATOM   2039  C    ASP  271    -8.449  38.727  33.810  1.00  24.98      1DIK2131
ATOM   2040  O    ASP  271    -7.903  37.632  33.587  1.00  23.79      1DIK2132
ATOM   2041  CB   ASP  271    -9.214  40.259  31.972  1.00  19.82      1DIK2133
ATOM   2042  CG   ASP  271    -8.135  39.762  31.028  1.00  25.01      1DIK2134
ATOM   2043  OD1  ASP  271    -8.467  38.997  30.098  1.00  25.69      1DIK2135
ATOM   2044  OD2  ASP  271    -6.955  40.130  31.215  1.00  22.99      1DIK2136
ATOM   2045  N    TYR  272    -8.042  39.565  34.766  1.00  26.52      1DIK2137
ATOM   2046  CA   TYR  272    -6.912  39.257  35.627  1.00  24.36      1DIK2138
ATOM   2047  C    TYR  272    -7.201  38.031  36.498  1.00  25.48      1DIK2139
ATOM   2048  O    TYR  272    -6.308  37.209  36.738  1.00  27.60      1DIK2140
ATOM   2049  CB   TYR  272    -6.546  40.458  36.501  1.00  25.93      1DIK2141
ATOM   2050  CG   TYR  272    -5.236  40.246  37.210  1.00  24.39      1DIK2142
ATOM   2051  CD1  TYR  272    -4.042  40.250  36.495  1.00  24.69      1DIK2143
ATOM   2052  CD2  TYR  272    -5.186  40.001  38.587  1.00  24.58      1DIK2144
ATOM   2053  CE1  TYR  272    -2.825  40.014  37.120  1.00  24.93      1DIK2145
ATOM   2054  CE2  TYR  272    -3.970  39.762  39.230  1.00  23.27      1DIK2146
ATOM   2055  CZ   TYR  272    -2.794  39.770  38.482  1.00  25.13      1DIK2147
ATOM   2056  OH   TYR  272    -1.577  39.541  39.073  1.00  27.21      1DIK2148
ATOM   2057  N    LEU  273    -8.441  37.900  36.969  1.00  24.96      1DIK2149
ATOM   2058  CA   LEU  273    -8.834  36.743  37.778  1.00  24.02      1DIK2150
ATOM   2059  C    LEU  273    -8.624  35.455  36.964  1.00  25.27      1DIK2151
ATOM   2060  O    LEU  273    -8.159  34.454  37.503  1.00  29.71      1DIK2152
ATOM   2061  CB   LEU  273   -10.302  36.858  38.214  1.00  20.23      1DIK2153
ATOM   2062  CG   LEU  273   -10.976  35.622  38.826  1.00  23.41      1DIK2154
ATOM   2063  CD1  LEU  273   -10.254  35.191  40.104  1.00  20.60      1DIK2155
ATOM   2064  CD2  LEU  273   -12.440  35.922  39.108  1.00  17.70      1DIK2156
ATOM   2065  N    GLN  274    -8.962  35.478  35.672  1.00  23.99      1DIK2157
ATOM   2066  CA   GLN  274    -8.778  34.303  34.811  1.00  21.73      1DIK2158
ATOM   2067  C    GLN  274    -7.290  33.944  34.655  1.00  21.38      1DIK2159
ATOM   2068  O    GLN  274    -6.928  32.763  34.650  1.00  19.72      1DIK2160
ATOM   2069  CB   GLN  274    -9.415  34.530  33.442  1.00  20.31      1DIK2161
ATOM   2070  CG   GLN  274   -10.881  34.906  33.505  1.00  23.01      1DIK2162
ATOM   2071  CD   GLN  274   -11.710  34.017  34.424  1.00  25.47      1DIK2163
ATOM   2072  OE1  GLN  274   -11.536  32.805  34.477  1.00  23.72      1DIK2164
ATOM   2073  NE2  GLN  274   -12.622  34.629  35.154  1.00  32.39      1DIK2165
ATOM   2074  N    SER  275    -6.436  34.961  34.526  1.00  20.92      1DIK2166
ATOM   2075  CA   SER  275    -4.991  34.751  34.433  1.00  20.81      1DIK2167
ATOM   2076  C    SER  275    -4.472  34.099  35.725  1.00  24.14      1DIK2168
ATOM   2077  O    SER  275    -3.612  33.208  35.684  1.00  27.93      1DIK2169
ATOM   2078  CB   SER  275    -4.271  36.078  34.205  1.00  15.74      1DIK2170
ATOM   2079  OG   SER  275    -4.640  36.626  32.950  1.00  24.68      1DIK2171
ATOM   2080  N    LEU  276    -4.991  34.537  36.873  1.00  25.40      1DIK2172
ATOM   2081  CA   LEU  276    -4.571  33.969  38.157  1.00  25.08      1DIK2173
ATOM   2082  C    LEU  276    -4.956  32.500  38.259  1.00  22.91      1DIK2174
ATOM   2083  O    LEU  276    -4.132  31.675  38.619  1.00  24.12      1DIK2175
ATOM   2084  CB   LEU  276    -5.173  34.753  39.333  1.00  25.80      1DIK2176
ATOM   2085  CG   LEU  276    -4.558  36.123  39.596  1.00  23.07      1DIK2177
ATOM   2086  CD1  LEU  276    -5.418  36.893  40.560  1.00  23.03      1DIK2178
ATOM   2087  CD2  LEU  276    -3.158  35.948  40.144  1.00  24.41      1DIK2179
ATOM   2088  N    LYS  277    -6.204  32.174  37.943  1.00  24.32      1DIK2180
ATOM   2089  CA   LYS  277    -6.656  30.790  38.001  1.00  25.45      1DIK2181
ATOM   2090  C    LYS  277    -5.722  29.874  37.204  1.00  24.92      1DIK2182
ATOM   2091  O    LYS  277    -5.302  28.835  37.703  1.00  26.63      1DIK2183
ATOM   2092  CB   LYS  277    -8.049  30.647  37.417  1.00  26.65      1DIK2184
ATOM   2093  CG   LYS  277    -9.226  31.126  38.222  1.00  30.58      1DIK2185
ATOM   2094  CD   LYS  277   -10.424  30.639  37.399  1.00  36.27      1DIK2186
ATOM   2095  CE   LYS  277   -11.754  31.247  37.737  1.00  39.17      1DIK2187
ATOM   2096  NZ   LYS  277   -12.677  30.913  36.604  1.00  37.60      1DIK2188
ATOM   2097  N    LYS  278    -5.408  30.250  35.964  1.00  24.38      1DIK2189
ATOM   2098  CA   LYS  278    -4.523  29.440  35.111  1.00  24.41      1DIK2190
ATOM   2099  C    LYS  278    -3.073  29.414  35.598  1.00  24.27      1DIK2191
ATOM   2100  O    LYS  278    -2.429  28.360  35.590  1.00  24.08      1DIK2192
```

FIG. 8-33

```
ATOM  2101  CB   LYS  278   -4.544  29.948  33.658  1.00  23.48      1DIK2193
ATOM  2102  CG   LYS  278   -5.880  29.828  32.975  1.00  20.48      1DIK2194
ATOM  2103  CD   LYS  278   -6.423  28.428  33.097  1.00  19.64      1DIK2195
ATOM  2104  CE   LYS  278   -7.859  28.389  32.661  1.00  24.74      1DIK2196
ATOM  2105  NZ   LYS  278   -8.431  27.043  32.798  1.00  22.55      1DIK2197
ATOM  2106  N    TYR  279   -2.565  30.573  36.016  1.00  22.37      1DIK2198
ATOM  2107  CA   TYR  279   -1.194  30.686  36.488  1.00  22.48      1DIK2199
ATOM  2108  C    TYR  279   -0.880  29.887  37.749  1.00  24.45      1DIK2200
ATOM  2109  O    TYR  279    0.165  29.237  37.826  1.00  25.51      1DIK2201
ATOM  2110  CB   TYR  279   -0.828  32.141  36.724  1.00  23.08      1DIK2202
ATOM  2111  CG   TYR  279    0.618  32.318  37.123  1.00  25.86      1DIK2203
ATOM  2112  CD1  TYR  279    1.631  32.222  36.179  1.00  21.81      1DIK2204
ATOM  2113  CD2  TYR  279    0.973  32.570  38.452  1.00  24.65      1DIK2205
ATOM  2114  CE1  TYR  279    2.956  32.368  36.540  1.00  26.71      1DIK2206
ATOM  2115  CE2  TYR  279    2.294  32.718  38.824  1.00  21.38      1DIK2207
ATOM  2116  CZ   TYR  279    3.281  32.616  37.863  1.00  25.91      1DIK2208
ATOM  2117  OH   TYR  279    4.596  32.746  38.217  1.00  28.30      1DIK2209
ATOM  2118  N    TYR  280   -1.764  29.938  38.740  1.00  24.59      1DIK2210
ATOM  2119  CA   TYR  280   -1.536  29.208  39.981  1.00  26.07      1DIK2211
ATOM  2120  C    TYR  280   -2.136  27.822  39.951  1.00  26.49      1DIK2212
ATOM  2121  O    TYR  280   -1.889  27.011  40.845  1.00  28.70      1DIK2213
ATOM  2122  CB   TYR  280   -2.045  30.002  41.188  1.00  25.05      1DIK2214
ATOM  2123  CG   TYR  280   -1.148  31.180  41.507  1.00  28.69      1DIK2215
ATOM  2124  CD1  TYR  280    0.047  30.997  42.214  1.00  24.61      1DIK2216
ATOM  2125  CD2  TYR  280   -1.466  32.475  41.065  1.00  27.52      1DIK2217
ATOM  2126  CE1  TYR  280    0.911  32.069  42.466  1.00  25.31      1DIK2218
ATOM  2127  CE2  TYR  280   -0.608  33.556  41.313  1.00  28.66      1DIK2219
ATOM  2128  CZ   TYR  280    0.578  33.342  42.011  1.00  28.71      1DIK2220
ATOM  2129  OH   TYR  280    1.444  34.385  42.212  1.00  29.16      1DIK2221
ATOM  2130  N    GLY  281   -2.922  27.548  38.916  1.00  26.31      1DIK2222
ATOM  2131  CA   GLY  281   -3.530  26.240  38.780  1.00  22.80      1DIK2223
ATOM  2132  C    GLY  281   -2.680  25.285  37.960  1.00  25.18      1DIK2224
ATOM  2133  O    GLY  281   -2.512  24.122  38.342  1.00  29.22      1DIK2225
ATOM  2134  N    HIS  282   -2.141  25.771  36.841  1.00  22.24      1DIK2226
ATOM  2135  CA   HIS  282   -1.342  24.943  35.939  1.00  24.32      1DIK2227
ATOM  2136  C    HIS  282   -0.042  25.561  35.448  1.00  26.33      1DIK2228
ATOM  2137  O    HIS  282    0.770  24.877  34.817  1.00  27.62      1DIK2229
ATOM  2138  CB   HIS  282   -2.190  24.543  34.733  1.00  21.27      1DIK2230
ATOM  2139  CG   HIS  282   -3.524  23.985  35.112  1.00  29.02      1DIK2231
ATOM  2140  ND1  HIS  282   -3.765  22.631  35.222  1.00  29.69      1DIK2232
ATOM  2141  CD2  HIS  282   -4.685  24.602  35.444  1.00  29.92      1DIK2233
ATOM  2142  CE1  HIS  282   -5.015  22.437  35.605  1.00  30.68      1DIK2234
ATOM  2143  NE2  HIS  282   -5.595  23.617  35.747  1.00  30.72      1DIK2235
ATOM  2144  N    GLY  283    0.155  26.846  35.722  1.00  27.84      1DIK2236
ATOM  2145  CA   GLY  283    1.370  27.508  35.292  1.00  26.80      1DIK2237
ATOM  2146  C    GLY  283    2.436  27.399  36.365  1.00  30.11      1DIK2238
ATOM  2147  O    GLY  283    2.324  26.566  37.272  1.00  26.73      1DIK2239
ATOM  2148  N    ALA  284    3.461  28.249  36.259  1.00  31.03      1DIK2240
ATOM  2149  CA   ALA  284    4.579  28.284  37.196  1.00  28.74      1DIK2241
ATOM  2150  C    ALA  284    4.178  28.654  38.621  1.00  32.24      1DIK2242
ATOM  2151  O    ALA  284    4.955  28.464  39.553  1.00  36.63      1DIK2243
ATOM  2152  CB   ALA  284    5.626  29.240  36.702  1.00  26.23      1DIK2244
ATOM  2153  N    GLY  285    2.974  29.182  38.800  1.00  31.80      1DIK2245
ATOM  2154  CA   GLY  285    2.534  29.541  40.133  1.00  30.04      1DIK2246
ATOM  2155  C    GLY  285    2.289  28.305  40.969  1.00  32.15      1DIK2247
ATOM  2156  O    GLY  285    2.274  28.364  42.201  1.00  39.54      1DIK2248
ATOM  2157  N    ASN  286    2.090  27.174  40.307  1.00  29.49      1DIK2249
ATOM  2158  CA   ASN  286    1.844  25.921  41.001  1.00  26.41      1DIK2250
ATOM  2159  C    ASN  286    3.140  25.106  41.045  1.00  28.02      1DIK2251
ATOM  2160  O    ASN  286    3.825  24.958  40.031  1.00  29.27      1DIK2252
ATOM  2161  CB   ASN  286    0.747  25.148  40.278  1.00  22.60      1DIK2253
ATOM  2162  CG   ASN  286    0.176  24.038  41.118  1.00  25.66      1DIK2254
ATOM  2163  OD1  ASN  286    0.822  23.009  41.330  1.00  27.94      1DIK2255
ATOM  2164  ND2  ASN  286   -1.039  24.236  41.611  1.00  22.58      1DIK2256
ATOM  2165  N    PRO  287    3.506  24.576  42.225  1.00  30.51      1DIK2257
ATOM  2166  CA   PRO  287    4.739  23.780  42.340  1.00  31.36      1DIK2258
```

FIG. 8-34

```
ATOM   2167  C    PRO  287      4.852  22.670  41.288  1.00  31.71      1DIK2259
ATOM   2168  O    PRO  287      5.931  22.427  40.750  1.00  34.15      1DIK2260
ATOM   2169  CB   PRO  287      4.658  23.221  43.762  1.00  29.15      1DIK2261
ATOM   2170  CG   PRO  287      3.923  24.320  44.499  1.00  32.66      1DIK2262
ATOM   2171  CD   PRO  287      2.821  24.691  43.527  1.00  29.14      1DIK2263
ATOM   2172  N    LEU  288      3.741  22.000  40.992  1.00  31.66      1DIK2264
ATOM   2173  CA   LEU  288      3.734  20.926  39.999  1.00  30.96      1DIK2265
ATOM   2174  C    LEU  288      3.054  21.320  38.673  1.00  31.70      1DIK2266
ATOM   2175  O    LEU  288      2.710  20.447  37.861  1.00  32.44      1DIK2267
ATOM   2176  CB   LEU  288      3.071  19.673  40.584  1.00  27.59      1DIK2268
ATOM   2177  CG   LEU  288      3.854  19.025  41.731  1.00  27.62      1DIK2269
ATOM   2178  CD1  LEU  288      3.039  17.913  42.364  1.00  28.75      1DIK2270
ATOM   2179  CD2  LEU  288      5.177  18.502  41.206  1.00  25.46      1DIK2271
ATOM   2180  N    GLY  289      2.877  22.626  38.458  1.00  29.27      1DIK2272
ATOM   2181  CA   GLY  289      2.240  23.121  37.245  1.00  28.87      1DIK2273
ATOM   2182  C    GLY  289      3.038  22.806  35.990  1.00  28.45      1DIK2274
ATOM   2183  O    GLY  289      2.591  22.015  35.152  1.00  25.00      1DIK2275
ATOM   2184  N    PRO  290      4.227  23.414  35.827  1.00  26.67      1DIK2276
ATOM   2185  CA   PRO  290      5.075  23.169  34.654  1.00  27.05      1DIK2277
ATOM   2186  C    PRO  290      5.420  21.667  34.473  1.00  27.87      1DIK2278
ATOM   2187  O    PRO  290      5.590  21.194  33.349  1.00  28.39      1DIK2279
ATOM   2188  CB   PRO  290      6.312  24.034  34.945  1.00  25.95      1DIK2280
ATOM   2189  CG   PRO  290      5.756  25.161  35.778  1.00  22.17      1DIK2281
ATOM   2190  CD   PRO  290      4.851  24.402  36.728  1.00  24.69      1DIK2282
ATOM   2191  N    THR  291      5.521  20.925  35.576  1.00  28.55      1DIK2283
ATOM   2192  CA   THR  291      5.807  19.495  35.525  1.00  23.19      1DIK2284
ATOM   2193  C    THR  291      4.778  18.742  34.668  1.00  23.08      1DIK2285
ATOM   2194  O    THR  291      5.106  17.718  34.067  1.00  23.15      1DIK2286
ATOM   2195  CB   THR  291      5.862  18.902  36.958  1.00  21.42      1DIK2287
ATOM   2196  OG1  THR  291      7.129  19.213  37.530  1.00  19.92      1DIK2288
ATOM   2197  CG2  THR  291      5.684  17.395  36.968  1.00  14.25      1DIK2289
ATOM   2197  N    GLN  292      3.543  19.243  34.599  1.00  22.57      1DIK2290
ATOM   2198  CA   GLN  292      2.509  18.584  33.791  1.00  21.65      1DIK2291
ATOM   2199  C    GLN  292      2.805  18.650  32.283  1.00  19.91      1DIK2292
ATOM   2201  O    GLN  292      2.227  17.904  31.494  1.00  23.11      1DIK2293
ATOM   2202  CB   GLN  292      1.119  19.190  34.046  1.00  18.92      1DIK2294
ATOM   2203  CG   GLN  292      0.656  19.202  35.487  1.00  23.26      1DIK2295
ATOM   2204  CD   GLN  292      0.821  17.867  36.187  1.00  24.01      1DIK2296
ATOM   2205  OE1  GLN  292      0.122  16.902  35.892  1.00  25.86      1DIK2297
ATOM   2206  NE2  GLN  292      1.752  17.809  37.127  1.00  26.50      1DIK2298
ATOM   2207  N    GLY  293      3.709  19.528  31.879  1.00  17.82      1DIK2299
ATOM   2208  CA   GLY  293      3.993  19.650  30.472  1.00  17.52      1DIK2300
ATOM   2209  C    GLY  293      5.284  19.050  29.990  1.00  21.21      1DIK2301
ATOM   2210  O    GLY  293      5.581  19.184  28.799  1.00  23.37      1DIK2302
ATOM   2211  N    VAL  294      6.054  18.391  30.859  1.00  19.02      1DIK2303
ATOM   2212  CA   VAL  294      7.329  17.838  30.403  1.00  17.89      1DIK2304
ATOM   2213  C    VAL  294      7.202  16.680  29.426  1.00  18.74      1DIK2305
ATOM   2214  O    VAL  294      8.009  16.588  28.495  1.00  25.27      1DIK2306
ATOM   2215  CB   VAL  294      8.292  17.477  31.558  1.00  18.75      1DIK2307
ATOM   2216  CG1  VAL  294      8.596  18.722  32.382  1.00  19.92      1DIK2308
ATOM   2217  CG2  VAL  294      7.707  16.415  32.425  1.00  24.87      1DIK2309
ATOM   2218  N    GLY  295      6.205  15.815  26.609  1.00  17.01      1DIK2310
ATOM   2219  CA   GLY  295      6.003  14.701  28.692  1.00  16.78      1DIK2311
ATOM   2220  C    GLY  295      5.870  15.193  27.258  1.00  21.51      1DIK2312
ATOM   2221  O    GLY  295      6.561  14.697  26.345  1.00  20.80      1DIK2313
ATOM   2222  N    TYR  296      4.988  16.177  27.055  1.00  16.60      1DIK2314
ATOM   2223  CA   TYR  296      4.780  16.767  25.739  1.00  16.58      1DIK2315
ATOM   2224  C    TYR  296      6.063  17.410  25.193  1.00  20.08      1DIK2316
ATOM   2225  O    TYR  296      6.371  17.314  23.996  1.00  20.96      1DIK2317
ATOM   2226  CB   TYR  296      3.686  17.823  25.803  1.00  17.05      1DIK2318
ATOM   2227  CG   TYR  296      3.273  18.295  24.437  1.00  16.86      1DIK2319
ATOM   2228  CD1  TYR  296      2.388  17.541  23.676  1.00  17.02      1DIK2320
ATOM   2229  CD2  TYR  296      3.774  19.483  23.896  1.00  15.90      1DIK2321
ATOM   2230  CE1  TYR  296      2.006  17.942  22.418  1.00  16.51      1DIK2322
ATOM   2231  CE2  TYR  296      3.399  19.897  22.637  1.00  17.02      1DIK2323
ATOM   2232  CZ   TYR  296      2.510  19.117  21.899  1.00  20.60      1DIK2324
```

FIG. 8-35

```
ATOM   2233  OH   TYR   296      2.101  19.495  20.640  1.00  22.06      1DIK2325
ATOM   2234  N    ALA   297      6.798  18.076  26.081  1.00  20.78      1DIK2326
ATOM   2235  CA   ALA   297      8.054  18.726  25.730  1.00  20.65      1DIK2327
ATOM   2236  C    ALA   297      9.079  17.698  25.239  1.00  18.75      1DIK2328
ATOM   2237  O    ALA   297      9.795  17.942  24.267  1.00  20.26      1DIK2329
ATOM   2238  CB   ALA   297      8.599  19.487  26.934  1.00  20.11      1DIK2330
ATOM   2239  N    ASN   298      9.156  16.549  25.904  1.00  14.67      1DIK2331
ATOM   2240  CA   ASN   298     10.088  15.507  25.479  1.00  15.91      1DIK2332
ATOM   2241  C    ASN   298      9.656  14.898  24.146  1.00  17.04      1DIK2333
ATOM   2242  O    ASN   298     10.498  14.429  23.373  1.00  18.62      1DIK2334
ATOM   2243  CB   ASN   298     10.226  14.433  26.553  1.00  16.51      1DIK2335
ATOM   2244  CG   ASN   298     11.093  14.888  27.702  1.00  19.39      1DIK2336
ATOM   2245  OD1  ASN   298     12.127  15.533  27.494  1.00  18.34      1DIK2337
ATOM   2246  ND2  ASN   298     10.686  14.559  28.919  1.00  10.95      1DIK2338
ATOM   2247  N    GLU   299      8.348  14.900  23.879  1.00  18.29      1DIK2339
ATOM   2248  CA   GLU   299      7.828  14.403  22.608  1.00  20.08      1DIK2340
ATOM   2249  C    GLU   299      8.214  15.404  21.515  1.00  19.66      1DIK2341
ATOM   2250  O    GLU   299      8.519  15.012  20.385  1.00  18.23      1DIK2342
ATOM   2251  CB   GLU   299      6.309  14.226  22.649  1.00  17.35      1DIK2343
ATOM   2252  CG   GLU   299      5.877  13.046  23.478  1.00  20.50      1DIK2344
ATOM   2253  CD   GLU   299      4.383  12.754  23.393  1.00  24.46      1DIK2345
ATOM   2254  OE1  GLU   299      3.576  13.690  23.181  1.00  17.82      1DIK2346
ATOM   2255  OE2  GLU   299      4.013  11.572  23.542  1.00  22.37      1DIK2347
ATOM   2256  N    LEU   300      8.206  16.693  21.859  1.00  19.59      1DIK2348
ATOM   2257  CA   LEU   300      8.596  17.739  20.917  1.00  20.13      1DIK2349
ATOM   2258  C    LEU   300     10.095  17.600  20.593  1.00  20.28      1DIK2350
ATOM   2259  O    LEU   300     10.487  17.665  19.422  1.00  22.61      1DIK2351
ATOM   2260  CB   LEU   300      8.289  19.125  21.488  1.00  21.25      1DIK2352
ATOM   2261  CG   LEU   300      8.649  20.287  20.559  1.00  24.96      1DIK2353
ATOM   2262  CD1  LEU   300      7.930  20.151  19.230  1.00  24.02      1DIK2354
ATOM   2263  CD2  LEU   300      8.269  21.578  21.219  1.00  16.85      1DIK2355
ATOM   2264  N    ILE   301     10.926  17.400  21.624  1.00  18.80      1DIK2356
ATOM   2265  CA   ILE   301     12.373  17.213  21.444  1.00  15.04      1DIK2357
ATOM   2266  C    ILE   301     12.587  16.017  20.484  1.00  20.56      1DIK2358
ATOM   2267  O    ILE   301     13.429  16.056  19.575  1.00  18.58      1DIK2359
ATOM   2268  CB   ILE   301     13.059  16.937  22.812  1.00  16.02      1DIK2360
ATOM   2269  CG1  ILE   301     13.004  18.194  23.686  1.00  17.32      1DIK2361
ATOM   2270  CG2  ILE   301     14.498  16.487  22.626  1.00   6.56      1DIK2362
ATOM   2271  CD1  ILE   301     13.594  18.005  25.064  1.00  14.26      1DIK2363
ATOM   2272  N    ALA   302     11.806  14.958  20.685  1.00  20.02      1DIK2364
ATOM   2273  CA   ALA   302     11.891  13.776  19.840  1.00  20.23      1DIK2365
ATOM   2274  C    ALA   302     11.610  14.139  18.375  1.00  21.81      1DIK2366
ATOM   2275  O    ALA   302     12.326  13.708  17.470  1.00  19.81      1DIK2367
ATOM   2276  CB   ALA   302     10.912  12.718  20.327  1.00  20.45      1DIK2368
ATOM   2277  N    ARG   303     10.577  14.943  18.138  1.00  20.13      1DIK2369
ATOM   2278  CA   ARG   303     10.227  15.329  16.774  1.00  17.34      1DIK2370
ATOM   2279  C    ARG   303     11.245  16.267  16.093  1.00  19.34      1DIK2371
ATOM   2280  O    ARG   303     11.569  16.095  14.907  1.00  15.37      1DIK2372
ATOM   2281  CB   ARG   303      8.816  15.934  16.750  1.00  15.85      1DIK2373
ATOM   2282  CG   ARG   303      7.715  14.914  17.021  1.00  12.30      1DIK2374
ATOM   2283  CD   ARG   303      6.353  15.572  17.215  1.00  11.98      1DIK2375
ATOM   2284  NE   ARG   303      5.287  14.572  17.315  1.00  11.60      1DIK2376
ATOM   2285  CZ   ARG   303      3.989  14.836  17.456  1.00  15.17      1DIK2377
ATOM   2286  NH1  ARG   303      3.538  16.088  17.540  1.00  11.46      1DIK2378
ATOM   2287  NH2  ARG   303      3.132  13.830  17.519  1.00  15.32      1DIK2379
ATOM   2288  N    LEU   304     11.752  17.247  16.838  1.00  16.06      1DIK2380
ATOM   2289  CA   LEU   304     12.722  18.188  16.289  1.00  18.27      1DIK2381
ATOM   2290  C    LEU   304     14.026  17.480  15.922  1.00  20.93      1DIK2382
ATOM   2291  O    LEU   304     14.638  17.772  14.897  1.00  23.62      1DIK2383
ATOM   2292  CB   LEU   304     13.020  19.309  17.292  1.00  12.77      1DIK2384
ATOM   2293  CG   LEU   304     11.882  20.262  17.643  1.00  20.49      1DIK2385
ATOM   2294  CD1  LEU   304     12.289  21.157  18.805  1.00  17.27      1DIK2386
ATOM   2295  CD2  LEU   304     11.509  21.083  16.416  1.00  22.28      1DIK2387
ATOM   2296  N    THR   305     14.450  16.546  16.763  1.00  21.43      1DIK2388
ATOM   2297  CA   THR   305     15.686  15.823  16.518  1.00  22.45      1DIK2389
ATOM   2298  C    THR   305     15.510  14.475  15.803  1.00  23.67      1DIK2390
```

FIG. 8-36

| | | | | | | | | | | |
|---|---|---|---|---|---|---|---|---|---|---|
| ATOM | 2299 | O | THR | 305 | 16.491 | 13.788 | 15.552 | 1.00 | 25.10 | 1DIK2391 |
| ATOM | 2300 | CB | THR | 305 | 16.429 | 15.589 | 17.843 | 1.00 | 21.99 | 1DIK2392 |
| ATOM | 2301 | OG1 | THR | 305 | 15.622 | 14.782 | 18.711 | 1.00 | 26.81 | 1DIK2393 |
| ATOM | 2302 | CG2 | THR | 305 | 16.712 | 16.906 | 18.530 | 1.00 | 16.41 | 1DIK2394 |
| ATOM | 2303 | N | HIS | 306 | 14.276 | 14.100 | 15.476 | 1.00 | 24.74 | 1DIK2395 |
| ATOM | 2304 | CA | HIS | 306 | 13.982 | 12.815 | 14.815 | 1.00 | 28.44 | 1DIK2396 |
| ATOM | 2305 | C | HIS | 306 | 14.566 | 11.628 | 15.600 | 1.00 | 27.46 | 1DIK2397 |
| ATOM | 2306 | O | HIS | 306 | 15.122 | 10.704 | 15.012 | 1.00 | 33.56 | 1DIK2398 |
| ATOM | 2307 | CB | HIS | 306 | 14.519 | 12.796 | 13.374 | 1.00 | 27.83 | 1DIK2399 |
| ATOM | 2308 | CG | HIS | 306 | 14.236 | 14.053 | 12.613 | 1.00 | 33.95 | 1DIK2400 |
| ATOM | 2309 | ND1 | HIS | 306 | 12.959 | 14.447 | 12.268 | 1.00 | 35.48 | 1DIK2401 |
| ATOM | 2310 | CD2 | HIS | 306 | 15.065 | 15.022 | 12.155 | 1.00 | 32.87 | 1DIK2402 |
| ATOM | 2311 | CE1 | HIS | 306 | 13.013 | 15.604 | 11.633 | 1.00 | 35.66 | 1DIK2403 |
| ATOM | 2312 | NE2 | HIS | 306 | 14.280 | 15.974 | 11.552 | 1.00 | 35.02 | 1DIK2404 |
| ATOM | 2313 | N | SER | 307 | 14.429 | 11.654 | 16.919 | 1.00 | 22.90 | 1DIK2405 |
| ATOM | 2314 | CA | SER | 307 | 14.956 | 10.606 | 17.779 | 1.00 | 24.39 | 1DIK2406 |
| ATOM | 2315 | C | SER | 307 | 13.858 | 10.081 | 18.684 | 1.00 | 27.25 | 1DIK2407 |
| ATOM | 2316 | O | SER | 307 | 12.864 | 10.768 | 18.920 | 1.00 | 31.56 | 1DIK2408 |
| ATOM | 2317 | CB | SER | 307 | 16.050 | 11.175 | 18.662 | 1.00 | 22.96 | 1DIK2409 |
| ATOM | 2318 | OG | SER | 307 | 16.779 | 12.147 | 17.948 | 1.00 | 39.77 | 1DIK2410 |
| ATOM | 2319 | N | PRO | 308 | 14.014 | 8.845 | 19.201 | 1.00 | 28.75 | 1DIK2411 |
| ATOM | 2320 | CA | PRO | 308 | 13.004 | 8.260 | 20.094 | 1.00 | 26.08 | 1DIK2412 |
| ATOM | 2321 | C | PRO | 308 | 12.764 | 9.127 | 21.322 | 1.00 | 23.85 | 1DIK2413 |
| ATOM | 2322 | O | PRO | 308 | 13.614 | 9.921 | 21.711 | 1.00 | 22.93 | 1DIK2414 |
| ATOM | 2323 | CB | PRO | 308 | 13.609 | 6.899 | 20.450 | 1.00 | 25.36 | 1DIK2415 |
| ATOM | 2324 | CG | PRO | 308 | 14.416 | 6.567 | 19.204 | 1.00 | 24.66 | 1DIK2416 |
| ATOM | 2325 | CD | PRO | 308 | 15.109 | 7.886 | 18.963 | 1.00 | 25.37 | 1DIK2417 |
| ATOM | 2326 | N | VAL | 309 | 11.601 | 8.968 | 21.932 | 1.00 | 25.92 | 1DIK2418 |
| ATOM | 2327 | CA | VAL | 309 | 11.250 | 9.744 | 23.105 | 1.00 | 23.97 | 1DIK2419 |
| ATOM | 2328 | C | VAL | 309 | 11.959 | 9.207 | 24.348 | 1.00 | 28.96 | 1DIK2420 |
| ATOM | 2329 | O | VAL | 309 | 12.050 | 7.990 | 24.554 | 1.00 | 28.02 | 1DIK2421 |
| ATOM | 2330 | CB | VAL | 309 | 9.725 | 9.692 | 23.367 | 1.00 | 19.99 | 1DIK2422 |
| ATOM | 2331 | CG1 | VAL | 309 | 9.351 | 10.630 | 24.506 | 1.00 | 14.96 | 1DIK2423 |
| ATOM | 2332 | CG2 | VAL | 309 | 8.963 | 10.053 | 22.112 | 1.00 | 21.23 | 1DIK2424 |
| ATOM | 2333 | N | HIS | 310 | 12.480 | 10.118 | 25.166 | 1.00 | 32.25 | 1DIK2425 |
| ATOM | 2334 | CA | HIS | 310 | 13.101 | 9.751 | 26.433 | 1.00 | 30.63 | 1DIK2426 |
| ATOM | 2335 | C | HIS | 310 | 12.270 | 10.503 | 27.447 | 1.00 | 28.25 | 1DIK2427 |
| ATOM | 2336 | O | HIS | 310 | 12.459 | 11.699 | 27.668 | 1.00 | 29.12 | 1DIK2428 |
| ATOM | 2337 | CB | HIS | 310 | 14.573 | 10.160 | 26.502 | 1.00 | 35.26 | 1DIK2429 |
| ATOM | 2338 | CG | HIS | 310 | 15.477 | 9.219 | 25.772 | 1.00 | 46.85 | 1DIK2430 |
| ATOM | 2339 | ND1 | HIS | 310 | 15.732 | 9.329 | 24.418 | 1.00 | 53.75 | 1DIK2431 |
| ATOM | 2340 | CD2 | HIS | 310 | 16.148 | 8.117 | 26.191 | 1.00 | 52.66 | 1DIK2432 |
| ATOM | 2341 | CE1 | HIS | 310 | 16.517 | 8.339 | 24.032 | 1.00 | 54.18 | 1DIK2433 |
| ATOM | 2342 | NE2 | HIS | 310 | 16.784 | 7.588 | 25.089 | 1.00 | 57.76 | 1DIK2434 |
| ATOM | 2343 | N | ASP | 311 | 11.326 | 9.795 | 28.047 | 1.00 | 25.80 | 1DIK2435 |
| ATOM | 2344 | CA | ASP | 311 | 10.450 | 10.404 | 29.019 | 1.00 | 24.79 | 1DIK2436 |
| ATOM | 2345 | C | ASP | 311 | 9.947 | 9.348 | 29.959 | 1.00 | 26.98 | 1DIK2437 |
| ATOM | 2346 | O | ASP | 311 | 9.707 | 8.212 | 29.564 | 1.00 | 29.31 | 1DIK2438 |
| ATOM | 2347 | CB | ASP | 311 | 9.257 | 11.064 | 28.317 | 1.00 | 25.99 | 1DIK2439 |
| ATOM | 2348 | CG | ASP | 311 | 8.239 | 11.619 | 29.292 | 1.00 | 24.92 | 1DIK2440 |
| ATOM | 2349 | OD1 | ASP | 311 | 8.498 | 12.703 | 29.844 | 1.00 | 24.37 | 1DIK2441 |
| ATOM | 2350 | OD2 | ASP | 311 | 7.184 | 10.982 | 29.512 | 1.00 | 21.07 | 1DIK2442 |
| ATOM | 2351 | N | ASP | 312 | 9.779 | 9.740 | 31.210 | 1.00 | 29.33 | 1DIK2443 |
| ATOM | 2352 | CA | ASP | 312 | 9.269 | 8.849 | 32.217 | 1.00 | 29.81 | 1DIK2444 |
| ATOM | 2353 | C | ASP | 312 | 8.262 | 9.626 | 33.072 | 1.00 | 32.06 | 1DIK2445 |
| ATOM | 2354 | O | ASP | 312 | 8.201 | 9.465 | 34.294 | 1.00 | 33.19 | 1DIK2446 |
| ATOM | 2355 | CB | ASP | 312 | 10.422 | 8.309 | 33.061 | 1.00 | 32.29 | 1DIK2447 |
| ATOM | 2356 | CG | ASP | 312 | 10.034 | 7.062 | 33.861 | 1.00 | 40.96 | 1DIK2448 |
| ATOM | 2357 | OD1 | ASP | 312 | 8.902 | 6.523 | 33.695 | 1.00 | 37.90 | 1DIK2449 |
| ATOM | 2358 | OD2 | ASP | 312 | 10.882 | 6.616 | 34.668 | 1.00 | 46.83 | 1DIK2450 |
| ATOM | 2359 | N | THR | 313 | 7.470 | 10.475 | 32.424 | 1.00 | 28.45 | 1DIK2451 |
| ATOM | 2360 | CA | THR | 313 | 6.472 | 11.250 | 33.143 | 1.00 | 26.99 | 1DIK2452 |
| ATOM | 2361 | C | THR | 313 | 5.040 | 10.924 | 32.685 | 1.00 | 27.21 | 1DIK2453 |
| ATOM | 2362 | O | THR | 313 | 4.455 | 9.940 | 33.145 | 1.00 | 25.95 | 1DIK2454 |
| ATOM | 2363 | CB | THR | 313 | 6.762 | 12.771 | 33.043 | 1.00 | 27.49 | 1DIK2455 |
| ATOM | 2364 | OG1 | THR | 313 | 6.694 | 13.193 | 31.671 | 1.00 | 21.29 | 1DIK2456 |

FIG. 8-37

```
ATOM   2365  CG2 THR   313       8.164  13.075  33.597  1.00 23.59      1DIK2457
ATOM   2366  N   SER   314       4.476  11.726  31.785  1.00 24.25      1DIK2458
ATOM   2367  CA  SER   314       3.105  11.510  31.326  1.00 20.48      1DIK2459
ATOM   2368  C   SER   314       2.936  10.702  30.042  1.00 20.74      1DIK2460
ATOM   2369  O   SER   314       1.821  10.289  29.712  1.00 20.71      1DIK2461
ATOM   2370  CB  SER   314       2.409  12.867  31.160  1.00 20.21      1DIK2462
ATOM   2371  OG  SER   314       3.137  13.722  30.286  1.00 23.16      1DIK2463
ATOM   2372  N   SER   315       4.028  10.468  29.317  1.00 21.85      1DIK2464
ATOM   2373  CA  SER   315       3.923   9.757  28.055  1.00 20.97      1DIK2465
ATOM   2374  C   SER   315       3.568   8.288  28.141  1.00 23.67      1DIK2466
ATOM   2375  O   SER   315       3.890   7.593  29.111  1.00 26.91      1DIK2467
ATOM   2376  CB  SER   315       5.187   9.953  27.200  1.00 18.40      1DIK2468
ATOM   2377  OG  SER   315       6.313   9.245  27.685  1.00 18.66      1DIK2469
ATOM   2378  N   ASN   316       2.885   7.830  27.102  1.00 23.83      1DIK2470
ATOM   2379  CA  ASN   316       2.489   6.440  26.964  1.00 24.79      1DIK2471
ATOM   2380  C   ASN   316       3.689   5.793  26.225  1.00 23.66      1DIK2472
ATOM   2381  O   ASN   316       3.929   6.088  25.047  1.00 24.08      1DIK2473
ATOM   2382  CB  ASN   316       1.205   6.394  26.130  1.00 24.17      1DIK2474
ATOM   2383  CG  ASN   316       0.621   5.012  26.011  1.00 20.87      1DIK2475
ATOM   2384  OD1 ASN   316       1.331   4.026  25.849  1.00 26.91      1DIK2476
ATOM   2385  ND2 ASN   316      -0.690   4.936  26.081  1.00 24.90      1DIK2477
ATOM   2386  N   HIS   317       4.439   4.930  26.918  1.00 19.55      1DIK2478
ATOM   2387  CA  HIS   317       5.627   4.274  26.341  1.00 17.40      1DIK2479
ATOM   2388  C   HIS   317       5.289   3.406  25.149  1.00 18.22      1DIK2480
ATOM   2389  O   HIS   317       6.015   3.392  24.152  1.00 21.43      1DIK2481
ATOM   2390  CB  HIS   317       6.341   3.401  27.380  1.00 19.52      1DIK2482
ATOM   2391  CG  HIS   317       6.708   4.125  28.640  1.00 25.20      1DIK2483
ATOM   2392  ND1 HIS   317       7.379   5.332  28.643  1.00 28.94      1DIK2484
ATOM   2393  CD2 HIS   317       6.503   3.808  29.940  1.00 26.03      1DIK2485
ATOM   2394  CE1 HIS   317       7.571   5.728  29.888  1.00 27.28      1DIK2486
ATOM   2395  NE2 HIS   317       7.049   4.821  30.694  1.00 31.03      1DIK2487
ATOM   2396  N   THR   318       4.187   2.670  25.255  1.00 18.44      1DIK2488
ATOM   2397  CA  THR   318       3.740   1.800  24.180  1.00 18.99      1DIK2489
ATOM   2398  C   THR   318       3.329   2.644  22.978  1.00 21.41      1DIK2490
ATOM   2399  O   THR   318       3.764   2.399  21.851  1.00 20.04      1DIK2491
ATOM   2400  CB  THR   318       2.544   0.955  24.632  1.00 18.88      1DIK2492
ATOM   2401  OG1 THR   318       2.889   0.310  25.857  1.00 18.06      1DIK2493
ATOM   2402  CG2 THR   318       2.188  -0.116  23.594  1.00 14.25      1DIK2494
ATOM   2403  N   LEU   319       2.500   3.650  23.221  1.00 20.99      1DIK2495
ATOM   2404  CA  LEU   319       2.030   4.509  22.151  1.00 21.53      1DIK2496
ATOM   2405  C   LEU   319       3.171   5.205  21.383  1.00 25.80      1DIK2497
ATOM   2406  O   LEU   319       3.091   5.371  20.165  1.00 25.17      1DIK2498
ATOM   2407  CB  LEU   319       1.085   5.541  22.733  1.00 20.62      1DIK2499
ATOM   2408  CG  LEU   319       0.100   6.148  21.761  1.00 22.28      1DIK2500
ATOM   2409  CD1 LEU   319      -0.686   5.029  21.099  1.00 23.07      1DIK2501
ATOM   2410  CD2 LEU   319      -0.819   7.079  22.522  1.00 20.45      1DIK2502
ATOM   2411  N   ASP   320       4.234   5.603  22.085  1.00 24.35      1DIK2503
ATOM   2412  CA  ASP   320       5.360   6.297  21.445  1.00 22.47      1DIK2504
ATOM   2413  C   ASP   320       6.493   5.459  20.884  1.00 21.00      1DIK2505
ATOM   2414  O   ASP   320       7.437   6.005  20.317  1.00 17.90      1DIK2506
ATOM   2415  CB  ASP   320       5.956   7.325  22.403  1.00 19.58      1DIK2507
ATOM   2416  CG  ASP   320       5.061   8.531  22.582  1.00 22.62      1DIK2508
ATOM   2417  OD1 ASP   320       3.909   8.509  22.092  1.00 22.05      1DIK2509
ATOM   2418  OD2 ASP   320       5.509   9.505  23.214  1.00 18.12      1DIK2510
ATOM   2419  N   SER   321       6.407   4.143  21.024  1.00 22.21      1DIK2511
ATOM   2420  CA  SER   321       7.477   3.271  20.556  1.00 25.24      1DIK2512
ATOM   2421  C   SER   321       7.416   2.869  19.082  1.00 25.75      1DIK2513
ATOM   2422  O   SER   321       8.382   2.315  18.539  1.00 25.63      1DIK2514
ATOM   2423  CB  SER   321       7.496   2.023  21.417  1.00 23.95      1DIK2515
ATOM   2424  OG  SER   321       6.265   1.358  21.278  1.00 33.89      1DIK2516
ATOM   2425  N   SER   322       6.288   3.155  18.441  1.00 27.36      1DIK2517
ATOM   2426  CA  SER   322       6.084   2.776  17.053  1.00 27.84      1DIK2518
ATOM   2427  C   SER   322       5.695   3.928  16.118  1.00 27.85      1DIK2519
ATOM   2428  O   SER   322       4.948   4.838  16.502  1.00 26.35      1DIK2520
ATOM   2429  CB  SER   322       5.016   1.677  17.007  1.00 27.18      1DIK2521
ATOM   2430  OG  SER   322       4.568   1.439  15.688  1.00 34.11      1DIK2522
```

FIG. 8-38

```
ATOM   2431  N   PRO 323       6.206   3.895  14.872  1.00 27.40      1DIK2523
ATOM   2432  CA  PRO 323       5.967   4.880  13.807  1.00 27.34      1DIK2524
ATOM   2433  C   PRO 323       4.471   5.053  13.496  1.00 26.66      1DIK2525
ATOM   2434  O   PRO 323       4.037   6.111  13.049  1.00 29.69      1DIK2526
ATOM   2435  CB  PRO 323       6.713   4.276  12.611  1.00 27.47      1DIK2527
ATOM   2436  CG  PRO 323       7.827   3.522  13.251  1.00 26.17      1DIK2528
ATOM   2437  CD  PRO 323       7.121   2.840  14.398  1.00 25.07      1DIK2529
ATOM   2438  N   ALA 324       3.685   4.014  13.732  1.00 23.94      1DIK2530
ATOM   2439  CA  ALA 324       2.258   4.086  13.465  1.00 24.16      1DIK2531
ATOM   2440  C   ALA 324       1.558   5.072  14.381  1.00 21.32      1DIK2532
ATOM   2441  O   ALA 324       0.598   5.712  13.984  1.00 24.85      1DIK2533
ATOM   2442  CB  ALA 324       1.615   2.709  13.615  1.00 23.92      1DIK2534
ATOM   2443  N   THR 325       2.024   5.194  15.612  1.00 19.68      1DIK2535
ATOM   2444  CA  THR 325       1.379   6.097  16.537  1.00 18.15      1DIK2536
ATOM   2445  C   THR 325       2.260   7.256  16.940  1.00 20.32      1DIK2537
ATOM   2446  O   THR 325       1.791   8.183  17.602  1.00 20.91      1DIK2538
ATOM   2447  CB  THR 325       0.898   5.350  17.764  1.00 18.83      1DIK2539
ATOM   2448  OG1 THR 325       1.907   4.428  18.161  1.00 23.06      1DIK2540
ATOM   2449  CG2 THR 325      -0.375   4.579  17.451  1.00 18.83      1DIK2541
ATOM   2450  N   PHE 326       3.532   7.202  16.548  1.00 19.80      1DIK2542
ATOM   2451  CA  PHE 326       4.467   8.282  16.824  1.00 18.01      1DIK2543
ATOM   2452  C   PHE 326       5.605   8.328  15.787  1.00 18.87      1DIK2544
ATOM   2453  O   PHE 326       6.725   7.875  16.046  1.00 20.23      1DIK2545
ATOM   2454  CB  PHE 326       5.024   8.183  18.256  1.00 22.80      1DIK2546
ATOM   2455  CG  PHE 326       5.620   9.478  18.761  1.00 20.42      1DIK2547
ATOM   2456  CD1 PHE 326       4.810  10.445  19.362  1.00 19.30      1DIK2548
ATOM   2457  CD2 PHE 326       6.979   9.755  18.595  1.00 15.81      1DIK2549
ATOM   2458  CE1 PHE 326       5.340  11.680  19.790  1.00 12.22      1DIK2550
ATOM   2459  CE2 PHE 326       7.515  10.984  19.018  1.00 18.58      1DIK2551
ATOM   2460  CZ  PHE 326       6.686  11.948  19.617  1.00 14.93      1DIK2552
ATOM   2461  N   PRO 327       5.323   8.876  14.588  1.00 18.42      1DIK2553
ATOM   2462  CA  PRO 327       6.270   9.017  13.473  1.00 19.53      1DIK2554
ATOM   2463  C   PRO 327       7.260  10.121  13.791  1.00 21.71      1DIK2555
ATOM   2464  O   PRO 327       6.875  11.203  14.245  1.00 21.90      1DIK2556
ATOM   2465  CB  PRO 327       5.388   9.449  12.300  1.00 16.34      1DIK2557
ATOM   2466  CG  PRO 327       3.995   9.168  12.745  1.00 17.33      1DIK2558
ATOM   2467  CD  PRO 327       4.013   9.422  14.211  1.00 16.80      1DIK2559
ATOM   2468  N   LEU 328       8.532   9.855  13.539  1.00 24.26      1DIK2560
ATOM   2469  CA  LEU 328       9.569  10.836  13.812  1.00 23.81      1DIK2561
ATOM   2470  C   LEU 328       9.967  11.618  12.566  1.00 24.00      1DIK2562
ATOM   2471  O   LEU 328      10.721  12.580  12.654  1.00 26.13      1DIK2563
ATOM   2472  CB  LEU 328      10.801  10.135  14.384  1.00 22.63      1DIK2564
ATOM   2473  CG  LEU 328      10.576   9.272  15.625  1.00 25.54      1DIK2565
ATOM   2474  CD1 LEU 328      11.869   8.560  15.990  1.00 24.58      1DIK2566
ATOM   2475  CD2 LEU 328      10.092  10.137  16.782  1.00 22.69      1DIK2567
ATOM   2476  N   ASN 329       9.473  11.220  11.403  1.00 26.61      1DIK2568
ATOM   2477  CA  ASN 329       9.865  11.919  10.198  1.00 29.63      1DIK2569
ATOM   2478  C   ASN 329       8.759  12.578   9.413  1.00 27.72      1DIK2570
ATOM   2479  O   ASN 329       8.941  12.876   8.243  1.00 32.13      1DIK2571
ATOM   2480  CB  ASN 329      10.686  11.001   9.288  1.00 36.18      1DIK2572
ATOM   2481  CG  ASN 329      12.075  10.733   9.843  1.00 48.05      1DIK2573
ATOM   2482  OD1 ASN 329      12.927  11.632   9.873  1.00 52.99      1DIK2574
ATOM   2483  ND2 ASN 329      12.315   9.494  10.290  1.00 53.32      1DIK2575
ATOM   2484  N   SER 330       7.601  12.797  10.020  1.00 28.90      1DIK2576
ATOM   2485  CA  SER 330       6.550  13.530   9.313  1.00 30.10      1DIK2577
ATOM   2486  C   SER 330       7.141  14.938   9.429  1.00 33.67      1DIK2578
ATOM   2487  O   SER 330       8.041  15.193  10.257  1.00 39.71      1DIK2579
ATOM   2488  CB  SER 330       5.212  13.489  10.054  1.00 27.33      1DIK2580
ATOM   2489  OG  SER 330       4.824  12.169  10.372  1.00 30.99      1DIK2581
ATOM   2490  N   THR 331       6.670  15.869   8.633  1.00 29.23      1DIK2582
ATOM   2491  CA  THR 331       7.260  17.198   8.729  1.00 29.49      1DIK2583
ATOM   2492  C   THR 331       6.303  18.150   9.420  1.00 25.32      1DIK2584
ATOM   2493  O   THR 331       6.714  19.147  10.005  1.00 22.51      1DIK2585
ATOM   2494  CB  THR 331       7.590  17.690   7.321  1.00 31.50      1DIK2586
ATOM   2495  OG1 THR 331       8.453  16.737   6.705  1.00 27.95      1DIK2587
ATOM   2496  CG2 THR 331       8.242  19.035   7.343  1.00 36.14      1DIK2588
```

FIG. 8-39

| | | | | | | | | | |
|---|---|---|---|---|---|---|---|---|---|
| ATOM | 2497 | N | LEU | 332 | 5.021 | 17.804 | 9.334 | 1.00 24.55 | 1DIK2589 |
| ATOM | 2498 | CA | LEU | 332 | 3.930 | 18.578 | 9.885 | 1.00 23.43 | 1DIK2590 |
| ATOM | 2499 | C | LEU | 332 | 3.168 | 17.760 | 10.916 | 1.00 21.17 | 1DIK2591 |
| ATOM | 2500 | O | LEU | 332 | 2.814 | 16.606 | 10.655 | 1.00 20.55 | 1DIK2592 |
| ATOM | 2501 | CB | LEU | 332 | 2.965 | 18.972 | 8.756 | 1.00 23.10 | 1DIK2593 |
| ATOM | 2502 | CG | LEU | 332 | 3.542 | 19.823 | 7.625 | 1.00 25.75 | 1DIK2594 |
| ATOM | 2503 | CD1 | LEU | 332 | 2.598 | 19.836 | 6.431 | 1.00 21.25 | 1DIK2595 |
| ATOM | 2504 | CD2 | LEU | 332 | 3.802 | 21.223 | 8.145 | 1.00 19.61 | 1DIK2596 |
| ATOM | 2505 | N | TYR | 333 | 2.916 | 18.361 | 12.076 | 1.00 19.69 | 1DIK2597 |
| ATOM | 2506 | CA | TYR | 333 | 2.154 | 17.720 | 13.152 | 1.00 17.57 | 1DIK2598 |
| ATOM | 2507 | C | TYR | 333 | 1.101 | 18.691 | 13.706 | 1.00 14.59 | 1DIK2599 |
| ATOM | 2508 | O | TYR | 333 | 1.304 | 19.910 | 13.718 | 1.00 17.04 | 1DIK2600 |
| ATOM | 2509 | CB | TYR | 333 | 3.076 | 17.317 | 14.301 | 1.00 16.40 | 1DIK2601 |
| ATOM | 2510 | CG | TYR | 333 | 4.150 | 16.329 | 13.944 | 1.00 15.46 | 1DIK2602 |
| ATOM | 2511 | CD1 | TYR | 333 | 3.927 | 14.962 | 14.058 | 1.00 16.50 | 1DIK2603 |
| ATOM | 2512 | CD2 | TYR | 333 | 5.399 | 16.758 | 13.519 | 1.00 15.19 | 1DIK2604 |
| ATOM | 2513 | CE1 | TYR | 333 | 4.929 | 14.039 | 13.758 | 1.00 19.21 | 1DIK2605 |
| ATOM | 2514 | CE2 | TYR | 333 | 6.412 | 15.845 | 13.214 | 1.00 19.07 | 1DIK2606 |
| ATOM | 2515 | CZ | TYR | 333 | 6.170 | 14.487 | 13.338 | 1.00 20.05 | 1DIK2607 |
| ATOM | 2516 | OH | TYR | 333 | 7.165 | 13.580 | 13.056 | 1.00 20.29 | 1DIK2608 |
| ATOM | 2517 | N | ALA | 334 | -0.022 | 18.154 | 14.161 | 1.00 11.62 | 1DIK2609 |
| ATOM | 2518 | CA | ALA | 334 | -1.072 | 18.971 | 14.764 | 1.00 14.11 | 1DIK2610 |
| ATOM | 2519 | C | ALA | 334 | -1.642 | 18.190 | 15.952 | 1.00 17.81 | 1DIK2611 |
| ATOM | 2520 | O | ALA | 334 | -2.001 | 17.014 | 15.808 | 1.00 20.52 | 1DIK2612 |
| ATOM | 2521 | CB | ALA | 334 | -2.169 | 19.291 | 13.763 | 1.00 6.64 | 1DIK2613 |
| ATOM | 2522 | N | ASP | 335 | -1.706 | 18.842 | 17.117 | 1.00 15.89 | 1DIK2614 |
| ATOM | 2523 | CA | ASP | 335 | -2.234 | 18.234 | 18.334 | 1.00 15.85 | 1DIK2615 |
| ATOM | 2524 | C | ASP | 335 | -3.350 | 19.116 | 18.877 | 1.00 19.02 | 1DIK2616 |
| ATOM | 2525 | O | ASP | 335 | -3.261 | 20.350 | 18.823 | 1.00 17.86 | 1DIK2617 |
| ATOM | 2526 | CB | ASP | 335 | -1.126 | 18.059 | 19.392 | 1.00 16.00 | 1DIK2618 |
| ATOM | 2527 | CG | ASP | 335 | -0.099 | 16.997 | 19.001 | 1.00 20.47 | 1DIK2619 |
| ATOM | 2528 | OD1 | ASP | 335 | -0.502 | 15.948 | 18.466 | 1.00 22.42 | 1DIK2620 |
| ATOM | 2529 | OD2 | ASP | 335 | 1.112 | 17.201 | 19.224 | 1.00 20.56 | 1DIK2621 |
| ATOM | 2530 | N | PHE | 336 | -4.402 | 18.481 | 19.395 | 1.00 18.17 | 1DIK2622 |
| ATOM | 2531 | CA | PHE | 336 | -5.543 | 19.200 | 19.937 | 1.00 17.35 | 1DIK2623 |
| ATOM | 2532 | C | PHE | 336 | -5.774 | 18.839 | 21.402 | 1.00 19.88 | 1DIK2624 |
| ATOM | 2533 | O | PHE | 336 | -5.815 | 17.655 | 21.776 | 1.00 19.43 | 1DIK2625 |
| ATOM | 2534 | CB | PHE | 336 | -6.778 | 18.940 | 19.066 | 1.00 17.54 | 1DIK2626 |
| ATOM | 2535 | CG | PHE | 336 | -6.594 | 19.394 | 17.655 | 1.00 14.71 | 1DIK2627 |
| ATOM | 2536 | CD1 | PHE | 336 | -5.954 | 18.577 | 16.728 | 1.00 14.86 | 1DIK2628 |
| ATOM | 2537 | CD2 | PHE | 336 | -6.978 | 20.676 | 17.271 | 1.00 14.13 | 1DIK2629 |
| ATOM | 2538 | CE1 | PHE | 336 | -5.688 | 19.036 | 15.434 | 1.00 19.47 | 1DIK2630 |
| ATOM | 2539 | CE2 | PHE | 336 | -6.721 | 21.148 | 15.987 | 1.00 13.80 | 1DIK2631 |
| ATOM | 2540 | CZ | PHE | 336 | -6.072 | 20.328 | 15.065 | 1.00 15.97 | 1DIK2632 |
| ATOM | 2541 | N | SER | 337 | -5.933 | 19.881 | 22.219 | 1.00 16.75 | 1DIK2633 |
| ATOM | 2542 | CA | SER | 337 | -6.096 | 19.713 | 23.642 | 1.00 15.92 | 1DIK2634 |
| ATOM | 2543 | C | SER | 337 | -6.962 | 20.793 | 24.331 | 1.00 17.12 | 1DIK2635 |
| ATOM | 2544 | O | SER | 337 | -7.708 | 21.549 | 23.684 | 1.00 15.10 | 1DIK2636 |
| ATOM | 2545 | CB | SER | 337 | -4.696 | 19.692 | 24.251 | 1.00 13.71 | 1DIK2637 |
| ATOM | 2546 | OG | SER | 337 | -4.698 | 18.968 | 25.455 | 1.00 18.65 | 1DIK2638 |
| ATOM | 2547 | N | HIS | 338 | -6.843 | 20.836 | 25.658 | 1.00 16.73 | 1DIK2639 |
| ATOM | 2548 | CA | HIS | 338 | -7.546 | 21.772 | 26.536 | 1.00 18.64 | 1DIK2640 |
| ATOM | 2549 | C | HIS | 338 | -6.616 | 22.900 | 26.998 | 1.00 20.65 | 1DIK2641 |
| ATOM | 2550 | O | HIS | 338 | -5.392 | 22.785 | 26.917 | 1.00 23.22 | 1DIK2642 |
| ATOM | 2551 | CB | HIS | 338 | -8.055 | 21.039 | 27.785 | 1.00 17.35 | 1DIK2643 |
| ATOM | 2552 | CG | HIS | 338 | -8.942 | 19.871 | 27.483 | 1.00 21.37 | 1DIK2644 |
| ATOM | 2553 | ND1 | HIS | 338 | -10.309 | 19.990 | 27.345 | 1.00 21.44 | 1DIK2645 |
| ATOM | 2554 | CD2 | HIS | 338 | -8.654 | 18.566 | 27.265 | 1.00 16.55 | 1DIK2646 |
| ATOM | 2555 | CE1 | HIS | 338 | -10.824 | 18.809 | 27.053 | 1.00 21.79 | 1DIK2647 |
| ATOM | 2556 | NE2 | HIS | 338 | -9.841 | 17.931 | 26.998 | 1.00 19.02 | 1DIK2648 |
| ATOM | 2557 | N | ASP | 339 | -7.204 | 23.981 | 27.504 | 1.00 21.52 | 1DIK2649 |
| ATOM | 2558 | CA | ASP | 339 | -6.436 | 25.120 | 27.983 | 1.00 19.43 | 1DIK2650 |
| ATOM | 2559 | C | ASP | 339 | -5.452 | 24.739 | 29.079 | 1.00 18.53 | 1DIK2651 |
| ATOM | 2560 | O | ASP | 339 | -4.301 | 25.170 | 29.052 | 1.00 22.28 | 1DIK2652 |
| ATOM | 2561 | CB | ASP | 339 | -7.364 | 26.275 | 28.452 | 1.00 23.01 | 1DIK2653 |
| ATOM | 2562 | CG | ASP | 339 | -8.397 | 25.856 | 29.528 | 1.00 25.24 | 1DIK2654 |

FIG. 8-40

```
ATOM   2563  OD1 ASP 339     -8.560  24.654  29.838  1.00  27.53      1DIK2655
ATOM   2564  OD2 ASP 339     -9.066  26.759  30.075  1.00  27.85      1DIK2656
ATOM   2565  N   ASN 340     -5.892  23.922  30.032  1.00  16.85      1DIK2657
ATOM   2566  CA  ASN 340     -5.035  23.514  31.141  1.00  17.73      1DIK2658
ATOM   2567  C   ASN 340     -3.750  22.830  30.712  1.00  19.02      1DIK2659
ATOM   2568  O   ASN 340     -2.666  23.210  31.161  1.00  21.77      1DIK2660
ATOM   2569  CB  ASN 340     -5.810  22.643  32.111  1.00  19.49      1DIK2661
ATOM   2570  CG  ASN 340     -6.815  23.443  32.908  1.00  22.56      1DIK2662
ATOM   2571  OD1 ASN 340     -6.752  24.662  32.945  1.00  25.89      1DIK2663
ATOM   2572  ND2 ASN 340     -7.743  22.762  33.552  1.00  28.53      1DIK2664
ATOM   2573  N   GLY 341     -3.858  21.831  29.845  1.00  17.89      1DIK2665
ATOM   2574  CA  GLY 341     -2.665  21.160  29.364  1.00  15.63      1DIK2666
ATOM   2575  C   GLY 341     -1.764  22.118  28.600  1.00  11.99      1DIK2667
ATOM   2576  O   GLY 341     -0.549  22.077  28.735  1.00  16.11      1DIK2668
ATOM   2577  N   ILE 342     -2.344  22.996  27.797  1.00  13.11      1DIK2669
ATOM   2578  CA  ILE 342     -1.525  23.941  27.036  1.00  17.14      1DIK2670
ATOM   2579  C   ILE 342     -0.755  24.910  27.946  1.00  17.23      1DIK2671
ATOM   2580  O   ILE 342      0.410  25.214  27.694  1.00  17.60      1DIK2672
ATOM   2581  CB  ILE 342     -2.399  24.690  25.990  1.00  16.48      1DIK2673
ATOM   2582  CG1 ILE 342     -2.982  23.663  25.015  1.00  11.17      1DIK2674
ATOM   2583  CG2 ILE 342     -1.574  25.710  25.221  1.00  12.60      1DIK2675
ATOM   2584  CD1 ILE 342     -4.052  24.199  24.138  1.00  14.25      1DIK2676
ATOM   2585  N   ILE 343     -1.397  25.384  29.010  1.00  20.72      1DIK2677
ATOM   2586  CA  ILE 343     -0.747  26.296  29.948  1.00  20.28      1DIK2678
ATOM   2587  C   ILE 343      0.531  25.647  30.503  1.00  21.94      1DIK2679
ATOM   2588  O   ILE 343      1.617  26.243  30.467  1.00  23.12      1DIK2680
ATOM   2589  CB  ILE 343     -1.703  26.677  31.124  1.00  17.08      1DIK2681
ATOM   2590  CG1 ILE 343     -2.757  27.671  30.638  1.00  12.06      1DIK2682
ATOM   2591  CG2 ILE 343     -0.911  27.321  32.277  1.00  12.92      1DIK2683
ATOM   2592  CD1 ILE 343     -2.152  29.042  30.271  1.00  11.66      1DIK2684
ATOM   2593  N   SER 344      0.394  24.424  31.006  1.00  20.30      1DIK2685
ATOM   2594  CA  SER 344      1.519  23.690  31.564  1.00  17.86      1DIK2686
ATOM   2595  C   SER 344      2.636  23.482  30.544  1.00  20.31      1DIK2687
ATOM   2596  O   SER 344      3.825  23.604  30.881  1.00  19.02      1DIK2688
ATOM   2597  CB  SER 344      1.036  22.344  32.081  1.00  18.82      1DIK2689
ATOM   2598  OG  SER 344      0.137  22.512  33.164  1.00  19.78      1DIK2690
ATOM   2599  N   ILE 345      2.248  23.170  29.302  1.00  19.86      1DIK2691
ATOM   2600  CA  ILE 345      3.194  22.940  28.205  1.00  19.61      1DIK2692
ATOM   2601  C   ILE 345      3.990  24.211  27.877  1.00  22.16      1DIK2693
ATOM   2602  O   ILE 345      5.211  24.156  27.678  1.00  21.36      1DIK2694
ATOM   2603  CB  ILE 345      2.460  22.420  26.936  1.00  17.67      1DIK2695
ATOM   2604  CG1 ILE 345      1.926  21.009  27.194  1.00  17.47      1DIK2696
ATOM   2605  CG2 ILE 345      3.389  22.402  25.738  1.00  10.81      1DIK2697
ATOM   2606  CD1 ILE 345      1.129  20.443  26.052  1.00  20.20      1DIK2698
ATOM   2607  N   LEU 346      3.290  25.347  27.828  1.00  21.51      1DIK2699
ATOM   2608  CA  LEU 346      3.906  26.645  27.558  1.00  21.18      1DIK2700
ATOM   2609  C   LEU 346      4.987  26.936  28.610  1.00  19.82      1DIK2701
ATOM   2610  O   LEU 346      6.078  27.401  28.281  1.00  22.60      1DIK2702
ATOM   2611  CB  LEU 346      2.838  27.754  27.559  1.00  21.21      1DIK2703
ATOM   2612  CG  LEU 346      1.787  27.761  26.430  1.00  25.27      1DIK2704
ATOM   2613  CD1 LEU 346      0.797  28.905  26.655  1.00  22.27      1DIK2705
ATOM   2614  CD2 LEU 346      2.457  27.910  25.067  1.00  19.78      1DIK2706
ATOM   2615  N   PHE 347      4.694  26.658  29.875  1.00  21.86      1DIK2707
ATOM   2616  CA  PHE 347      5.679  26.878  30.929  1.00  21.46      1DIK2708
ATOM   2617  C   PHE 347      6.825  25.881  30.884  1.00  24.47      1DIK2709
ATOM   2618  O   PHE 347      7.981  26.282  31.064  1.00  23.78      1DIK2710
ATOM   2619  CB  PHE 347      5.006  26.903  32.300  1.00  22.55      1DIK2711
ATOM   2620  CG  PHE 347      4.289  28.189  32.566  1.00  19.15      1DIK2712
ATOM   2621  CD1 PHE 347      4.977  29.283  33.088  1.00  19.76      1DIK2713
ATOM   2622  CD2 PHE 347      2.953  28.332  32.233  1.00  17.59      1DIK2714
ATOM   2623  CE1 PHE 347      4.341  30.508  33.268  1.00  18.90      1DIK2715
ATOM   2624  CE2 PHE 347      2.311  29.542  32.407  1.00  21.97      1DIK2716
ATOM   2625  CZ  PHE 347      3.007  30.638  32.926  1.00  20.72      1DIK2717
ATOM   2626  N   ALA 348      6.517  24.599  30.634  1.00  25.00      1DIK2718
ATOM   2627  CA  ALA 348      7.547  23.551  30.533  1.00  23.63      1DIK2719
ATOM   2628  C   ALA 348      8.523  23.830  29.374  1.00  23.94      1DIK2720
```

FIG. 8-41

```
ATOM   2629  O    ALA  348    9.647  23.327  29.368  1.00  22.81    1DIK2721
ATOM   2630  CB   ALA  348    6.909  22.175  30.360  1.00  18.75    1DIK2722
ATOM   2631  N    LEU  349    8.096  24.624  28.394  1.00  23.18    1DIK2723
ATOM   2632  CA   LEU  349    8.969  24.977  27.279  1.00  24.76    1DIK2724
ATOM   2633  C    LEU  349    9.725  26.227  27.606  1.00  25.45    1DIK2725
ATOM   2634  O    LEU  349   10.538  26.708  26.760  1.00  26.63    1DIK2726
ATOM   2635  CB   LEU  349    8.11   25.197  25.990  1.00  24.37    1DIK2727
ATOM   2636  CG   LEU  349    7.530  23.958  25.332  1.00  27.98    1DIK2728
ATOM   2637  CD1  LEU  349    6.813  24.399  24.054  1.00  24.59    1DIK2729
ATOM   2638  CD2  LEU  349    8.578  22.871  25.023  1.00  19.81    1DIK2730
ATOM   2639  N    GLY  350    9.625  26.745  28.827  1.00  25.68    1DIK2731
ATOM   2640  CA   GLY  350   10.370  27.916  29.269  1.00  27.97    1DIK2732
ATOM   2641  C    GLY  350   10.009  29.236  28.611  1.00  30.96    1DIK2733
ATOM   2642  O    GLY  350   10.781  30.197  28.671  1.00  31.89    1DIK2734
ATOM   2643  N    LEU  351    8.830  29.292  27.997  1.00  31.09    1DIK2735
ATOM   2644  CA   LEU  351    8.367  30.486  27.301  1.00  29.39    1DIK2736
ATOM   2645  C    LEU  351    8.048  31.700  28.184  1.00  30.29    1DIK2737
ATOM   2646  O    LEU  351    8.092  32.841  27.722  1.00  28.55    1DIK2738
ATOM   2647  CB   LEU  351    7.147  30.132  26.456  1.00  31.14    1DIK2739
ATOM   2648  CG   LEU  351    7.359  28.989  25.467  1.00  29.30    1DIK2740
ATOM   2649  CD1  LEU  351    6.063  28.718  24.722  1.00  28.64    1DIK2741
ATOM   2650  CD2  LEU  351    8.483  29.347  24.501  1.00  25.72    1DIK2742
ATOM   2651  N    TYR  352    7.731  31.474  29.453  1.00  31.04    1DIK2743
ATOM   2652  CA   TYR  352    7.410  32.594  30.325  1.00  31.74    1DIK2744
ATOM   2653  C    TYR  352    8.350  32.747  31.502  1.00  34.72    1DIK2745
ATOM   2654  O    TYR  352    7.942  33.102  32.613  1.00  33.44    1DIK2746
ATOM   2655  CB   TYR  352    5.953  32.484  30.752  1.00  26.97    1DIK2747
ATOM   2656  CG   TYR  352    5.090  32.667  29.552  1.00  28.46    1DIK2748
ATOM   2657  CD1  TYR  352    4.916  33.932  29.003  1.00  27.92    1DIK2749
ATOM   2658  CD2  TYR  352    4.506  31.574  28.910  1.00  29.60    1DIK2750
ATOM   2659  CE1  TYR  352    4.190  34.118  27.846  1.00  30.02    1DIK2751
ATOM   2660  CE2  TYR  352    3.773  31.745  27.745  1.00  30.26    1DIK2752
ATOM   2661  CZ   TYR  352    3.622  33.029  27.220  1.00  32.93    1DIK2753
ATOM   2662  OH   TYR  352    2.903  33.228  26.067  1.00  33.54    1DIK2754
ATOM   2663  N    ASN  353    9.626  32.484  31.236  1.00  40.74    1DIK2755
ATOM   2664  CA   ASN  353   10.669  32.582  32.251  1.00  47.39    1DIK2756
ATOM   2665  C    ASN  353   10.941  34.011  32.729  1.00  47.72    1DIK2757
ATOM   2666  O    ASN  353   11.505  34.206  33.802  1.00  46.72    1DIK2758
ATOM   2667  CB   ASN  353   11.966  31.932  31.749  1.00  49.39    1DIK2759
ATOM   2668  CG   ASN  353   11.931  30.406  31.832  1.00  53.90    1DIK2760
ATOM   2669  OD1  ASN  353   10.895  29.801  32.155  1.00  51.32    1DIK2761
ATOM   2670  ND2  ASN  353   13.071  29.774  31.537  1.00  57.79    1DIK2762
ATOM   2671  N    GLY  354   10.535  35.002  31.937  1.00  48.40    1DIK2763
ATOM   2672  CA   GLY  354   10.741  36.390  32.319  1.00  49.75    1DIK2764
ATOM   2673  C    GLY  354    9.531  36.974  33.032  1.00  49.81    1DIK2765
ATOM   2674  O    GLY  354    9.424  38.193  33.203  1.00  55.38    1DIK2766
ATOM   2675  N    THR  355    8.622  36.101  33.449  1.00  46.75    1DIK2767
ATOM   2676  CA   THR  355    7.396  36.496  34.135  1.00  46.22    1DIK2768
ATOM   2677  C    THR  355    7.536  36.191  35.631  1.00  47.74    1DIK2769
ATOM   2678  O    THR  355    7.789  35.042  36.007  1.00  47.46    1DIK2770
ATOM   2679  CB   THR  355    6.180  35.691  33.556  1.00  42.82    1DIK2771
ATOM   2680  OG1  THR  355    6.147  35.847  32.131  1.00  43.08    1DIK2772
ATOM   2681  CG2  THR  355    4.853  36.160  34.154  1.00  35.74    1DIK2773
ATOM   2682  N    LYS  356    7.388  37.202  36.486  1.00  44.73    1DIK2774
ATOM   2683  CA   LYS  356    7.478  36.960  37.926  1.00  42.43    1DIK2775
ATOM   2684  C    LYS  356    6.116  36.530  38.437  1.00  40.86    1DIK2776
ATOM   2685  O    LYS  356    5.103  36.849  37.813  1.00  42.40    1DIK2777
ATOM   2686  CB   LYS  356    7.942  38.210  38.664  1.00  41.47    1DIK2778
ATOM   2687  CG   LYS  356    9.438  38.349  38.668  1.00  42.08    1DIK2779
ATOM   2688  CD   LYS  356    9.866  39.579  39.406  1.00  42.64    1DIK2780
ATOM   2689  CE   LYS  356   11.351  39.719  39.346  1.00  42.34    1DIK2781
ATOM   2690  NZ   LYS  356   11.693  41.124  39.631  1.00  48.71    1DIK2782
ATOM   2691  N    PRO  357    6.069  35.806  39.577  1.00  38.87    1DIK2783
ATOM   2692  CA   PRO  357    4.777  35.358  40.120  1.00  39.88    1DIK2784
ATOM   2693  C    PRO  357    3.771  36.512  40.134  1.00  42.03    1DIK2785
ATOM   2694  O    PRO  357    4.092  37.629  40.564  1.00  44.16    1DIK2786
```

FIG. 8-42

```
ATOM   2695  CB   PRO  357    5.149  34.869  41.517  1.00  38.17    1DIK2787
ATOM   2696  CG   PRO  357    6.526  34.306  41.295  1.00  34.95    1DIK2788
ATOM   2697  CD   PRO  357    7.183  35.366  40.438  1.00  33.26    1DIK2789
ATOM   2698  N    LEU  358    2.562  36.252  39.649  1.00  40.53    1DIK2790
ATOM   2699  CA   LEU  358    1.555  37.298  39.584  1.00  39.23    1DIK2791
ATOM   2700  C    LEU  358    1.075  37.682  40.975  1.00  40.76    1DIK2792
ATOM   2701  O    LEU  358    0.861  36.815  41.821  1.00  40.81    1DIK2793
ATOM   2702  CB   LEU  358    0.355  36.864  38.732  1.00  37.58    1DIK2794
ATOM   2703  CG   LEU  358    0.499  36.397  37.283  1.00  34.63    1DIK2795
ATOM   2704  CD1  LEU  358   -0.862  36.528  36.631  1.00  32.21    1DIK2796
ATOM   2705  CD2  LEU  358    1.512  37.210  36.528  1.00  33.59    1DIK2797
ATOM   2706  N    SER  359    0.900  38.979  41.205  1.00  39.69    1DIK2798
ATOM   2707  CA   SER  359    0.432  39.461  42.494  1.00  40.29    1DIK2799
ATOM   2708  C    SER  359   -0.963  38.910  42.687  1.00  38.32    1DIK2800
ATOM   2709  O    SER  359   -1.763  38.923  41.758  1.00  38.66    1DIK2801
ATOM   2710  CB   SER  359    0.376  40.989  42.515  1.00  43.59    1DIK2802
ATOM   2711  OG   SER  359   -0.234  41.445  43.720  1.00  51.02    1DIK2803
ATOM   2712  N    THR  360   -1.254  38.432  43.889  1.00  37.92    1DIK2804
ATOM   2713  CA   THR  360   -2.564  37.870  44.189  1.00  40.16    1DIK2805
ATOM   2714  C    THR  360   -3.564  38.907  44.709  1.00  39.58    1DIK2806
ATOM   2715  O    THR  360   -4.736  38.589  44.952  1.00  38.55    1DIK2807
ATOM   2716  CB   THR  360   -2.425  36.709  45.206  1.00  42.37    1DIK2808
ATOM   2717  OG1  THR  360   -1.519  37.095  46.255  1.00  47.97    1DIK2809
ATOM   2718  CG2  THR  360   -1.877  35.462  44.515  1.00  40.43    1DIK2810
ATOM   2719  N    THR  361   -3.104  40.144  44.875  1.00  40.07    1DIK2811
ATOM   2720  CA   THR  361   -3.964  41.214  45.381  1.00  42.85    1DIK2812
ATOM   2721  C    THR  361   -4.164  42.376  44.414  1.00  44.11    1DIK2813
ATOM   2722  O    THR  361   -5.183  43.053  44.469  1.00  44.52    1DIK2814
ATOM   2723  CB   THR  361   -3.432  41.787  46.728  1.00  42.66    1DIK2815
ATOM   2724  OG1  THR  361   -1.993  41.834  46.720  1.00  42.42    1DIK2816
ATOM   2725  CG2  THR  361   -3.909  40.934  47.877  1.00  45.08    1DIK2817
ATOM   2726  N    THR  362   -3.201  42.595  43.524  1.00  45.47    1DIK2818
ATOM   2727  CA   THR  362   -3.272  43.703  42.582  1.00  45.00    1DIK2819
ATOM   2728  C    THR  362   -3.134  43.247  41.138  1.00  42.73    1DIK2820
ATOM   2729  O    THR  362   -2.368  42.332  40.846  1.00  43.39    1DIK2821
ATOM   2730  CB   THR  362   -2.142  44.689  42.867  1.00  49.03    1DIK2822
ATOM   2731  OG1  THR  362   -2.006  44.846  44.287  1.00  56.76    1DIK2823
ATOM   2732  CG2  THR  362   -2.434  46.036  42.227  1.00  50.37    1DIK2824
ATOM   2733  N    VAL  363   -3.879  43.901  40.249  1.00  40.72    1DIK2825
ATOM   2734  CA   VAL  363   -3.860  43.616  38.815  1.00  37.30    1DIK2826
ATOM   2735  C    VAL  363   -2.524  44.081  38.243  1.00  39.07    1DIK2827
ATOM   2736  O    VAL  363   -2.045  45.160  38.603  1.00  40.33    1DIK2828
ATOM   2737  CB   VAL  363   -4.982  44.402  38.070  1.00  34.35    1DIK2829
ATOM   2738  CG1  VAL  363   -4.928  44.143  36.562  1.00  33.50    1DIK2830
ATOM   2739  CG2  VAL  363   -6.332  44.034  38.625  1.00  32.51    1DIK2831
ATOM   2740  N    GLU  364   -1.934  43.269  37.366  1.00  38.65    1DIK2832
ATOM   2741  CA   GLU  364   -0.676  43.602  36.694  1.00  40.15    1DIK2833
ATOM   2742  C    GLU  364   -0.961  43.550  35.199  1.00  41.61    1DIK2834
ATOM   2743  O    GLU  364   -1.619  42.628  34.714  1.00  42.19    1DIK2835
ATOM   2744  CB   GLU  364    0.421  42.606  37.040  1.00  39.16    1DIK2836
ATOM   2745  CG   GLU  364    0.621  42.449  38.515  1.00  45.46    1DIK2837
ATOM   2746  CD   GLU  364    1.956  41.863  38.842  1.00  46.24    1DIK2838
ATOM   2747  OE1  GLU  364    2.953  42.609  38.751  1.00  54.58    1DIK2839
ATOM   2748  OE2  GLU  364    2.013  40.666  39.187  1.00  43.12    1DIK2840
ATOM   2749  N    ASN  365   -0.475  44.540  34.466  1.00  41.88    1DIK2841
ATOM   2750  CA   ASN  365   -0.727  44.587  33.037  1.00  41.03    1DIK2842
ATOM   2751  C    ASN  365    0.218  43.661  32.288  1.00  39.55    1DIK2843
ATOM   2752  O    ASN  365    1.181  43.141  32.866  1.00  34.92    1DIK2844
ATOM   2753  CB   ASN  365   -0.615  46.025  32.513  1.00  46.26    1DIK2845
ATOM   2754  CG   ASN  365    0.786  46.589  32.649  1.00  49.70    1DIK2846
ATOM   2755  OD1  ASN  365    1.646  46.361  31.798  1.00  52.55    1DIK2847
ATOM   2756  ND2  ASN  365    1.024  47.323  33.719  1.00  56.03    1DIK2848
ATOM   2757  N    ILE  366   -0.075  43.481  30.999  1.00  38.20    1DIK2849
ATOM   2758  CA   ILE  366    0.671  42.603  30.103  1.00  36.15    1DIK2850
ATOM   2759  C    ILE  366    2.160  42.944  29.939  1.00  37.55    1DIK2851
ATOM   2760  O    ILE  366    2.947  42.107  29.489  1.00  38.87    1DIK2852
```

FIG. 8-43

```
ATOM   2761  CB   ILE 366      -0.068  42.489  28.713  1.00  33.38      1DIK2853
ATOM   2762  CG1  ILE 366       0.239  41.136  28.084  1.00  29.94      1DIK2854
ATOM   2763  CG2  ILE 366       0.273  43.652  27.786  1.00  24.77      1DIK2855
ATOM   2764  CD1  ILE 366      -0.332  39.987  28.874  1.00  22.62      1DIK2856
ATOM   2765  N    THR 367       2.542  44.165  30.302  1.00  37.95      1DIK2857
ATOM   2766  CA   THR 367       3.944  44.592  30.243  1.00  40.36      1DIK2858
ATOM   2767  C    THR 367       4.654  44.030  31.486  1.00  40.59      1DIK2859
ATOM   2768  O    THR 367       5.775  43.512  31.406  1.00  40.36      1DIK2860
ATOM   2769  CB   THR 367       4.058  46.149  30.248  1.00  41.59      1DIK2861
ATOM   2770  OG1  THR 367       3.625  46.663  28.983  1.00  38.58      1DIK2862
ATOM   2771  CG2  THR 367       5.488  46.602  30.535  1.00  43.44      1DIK2863
ATOM   2772  N    GLN 368       3.985  44.135  32.630  1.00  39.60      1DIK2864
ATOM   2773  CA   GLN 368       4.532  43.647  33.880  1.00  42.39      1DIK2865
ATOM   2774  C    GLN 368       4.656  42.133  33.876  1.00  43.99      1DIK2866
ATOM   2775  O    GLN 368       5.613  41.598  34.438  1.00  47.07      1DIK2867
ATOM   2776  CB   GLN 368       3.650  44.055  35.050  1.00  46.02      1DIK2868
ATOM   2777  CG   GLN 368       3.575  45.543  35.313  1.00  52.12      1DIK2869
ATOM   2778  CD   GLN 368       2.605  45.854  36.439  1.00  55.80      1DIK2870
ATOM   2779  OE1  GLN 368       1.553  46.460  36.223  1.00  53.21      1DIK2871
ATOM   2780  NE2  GLN 368       2.953  45.432  37.649  1.00  58.79      1DIK2872
ATOM   2781  N    THR 369       3.691  41.447  33.250  1.00  42.31      1DIK2873
ATOM   2782  CA   THR 369       3.691  39.980  33.195  1.00  37.86      1DIK2874
ATOM   2783  C    THR 369       4.457  39.399  32.018  1.00  35.95      1DIK2875
ATOM   2784  O    THR 369       4.415  38.186  31.776  1.00  32.63      1DIK2876
ATOM   2785  CB   THR 369       2.273  39.404  33.156  1.00  37.12      1DIK2877
ATOM   2786  OG1  THR 369       1.626  39.815  31.940  1.00  40.70      1DIK2878
ATOM   2787  CG2  THR 369       1.475  39.871  34.368  1.00  28.31      1DIK2879
ATOM   2788  N    ASP 370       5.149  40.269  31.291  1.00  33.39      1DIK2880
ATOM   2789  CA   ASP 370       5.954  39.864  30.153  1.00  32.87      1DIK2881
ATOM   2790  C    ASP 370       5.170  39.043  29.104  1.00  31.05      1DIK2882
ATOM   2791  O    ASP 370       5.608  37.979  28.656  1.00  31.02      1DIK2883
ATOM   2792  CB   ASP 370       7.191  39.099  30.655  1.00  35.44      1DIK2884
ATOM   2793  CG   ASP 370       8.319  39.065  29.629  1.00  40.37      1DIK2885
ATOM   2794  OD1  ASP 370       8.469  40.065  28.893  1.00  35.88      1DIK2886
ATOM   2795  OD2  ASP 370       9.052  38.043  29.558  1.00  39.79      1DIK2887
ATOM   2796  N    GLY 371       4.003  39.548  28.721  1.00  29.15      1DIK2888
ATOM   2797  CA   GLY 371       3.203  38.883  27.717  1.00  26.42      1DIK2889
ATOM   2798  C    GLY 371       2.322  37.745  28.178  1.00  29.16      1DIK2890
ATOM   2799  O    GLY 371       1.686  37.105  27.350  1.00  31.15      1DIK2891
ATOM   2800  N    PHE 372       2.260  37.470  29.475  1.00  29.53      1DIK2892
ATOM   2801  CA   PHE 372       1.397  36.390  29.921  1.00  26.79      1DIK2893
ATOM   2802  C    PHE 372       0.035  36.824  30.426  1.00  28.06      1DIK2894
ATOM   2803  O    PHE 372      -0.065  37.740  31.243  1.00  32.94      1DIK2895
ATOM   2804  CB   PHE 372       2.038  35.542  31.025  1.00  23.34      1DIK2896
ATOM   2805  CG   PHE 372       1.130  34.436  31.508  1.00  24.56      1DIK2897
ATOM   2806  CD1  PHE 372       0.994  33.257  30.772  1.00  22.68      1DIK2898
ATOM   2807  CD2  PHE 372       0.355  34.601  32.648  1.00  22.77      1DIK2899
ATOM   2808  CE1  PHE 372       0.095  32.268  31.161  1.00  23.69      1DIK2900
ATOM   2809  CE2  PHE 372      -0.553  33.614  33.048  1.00  26.64      1DIK2901
ATOM   2810  CZ   PHE 372      -0.684  32.447  32.303  1.00  24.28      1DIK2902
ATOM   2811  N    SER 373      -1.006  36.149  29.941  1.00  27.69      1DIK2903
ATOM   2812  CA   SER 373      -2.394  36.361  30.377  1.00  24.96      1DIK2904
ATOM   2813  C    SER 373      -3.191  35.201  29.772  1.00  25.82      1DIK2905
ATOM   2814  O    SER 373      -2.776  34.638  28.753  1.00  26.67      1DIK2906
ATOM   2815  CB   SER 373      -2.945  37.716  29.914  1.00  20.86      1DIK2907
ATOM   2816  OG   SER 373      -3.520  37.661  28.620  1.00  26.28      1DIK2908
ATOM   2817  N    SER 374      -4.310  34.820  30.378  1.00  23.66      1DIK2909
ATOM   2818  CA   SER 374      -5.092  33.728  29.816  1.00  23.58      1DIK2910
ATOM   2819  C    SER 374      -5.576  34.063  28.418  1.00  21.38      1DIK2911
ATOM   2820  O    SER 374      -5.596  33.201  27.552  1.00  24.01      1DIK2912
ATOM   2821  CB   SER 374      -6.295  33.404  30.688  1.00  24.78      1DIK2913
ATOM   2822  OG   SER 374      -5.868  32.729  31.846  1.00  36.24      1DIK2914
ATOM   2823  N    ALA 375      -5.965  35.316  28.209  1.00  19.17      1DIK2915
ATOM   2824  CA   ALA 375      -6.462  35.774  26.919  1.00  18.77      1DIK2916
ATOM   2825  C    ALA 375      -5.377  35.768  25.839  1.00  19.10      1DIK2917
```

FIG. 8-44

```
ATOM   2826  O    ALA  375    -5.674  35.603  24.662  1.00  17.13      1DIK2918
ATOM   2827  CB   ALA  375    -7.066  37.176  27.060  1.00  17.12      1DIK2919
ATOM   2828  N    TRP  376    -4.124  35.948  26.241  1.00  18.21      1DIK2920
ATOM   2829  CA   TRP  376    -3.028  35.956  25.285  1.00  20.78      1DIK2921
ATOM   2830  C    TRP  376    -2.419  34.585  25.036  1.00  22.76      1DIK2922
ATOM   2831  O    TRP  376    -1.724  34.391  24.032  1.00  24.41      1DIK2923
ATOM   2832  CB   TRP  376    -1.922  36.932  25.720  1.00  20.50      1DIK2924
ATOM   2833  CG   TRP  376    -2.236  38.359  25.406  1.00  21.91      1DIK2925
ATOM   2834  CD1  TRP  376    -3.465  38.941  25.432  1.00  21.75      1DIK2926
ATOM   2835  CD2  TRP  376    -1.309  39.389  25.017  1.00  23.53      1DIK2927
ATOM   2836  NE1  TRP  376    -3.368  40.265  25.085  1.00  23.80      1DIK2928
ATOM   2837  CE2  TRP  376    -2.060  40.572  24.824  1.00  24.79      1DIK2929
ATOM   2838  CE3  TRP  376     0.082  39.429  24.814  1.00  26.46      1DIK2930
ATOM   2839  CZ2  TRP  376    -1.468  41.794  24.435  1.00  25.72      1DIK2931
ATOM   2840  CZ3  TRP  376     0.676  40.649  24.425  1.00  24.82      1DIK2932
ATOM   2841  CH2  TRP  376    -0.106  41.812  24.242  1.00  24.72      1DIK2933
ATOM   2842  N    THR  377    -2.670  33.631  25.931  1.00  23.05      1DIK2934
ATOM   2843  CA   THR  377    -2.105  32.296  25.770  1.00  20.73      1DIK2935
ATOM   2844  C    THR  377    -3.128  31.212  25.438  1.00  21.78      1DIK2936
ATOM   2845  O    THR  377    -2.917  30.422  24.499  1.00  22.28      1DIK2937
ATOM   2846  CB   THR  377    -1.282  31.891  27.015  1.00  21.05      1DIK2938
ATOM   2847  OG1  THR  377    -2.125  31.885  28.181  1.00  20.07      1DIK2939
ATOM   2848  OG2  THR  377    -0.122  32.871  27.215  1.00  17.56      1DIK2940
ATOM   2849  N    VAL  378    -4.232  31.177  26.187  1.00  19.66      1DIK2941
ATOM   2850  CA   VAL  378    -5.266  30.173  25.960  1.00  17.69      1DIK2942
ATOM   2851  C    VAL  378    -6.712  30.611  25.663  1.00  19.05      1DIK2943
ATOM   2852  O    VAL  378    -7.657  30.160  26.323  1.00  18.97      1DIK2944
ATOM   2853  CB   VAL  378    -5.290  29.124  27.103  1.00  19.46      1DIK2945
ATOM   2854  CG1  VAL  378    -4.018  28.291  27.061  1.00  16.35      1DIK2946
ATOM   2855  CG2  VAL  378    -5.461  29.811  28.459  1.00  17.47      1DIK2947
ATOM   2856  N    PRO  379    -6.909  31.510  24.681  1.00  19.03      1DIK2948
ATOM   2857  CA   PRO  379    -8.300  31.878  24.405  1.00  17.80      1DIK2949
ATOM   2858  C    PRO  379    -8.910  30.654  23.696  1.00  19.39      1DIK2950
ATOM   2859  O    PRO  379    -8.215  29.655  23.472  1.00  21.31      1DIK2951
ATOM   2860  CB   PRO  379    -8.149  33.045  23.438  1.00  16.10      1DIK2952
ATOM   2861  CG   PRO  379    -6.877  32.691  22.677  1.00  17.21      1DIK2953
ATOM   2862  CD   PRO  379    -5.979  32.249  23.798  1.00  19.06      1DIK2954
ATOM   2863  N    PHE  380   -10.188  30.704  23.344  1.00  18.52      1DIK2955
ATOM   2864  CA   PHE  380   -10.784  29.588  22.608  1.00  18.85      1DIK2956
ATOM   2865  C    PHE  380   -10.052  29.506  21.263  1.00  21.10      1DIK2957
ATOM   2866  O    PHE  380    -9.733  30.535  20.669  1.00  24.26      1DIK2958
ATOM   2867  CB   PHE  380   -12.260  29.843  22.329  1.00  17.78      1DIK2959
ATOM   2868  CG   PHE  380   -13.150  29.637  23.509  1.00  20.97      1DIK2960
ATOM   2869  CD1  PHE  380   -13.089  28.461  24.247  1.00  18.51      1DIK2961
ATOM   2870  CD2  PHE  380   -14.084  30.615  23.868  1.00  22.13      1DIK2962
ATOM   2871  CE1  PHE  380   -13.945  28.252  25.327  1.00  23.16      1DIK2963
ATOM   2872  CE2  PHE  380   -14.942  30.419  24.941  1.00  20.92      1DIK2964
ATOM   2873  CZ   PHE  380   -14.874  29.229  25.677  1.00  18.80      1DIK2965
ATOM   2874  N    ALA  381    -9.790  28.296  20.785  1.00  19.83      1DIK2966
ATOM   2875  CA   ALA  381    -9.106  28.103  19.514  1.00  17.83      1DIK2967
ATOM   2876  C    ALA  381    -7.703  28.731  19.476  1.00  21.42      1DIK2968
ATOM   2877  O    ALA  381    -7.225  29.148  18.414  1.00  23.62      1DIK2969
ATOM   2878  CB   ALA  381    -9.968  28.641  18.369  1.00  16.06      1DIK2970
ATOM   2879  N    SER  382    -7.035  28.809  20.622  1.00  16.01      1DIK2971
ATOM   2880  CA   SER  382    -5.699  29.359  20.625  1.00  16.41      1DIK2972
ATOM   2881  C    SER  382    -4.814  28.403  19.850  1.00  16.99      1DIK2973
ATOM   2882  O    SER  382    -5.165  27.240  19.674  1.00  21.80      1DIK2974
ATOM   2883  CB   SER  382    -5.170  29.462  22.046  1.00  18.69      1DIK2975
ATOM   2884  OG   SER  382    -5.083  28.174  22.612  1.00  19.41      1DIK2976
ATOM   2885  N    ARG  383    -3.666  28.882  19.383  1.00  19.86      1DIK2977
ATOM   2886  CA   ARG  383    -2.724  28.025  18.678  1.00  16.82      1DIK2978
ATOM   2887  C    ARG  383    -1.299  28.454  18.979  1.00  19.46      1DIK2979
ATOM   2888  O    ARG  383    -1.000  29.648  19.103  1.00  22.02      1DIK2980
ATOM   2889  CB   ARG  383    -2.971  28.002  17.153  1.00  17.09      1DIK2981
ATOM   2890  CG   ARG  383    -2.591  29.257  16.352  1.00  17.29      1DIK2982
ATOM   2891  CD   ARG  383    -3.451  30.487  16.688  1.00  16.60      1DIK2983
```

FIG. 8-45

```
ATOM  2892  NE   ARG  383   -4.896  30.223  16.669  1.00  15.07  1DIK2984
ATOM  2893  CZ   ARG  383   -5.716  30.480  15.645  1.00  14.92  1DIK2985
ATOM  2894  NH1  ARG  383   -5.272  31.002  14.508  1.00   8.26  1DIK2986
ATOM  2895  NH2  ARG  383   -7.005  30.209  15.757  1.00  12.00  1DIK2987
ATOM  2896  N    LEU  384   -0.432  27.456  19.113  1.00  20.14  1DIK2988
ATOM  2897  CA   LEU  384    0.982  27.640  19.361  1.00  15.15  1DIK2989
ATOM  2898  C    LEU  384    1.632  26.976  18.156  1.00  17.51  1DIK2990
ATOM  2899  O    LEU  384    1.239  25.859  17.776  1.00  17.66  1DIK2991
ATOM  2900  CB   LEU  384    1.384  26.904  20.641  1.00  14.47  1DIK2992
ATOM  2901  CG   LEU  384    2.834  26.416  20.797  1.00  23.97  1DIK2993
ATOM  2902  CD1  LEU  384    3.761  27.555  21.205  1.00  22.30  1DIK2994
ATOM  2903  CD2  LEU  384    2.880  25.312  21.859  1.00  26.10  1DIK2995
ATOM  2904  N    TYR  385    2.601  27.658  17.546  1.00  17.61  1DIK2996
ATOM  2905  CA   TYR  385    3.336  27.110  16.402  1.00  14.96  1DIK2997
ATOM  2906  C    TYR  385    4.794  26.962  16.803  1.00  17.08  1DIK2998
ATOM  2907  O    TYR  385    5.379  27.860  17.428  1.00  15.24  1DIK2999
ATOM  2908  CB   TYR  385    3.341  28.047  15.186  1.00  12.27  1DIK3000
ATOM  2909  CG   TYR  385    2.021  28.338  14.532  1.00  14.64  1DIK3001
ATOM  2910  CD1  TYR  385    1.004  27.383  14.479  1.00  15.16  1DIK3002
ATOM  2911  CD2  TYR  385    1.795  29.580  13.942  1.00  17.04  1DIK3003
ATOM  2912  CE1  TYR  385   -0.209  27.657  13.854  1.00  16.98  1DIK3004
ATOM  2913  CE2  TYR  385    0.584  29.870  13.309  1.00  18.46  1DIK3005
ATOM  2914  CZ   TYR  385   -0.418  28.910  13.265  1.00  21.91  1DIK3006
ATOM  2915  OH   TYR  385   -1.620  29.216  12.637  1.00  13.55  1DIK3007
ATOM  2916  N    VAL  386    5.381  25.829  16.448  1.00  18.39  1DIK3008
ATOM  2917  CA   VAL  386    6.793  25.606  16.681  1.00  16.56  1DIK3009
ATOM  2918  C    VAL  386    7.285  25.311  15.279  1.00  17.90  1DIK3010
ATOM  2919  O    VAL  386    6.893  24.298  14.680  1.00  20.76  1DIK3011
ATOM  2920  CB   VAL  386    7.067  24.404  17.577  1.00  16.14  1DIK3012
ATOM  2921  CG1  VAL  386    8.572  24.270  17.787  1.00   6.88  1DIK3013
ATOM  2922  CG2  VAL  386    6.346  24.565  18.910  1.00  15.11  1DIK3014
ATOM  2923  N    GLU  387    8.116  26.198  14.745  1.00  17.38  1DIK3015
ATOM  2924  CA   GLU  387    8.656  26.029  13.400  1.00  19.62  1DIK3016
ATOM  2925  C    GLU  387   10.169  25.935  13.407  1.00  19.53  1DIK3017
ATOM  2926  O    GLU  387   10.834  26.508  14.269  1.00  21.49  1DIK3018
ATOM  2927  CB   GLU  387    8.211  27.185  12.488  1.00  19.65  1DIK3019
ATOM  2928  CG   GLU  387    8.456  28.572  13.064  1.00  24.89  1DIK3020
ATOM  2929  CD   GLU  387    7.839  29.707  12.237  1.00  25.32  1DIK3021
ATOM  2930  OE1  GLU  387    6.675  29.590  11.802  1.00  18.28  1DIK3022
ATOM  2931  OE2  GLU  387    8.531  30.726  12.030  1.00  24.15  1DIK3023
ATOM  2932  N    MET  388   10.708  25.196  12.448  1.00  22.89  1DIK3024
ATOM  2933  CA   MET  388   12.148  25.047  12.306  1.00  24.50  1DIK3025
ATOM  2934  C    MET  388   12.420  25.506  10.872  1.00  25.97  1DIK3026
ATOM  2935  O    MET  388   11.629  25.226   9.962  1.00  24.86  1DIK3027
ATOM  2936  CB   MET  388   12.564  23.596  12.542  1.00  24.86  1DIK3028
ATOM  2937  CG   MET  388   14.045  23.405  12.736  1.00  28.49  1DIK3029
ATOM  2938  SD   MET  388   14.420  21.945  13.737  1.00  32.00  1DIK3030
ATOM  2939  CE   MET  388   13.569  20.648  12.835  1.00  25.36  1DIK3031
ATOM  2940  N    MET  389   13.517  26.233  10.673  1.00  26.04  1DIK3032
ATOM  2941  CA   MET  389   13.863  26.749   9.351  1.00  27.38  1DIK3033
ATOM  2942  C    MET  389   15.354  26.673   9.063  1.00  31.05  1DIK3034
ATOM  2943  O    MET  389   16.186  26.532   9.970  1.00  28.80  1DIK3035
ATOM  2944  CB   MET  389   13.388  28.200   9.188  1.00  21.65  1DIK3036
ATOM  2945  CG   MET  389   13.986  29.170  10.190  1.00  20.31  1DIK3037
ATOM  2946  SD   MET  389   13.301  30.826  10.047  1.00  27.29  1DIK3038
ATOM  2947  CE   MET  389   11.760  30.668  10.980  1.00  23.61  1DIK3039
ATOM  2948  N    GLN  390   15.683  26.752   7.782  1.00  33.50  1DIK3040
ATOM  2949  CA   GLN  390   17.064  26.722   7.352  1.00  39.30  1DIK3041
ATOM  2950  C    GLN  390   17.218  28.001   6.560  1.00  37.68  1DIK3042
ATOM  2951  O    GLN  390   16.399  28.306   5.687  1.00  38.67  1DIK3043
ATOM  2952  CB   GLN  390   17.336  25.488   6.493  1.00  42.00  1DIK3044
ATOM  2953  CG   GLN  390   18.614  24.779   6.890  1.00  53.74  1DIK3045
ATOM  2954  CD   GLN  390   18.668  23.361   6.364  1.00  63.83  1DIK3046
ATOM  2955  OE1  GLN  390   18.355  23.105   5.191  1.00  68.11  1DIK3047
ATOM  2956  NE2  GLN  390   19.065  22.421   7.224  1.00  63.91  1DIK3048
```

FIG. 8-46

```
ATOM   2957  N    CYS   391      18.250  28.767   6.876  1.00 40.00      1DIK3049
ATOM   2958  CA   CYS   391      18.462  30.027   6.186  1.00 45.20      1DIK3050
ATOM   2959  C    CYS   391      19.823  30.061   5.521  1.00 49.70      1DIK3051
ATOM   2960  O    CYS   391      20.750  29.371   5.932  1.00 49.75      1DIK3052
ATOM   2961  CB   CYS   391      18.301  31.213   7.149  1.00 39.14      1DIK3053
ATOM   2962  SG   CYS   391      16.773  31.195   8.142  1.00 30.19      1DIK3054
ATOM   2963  N    GLN   392      19.917  30.883   4.488  1.00 59.92      1DIK3055
ATOM   2964  CA   GLN   392      21.121  31.044   3.685  1.00 68.58      1DIK3056
ATOM   2965  C    GLN   392      22.430  31.262   4.455  1.00 71.02      1DIK3057
ATOM   2966  O    GLN   392      23.442  30.618   4.166  1.00 72.41      1DIK3058
ATOM   2967  CB   GLN   392      20.883  32.199   2.724  1.00 73.43      1DIK3059
ATOM   2968  CG   GLN   392      21.760  32.223   1.498  1.00 80.79      1DIK3060
ATOM   2969  CD   GLN   392      21.489  33.465   0.686  1.00 83.73      1DIK3061
ATOM   2970  OE1  GLN   392      20.888  34.420   1.193  1.00 85.73      1DIK3062
ATOM   2971  NE2  GLN   392      21.920  33.471  -0.571  1.00 84.40      1DIK3063
ATOM   2972  N    ALA   393      22.408  32.169   5.425  1.00 72.05      1DIK3064
ATOM   2973  CA   ALA   393      23.604  32.467   6.207  1.00 74.09      1DIK3065
ATOM   2974  C    ALA   393      23.989  31.392   7.241  1.00 74.58      1DIK3066
ATOM   2975  O    ALA   393      25.159  31.020   7.345  1.00 74.91      1DIK3067
ATOM   2976  CB   ALA   393      23.440  33.820   6.895  1.00 75.97      1DIK3068
ATOM   2977  N    GLU   394      23.007  30.905   7.998  1.00 73.28      1DIK3069
ATOM   2978  CA   GLU   394      23.229  29.902   9.041  1.00 72.21      1DIK3070
ATOM   2979  C    GLU   394      23.418  28.461   8.528  1.00 70.24      1DIK3071
ATOM   2980  O    GLU   394      22.973  28.131   7.437  1.00 72.41      1DIK3072
ATOM   2981  CB   GLU   394      22.055  29.955  10.018  1.00 74.31      1DIK3073
ATOM   2982  CG   GLU   394      22.266  29.170  11.307  1.00 81.75      1DIK3074
ATOM   2983  CD   GLU   394      23.361  29.761  12.187  1.00 84.86      1DIK3075
ATOM   2984  OE1  GLU   394      23.242  30.948  12.578  1.00 86.06      1DIK3076
ATOM   2985  OE2  GLU   394      24.338  29.038  12.489  1.00 86.34      1DIK3077
ATOM   2986  N    GLN   395      24.077  27.608   9.314  1.00 67.62      1DIK3078
ATOM   2987  CA   GLN   395      24.296  26.203   8.924  1.00 67.27      1DIK3079
ATOM   2988  C    GLN   395      23.313  25.261   9.625  1.00 64.99      1DIK3080
ATOM   2989  O    GLN   395      22.818  24.294   9.034  1.00 65.93      1DIK3081
ATOM   2990  CB   GLN   395      25.704  25.752   9.288  1.00 70.58      1DIK3082
ATOM   2991  CG   GLN   395      26.799  26.627   8.760  1.00 80.49      1DIK3083
ATOM   2992  CD   GLN   395      28.085  26.437   9.542  1.00 86.58      1DIK3084
ATOM   2993  OE1  GLN   395      28.185  25.537  10.385  1.00 87.92      1DIK3085
ATOM   2994  NE2  GLN   395      29.077  27.280   9.272  1.00 90.05      1DIK3086
ATOM   2995  N    GLU   396      23.051  25.546  10.900  1.00 59.17      1DIK3087
ATOM   2996  CA   GLU   396      22.127  24.760  11.707  1.00 52.18      1DIK3088
ATOM   2997  C    GLU   396      20.694  25.250  11.536  1.00 45.17      1DIK3089
ATOM   2998  O    GLU   396      20.450  26.432  11.232  1.00 42.88      1DIK3090
ATOM   2999  CB   GLU   396      22.442  24.917  13.192  1.00 58.64      1DIK3091
ATOM   3000  CG   GLU   396      23.637  24.200  13.749  1.00 65.48      1DIK3092
ATOM   3001  CD   GLU   396      23.588  24.204  15.279  1.00 72.96      1DIK3093
ATOM   3002  OE1  GLU   396      22.721  23.485  15.849  1.00 75.18      1DIK3094
ATOM   3003  OE2  GLU   396      24.402  24.925  15.908  1.00 73.08      1DIK3095
ATOM   3004  N    PRO   397      19.723  24.344  11.708  1.00 37.24      1DIK3096
ATOM   3005  CA   PRO   397      18.346  24.817  11.572  1.00 33.03      1DIK3097
ATOM   3006  C    PRO   397      18.015  25.696  12.806  1.00 27.77      1DIK3098
ATOM   3007  O    PRO   397      18.547  25.491  13.912  1.00 23.86      1DIK3099
ATOM   3008  CB   PRO   397      17.537  23.515  11.499  1.00 30.60      1DIK3100
ATOM   3009  CG   PRO   397      18.343  22.572  12.325  1.00 34.10      1DIK3101
ATOM   3010  CD   PRO   397      19.779  22.897  11.975  1.00 33.21      1DIK3102
ATOM   3011  N    LEU   398      17.151  26.680  12.599  1.00 24.89      1DIK3103
ATOM   3012  CA   LEU   398      16.743  27.603  13.644  1.00 22.58      1DIK3104
ATOM   3013  C    LEU   398      15.287  27.333  14.072  1.00 23.54      1DIK3105
ATOM   3014  O    LEU   398      14.420  27.074  13.239  1.00 23.76      1DIK3106
ATOM   3015  CB   LEU   398      16.904  29.033  13.129  1.00 19.29      1DIK3107
ATOM   3016  CG   LEU   398      18.296  29.357  12.572  1.00 21.68      1DIK3108
ATOM   3017  CD1  LEU   398      18.210  30.505  11.590  1.00 21.80      1DIK3109
ATOM   3018  CD2  LEU   398      19.252  29.681  13.695  1.00 17.36      1DIK3110
ATOM   3019  N    VAL   399      15.039  27.395  15.374  1.00 23.51      1DIK3111
ATOM   3020  CA   VAL   399      13.727  27.149  15.959  1.00 23.57      1DIK3112
ATOM   3021  C    VAL   399      13.084  28.478  16.379  1.00 25.60      1DIK3113
ATOM   3022  O    VAL   399      13.767  29.398  16.832  1.00 28.79      1DIK3114
```

FIG. 8-47

```
ATOM  3023  CB   VAL  399   13.864  26.226  17.220  1.00  23.92   1DIK3115
ATOM  3024  CG1  VAL  399   12.510  25.978  17.867  1.00  19.35   1DIK3116
ATOM  3025  CG2  VAL  399   14.525  24.906  16.844  1.00  19.06   1DIK3117
ATOM  3026  N    ARG  400   11.770  28.576  16.223  1.00  24.81   1DIK3118
ATOM  3027  CA   ARG  400   11.038  29.766  16.612  1.00  20.32   1DIK3119
ATOM  3028  C    ARG  400    9.642  29.348  17.060  1.00  20.66   1DIK3120
ATOM  3029  O    ARG  400    9.065  28.407  16.511  1.00  21.08   1DIK3121
ATOM  3030  CB   ARG  400   10.950  30.754  15.457  1.00  21.26   1DIK3122
ATOM  3031  CG   ARG  400   10.227  32.002  15.867  1.00  24.84   1DIK3123
ATOM  3032  CD   ARG  400   10.446  33.098  14.903  1.00  22.49   1DIK3124
ATOM  3033  NE   ARG  400    9.769  32.864  13.643  1.00  24.64   1DIK3125
ATOM  3034  CZ   ARG  400    9.536  33.835  12.763  1.00  33.02   1DIK3126
ATOM  3035  NH1  ARG  400    9.930  35.079  13.042  1.00  30.42   1DIK3127
ATOM  3036  NH2  ARG  400    8.915  33.576  11.614  1.00  30.09   1DIK3128
ATOM  3037  N    VAL  401    9.109  30.044  18.058  1.00  19.00   1DIK3129
ATOM  3038  CA   VAL  401    7.795  29.757  18.606  1.00  18.61   1DIK3130
ATOM  3039  C    VAL  401    6.882  30.980  18.554  1.00  21.25   1DIK3131
ATOM  3040  O    VAL  401    7.260  32.059  19.003  1.00  23.23   1DIK3132
ATOM  3041  CB   VAL  401    7.908  29.318  20.087  1.00  20.03   1DIK3133
ATOM  3042  CG1  VAL  401    6.529  29.173  20.701  1.00  17.45   1DIK3134
ATOM  3043  CG2  VAL  401    8.673  28.006  20.195  1.00  16.44   1DIK3135
ATOM  3044  N    LEU  402    5.683  30.812  18.006  1.00  20.98   1DIK3136
ATOM  3045  CA   LEU  402    4.701  31.888  17.948  1.00  17.41   1DIK3137
ATOM  3046  C    LEU  402    3.540  31.418  18.804  1.00  19.37   1DIK3138
ATOM  3047  O    LEU  402    3.165  30.249  18.728  1.00  22.64   1DIK3139
ATOM  3048  CB   LEU  402    4.206  32.128  16.519  1.00  14.63   1DIK3140
ATOM  3049  CG   LEU  402    5.213  32.709  15.523  1.00  17.85   1DIK3141
ATOM  3050  CD1  LEU  402    6.046  31.608  14.893  1.00  12.36   1DIK3142
ATOM  3051  CD2  LEU  402    4.464  33.480  14.461  1.00  15.05   1DIK3143
ATOM  3052  N    VAL  403    2.984  32.305  19.626  1.00  18.51   1DIK3144
ATOM  3053  CA   VAL  403    1.831  31.962  20.472  1.00  18.78   1DIK3145
ATOM  3054  C    VAL  403    0.710  32.925  20.081  1.00  21.06   1DIK3146
ATOM  3055  O    VAL  403    0.793  34.129  20.357  1.00  20.63   1DIK3147
ATOM  3056  CB   VAL  403    2.150  32.111  21.993  1.00  17.73   1DIK3148
ATOM  3057  CG1  VAL  403    0.904  31.836  22.840  1.00  12.73   1DIK3149
ATOM  3058  CG2  VAL  403    3.266  31.146  22.388  1.00  16.54   1DIK3150
ATOM  3059  N    ASN  404   -0.327  32.397  19.429  1.00  18.48   1DIK3151
ATOM  3060  CA   ASN  404   -1.455  33.216  18.967  1.00  21.00   1DIK3152
ATOM  3061  C    ASN  404   -0.986  34.403  18.116  1.00  21.42   1DIK3153
ATOM  3062  O    ASN  404   -1.507  35.522  18.221  1.00  18.49   1DIK3154
ATOM  3063  CB   ASN  404   -2.323  33.679  20.142  1.00  17.93   1DIK3155
ATOM  3064  CG   ASN  404   -3.007  32.525  20.825  1.00  16.64   1DIK3156
ATOM  3065  OD1  ASN  404   -3.675  31.726  20.177  1.00  18.50   1DIK3157
ATOM  3066  ND2  ASN  404   -2.841  32.421  22.132  1.00  13.25   1DIK3158
ATOM  3067  N    ASP  405    0.011  34.103  17.277  1.00  20.77   1DIK3159
ATOM  3068  CA   ASP  405    0.657  35.003  16.317  1.00  21.55   1DIK3160
ATOM  3069  C    ASP  405    1.704  35.960  16.838  1.00  24.70   1DIK3161
ATOM  3070  O    ASP  405    2.244  36.765  16.078  1.00  27.69   1DIK3162
ATOM  3071  CB   ASP  405   -0.374  35.753  15.481  1.00  19.33   1DIK3163
ATOM  3072  CG   ASP  405   -1.249  34.821  14.694  1.00  21.06   1DIK3164
ATOM  3073  OD1  ASP  405   -0.824  33.668  14.469  1.00  22.07   1DIK3165
ATOM  3074  OD2  ASP  405   -2.359  35.231  14.303  1.00  23.53   1DIK3166
ATOM  3075  N    ARG  406    1.999  35.874  18.126  1.00  24.97   1DIK3167
ATOM  3076  CA   ARG  406    3.022  36.732  18.709  1.00  25.69   1DIK3168
ATOM  3077  C    ARG  406    4.317  35.917  18.738  1.00  24.24   1DIK3169
ATOM  3078  O    ARG  406    4.313  34.767  19.213  1.00  24.35   1DIK3170
ATOM  3079  CB   ARG  406    2.619  37.141  20.139  1.00  26.35   1DIK3171
ATOM  3080  CG   ARG  406    3.618  38.049  20.840  1.00  26.41   1DIK3172
ATOM  3081  CD   ARG  406    3.315  38.224  22.331  1.00  28.94   1DIK3173
ATOM  3082  NE   ARG  406    4.501  38.715  23.031  1.00  32.36   1DIK3174
ATOM  3083  CZ   ARG  406    5.099  38.092  24.047  1.00  36.19   1DIK3175
ATOM  3084  NH1  ARG  406    4.613  36.950  24.521  1.00  35.65   1DIK3176
ATOM  3085  NH2  ARG  406    6.188  38.618  24.601  1.00  38.62   1DIK3177
ATOM  3086  N    VAL  407    5.410  36.483  18.226  1.00  20.04   1DIK3178
ATOM  3087  CA   VAL  407    6.689  35.779  18.266  1.00  19.32   1DIK3179
```

FIG. 8-48

| | | | | | | | | | |
|---|---|---|---|---|---|---|---|---|---|
| ATOM | 3088 | C | VAL | 407 | 7.183 | 35.895 | 19.710 | 1.00 22.20 | 1DIK3180 |
| ATOM | 3089 | O | VAL | 407 | 7.481 | 36.974 | 20.198 | 1.00 26.19 | 1DIK3181 |
| ATOM | 3090 | CB | VAL | 407 | 7.743 | 36.372 | 17.276 | 1.00 17.66 | 1DIK3182 |
| ATOM | 3091 | CG1 | VAL | 407 | 9.143 | 35.815 | 17.606 | 1.00 12.58 | 1DIK3183 |
| ATOM | 3092 | CG2 | VAL | 407 | 7.367 | 36.031 | 15.826 | 1.00 8.62 | 1DIK3184 |
| ATOM | 3093 | N | VAL | 408 | 7.245 | 34.767 | 20.391 | 1.00 27.04 | 1DIK3185 |
| ATOM | 3094 | CA | VAL | 408 | 7.682 | 34.718 | 21.779 | 1.00 30.49 | 1DIK3186 |
| ATOM | 3095 | C | VAL | 408 | 9.169 | 34.371 | 21.845 | 1.00 33.80 | 1DIK3187 |
| ATOM | 3096 | O | VAL | 408 | 9.576 | 33.273 | 21.468 | 1.00 36.38 | 1DIK3188 |
| ATOM | 3097 | CB | VAL | 408 | 6.869 | 33.645 | 22.575 | 1.00 27.31 | 1DIK3189 |
| ATOM | 3098 | CG1 | VAL | 408 | 7.310 | 33.590 | 24.026 | 1.00 26.14 | 1DIK3190 |
| ATOM | 3099 | CG2 | VAL | 408 | 5.392 | 33.950 | 22.493 | 1.00 25.33 | 1DIK3191 |
| ATOM | 3100 | N | PRO | 409 | 10.007 | 35.312 | 22.298 | 1.00 39.45 | 1DIK3192 |
| ATOM | 3101 | CA | PRO | 409 | 11.453 | 35.048 | 22.405 | 1.00 39.88 | 1DIK3193 |
| ATOM | 3102 | C | PRO | 409 | 11.740 | 33.855 | 23.348 | 1.00 38.92 | 1DIK3194 |
| ATOM | 3103 | O | PRO | 409 | 11.135 | 33.707 | 24.423 | 1.00 36.45 | 1DIK3195 |
| ATOM | 3104 | CB | PRO | 409 | 12.005 | 36.368 | 22.948 | 1.00 42.97 | 1DIK3196 |
| ATOM | 3105 | CG | PRO | 409 | 10.992 | 37.396 | 22.418 | 1.00 44.48 | 1DIK3197 |
| ATOM | 3106 | CD | PRO | 410 | 9.688 | 36.692 | 22.702 | 1.00 40.36 | 1DIK3198 |
| ATOM | 3107 | N | LEU | 410 | 12.668 | 33.009 | 22.921 | 1.00 38.46 | 1DIK3199 |
| ATOM | 3108 | CA | LEU | 410 | 13.041 | 31.814 | 23.660 | 1.00 34.48 | 1DIK3200 |
| ATOM | 3109 | C | LEU | 410 | 13.959 | 32.117 | 24.846 | 1.00 33.51 | 1DIK3201 |
| ATOM | 3110 | O | LEU | 410 | 14.710 | 33.092 | 24.839 | 1.00 31.11 | 1DIK3202 |
| ATOM | 3111 | CB | LEU | 410 | 13.707 | 30.810 | 22.697 | 1.00 32.83 | 1DIK3203 |
| ATOM | 3112 | CG | LEU | 410 | 12.875 | 30.372 | 21.476 | 1.00 29.37 | 1DIK3204 |
| ATOM | 3113 | CD1 | LEU | 410 | 13.725 | 29.543 | 20.528 | 1.00 28.62 | 1DIK3205 |
| ATOM | 3114 | CD2 | LEU | 410 | 11.661 | 29.584 | 21.937 | 1.00 24.58 | 1DIK3206 |
| ATOM | 3115 | N | HIS | 411 | 13.888 | 31.275 | 25.867 | 1.00 32.47 | 1DIK3207 |
| ATOM | 3116 | CA | HIS | 411 | 14.725 | 31.432 | 27.041 | 1.00 34.54 | 1DIK3208 |
| ATOM | 3117 | C | HIS | 411 | 15.585 | 30.188 | 27.209 | 1.00 33.85 | 1DIK3209 |
| ATOM | 3118 | O | HIS | 411 | 15.168 | 29.088 | 26.854 | 1.00 36.81 | 1DIK3210 |
| ATOM | 3119 | CB | HIS | 411 | 13.865 | 31.652 | 28.288 | 1.00 40.62 | 1DIK3211 |
| ATOM | 3120 | CG | HIS | 411 | 13.249 | 33.012 | 28.352 | 1.00 43.65 | 1DIK3212 |
| ATOM | 3121 | ND1 | HIS | 411 | 11.994 | 33.287 | 27.854 | 1.00 46.21 | 1DIK3213 |
| ATOM | 3122 | CD2 | HIS | 411 | 13.371 | 34.185 | 28.822 | 1.00 43.54 | 1DIK3214 |
| ATOM | 3123 | CE1 | HIS | 411 | 11.731 | 34.571 | 28.012 | 1.00 46.39 | 1DIK3215 |
| ATOM | 3124 | NE2 | HIS | 411 | 12.771 | 35.138 | 28.598 | 1.00 43.29 | 1DIK3216 |
| ATOM | 3125 | N | GLY | 412 | 16.786 | 30.372 | 27.747 | 1.00 32.45 | 1DIK3217 |
| ATOM | 3126 | CA | GLY | 412 | 17.690 | 29.258 | 27.961 | 1.00 27.18 | 1DIK3218 |
| ATOM | 3127 | C | GLY | 412 | 18.642 | 29.036 | 26.807 | 1.00 28.45 | 1DIK3219 |
| ATOM | 3128 | O | GLY | 412 | 19.530 | 28.180 | 26.880 | 1.00 32.18 | 1DIK3220 |
| ATOM | 3129 | N | CYS | 413 | 18.470 | 29.797 | 25.734 | 1.00 25.33 | 1DIK3221 |
| ATOM | 3130 | CA | CYS | 413 | 19.334 | 29.669 | 24.570 | 1.00 24.44 | 1DIK3222 |
| ATOM | 3131 | C | CYS | 413 | 19.542 | 31.073 | 24.032 | 1.00 23.08 | 1DIK3223 |
| ATOM | 3132 | O | CYS | 413 | 18.723 | 31.967 | 24.278 | 1.00 23.15 | 1DIK3224 |
| ATOM | 3133 | CB | CYS | 413 | 18.691 | 28.751 | 23.511 | 1.00 26.97 | 1DIK3225 |
| ATOM | 3134 | SG | CYS | 413 | 17.010 | 29.217 | 22.959 | 1.00 26.06 | 1DIK3226 |
| ATOM | 3135 | N | PRO | 414 | 20.640 | 31.289 | 23.299 | 1.00 22.53 | 1DIK3227 |
| ATOM | 3136 | CA | PRO | 414 | 21.000 | 32.586 | 22.706 | 1.00 25.51 | 1DIK3228 |
| ATOM | 3137 | C | PRO | 414 | 20.086 | 32.989 | 21.542 | 1.00 26.43 | 1DIK3229 |
| ATOM | 3138 | O | PRO | 414 | 20.303 | 32.531 | 20.415 | 1.00 24.37 | 1DIK3230 |
| ATOM | 3139 | CB | PRO | 414 | 22.438 | 32.359 | 22.202 | 1.00 27.32 | 1DIK3231 |
| ATOM | 3140 | CG | PRO | 414 | 22.904 | 31.083 | 22.891 | 1.00 26.89 | 1DIK3232 |
| ATOM | 3141 | CD | PRO | 414 | 21.649 | 30.264 | 22.972 | 1.00 25.24 | 1DIK3233 |
| ATOM | 3142 | N | VAL | 415 | 19.080 | 33.829 | 21.801 | 1.00 24.39 | 1DIK3234 |
| ATOM | 3143 | CA | VAL | 415 | 18.180 | 34.258 | 20.732 | 1.00 23.17 | 1DIK3235 |
| ATOM | 3144 | C | VAL | 415 | 18.762 | 35.328 | 19.817 | 1.00 23.33 | 1DIK3236 |
| ATOM | 3145 | O | VAL | 415 | 19.498 | 36.213 | 20.262 | 1.00 23.01 | 1DIK3237 |
| ATOM | 3146 | CB | VAL | 415 | 16.827 | 34.801 | 21.256 | 1.00 20.98 | 1DIK3238 |
| ATOM | 3147 | CG1 | VAL | 415 | 15.937 | 33.675 | 21.666 | 1.00 22.55 | 1DIK3239 |
| ATOM | 3148 | CG2 | VAL | 415 | 17.051 | 35.763 | 22.391 | 1.00 26.59 | 1DIK3240 |
| ATOM | 3149 | N | ASP | 416 | 18.434 | 35.236 | 18.532 | 1.00 21.89 | 1DIK3241 |
| ATOM | 3150 | CA | ASP | 416 | 18.881 | 36.224 | 17.569 | 1.00 23.29 | 1DIK3242 |
| ATOM | 3151 | C | ASP | 416 | 17.798 | 37.307 | 17.436 | 1.00 25.15 | 1DIK3243 |
| ATOM | 3152 | O | ASP | 416 | 16.739 | 37.209 | 18.070 | 1.00 23.71 | 1DIK3244 |

FIG. 8-49

```
ATOM   3153  CB  ASP 416    19.265 35.579 16.207  1.00 22.64      1DIK3245
ATOM   3154  CG  ASP 416    18.085 34.947 15.445  1.00 25.90      1DIK3246
ATOM   3155  OD1 ASP 416    16.896 35.237 15.713  1.00 28.90      1DIK3247
ATOM   3156  OD2 ASP 416    18.366 34.135 14.540  1.00 24.59      1DIK3248
ATOM   3157  N   ALA 417    18.062 38.327 16.619  1.00 25.89      1DIK3249
ATOM   3158  CA  ALA 417    17.137 39.443 16.411  1.00 26.04      1DIK3250
ATOM   3159  C   ALA 417    15.717 39.053 15.986  1.00 27.35      1DIK3251
ATOM   3160  O   ALA 417    14.779 39.837 16.165  1.00 28.16      1DIK3252
ATOM   3161  CB  ALA 417    17.738 40.443 15.403  1.00 22.45      1DIK3253
ATOM   3162  N   LEU 418    15.553 37.852 15.428  1.00 28.60      1DIK3254
ATOM   3163  CA  LEU 418    14.238 37.384 14.991  1.00 26.36      1DIK3255
ATOM   3164  C   LEU 418    13.552 36.391 15.952  1.00 26.54      1DIK3256
ATOM   3165  O   LEU 418    12.533 35.795 15.608  1.00 26.72      1DIK3257
ATOM   3166  CB  LEU 418    14.329 36.829 13.564  1.00 25.45      1DIK3258
ATOM   3167  CG  LEU 418    14.649 37.875 12.474  1.00 28.70      1DIK3259
ATOM   3168  CD1 LEU 418    14.842 37.187 11.139  1.00 27.85      1DIK3260
ATOM   3169  CD2 LEU 418    13.525 38.908 12.354  1.00 23.85      1DIK3261
ATOM   3170  N   GLY 419    14.118 36.234 17.154  1.00 27.13      1DIK3262
ATOM   3171  CA  GLY 419    13.556 35.364 18.182  1.00 22.28      1DIK3263
ATOM   3172  C   GLY 419    13.913 33.894 18.094  1.00 25.13      1DIK3264
ATOM   3173  O   GLY 419    13.347 33.077 18.827  1.00 29.64      1DIK3265
ATOM   3174  N   ARG 420    14.852 33.555 17.218  1.00 18.88      1DIK3266
ATOM   3175  CA  ARG 420    15.252 32.173 17.004  1.00 21.64      1DIK3267
ATOM   3176  C   ARG 420    16.483 31.695 17.768  1.00 23.83      1DIK3268
ATOM   3177  O   ARG 420    17.306 32.495 18.193  1.00 26.72      1DIK3269
ATOM   3178  CB  ARG 420    15.504 31.959 15.515  1.00 23.45      1DIK3270
ATOM   3179  CG  ARG 420    14.413 32.532 14.623  1.00 27.05      1DIK3271
ATOM   3180  CD  ARG 420    14.827 32.520 13.166  1.00 25.37      1DIK3272
ATOM   3181  NE  ARG 420    16.019 33.333 12.915  1.00 30.86      1DIK3273
ATOM   3182  CZ  ARG 420    16.435 33.730 11.708  1.00 28.82      1DIK3274
ATOM   3183  NH1 ARG 420    15.775 33.407 10.599  1.00 25.15      1DIK3275
ATOM   3184  NH2 ARG 420    17.528 34.463 11.608  1.00 28.95      1DIK3276
ATOM   3185  N   CYS 421    16.590 30.377 17.927  1.00 24.78      1DIK3277
ATOM   3186  CA  CYS 421    17.726 29.704 18.570  1.00 22.57      1DIK3278
ATOM   3187  C   CYS 421    18.039 28.519 17.679  1.00 23.03      1DIK3279
ATOM   3188  O   CYS 421    17.144 27.988 17.035  1.00 22.43      1DIK3280
ATOM   3189  CB  CYS 421    17.366 29.144 19.944  1.00 22.26      1DIK3281
ATOM   3190  SG  CYS 421    17.337 30.349 21.302  1.00 27.11      1DIK3282
ATOM   3191  N   THR 422    19.294 28.098 17.623  1.00 26.80      1DIK3283
ATOM   3192  CA  THR 422    19.624 26.935 16.816  1.00 26.97      1DIK3284
ATOM   3193  C   THR 422    18.879 25.795 17.511  1.00 30.20      1DIK3285
ATOM   3194  O   THR 422    18.636 25.857 18.731  1.00 30.05      1DIK3286
ATOM   3195  CB  THR 422    21.146 26.649 16.799  1.00 25.67      1DIK3287
ATOM   3196  OG1 THR 422    21.615 26.400 18.133  1.00 25.43      1DIK3288
ATOM   3197  CG2 THR 422    21.895 27.827 16.200  1.00 23.71      1DIK3289
ATOM   3198  N   ARG 423    18.505 24.767 16.752  1.00 30.48      1DIK3290
ATOM   3199  CA  ARG 423    17.781 23.650 17.331  1.00 28.62      1DIK3291
ATOM   3200  C   ARG 423    18.528 23.048 18.518  1.00 29.61      1DIK3292
ATOM   3201  O   ARG 423    17.934 22.791 19.567  1.00 29.29      1DIK3293
ATOM   3202  CB  ARG 423    17.536 22.573 16.281  1.00 27.71      1DIK3294
ATOM   3203  CG  ARG 423    16.711 21.420 16.820  1.00 30.71      1DIK3295
ATOM   3204  CD  ARG 423    16.689 20.273 15.857  1.00 31.47      1DIK3296
ATOM   3205  NE  ARG 423    18.046 19.852 15.553  1.00 33.67      1DIK3297
ATOM   3206  CZ  ARG 423    18.406 19.262 14.422  1.00 33.99      1DIK3298
ATOM   3207  NH1 ARG 423    17.510 19.012 13.476  1.00 35.49      1DIK3299
ATOM   3208  NH2 ARG 423    19.671 18.921 14.241  1.00 38.78      1DIK3300
ATOM   3209  N   ASP 424    19.830 22.838 18.351  1.00 29.32      1DIK3301
ATOM   3210  CA  ASP 424    20.654 22.238 19.393  1.00 32.19      1DIK3302
ATOM   3211  C   ASP 424    20.729 22.998 20.704  1.00 30.97      1DIK3303
ATOM   3212  O   ASP 424    20.614 22.391 21.772  1.00 35.15      1DIK3304
ATOM   3213  CB  ASP 424    22.057 21.954 18.858  1.00 37.79      1DIK3305
ATOM   3214  CG  ASP 424    22.087 20.758 17.900  1.00 49.74      1DIK3306
ATOM   3215  OD1 ASP 424    21.108 20.531 17.136  1.00 52.55      1DIK3307
ATOM   3216  OD2 ASP 424    23.101 20.034 17.911  1.00 52.75      1DIK3308
ATOM   3217  N   SER 425    20.919 24.311 24.653  1.00 28.34      1DIK3309
```

FIG. 8-50

```
ATOM   3218  CA   SER  425    20.976  25.071  21.893  1.00  28.79   1DIK3310
ATOM   3219  C    SER  425    19.568  25.148  22.504  1.00  28.14   1DIK3311
ATOM   3220  O    SER  425    19.422  25.177  23.731  1.00  27.74   1DIK3312
ATOM   3221  CB   SER  425    21.584  26.470  21.674  1.00  27.42   1DIK3313
ATOM   3222  OG   SER  425    20.849  27.235  20.742  1.00  31.04   1DIK3314
ATOM   3223  N    PHE  426    18.538  25.170  21.651  1.00  26.40   1DIK3315
ATOM   3224  CA   PHE  426    17.152  25.203  22.129  1.00  26.40   1DIK3316
ATOM   3225  C    PHE  426    16.839  23.931  22.941  1.00  26.61   1DIK3317
ATOM   3226  O    PHE  426    16.311  23.996  24.064  1.00  23.72   1DIK3318
ATOM   3227  CB   PHE  426    16.149  25.327  20.961  1.00  24.80   1DIK3319
ATOM   3228  CG   PHE  426    14.698  25.227  21.399  1.00  24.49   1DIK3320
ATOM   3229  CD1  PHE  426    14.123  26.225  22.185  1.00  23.07   1DIK3321
ATOM   3230  CD2  PHE  426    13.925  24.117  21.061  1.00  22.45   1DIK3322
ATOM   3231  CE1  PHE  426    12.809  26.112  22.632  1.00  20.13   1DIK3323
ATOM   3232  CE2  PHE  426    12.609  23.999  21.506  1.00  19.45   1DIK3324
ATOM   3233  CZ   PHE  426    12.053  24.993  22.293  1.00  20.49   1DIK3325
ATOM   3234  N    VAL  427    17.161  22.780  22.354  1.00  27.03   1DIK3326
ATOM   3235  CA   VAL  427    16.948  21.491  22.996  1.00  27.17   1DIK3327
ATOM   3236  C    VAL  427    17.788  21.444  24.267  1.00  29.37   1DIK3328
ATOM   3237  O    VAL  427    17.327  21.011  25.323  1.00  32.09   1DIK3329
ATOM   3238  CB   VAL  427    17.348  20.346  22.047  1.00  28.39   1DIK3330
ATOM   3239  CG1  VAL  427    17.439  19.022  22.809  1.00  26.94   1DIK3331
ATOM   3240  CG2  VAL  427    16.326  20.256  20.901  1.00  24.93   1DIK3332
ATOM   3241  N    ARG  428    19.024  21.909  24.160  1.00  31.56   1DIK3333
ATOM   3242  CA   ARG  428    19.931  21.947  25.292  1.00  33.59   1DIK3334
ATOM   3243  C    ARG  428    19.331  22.797  26.426  1.00  32.27   1DIK3335
ATOM   3244  O    ARG  428    19.489  22.472  27.598  1.00  31.56   1DIK3336
ATOM   3245  CB   ARG  428    21.257  22.518  24.819  1.00  40.23   1DIK3337
ATOM   3246  CG   ARG  428    22.404  22.306  25.750  1.00  55.44   1DIK3338
ATOM   3247  CD   ARG  428    23.706  22.643  25.043  1.00  69.03   1DIK3339
ATOM   3248  NE   ARG  428    24.726  23.025  26.013  1.00  83.02   1DIK3340
ATOM   3249  CZ   ARG  428    25.632  23.981  25.819  1.00  88.04   1DIK3341
ATOM   3250  NH1  ARG  428    25.659  24.656  24.674  1.00  89.88   1DIK3342
ATOM   3251  NH2  ARG  428    26.516  24.260  26.777  1.00  89.48   1DIK3343
ATOM   3252  N    GLY  429    18.634  23.875  26.068  1.00  31.73   1DIK3344
ATOM   3253  CA   GLY  429    18.011  24.754  27.049  1.00  29.88   1DIK3345
ATOM   3254  C    GLY  429    16.814  24.187  27.816  1.00  31.65   1DIK3346
ATOM   3255  O    GLY  429    16.434  24.718  28.871  1.00  29.27   1DIK3347
ATOM   3256  N    LEU  430    16.208  23.115  27.308  1.00  32.28   1DIK3348
ATOM   3257  CA   LEU  430    15.057  22.495  27.977  1.00  31.40   1DIK3349
ATOM   3258  C    LEU  430    15.546  21.456  29.009  1.00  30.50   1DIK3350
ATOM   3259  O    LEU  430    15.093  20.307  29.033  1.00  30.10   1DIK3351
ATOM   3260  CB   LEU  430    14.144  21.836  26.930  1.00  27.85   1DIK3352
ATOM   3261  CG   LEU  430    13.635  22.755  25.819  1.00  27.51   1DIK3353
ATOM   3262  CD1  LEU  430    12.980  21.956  24.702  1.00  21.48   1DIK3354
ATOM   3263  CD2  LEU  430    12.672  23.751  26.420  1.00  21.75   1DIK3355
ATOM   3264  N    SER  431    16.468  21.869  29.869  1.00  29.03   1DIK3356
ATOM   3265  CA   SER  431    17.028  20.960  30.864  1.00  31.21   1DIK3357
ATOM   3266  C    SER  431    15.991  20.465  31.871  1.00  28.76   1DIK3358
ATOM   3267  O    SER  431    16.037  19.308  32.290  1.00  29.64   1DIK3359
ATOM   3268  CB   SER  431    18.212  21.623  31.580  1.00  31.70   1DIK3360
ATOM   3269  OG   SER  431    17.837  22.857  32.169  1.00  36.73   1DIK3361
ATOM   3270  N    PHE  432    15.059  21.334  32.254  1.00  25.33   1DIK3362
ATOM   3271  CA   PHE  432    14.016  20.969  33.207  1.00  26.36   1DIK3363
ATOM   3272  C    PHE  432    13.170  19.796  32.681  1.00  30.38   1DIK3364
ATOM   3273  O    PHE  432    12.904  18.822  33.404  1.00  29.32   1DIK3365
ATOM   3274  CB   PHE  432    13.133  22.186  33.487  1.00  21.52   1DIK3366
ATOM   3275  CG   PHE  432    11.908  21.885  34.315  1.00  24.46   1DIK3367
ATOM   3276  CD1  PHE  432    12.022  21.567  35.670  1.00  22.91   1DIK3368
ATOM   3277  CD2  PHE  432    10.636  21.941  33.739  1.00  19.38   1DIK3369
ATOM   3278  CE1  PHE  432    10.883  21.311  36.441  1.00  24.30   1DIK3370
ATOM   3279  CE2  PHE  432     9.489  21.688  34.495  1.00  22.66   1DIK3371
ATOM   3280  CZ   PHE  432     9.606  21.372  35.846  1.00  26.15   1DIK3372
ATOM   3281  N    ALA  433    12.752  19.896  31.421  1.00  27.75   1DIK3373
ATOM   3282  CA   ALA  433    11.958  18.850  30.796  1.00  26.55   1DIK3374
```

FIG. 8-51

| | | | | | | | | | |
|---|---|---|---|---|---|---|---|---|---|
| ATOM | 3283 | C   | ALA | 433 | 12.789 | 17.577 | 30.597 | 1.00 25.17 | 1DIK3375 |
| ATOM | 3284 | O   | ALA | 433 | 12.350 | 16.492 | 30.974 | 1.00 28.47 | 1DIK3376 |
| ATOM | 3285 | CB  | ALA | 433 | 11.411 | 19.336 | 29.460 | 1.00 23.17 | 1DIK3377 |
| ATOM | 3286 | N   | ARG | 434 | 13.982 | 17.710 | 30.018 | 1.00 23.09 | 1DIK3378 |
| ATOM | 3287 | CA  | ARG | 434 | 14.849 | 16.557 | 29.754 | 1.00 24.40 | 1DIK3379 |
| ATOM | 3288 | C   | ARG | 434 | 15.156 | 15.725 | 30.992 | 1.00 24.98 | 1DIK3380 |
| ATOM | 3289 | O   | ARG | 434 | 15.416 | 14.525 | 30.889 | 1.00 25.10 | 1DIK3381 |
| ATOM | 3290 | CB  | ARG | 434 | 16.163 | 16.991 | 29.087 | 1.00 22.29 | 1DIK3382 |
| ATOM | 3291 | CG  | ARG | 434 | 16.013 | 17.379 | 27.610 | 1.00 27.82 | 1DIK3383 |
| ATOM | 3292 | CD  | ARG | 434 | 17.363 | 17.590 | 26.910 | 1.00 29.10 | 1DIK3384 |
| ATOM | 3293 | NE  | ARG | 434 | 18.090 | 18.741 | 27.446 | 1.00 36.82 | 1DIK3385 |
| ATOM | 3294 | CZ  | ARG | 434 | 19.087 | 18.664 | 28.332 | 1.00 39.13 | 1DIK3386 |
| ATOM | 3295 | NH1 | ARG | 434 | 19.487 | 17.480 | 28.784 | 1.00 39.16 | 1DIK3387 |
| ATOM | 3296 | NH2 | ARG | 434 | 19.688 | 19.770 | 28.766 | 1.00 30.93 | 1DIK3388 |
| ATOM | 3297 | N   | SER | 435 | 15.123 | 16.367 | 32.157 | 1.00 26.13 | 1DIK3389 |
| ATOM | 3298 | CA  | SER | 435 | 15.394 | 15.696 | 33.427 | 1.00 28.09 | 1DIK3390 |
| ATOM | 3299 | C   | SER | 435 | 14.126 | 15.122 | 34.088 | 1.00 26.80 | 1DIK3391 |
| ATOM | 3300 | O   | SER | 435 | 14.208 | 14.433 | 35.103 | 1.00 27.78 | 1DIK3392 |
| ATOM | 3301 | CB  | SER | 435 | 16.112 | 16.659 | 34.392 | 1.00 29.48 | 1DIK3393 |
| ATOM | 3302 | OG  | SER | 435 | 15.322 | 17.811 | 34.687 | 1.00 36.42 | 1DIK3394 |
| ATOM | 3303 | N   | GLY | 436 | 12.960 | 15.407 | 33.515 | 1.00 26.30 | 1DIK3395 |
| ATOM | 3304 | CA  | GLY | 436 | 11.719 | 14.894 | 34.068 | 1.00 24.08 | 1DIK3396 |
| ATOM | 3305 | C   | GLY | 436 | 11.003 | 15.827 | 35.025 | 1.00 25.00 | 1DIK3397 |
| ATOM | 3306 | O   | GLY | 436 | 10.114 | 15.383 | 35.763 | 1.00 25.04 | 1DIK3398 |
| ATOM | 3307 | N   | GLY | 437 | 11.376 | 17.107 | 35.015 | 1.00 24.66 | 1DIK3399 |
| ATOM | 3308 | CA  | GLY | 437 | 10.755 | 18.076 | 35.901 | 1.00 26.30 | 1DIK3400 |
| ATOM | 3309 | C   | GLY | 437 | 10.743 | 17.560 | 37.330 | 1.00 28.82 | 1DIK3401 |
| ATOM | 3310 | O   | GLY | 437 | 11.697 | 16.913 | 37.767 | 1.00 30.32 | 1DIK3402 |
| ATOM | 3311 | N   | ASP | 438 | 9.666  | 17.839 | 38.058 | 1.00 29.95 | 1DIK3403 |
| ATOM | 3312 | CA  | ASP | 438 | 9.516  | 17.374 | 39.438 | 1.00 31.82 | 1DIK3404 |
| ATOM | 3313 | C   | ASP | 438 | 8.453  | 16.273 | 39.477 | 1.00 32.65 | 1DIK3405 |
| ATOM | 3314 | O   | ASP | 438 | 7.674  | 16.197 | 40.434 | 1.00 29.97 | 1DIK3406 |
| ATOM | 3315 | CB  | ASP | 438 | 9.094  | 18.534 | 40.363 | 1.00 33.43 | 1DIK3407 |
| ATOM | 3316 | CG  | ASP | 438 | 10.174 | 19.610 | 40.499 | 1.00 37.98 | 1DIK3408 |
| ATOM | 3317 | OD1 | ASP | 438 | 11.372 | 19.271 | 40.545 | 1.00 43.62 | 1DIK3409 |
| ATOM | 3318 | OD2 | ASP | 438 | 9.834  | 20.806 | 40.563 | 1.00 40.73 | 1DIK3410 |
| ATOM | 3319 | N   | TRP | 439 | 8.423  | 15.420 | 38.446 | 1.00 32.12 | 1DIK3411 |
| ATOM | 3320 | CA  | TRP | 439 | 7.415  | 14.357 | 38.365 | 1.00 31.93 | 1DIK3412 |
| ATOM | 3321 | C   | TRP | 439 | 7.429  | 13.410 | 39.571 | 1.00 35.50 | 1DIK3413 |
| ATOM | 3322 | O   | TRP | 439 | 6.388  | 12.886 | 39.979 | 1.00 34.13 | 1DIK3414 |
| ATOM | 3323 | CB  | TRP | 439 | 7.545  | 13.573 | 37.045 | 1.00 23.82 | 1DIK3415 |
| ATOM | 3324 | CG  | TRP | 439 | 6.379  | 12.641 | 36.794 | 1.00 25.59 | 1DIK3416 |
| ATOM | 3325 | CD1 | TRP | 439 | 6.331  | 11.304 | 37.067 | 1.00 22.86 | 1DIK3417 |
| ATOM | 3326 | CD2 | TRP | 439 | 5.076  | 12.989 | 36.279 | 1.00 25.24 | 1DIK3418 |
| ATOM | 3327 | NE1 | TRP | 439 | 5.089  | 10.802 | 36.764 | 1.00 27.19 | 1DIK3419 |
| ATOM | 3328 | CE2 | TRP | 439 | 4.299  | 11.813 | 36.280 | 1.00 25.01 | 1DIK3420 |
| ATOM | 3329 | CE3 | TRP | 439 | 4.494  | 14.179 | 35.819 | 1.00 25.14 | 1DIK3421 |
| ATOM | 3330 | CZ2 | TRP | 439 | 2.967  | 11.790 | 35.842 | 1.00 26.41 | 1DIK3422 |
| ATOM | 3331 | CZ3 | TRP | 439 | 3.169  | 14.157 | 35.381 | 1.00 21.25 | 1DIK3423 |
| ATOM | 3332 | CH2 | TRP | 439 | 2.424  | 12.970 | 35.398 | 1.00 27.53 | 1DIK3424 |
| ATOM | 3333 | N   | ALA | 440 | 8.608  | 13.198 | 40.147 | 1.00 39.08 | 1DIK3425 |
| ATOM | 3334 | CA  | ALA | 440 | 8.740  | 12.325 | 41.304 | 1.00 40.38 | 1DIK3426 |
| ATOM | 3335 | C   | ALA | 440 | 7.783  | 12.771 | 42.429 | 1.00 42.18 | 1DIK3427 |
| ATOM | 3336 | O   | ALA | 440 | 7.072  | 11.948 | 43.026 | 1.00 44.41 | 1DIK3428 |
| ATOM | 3337 | CB  | ALA | 440 | 10.173 | 12.341 | 41.776 | 1.00 36.80 | 1DIK3429 |
| ATOM | 3338 | N   | GLU | 441 | 7.758  | 14.077 | 42.689 | 1.00 41.96 | 1DIK3430 |
| ATOM | 3339 | CA  | GLU | 441 | 6.903  | 14.687 | 43.713 | 1.00 42.69 | 1DIK3431 |
| ATOM | 3340 | C   | GLU | 441 | 5.397  | 14.402 | 43.529 | 1.00 42.04 | 1DIK3432 |
| ATOM | 3341 | O   | GLU | 441 | 4.575  | 14.766 | 44.373 | 1.00 42.51 | 1DIK3433 |
| ATOM | 3342 | CB  | GLU | 441 | 7.109  | 16.207 | 43.710 | 1.00 49.22 | 1DIK3434 |
| ATOM | 3343 | CG  | GLU | 441 | 8.554  | 16.671 | 43.787 | 1.00 56.93 | 1DIK3435 |
| ATOM | 3344 | CD  | GLU | 441 | 9.184  | 16.346 | 45.122 | 1.00 65.76 | 1DIK3436 |
| ATOM | 3345 | OE1 | GLU | 441 | 8.602  | 16.733 | 46.161 | 1.00 69.69 | 1DIK3437 |
| ATOM | 3346 | OE2 | GLU | 441 | 10.260 | 15.704 | 45.139 | 1.00 69.76 | 1DIK3438 |
| ATOM | 3347 | N   | CYS | 442 | 5.034  | 13.765 | 42.426 | 1.00 39.99 | 1DIK3439 |

FIG. 8-52

```
ATOM   3348 CA  CYS 442      3.638  13.468  42.160  1.00 40.48      1DIK3440
ATOM   3349 C   CYS 442      3.068  12.411  43.073  1.00 43.32      1DIK3441
ATOM   3350 O   CYS 442      1.859  12.405  43.337  1.00 43.60      1DIK3442
ATOM   3351 CB  CYS 442      3.452  12.982  40.715  1.00 39.39      1DIK3443
ATOM   3352 SG  CYS 442      3.541  14.265  39.429  1.00 32.94      1DIK3444
ATOM   3353 N   PHE 443      3.930  11.517  43.546  1.00 45.06      1DIK3445
ATOM   3354 CA  PHE 443      3.479  10.403  44.372  1.00 50.79      1DIK3446
ATOM   3355 C   PHE 443      3.941  10.416  45.813  1.00 55.76      1DIK3447
ATOM   3356 O   PHE 443      3.268   9.863  46.684  1.00 57.52      1DIK3448
ATOM   3357 CB  PHE 443      3.882   9.111  43.681  1.00 45.54      1DIK3449
ATOM   3358 CG  PHE 443      3.724   9.182  42.205  1.00 45.83      1DIK3450
ATOM   3359 CD1 PHE 443      2.453   9.192  41.636  1.00 43.41      1DIK3451
ATOM   3360 CD2 PHE 443      4.840   9.294  41.379  1.00 46.74      1DIK3452
ATOM   3361 CE1 PHE 443      2.292   9.315  40.262  1.00 43.31      1DIK3453
ATOM   3362 CE2 PHE 443      4.694   9.417  39.999  1.00 45.78      1DIK3454
ATOM   3363 CZ  PHE 443      3.416   9.428  39.441  1.00 45.42      1DIK3455
ATOM   3364 N   ALA 444      5.089  11.039  46.060  1.00 62.20      1DIK3456
ATOM   3365 CA  ALA 444      5.621  11.144  47.412  1.00 66.60      1DIK3457
ATOM   3366 C   ALA 444      4.893  12.333  48.043  1.00 68.05      1DIK3458
ATOM   3367 O   ALA 444      3.938  12.089  48.817  1.00 68.94      1DIK3459
ATOM   3368 CB  ALA 444      7.151  11.380  47.381  1.00 66.83      1DIK3460
ATOM   3369 OXT ALA 444      5.274  13.489  47.747  1.00 69.24      1DIK3461
TER    3370     ALA 444                                             1DIK3462
HETATM 3371 O   HOH   1      5.314  11.951  16.327  1.00 10.28      1DIK3463
HETATM 3372 O   HOH   2     -6.660  26.826  16.721  1.00 14.37      1DIK3464
HETATM 3373 O   HOH   3      0.327  31.364  16.394  1.00 14.78      1DIK3465
HETATM 3374 O   HOH   4    -11.448   9.894  26.651  1.00 15.14      1DIK3466
HETATM 3375 O   HOH   5     -1.808  14.907  36.587  1.00 15.18      1DIK3467
HETATM 3376 O   HOH   6    -16.607  13.889  26.028  1.00 15.50      1DIK3468
HETATM 3377 O   HOH   7      8.014   7.031  26.624  1.00 15.90      1DIK3469
HETATM 3378 O   HOH   8      2.890  16.506  29.187  1.00 16.33      1DIK3470
HETATM 3379 O   HOH   9     -3.509  12.674   9.344  1.00 16.84      1DIK3471
HETATM 3380 O   HOH  10     12.661  12.918  24.069  1.00 17.03      1DIK3472
HETATM 3381 O   HOH  11      0.759  15.125  16.187  1.00 18.48      1DIK3473
HETATM 3382 O   HOH  12     -4.619  39.381  32.613  1.00 18.74      1DIK3474
HETATM 3383 O   HOH  13     -9.462  31.056  14.118  1.00 18.80      1DIK3475
HETATM 3384 O   HOH  14     -5.677  35.681  21.397  1.00 19.53      1DIK3476
HETATM 3385 O   HOH  15    -11.372   5.811  26.977  1.00 20.29      1DIK3477
HETATM 3386 O   HOH  16      1.644   9.234  20.239  1.00 20.38      1DIK3478
HETATM 3387 O   HOH  17      7.980   5.282  24.219  1.00 20.45      1DIK3479
HETATM 3388 O   HOH  18     -2.840   6.618  26.553  1.00 21.48      1DIK3480
HETATM 3389 O   HOH  19     10.194   6.545  20.888  1.00 21.50      1DIK3481
HETATM 3390 O   HOH  20    -10.932   8.587  24.215  1.00 22.02      1DIK3482
HETATM 3391 O   HOH  21     -3.698  27.479  12.828  1.00 22.24      1DIK3483
HETATM 3392 O   HOH  22     -9.209   6.732  23.045  1.00 22.35      1DIK3484
HETATM 3393 O   HOH  23    -11.843  33.526  16.995  1.00 22.95      1DIK3485
HETATM 3394 O   HOH  24    -10.730  33.322  13.268  1.00 23.32      1DIK3486
HETATM 3395 O   HOH  25     -5.232   6.280  25.125  1.00 23.99      1DIK3487
HETATM 3396 O   HOH  26     -2.692  31.651  13.662  1.00 24.43      1DIK3488
HETATM 3397 O   HOH  27      9.007   7.301  10.872  1.00 24.65      1DIK3489
HETATM 3398 O   HOH  28      4.550  15.458  32.235  1.00 24.79      1DIK3490
HETATM 3399 O   HOH  29      0.579  35.238  22.968  1.00 24.95      1DIK3491
HETATM 3400 O   HOH  30      0.056  10.426  25.818  1.00 25.40      1DIK3492
HETATM 3401 O   HOH  31      2.362   9.432  24.562  1.00 26.19      1DIK3493
HETATM 3402 O   HOH  32      8.504   5.960  17.071  1.00 26.33      1DIK3494
HETATM 3403 O   HOH  33     -3.535  16.451   2.757  1.00 26.46      1DIK3495
HETATM 3404 O   HOH  34      1.506   9.018  33.598  1.00 26.96      1DIK3496
HETATM 3405 O   HOH  35    -18.820  19.116  20.350  1.00 27.18      1DIK3497
HETATM 3406 O   HOH  36      8.399   9.350   9.458  1.00 27.24      1DIK3498
HETATM 3407 O   HOH  37     -9.061  36.957   6.577  1.00 27.38      1DIK3599
HETATM 3408 O   HOH  38    -12.921  16.340   9.063  1.00 27.46      1DIK3500
HETATM 3409 O   HOH  39    -12.574  24.639  28.242  1.00 27.73      1DIK3501
HETATM 3410 O   HOH  40    -12.507  26.784  33.545  1.00 27.75      1DIK3502
HETATM 3411 O   HOH  41     -7.187  31.641  12.393  1.00 27.85      1DIK3503
HETATM 3412 O   HOH  42     10.571  32.202  19.033  1.00 28.02      1DIK3504
```

FIG. 8-53

| | | | | | | | | | | |
|---|---|---|---|---|---|---|---|---|---|---|
| HETATM | 3413 | O | HOH | 43 | 8.426 | 35.536 | 30.142 | 1.00 | 28.34 | 1DIK3505 |
| HETATM | 3414 | O | HOH | 44 | -6.691 | 36.766 | 30.786 | 1.00 | 28.87 | 1DIK3506 |
| HETATM | 3415 | O | HOH | 45 | 12.389 | 22.580 | 30.279 | 1.00 | 29.03 | 1DIK3507 |
| HETATM | 3416 | O | HOH | 46 | -16.222 | 15.844 | 27.511 | 1.00 | 29.03 | 1DIK3508 |
| HETATM | 3417 | O | HOH | 47 | -10.420 | 13.136 | 6.619 | 1.00 | 29.13 | 1DIK3509 |
| HETATM | 3418 | O | HOH | 48 | 6.987 | 21.974 | 38.216 | 1.00 | 29.26 | 1DIK3510 |
| HETATM | 3419 | O | HOH | 49 | -17.438 | 17.382 | 24.990 | 1.00 | 29.33 | 1DIK3511 |
| HETATM | 3420 | O | HOH | 50 | -22.489 | 30.175 | 17.758 | 1.00 | 29.51 | 1DIK3512 |
| HETATM | 3421 | O | HOH | 51 | -2.152 | 40.434 | 32.506 | 1.00 | 29.67 | 1DIK3513 |
| HETATM | 3422 | O | HOH | 52 | -10.794 | 11.992 | 11.258 | 1.00 | 29.84 | 1DIK3514 |
| HETATM | 3423 | O | HOH | 53 | -5.062 | 39.959 | 28.886 | 1.00 | 29.89 | 1DIK3515 |
| HETATM | 3424 | O | HOH | 54 | -19.008 | 30.051 | 23.934 | 1.00 | 29.97 | 1DIK3516 |
| HETATM | 3425 | O | HOH | 55 | 14.324 | 12.475 | 22.179 | 1.00 | 29.97 | 1DIK3517 |
| HETATM | 3426 | O | HOH | 56 | -15.744 | 47.285 | 28.530 | 1.00 | 29.97 | 1DIK3518 |
| HETATM | 3427 | O | HOH | 57 | -2.017 | 21.298 | 33.876 | 1.00 | 30.51 | 1DIK3519 |
| HETATM | 3428 | O | HOH | 58 | -10.164 | 23.699 | 27.468 | 1.00 | 30.66 | 1DIK3520 |
| HETATM | 3429 | O | HOH | 59 | 21.068 | 30.466 | 19.064 | 1.00 | 30.86 | 1DIK3521 |
| HETATM | 3430 | O | HOH | 60 | 15.633 | 26.247 | 25.288 | 1.00 | 31.46 | 1DIK3522 |
| HETATM | 3431 | O | HOH | 61 | 2.539 | 13.006 | 3.675 | 1.00 | 31.51 | 1DIK3523 |
| HETATM | 3432 | O | HOH | 62 | 0.718 | 11.503 | 8.049 | 1.00 | 31.69 | 1DIK3524 |
| HETATM | 3433 | O | HOH | 63 | 6.296 | 32.820 | 36.174 | 1.00 | 31.69 | 1DIK3525 |
| HETATM | 3434 | O | HOH | 64 | -6.588 | 42.450 | 32.884 | 1.00 | 31.91 | 1DIK3526 |
| HETATM | 3435 | O | HOH | 65 | 2.321 | 35.791 | 25.121 | 1.00 | 32.04 | 1DIK3527 |
| HETATM | 3436 | O | HOH | 66 | -11.516 | 36.087 | 6.335 | 1.00 | 32.59 | 1DIK3528 |
| HETATM | 3437 | O | HOH | 67 | -25.724 | 25.284 | 29.618 | 1.00 | 32.59 | 1DIK3529 |
| HETATM | 3438 | O | HOH | 68 | -18.133 | 26.391 | 31.970 | 1.00 | 32.62 | 1DIK3530 |
| HETATM | 3439 | O | HOH | 69 | -14.947 | 45.064 | 46.354 | 1.00 | 33.42 | 1DIK3531 |
| HETATM | 3440 | O | HOH | 70 | 21.082 | 26.576 | 25.533 | 1.00 | 33.44 | 1DIK3532 |
| HETATM | 3441 | O | HOH | 71 | 11.263 | 14.005 | 39.063 | 1.00 | 33.76 | 1DIK3533 |
| HETATM | 3442 | O | HOH | 72 | 6.695 | 36.561 | 26.464 | 1.00 | 33.92 | 1DIK3534 |
| HETATM | 3443 | O | HOH | 73 | -5.225 | 27.878 | -1.684 | 1.00 | 34.01 | 1DIK3535 |
| HETATM | 3444 | O | HOH | 74 | -0.802 | 9.860 | -0.093 | 1.00 | 34.16 | 1DIK3536 |
| HETATM | 3445 | O | HOH | 75 | -12.291 | 22.260 | 29.152 | 1.00 | 34.19 | 1DIK3537 |
| HETATM | 3446 | O | HOH | 76 | 9.096 | 28.265 | 3.852 | 1.00 | 35.19 | 1DIK3538 |
| HETATM | 3447 | O | HOH | 77 | 14.838 | 41.703 | 18.071 | 1.00 | 35.41 | 1DIK3539 |
| HETATM | 3448 | O | HOH | 78 | 7.786 | 14.132 | 5.764 | 1.00 | 35.54 | 1DIK3540 |
| HETATM | 3449 | O | HOH | 79 | 14.772 | 24.028 | 31.196 | 1.00 | 35.79 | 1DIK3541 |
| HETATM | 3450 | O | HOH | 80 | -6.978 | 43.656 | 22.677 | 1.00 | 35.90 | 1DIK3542 |
| HETATM | 3451 | O | HOH | 81 | -10.032 | 8.600 | 15.243 | 1.00 | 36.00 | 1DIK3543 |
| HETATM | 3452 | O | HOH | 82 | 24.248 | 25.836 | 18.908 | 1.00 | 36.04 | 1DIK3544 |
| HETATM | 3453 | O | HOH | 83 | -9.437 | 28.721 | 1.634 | 1.00 | 36.20 | 1DIK3545 |
| HETATM | 3454 | O | HOH | 84 | -2.779 | 26.774 | 21.988 | 1.00 | 36.25 | 1DIK3546 |
| HETATM | 3455 | O | HOH | 85 | -20.467 | 37.474 | 17.552 | 1.00 | 36.27 | 1DIK3547 |
| HETATM | 3456 | O | HOH | 86 | 8.166 | 29.232 | 31.117 | 1.00 | 36.46 | 1DIK3548 |
| HETATM | 3457 | O | HOH | 87 | -26.538 | 28.576 | 41.161 | 1.00 | 36.47 | 1DIK3549 |
| HETATM | 3458 | O | HOH | 88 | -2.580 | 22.992 | 47.692 | 1.00 | 36.48 | 1DIK3550 |
| HETATM | 3459 | O | HOH | 89 | 12.366 | 14.284 | 9.003 | 1.00 | 36.58 | 1DIK3551 |
| HETATM | 3460 | O | HOH | 90 | -21.790 | 30.576 | 46.190 | 1.00 | 36.67 | 1DIK3552 |
| HETATM | 3461 | O | HOH | 91 | -15.282 | 25.935 | 33.446 | 1.00 | 36.75 | 1DIK3553 |
| HETATM | 3462 | O | HOH | 92 | 14.144 | 14.560 | 25.959 | 1.00 | 36.89 | 1DIK3554 |
| HETATM | 3463 | O | HOH | 93 | -1.689 | 11.245 | 32.455 | 1.00 | 36.99 | 1DIK3555 |
| HETATM | 3464 | O | HOH | 94 | -15.117 | 10.158 | 15.158 | 1.00 | 37.08 | 1DIK3556 |
| HETATM | 3465 | O | HOH | 95 | -14.135 | 46.511 | 18.743 | 1.00 | 37.17 | 1DIK3557 |
| HETATM | 3466 | O | HOH | 96 | -4.814 | 10.202 | 6.231 | 1.00 | 37.24 | 1DIK3558 |
| HETATM | 3467 | O | HOH | 97 | 7.946 | 31.148 | 35.040 | 1.00 | 37.53 | 1DIK3559 |
| HETATM | 3468 | O | HOH | 98 | -6.586 | 41.003 | 26.383 | 1.00 | 37.57 | 1DIK3560 |
| HETATM | 3469 | O | HOH | 99 | -19.902 | 18.883 | 33.687 | 1.00 | 37.74 | 1DIK3561 |
| HETATM | 3470 | O | HOH | 100 | -18.028 | 40.102 | 50.829 | 1.00 | 37.89 | 1DIK3562 |
| HETATM | 3471 | O | HOH | 101 | -13.315 | 28.183 | 35.513 | 1.00 | 38.10 | 1DIK3563 |
| HETATM | 3472 | O | HOH | 102 | -28.008 | 45.248 | 30.179 | 1.00 | 38.86 | 1DIK3564 |
| HETATM | 3473 | O | HOH | 103 | 0.486 | 39.943 | 46.308 | 1.00 | 39.11 | 1DIK3565 |
| HETATM | 3474 | O | HOH | 104 | -2.576 | 4.959 | 28.921 | 1.00 | 39.13 | 1DIK3566 |
| HETATM | 3475 | O | HOH | 105 | -25.042 | 47.163 | 37.757 | 1.00 | 39.65 | 1DIK3567 |
| HETATM | 3476 | O | HOH | 106 | -13.645 | 35.978 | 48.302 | 1.00 | 40.20 | 1DIK3568 |
| HETATM | 3477 | O | HOH | 107 | 14.699 | 38.630 | 20.218 | 1.00 | 40.52 | 1DIK3569 |

FIG. 8-54

```
HETATM  3478  O   HOH  108     -8.278  44.086  42.473  1.00 41.00      1DIK3570
HETATM  3479  O   HOH  109     -5.494  11.036  32.617  1.00 42.26      1DIK3571
HETATM  3480  O   HOH  110      9.842  15.499  12.296  1.00 43.26      1DIK3572
HETATM  3481  O   HOH  111    -16.929  18.595  14.159  1.00 43.73      1DIK3573
HETATM  3482  O   HOH  112     -2.958  42.099  16.177  1.00 43.99      1DIK3574
HETATM  3483  O   HOH  113    -20.129  25.973  11.583  1.00 44.43      1DIK3575
HETATM  3484  O   HOH  114      8.119  26.656  -2.650  1.00 44.66      1DIK3576
HETATM  3485  O   HOH  115     17.556  35.041   8.367  1.00 45.27      1DIK3577
HETATM  3486  S   SO4  201     18.476  17.347  10.473  1.00 98.34      1DIK3578
HETATM  3487  O1  SO4  201     17.123  18.013  10.311  1.00 96.57      1DIK3579
HETATM  3488  O2  SO4  201     18.756  16.524   9.233  1.00 97.48      1DIK3580
HETATM  3489  O3  SO4  201     18.472  16.383  11.631  1.00 95.71      1DIK3581
HETATM  3490  O4  SO4  201     19.535  18.422  10.640  1.00 95.40      1DIK3582
CONECT  3486 3490 3489 3488 3487                                       1DIK3583
CONECT  3487 3486                                                      1DIK3584
CONECT  3488 3486                                                      1DIK3585
CONECT  3489 3486                                                      1DIK3586
CONECT  3490 3486                                                      1DIK3587
MASTER        46    0    1    0    0    0    0 3488    1    5   34    1DIK3588
END                                                                    1DIK3589
```

FIG. 8-55

PRIMER SET A

| PRIMER Q27L s | 5' | CAT | CTA | TGG | GGC | C_TG | TAC | TCG | CCA | TTC | 3' |
|---|---|---|---|---|---|---|---|---|---|---|---|
| PRIMER Q27L as | 3' | GTA | GAT | ACC | CCG | GA_C | ATG | AGC | GGT | AAG | 5' |
| | | H | L | W | G | $L_{27}$ | Y | S | P | F | |

PRIMER SET B

| PRIMER Q274L s | 5' | TAC | AAC | TAC | CTT | C_TG | TCC | TTG | GGC | AAG | 3' |
|---|---|---|---|---|---|---|---|---|---|---|---|
| PRIMER Q274L as | 3' | ATG | TTG | ATG | GAA | GA_C | AGG | AAC | CCG | TTC | 5' |
| | | Y | N | Y | L | $L_{274}$ | S | L | G | K | |

PRIMER SET C

| PRIMER G277D s | 5' | CTT | CAG | TCC | TTG | GA_C | AAG | TAC | TAC | GGC | 3' |
|---|---|---|---|---|---|---|---|---|---|---|---|
| PRIMER G277D as | 3' | GAA | GTC | AGG | AAC | C_TG | TTC | ATG | ATG | CCG | 5' |
| | | L | Q | S | L | $D_{277}$ | K | Y | Y | G | |

PRIMER SET D

| PRIMER G277D* s | 5' | CTT | CTG | TCC | TTG | GA_C | AAG | TAC | TAC | GGC | 3' |
|---|---|---|---|---|---|---|---|---|---|---|---|
| PRIMER G277D* as | 3' | GAA | GAC | AGG | AAC | C_TG | TTC | ATG | ATG | CCG | 5' |
| | | L | $L_{274}$ | S | L | $D_{277}$ | K | Y | Y | G | |

PRIMER SET E

| PRIMER N340S s | 5' | TTT | TCA | CAC | GAC | A_GC | AGC | ATG | GTT | TCC | 3' |
|---|---|---|---|---|---|---|---|---|---|---|---|
| PRIMER N340S as | 3' | AAA | AGT | GTG | CTG | T_CG | TCG | TAC | CAA | AGG | 5' |
| | | F | S | H | D | $S_{340}$ | S | M | V | I | |

FIG. 14a-1

PRIMER SET F

| PRIMER G277K s | 5' | C CTT CAG TCC TTG AAG AAG TAC TAC GGC TAC | 3' |
| PRIMER G277K as | 3' | G GAA GTC AGG AAC TTC TTC ATG ATG CCG ATG | 5' |

L    Q    S    L    $K_{277}$    K    Y    Y    G    Y

PRIMER SET G

| PRIMER A205E s | 5' | GGA GAT GAG GTT GAG GCC AAT TTC ACT G | 3' |
| PRIMER A205E as | 3' | CCT CTA CTC CAA CTC CGG TTA AAG TGA C | 5' |

G    D    E    V    $E_{205}$    A    N    F    T

PRIMER SET H

| PRIMER Y282H s | 5' | AAG TAC TAC GGC CAC GGC GCA GGC AAC | 3' |
| PRIMER Y282H as | 3' | TTC ATG ATG CCG GTG CCG CGT CCG TTG | 5' |

K    Y    Y    G    $H_{282}$    G    A    G    N

PRIMER SET I

| PRIMER AvrII s | 5' | GAT ACG GTA GAC CTA GGG TAC CAG TGC | 3' |
| PRIMER AvrII as | 3' | CTA TGC CAT CTG GAT CCC ATG GTC ACG | 5' |

D    T    V    D    L    G    Y    Q    C

PRIMER SET J

| PRIMER S66D s | 5' | CGG TAC CCA ACC GAT TCG AAG AGC AAA AAG | 3' |
| PRIMER S66D as | 3' | GCC ATG GGT TGG CTA AGC TTC TCG TTT TTC | 5' |

R    Y    P    T    $D_{66}$    S    K    S    K    K

PRIMER SET K

| PRIMER S140Y/D141G s | 5' | GC GCC TCA GGC TAC GGC CGG GTT ATT GC | 3' |
| PRIMER S140Y/D141G as | 3' | CG CGG AGT CCG ATG CCG GCC CAA TAA CG | 5' |

PRIMER SET L

PRIMER S130N s      5'  CTG GCG CGC A<u>A</u>T GTG GTG CCG TTT ATT C    3'

PRIMER S130N as     3'  GAC CGC GCG T<u>T</u>A CAC CAC GGC AAA TAA G     5'

L  A  R  N$_{130}$ V  V  P  F  I

PRIMER SET M

PRIMER R129L/S130N s    5'  GCT CTG GCG C<u>T</u>C A<u>A</u>T GTG GTG CCG TTT ATT C   3'

PRIMER R129L/S130N as   3'  CGA GAC CGC G<u>A</u>G T<u>T</u>A CAC CAC GGC AAA TAA G    5'

A  L  A  L$_{129}$ N$_{130}$ V  V  P  F  I

PRIMER SET N

PRIMER K167G/R168Q s    5'  GAC CAT GGC TCC <u>GGA</u> C<u>AA</u> GCT ACG CCA G   3'

PRIMER K167G/R168Q as   3'  CTG GTA CCG AGG <u>CCT</u> G<u>TT</u> CGA TGC GGT C   5'

PRIMER SET O

FumG27-s 5'- CTA GGG TAC CAG TGC TCC CCT GCG ACT TCT CAT CTA TGG GGC GGA TAC TCG CCA TTC TTT TCG C - 3'

FumG27-as 3'- CC ATG GTC ACG AGG GGA CGC TGA AGA GTA GAT ACC CCG CCT ATG AGC GGT AAG AAA AGC GAG CT - 5'

PRIMER SET P

FumV27-s 5'- CTA GGG TAC CAG TGC TCC CCT GCG ACT TCT CAT CTA TGG GGC GTG TAC TCG CCA TTC TTT TCG C - 3'

FumV27-as 3'- CC ATG GTC ACG AGG GGA CGC TGA AGA GTA GAT ACC CCG CAC ATG AGC GGT AAG AAA AGC GAG CT - 5'

PRIMER SET Q

FumN27-s 5'- CTA GGG TAC CAG TGC TCC CCT GCG ACT TCT CAT CTA TGG GGC AAC TAC TCG CCA TTC TTT TCG C - 3'

FumN27-as 3'- CC ATG GTC ACG AGG GGA CGC TGA AGA GTA GAT ACC CCG TTG ATG AGC GGT AAG AAA AGC GAG CT - 5'

PRIMER SET R

FumI27-s 5'- CTA GGG TAC CAG TGC TCC CCT GCG ACT TCT CAT CTA TGG GGC ATC TAC TCG CCA TTC TTT TCG C - 3'

FumI27-as 3'- CC ATG GTC ACG AGG GGA CGC TGA AGA GTA GAT ACC CCG TAG ATG AGC GGT AAG AAA AGC GAG CT - 5'

PRIMER SET S

FumA27-s 5'- CTA GGG TAC CAG TGC TCC CCT GCG ACT TCT CAT CTA TGG GGC GCG TAC TCG CCA TTC TTT TCG C - 3'

FumA27-as 3'- CC ATG GTC ACG AGG GGA CGC TGA AGA GTA GAT ACC CCG CGC ATG AGC GGT AAG AAA AGC GAG CT - 5'

PRIMER SET T

FumT27-s 5'- CTA GGG TAC CAG TGC TCC CCT GCG ACT TCT CAT CTA TGG GGC ACG TAC TCG CCA TTC TTT TCG C - 3'

FumgT27-as 3'- CC ATG GTC ACG AGG GGA CGC TGA AGA GTA GAT ACC CCG TGC ATG AGC GGT AAG AAA AGC GAG CT - 5'

```
        1
#13073  MVTLTFLLSA AYLLSGRVSA APSS-----A GSKSCDTVDL GYQCSPATSH LWGQYSPFFS LEDELSVSSK LPKDCRITLV
#32722  .......... .......... ....-----. .......... .......... .......... .......... ..........
#58128  .......... .......... ....-----. .......... .......... .......... .......... ..........
#26906  .GA....... ..V....... M...-----. .......... ...G...... .......... .......... ..........
#32239  .......... .......... .-AG...GCSAGS ...A....E. .......... .......... .......D.. ....V.F...

81
#13073  QVLSRHGARY PTSSKSKKYK KLVTAIQANA TDFKGKFAFL KTYNYTLGAD DLTPFGEQQL VNSGIKFYQR YKALARSVVP
#32722  .......... .......... .......... .......... .......... .......... .......... ..........
#58128  .......... ..A....... .......... ....K..... .......... ......A... .......... ..........
#26906  .......... .......... .......... .......... ......E... .......... .......... .....K....
#32239  .......... .......... .......... .......... .......... .......... .......... ......G...

161
#13073  FIRASGSDRV IASGEKFIEG FQQAKLADPG ATNRAAPAIS VIIPESETFN NTLDHGVCTK FEASQLGDEV AANFTALFAP
#32722  .......... .......... .......... .......... .......... .......... .......... ..........
#58128  .......... .......... .......... ........NV .......... .......... .......... ..........
#26906  ...S...... .......... .......... .......... .......V.. .......... ....Y..... ..........
#32239  .......... .......... .......... .......... .......... ......S..N .......E.. ..........

241
#13073  DIRARAEKHL PGVTLTDEDV VSLMDMCSFD TVARTSDASQ LSPFCQLFTH NEWKKYNYLQ SLGKYYGYGA GNPLGPAQGI
#32722  .......... .......... .......... .......... .......... .......... .......... ..........
#58128  .......K.. .......Q.D .......... ...A..E... .......... .......... .......... ..........
#26906  .......... .......... .......... .......... ......AI.. .......... .....D.... ..........
#32239  ....I..... .......... .......... .......... .......... .......... .......... ..........
```

```
        321
#13073  GFTNELIARL TRSPVQDHTS TNSTLVSNPA TFPLNATMYV DFSHDNSMVS IFFALGLYNG TEPLSRTSVE SAKELDGYSA
#32722  .......... .......... .......... .......... .......... .......... .......G.. ..........
#58128  .......... .......... .......... .......... .......... .......... .......... ..........
#26906  .......... .......... ....N..... .......... ...D.D.... .......I.. .......... ..........
#32239  .......... .......... .......... .......... ......G.IP .....M.... ...Q..E... .T..SN....
                                                                                            400

401                                                                        470
#13073  SWVVPFGARA YFETMQCKSE KEPLVRALIN DRVVPLHGCD VDKLGRCKLN DFVKGLSWAR SGGNWGECFS
#32722  .......... .......... .......... .......... .......... .......... ..........
#58128  .......... .......... ....S..... .......... .......... .......... ..........
#26906  .......... .......... .......... .......... .......... .......... ..........
#32239  ..A....... .......... .......... .......A.. .......K.. .......... ....SEQS..
```

FIG. 23-2

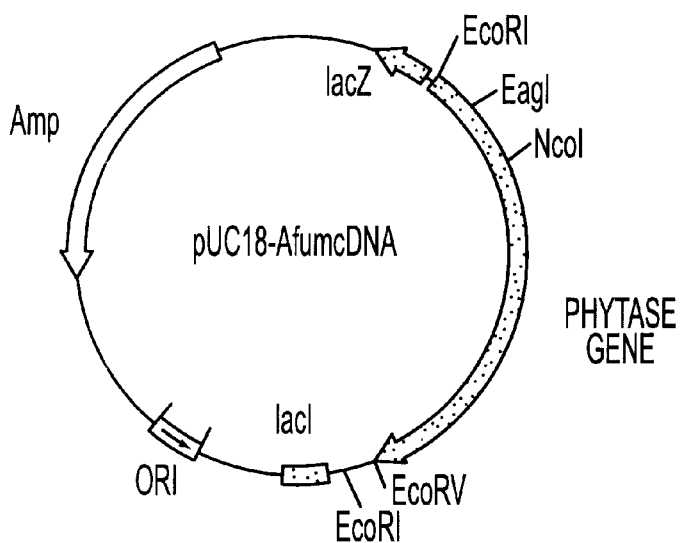
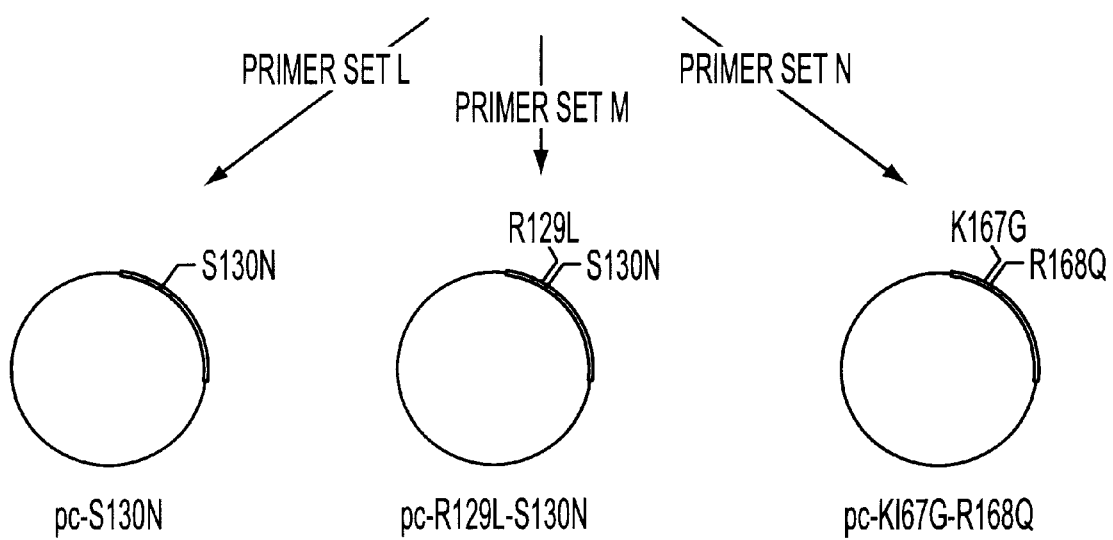
FIG. 26

MODIFIED PHYTASES

BACKGROUND OF THE INVENTION

Phytases (myo-inositol hexakisphosphate phosphohydrolases; EC 3.1.3.8) are enzymes that hydrolyze phytate (myo-inositol hexakisphosphate) to myo-inositol and inorganic phosphate and are known to be valuable feed additives.

A phytase was first described in rice bran in 1907 [Suzuki et al., Bull. Coll. Agr. Tokio Imp. Univ. 7, 495 (1907)] and phytases from Aspergillus species in 1911 [Dox and Golden, J. Biol. Chem. 10, 183–186 (1911)]. Phytases have also been found in wheat bran, plant seeds, animal intestines and in microorganisms [Howsen and Davis, Enzyme Microb. Technol. 5, 377–382 (1983), Lambrechts et al., Biotech. Lett. 14, 61–66 (1992), Shieh and Ware, Appl. Microbiol. 16, 1348–1351 (1968)].

The cloning and expression of the phytase from Aspergillus niger (ficuum) has been described by Van Hartingsveldt et al., in Gene, 127, 87–94 (1993) and in European Patent Application, Publication No. (EP) 420 358 and from Aspergillus niger var. awamori by Piddington et al., in Gene 133, 55–62 (1993).

Cloning, expression and purification of phytases with improved properties have been disclosed in EP 684 313. However, since there is a still ongoing need for further improved phytases, especially with respect to the activity properties, it is an object of the present invention to provide such improvements.

SUMMARY OF THE INVENTION

Accordingly, this invention is directed to a process for the production of a modified phytase with a desired property improved over the property of the corresponding unmodified phytase which comprises:

(a) determining the three dimensional structure of the unmodified phytase and of a second phytase which has the desired property by aligning the amino acid sequences of said phytases with the amino acid sequence of a third phytase which is the phytase of Aspergillus niger and using the three dimensional structure of the phytase of Aspergillus niger as a template based on the alignment to determine said three dimensional structures;

(b) determining from the structures of step (a) the amino acids of the active sites of the unmodified phytase and of the second phytase having the desired property which active site provides the desired property and comparing the amino acids which form the active sites to identify which amino acids are different in the active site of the second phytase from the amino acids in the active site of the unmodified phytase;

(c) constructing a DNA sequence coding for the modified phytase by obtaining the DNA sequence of the unmodified phytase and changing the nucleotides coding for the active site which provides the desired property for said unmodified phytase so that at least one of the amino acids in the active site which provides the desired property is substituted by one of the amino acids which was identified as being different in step (b);

(d) integrating such a DNA sequence into a vector capable of expression in a suitable host cell; and (e) transforming the suitable host cell by the DNA sequence of step (c) or the vector of step (d), growing said host cell under suitable growth conditions and isolating the modified phytase from the host cell or the culture medium.

Either or both of the unmodified phytase and the phytase with the desired property may be of eukaryotic origin, especially of fungal origin. Such phytases are preferably of Aspergillus origin, for example phytase from Aspergillus fumigatus. In a preferred process, the phytase with the desired property is a phytase from Aspergillus terreus. In another preferred process, the unmodified phytase is a phytase of Aspergillus fumigatus and the phytase with the desired property is the Aspergillus niger phytase. In yet another preferred process, the unmodified phytase is a phytase of Aspergillus fumigatus and the phytase with the desired property is the Aspergillus terreus phytase.

Also part of this invention is a modified phytase with a specific activity improved over the specific activity of the corresponding unmodified phytase (for example Aspergillus fumigatus) wherein the amino acid sequence of the corresponding unmodified phytase has been changed by one or more of deletion, substitution and addition by one or more amino acids to obtain the amino acid sequence of the modified phytase. A preferred phytase has an amino acid sequence homologous to that of the phytase of Aspergillus niger (SEQ ID NO. 1 and has an amino acid sequence that has been changed in at least one amino acid position selected from the following amino acid positions which correspond to positions of the amino acid sequence of the phytase of Aspergillus niger: 27, 66, 71, 103, 140, 141, 188, 205, 234, 235, 238, 274, 277, 282, 340 and 424, in particular wherein the amino acid position is selected from 27, 66, 140, 205, 274, 277, 282, and 340.

A preferred modified phytase has an amino acid sequence which has been changed at position 27 alone or in addition to other of the above positions, in particular at least at position 66 and/or position 140. Thus preferred phytases are modified at position 27 and 66 or 27 and 140.

For any such phytase, the amino acid at position 27 may be replaced by a specific amino acid selected from one of the following groups:

a) Ala, Val, Leu, Ile; or b) Thr; or c) Asn.

Particular modified phytases of this invention are characterized by at least one of the following changes in amino acids at positions: Q27L, Q27N, Q27T, Q27I, Q27V, Q27A, Q27G, S66D, S140Y, D141G, A205E, Q274L, G277D, G277K, Y282H and/or N340S.

Also part of this invention are polynucleotides comprising a DNA sequence coding for the modified phytases produced by the above method. Polynucleotides comprising DNA sequences coding for the phytases described above which are modified at particular amino acid positions are included.

Also included are vectors, especially expression vectors, which contain the polynucleotides of this invention, and host cells which contain these polynucleotides directly or within a vector.

Another aspect of this invention is a food or feed composition which contains modified phytases described above.

BRIEF DESCRIPTION OF THE FIGURES

FIG. 1: Primary sequence alignment of A. niger (ficuum), (SEQ ID NO:1) A. terreus cbs116.46 (SEQ ID NO:2) and A. fumigatus [ATCC 13073] (SEQ ID NO:3) phytase. Stars show identical residues within the active site and rectangles, non-identical residues within the active site.

FIG. 4: Complete coding sequence and encoded amino acid sequence of the Aspergillus nidulans phytase (SEQ ID NOS:4–6).

FIG. 5: Complete coding sequence (SEQ ID NO:7) and encoded amino acid sequence (SEQ ID NOs:8–9) of Talaromyces thermophilus phytase.

FIG. 6: Complete coding sequence (SEQ ID NO:10) and encoded amino acid sequence (SEQ ID NOs:11–12) of *Aspergillus fumigatus* [ATCC 13073] phytase.

FIG. 7: Complete coding sequence (SEQ ID NO:13) and encoded amino acid sequence (SEQ ID NOs:14–15) of *Aspergillus terreus* CBS 116.46 phytase.

FIG. 8: Crystallographic data of the structure of the *Aspergillus niger* phytase.

FIG. 14a: Primer sets A-N (SEQ ID NOs:24–65)used for site directed mutagenesis.

FIG. 14b: Primer sets O-T (SEQ ID NOs:66–77) used for site directed mutagenesis.

Open triangles: *A. fumigatus* [ATCC 13073] wild-type phytase; Open rhombs: *A. fumigatus* Q27G phytase; Filled squares: *A. fumigatus* Q27N phytase; Filled triangles: *A. fumigatus* Q27V phytase; Open squares: *A. fumigatus* Q27A phytase; Filled circles: *A. fumigatus* Q27I phytase; Open circles: *A. fumigatus* Q27T phytase; Dashed line: *A. fumigatus* Q27L phytase.

Figure 21:
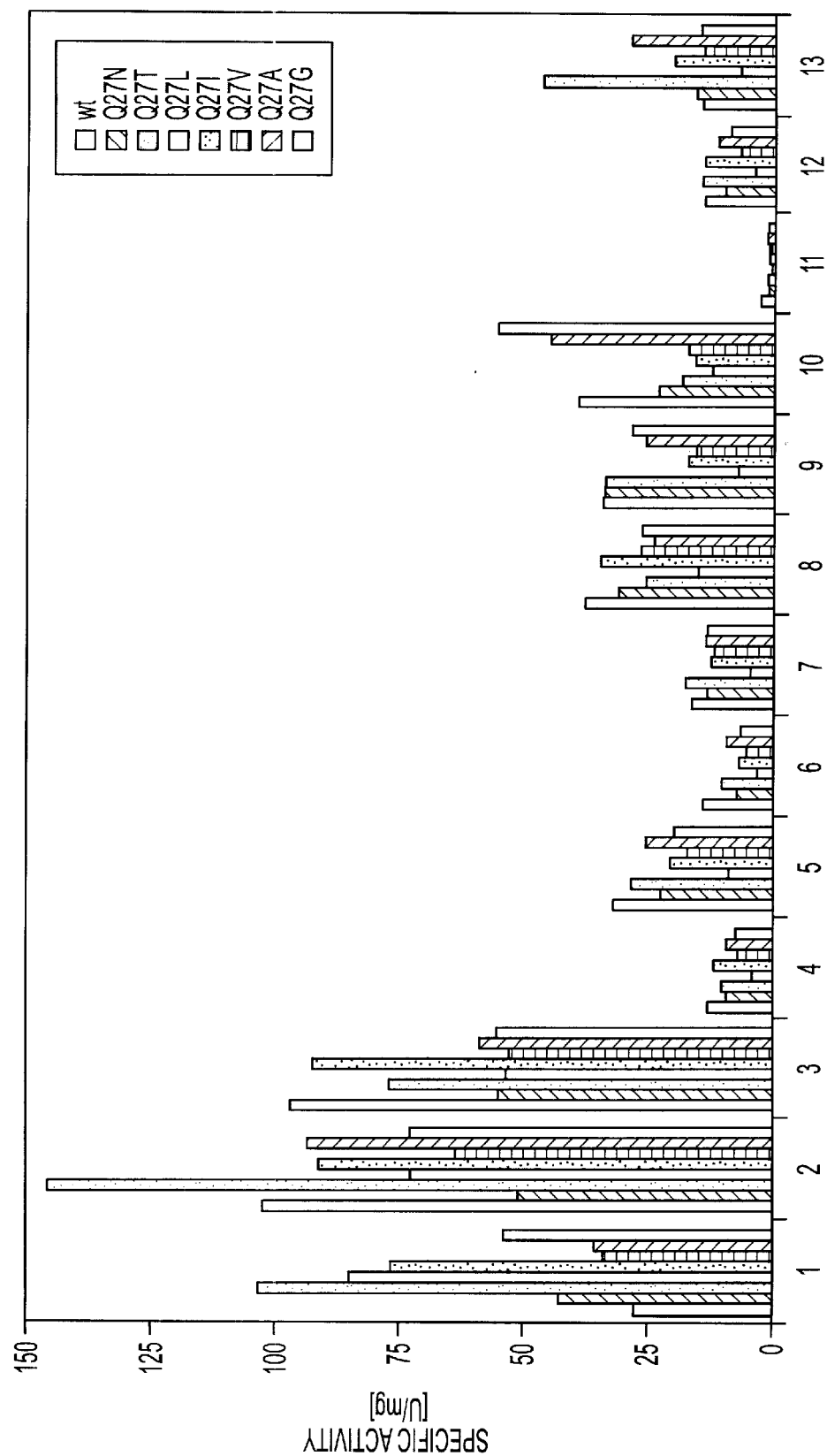

FIG. 21: Substrate specificities of wild-type and mutant *A. fumigatus* [ATCC 13073] phytases. The used substrates 1–13 are the same as mentioned in FIG. 3.

The specific activities of the different phytases with any one of the 13 substrates tested are given in the following order (from left to right): *A. fumigatus* wild-type phytase, *A. fumigatus* Q27N phytase, *A. fumigatus* Q27T phytase, *A. fumigatus* Q27L phytase, *A. fumigatus* Q27I phytase, *A. fumigatus* Q27V phytase, *A. fumigatus* Q27A phytase, *A. fumigatus* Q27G phytase.

Figure 22:
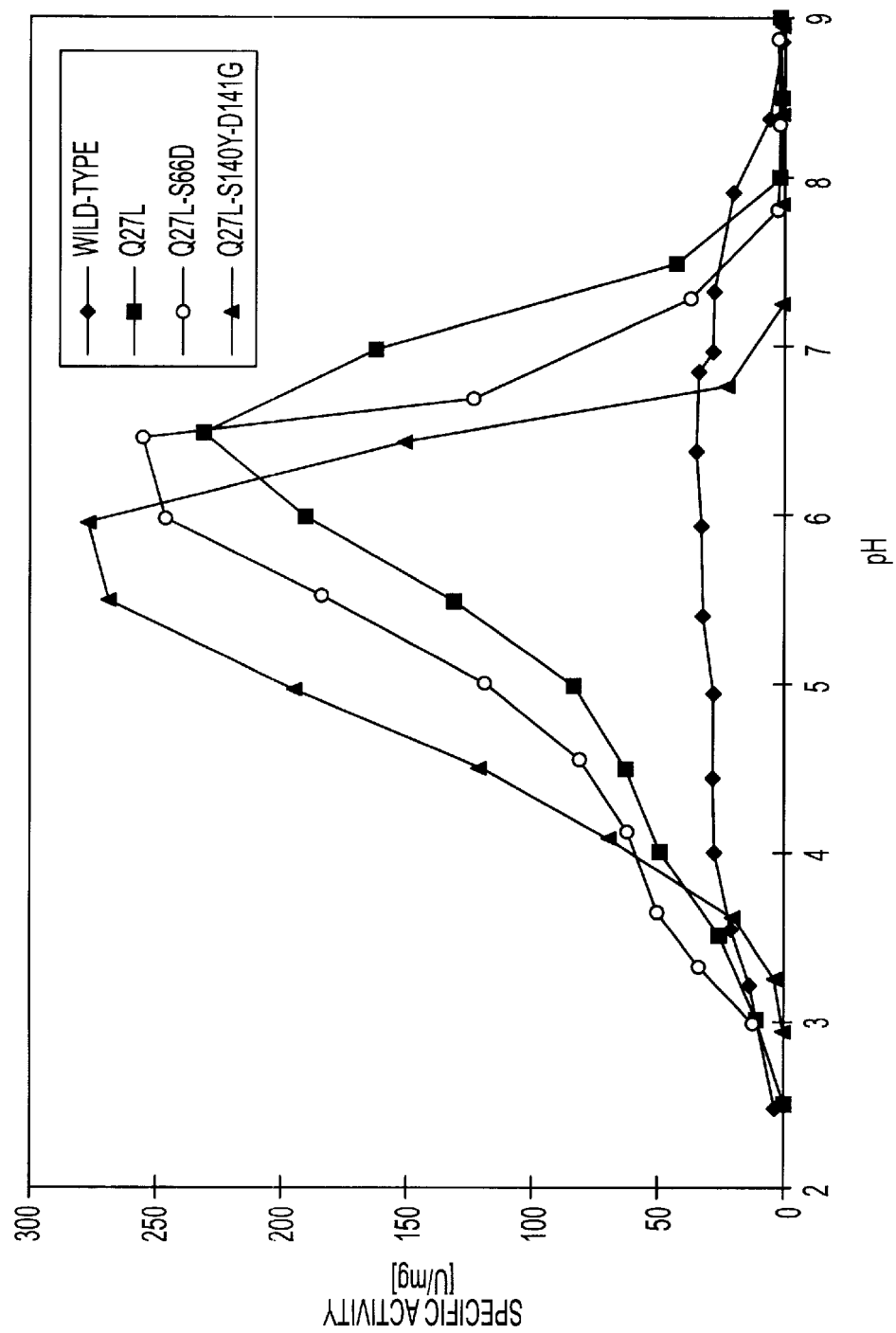

FIG. 22: pH optima curves. Specific activity of wild-type and mutant *A. fumigatus* [ATCC 13073] phytases is plotted against pH of incubation.

Filled rhombs: *A. fumigatus* wild-type phytase; Filled squares: *A. fumigatus* Q27L single mutant; Open circles: *A. fumigatus* Q27L-S66D double mutant; Filled triangles: *A. fumigatus* Q27L-S140Y-D141G triple mutant.

FIG. 23: Natural variation of phytases in different isolates of *A. fumigatus* [ATCC 13073]. The predicted protein sequences (SEQ ID NO:78–82) are shown and compared to that of the phytase from *A. fumigatus* strain ATCC 13073. Only the amino acids which differ from those in #13073 are shown.

Figure 24:
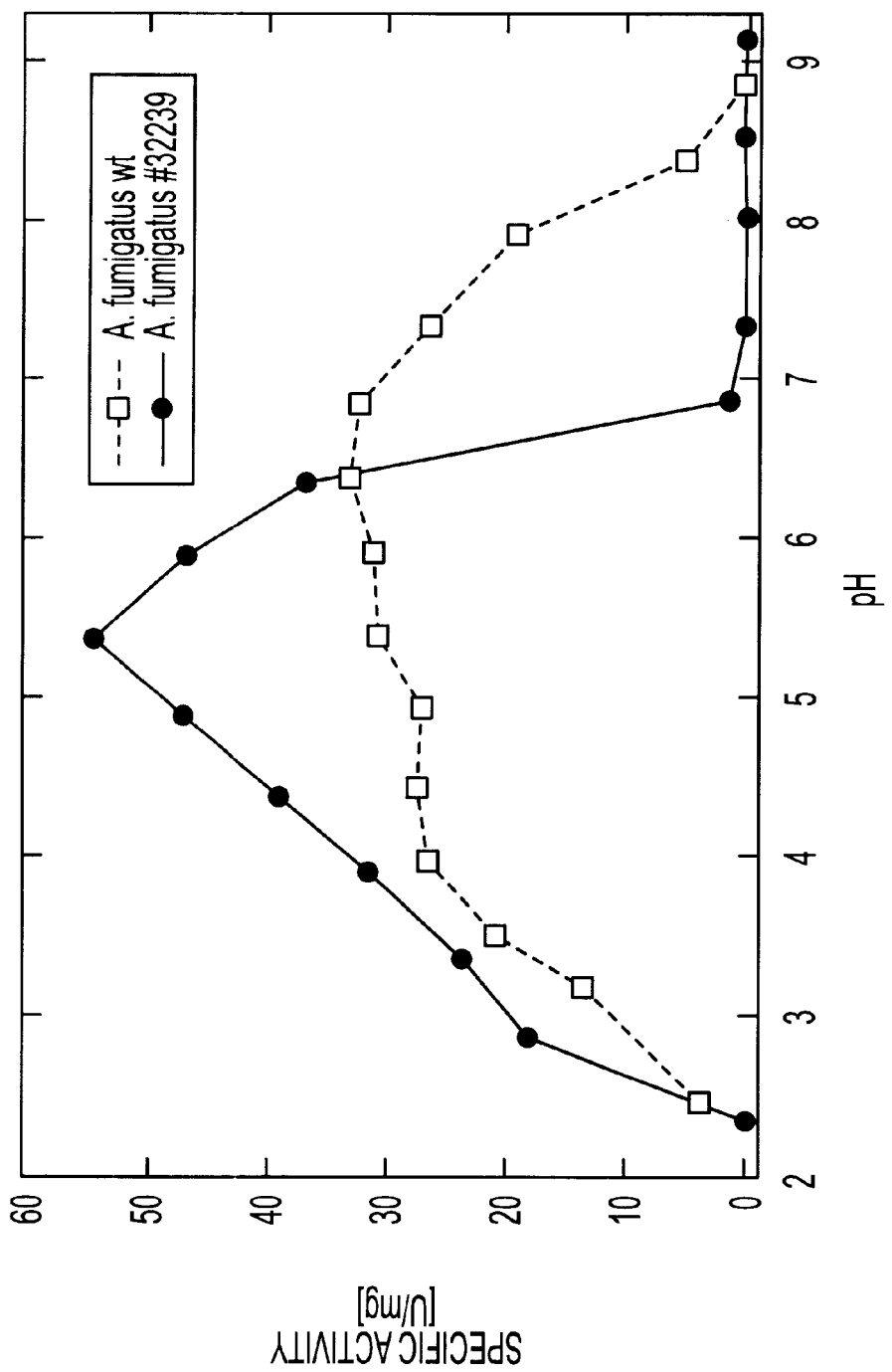

FIG. 24: pH dependent specific activity of phytases isolated from two different *A. fumigatus* wildtype strains. Open squares: wild-type strain ATCC 13073; Filled circles: strain ATCC 32239.

Figure 25:
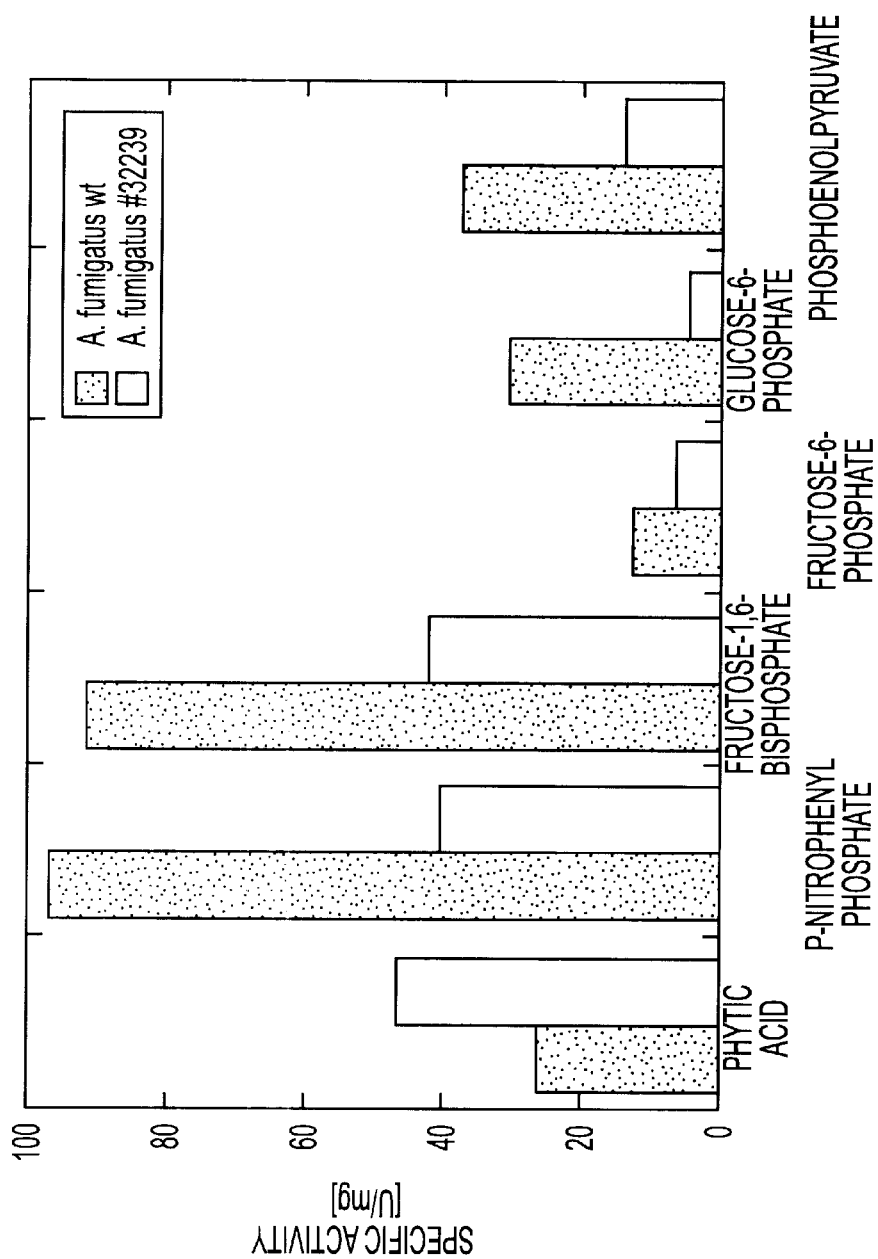

FIG. 25: Substrate specificities of phytases isolated from two different *A. fumigatus* wildtype strains. Black bars: wild-type strain ATCC 13073; White bars: strain ATCC 32239.

FIG. 26: Construction of plasmids pc-S13ON, pc-R129L-S13ON, pc-K167G-R168Q.

DETAILED DESCRIPTION OF THE INVENTION

The process of this invention allows the production of a modified phytase with improved activity by using structural information about phytases to design the improvement. First, the three dimensional structure of the phytase to be modified and, optionally of another phytase with activity properties which are more favorable than the ones of the phytase to be modified is/are computer modelled on the basis of the three dimensional structure of the phytase of *Aspergillus niger* (ficuum). Then, the structure of the active sites of the phytase to be modified and of the phytase with the more favorable activity properties are compared and those amino acid residues in both active sites which are different are identified, after which a DNA sequence coding for a modified phytase is constructed by changing the nucleotides coding for at least one of the amino acids by which both active sites differ. The modified phytase is then obtained by integrating such a DNA sequence into a vector capable of expression in a suitable host cell, transforming a suitable host cell by the DNA sequence or the vector, growing the host cell under suitable growth conditions and isolating the modified phytase from the host cell or the culture medium by methods known in the state of the art.

As stated above, this process is particularly useful where the phytase to be modified is of eukaryotic, preferably fungal, more preferably Aspergillus, e.g. *Aspergillus fumigatus* origin and the phytase with more favorable activity properties is of eukaryotic, preferably fungal, more preferably Aspergillus, e.g. *Aspergillus niger* or *Aspergillus terreus* (*Aspergillus terreus* cbs 116.46 or 9A1) origin, or the phytase to be modified is a phytase of *Aspergillus fumigatus* and the phytase with the more favorable activity properties is the Aspergillus terre us phytase or the phytase of *Aspergillus niger*.

Thus, the unmodified phytase (for example a wild-type phytase) which has a property to be improved, and the phytase which has that property in an improved version (i.e. the desired property which the modified phytase will be designed to possess) may be derived from any known source of phytases. Various plants and microorganisms are known to produce phytases [e.g. reviewed in Wodzinski, R. J. and Ullah, H. J., Advances in Applied Microbiology 42, 263 (1996)]. Thus any enzyme which may be isolated by conventional methods and determined to be a phytase by standard assays (see e.g. EP 420 358) is a suitable phytase for this invention. Sequence and structure information for such phytases may be obtained by conventional techniques or from publicly available databases.

Preferred phytases are those isolated from fungi such as Aspergillus species [Shieh, T. R. and Ware, J. H. Appl. Microbiology 16, 1348 (1968); Yamada et al., Agr. Biol. Chem. 32, 1275 (1968);Van Hartingsveldt et al., in Gene, 127, 87–94 (1993), European Patent Application, Publication No. (EP) 420 358, Piddington et al., in Gene 133, 55–62 (1993); Wodzinski, R. J. and Ullah, H. J. (s.a.) and Mitchell et al., Microbiology 143, 245 (1997)]. Aspergillus are well known fungi commonly isolated from natural sources by conventional methods. In addition, Aspergillus species may be obtained from depositories.

Once such a fungus is obtained, DNA expressing its phytase can be isolated by conventional methods [see Mitchell et al., Microbiology 143:245 (1997) Van Hartingsweldt et al. (s.a.); Dox and Golden (s.a.); EP 420 358; Piddington et al (s.a.) and WO 94/03612] (for example cloned, expressed, and assayed by phytase activity assays to obtain a clone expressing the phytase) for use in this invention. Specifically, the phytase DNA can be used to isolat the phytase, whose amino acid sequence and three-dimensional structures can also be obtained by known methods, such as crystallography or computer modelling. Alternatively, the phytase may be isolated by conventional methods for isolating proteins such as enzymes, and analyzed as described. Also, DNA and amino acid sequences may be obtained from publicly available databases.

Although other three-dimensional phytase structures may be obtained and used, it is preferred to use the three-dimensional of the *Aspergillus niger* phytase in the process of this invention (see Kostrewa et al., Nature Structural Biology 4:185 (1997) or of Aspergillus fumigatus. A useful strain of *Aspergillus niger* may be obtained from the American Type Culture Collection [address] under accession number ATCC 9142. Like any three-dimensional phytase structure useful in this invention, the three-dimensional structure of the *A. niger* phytase is obtained by techniques known to a skilled practitioner. Based on an amino acid sequence such as the *A. niger* amino acid sequence provided herein, (SEQ ID NO:1) computer programs can provide theoretical structures. Crystal structures can also be obtained, as in Example 1 below. From these three-dimensional structures, active sites can be defined, such as the part of the phytase which interacts with substrate. This active site can then be localized to the segment or segments of the amino acid sequence which together form the active site, which segment or segments can then be modified, the whole sequence expressed as a modified phytase which is then tested to see if the activity has been improved. By this means a desired property can be designed into an unmodified phytase, using the three dimensional structure of the *A. niger* phytase as a template based on the alignment.

Specifically, the structure of *A. niger* is analyzed to find out which amino acid residues form the active site which determines specific activity. Then, the amino acid sequence of an unmodified phytase with a given specific activity and that of a phytase which has a desired property, e.g. a higher specific activity, are aligned homologous (as defined below) to that of *A. niger* to provide a best fit, and the amino acid residues which correspond to the *A. niger* active site in the other phytases are determined and compared, to identify which amino acids are different in the active site of the phytase with the desired property. The active site amino acid residues of the unmodified phytase may then be changed by known methods to duplicate some or all of the active site amino acid residues of the phytase with the desired property. The modified phytase is then obtained by known methods (for example determining the DNA sequence, mutating the sequence to provide the desired amino acid sequence, and expressing the resulting protein), and is tested by assays for the desired property, e.g. specific activity, to confirm that the desired property is present.

In this context it should be mentioned that another possibility for producing phytases with improved properties is by isolating phytases from the same organism, like for example the Aspergillus ficuum, but different strains which can be found in nature and have been deposited by any of the known depository authorities. Their amino acid sequences can be determined by cloning their corresponding DNA sequences by methods as described, e.g. in European Patent Application No. (EP) 684 313. Once such sequences have been defined they can be modeled on the basis of the three-dimensional structure of the *A. niger* phytase and the active sites of both sequences can be compared to find out whether such phytase should have improved activity properties (see Example 8) or both active site sequences can be compared directly and than tested for increased and/or improved activity by the assays described in the present application.

It is furthermore an object of the present invention to provide a modified phytase which is obtainable by a process as described above.

It is in general an object of the present invention to provide a phytase which has been modified in a way that its activity property is more favorable than the one of the non-modified phytase, specifically such a phytase characterized therein that the amino acid sequence of the non-modified phytase has been changed by deletion, substitution and/or addition of one or more amino acids, more specifically such a phytase wherein changes have been made at at least one position which is homologous to one of the following positions of the amino acid sequence of the phytase of Aspergillus (*A.*) *niger* (see FIG. 1): 27, 66, 71, 103, 140, 141, 188, 205, 234, 235, 238, 274, 277, 282, 340 and/or 424, preferably 27, 66, 140, 205, 274, 277, 282 and/or 340, and even more specifically such a phytase which is the phytase of eukaryotic, preferably fungal, more preferably Aspergillus and most preferably *Aspergillus fumigatus*, origin.

It is furthermore an object of the present invention to provide such a phytase wherein at position 27 or at least at position 27 a change occurs, preferably a phytase wherein the amino acid at position 27 is replaced by one selected from one of the following groups:

a) Ala, Val, Leu, Ile; or b) Thr or c) Asn; and furthermore such a phytase wherein in addition to position 27 a change occurs also at position 66 or wherein in addition to position 27 a change occurs also at position 140 and/or at positions 274 and/or 277.

It is also an object of the present invention to provide a phytase as specified above which is characterized by at least one of the following mutations: Q27L, Q27N, Q27T, Q27I, Q27V, Q27A, Q27G, S66D, S140Y, D141G, A205E, Q274L, G277D, G277K, Y282H and/or N340S.

It is furthermore an object of the present invention to provide phytase muteins which are resistant against degradation by proteases of fungal, preferably Aspergillus and most preferably *Aspergillus niger* (ficuum) origin. Such muteins are characterized therein that at least at one of the following positions (which refers to the homologous position in the amino acid sequence of *A. niger*), namely position 130 or 129 and 130, preferably of the *Aspergillus fumigatus* or 167, 168 preferably of the *A. nidulans* phytase amino acid sequence, the amino acid which is present in the wild type sequence has been replaced against another amino acid which is known to change the protease sensitivity, e.g. in the case of *A. fumigatus* at position 130 from "S" to "N" and at position 129 from "R" to "L" and in case of *A. nidulans* at position 167 from "K" to "G" and at position 168 from R to Q. Such positions can be also combined with those providing for improved activity properties.

A desired property to be integrated into an unmodified phytase by sequence modification as described herein, may be a new property not present in the unmodified phytase, or may preferably be an existing property of the unmodified phytase which is to be improved, for example a specific activity over a broader pH range than in the unmodified phytase. The active site of the phytases is the part of the phytase which is the physical structure which provides all or part of the property. For example the binding site of the phytase provides the property of substrate specificity. Other parts of the phytase may have an influence on a given property, however the active site is the part which changes the property upon modification as described.

In this context a desired property which is to be improved, or an improved activity property means any type of improvement of the activity of the modified phytase as compared to the unmodified. This could mean for example a higher specific activity, preferably at least two fold or more preferably at least 3 to 4 fold higher in an assay known in the state of the art to measure phytase activity, see e.g. in EP 684 313 or described in the examples of the present application. Furthermore this could mean a different substrate specificity determined in an assay known in the state of the art or as described e.g. in the specific examples of the present invention. This could also mean a maximum of the specific activity at a different more favorable pH or a broad pH optimum ("improved pH profile") determined by an assay as known in the state of the art or as described e.g. in the examples. This also could mean improved resistance to protease degradation, as described above. Finally this could also mean any combination of such properties.

Figure 1:
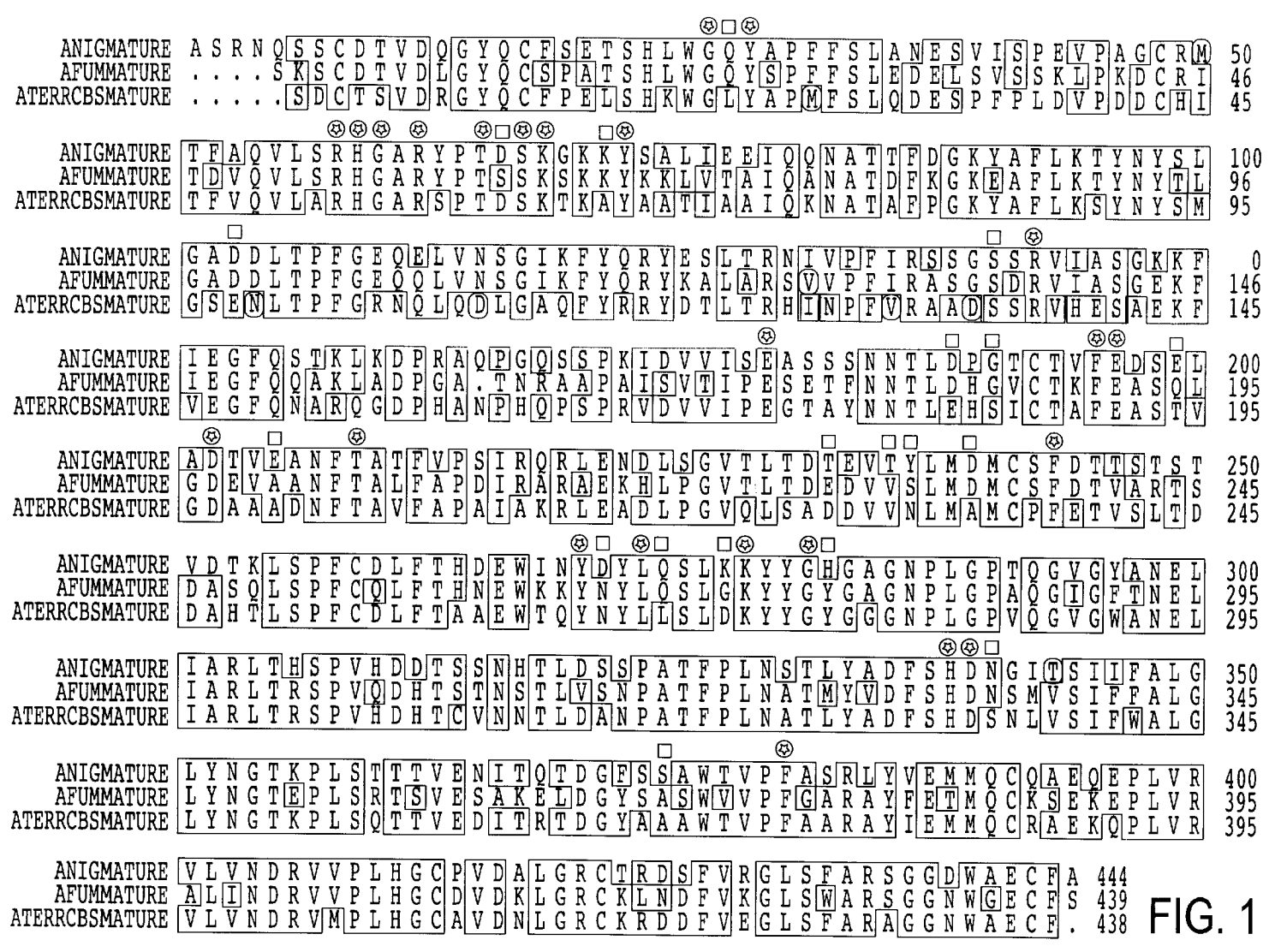

"Homologous" in the context of the present invention means the best fit of the primary, preferably also secondary and most preferably also tertiary structure of the phytase to be modified and the phytase of *Aspergillus niger*. How such best fit can be obtained is described in detail in Example 1 of the present invention. FIG. 1 gives an example of such best fit for the phytase amino acid sequences of *Aspergillus fumigatus* and *Aspergillus terreus* aligned on the basis of the *Aspergillus niger* amino acid sequence which latter sequence is also used as the reference to which the positions of the other sequences, e.g. the ones named before, are referred to. Furthermore the modified *Aspergillus fumigatus* phytase with the Q27L mutation, means nothing else than the phytase of *Aspergillus fumigatus* wherein at position 27 according to the assignment as defined above (which is in fact position 23 of the *Aspergillus fumigatus* amino acid sequence) the naturally occurring glutamine ("Q" refers to the standard UPAC one letter amino acid code) has been replaced by leucine ("L"). All muteins of the present invention are designated in this way independent from whether they are protease resistant muteins or muteins with improved activity properties.

Constructing a polynucleotide comprising a DNA sequence coding for the modified phytase whose amino acid sequence was obtained as described above is performed by known methods such as those described below. The nucleotides coding for the active site which provides the desired property are changed so that at least one of the amino acids now encoded corresponds to an amino acid which is different in the active site of the unmodified phytase and the active site of the phytase which has the desired property. Integrating such a polynucleotide into vectors and host cells so as to express the modified phytase is also part of this invention and may be accomplished by known methods and as described below.

Thus it is furthermore an object of the present invention to provide a polynucleotide comprising a DNA sequence coding for a phytase as described above, a vector, preferably an expression vector, comprising such a polynucleotide, a host cell which has been transformed by such a polynucleotide or vector, a process for the preparation of a phytase of the present invention wherein the host cell as described before is cultured under suitable culture conditions and the phytase is isolated from such host cell or the culture medium by methods known in the art, and a food or feed composition comprising a phytase of the present invention.

In this context it should be noted that it is also an object of the present invention to provide a DNA sequence which codes for a phytase carrying at least one of the specific mutations of the present invention and which hybridizes under standard conditions with the DNA sequences of the specific modified phytases of the present invention or a DNA sequence which, because of the degeneracy of the genetic code does not hybridize but which codes for a polypeptide with exactly the same amino acid sequence as the one encoded by the DNA sequence to which it does not hybridize or a DNA sequence which is a fragment of such DNA sequences which maintains the activity properties of the polypeptide of which it is a fragment.

"Standard conditions" for hybridization mean in the context the conditions which are generally used by a person skilled in the art to detect specific hybridization signals and which are described, e.g. by Sambrook et al., "Molecular Cloning", second edition, Cold Spring Harbor Laboratory Press 1989, New York, or preferably so called stringent hybridization and non-stringent washing conditions or more preferably so called stringent hybridization and stringent washing conditions a person skilled in the art is familiar with and which are described, e.g. in Sambrook et al. (s.a.).

It is furthermore an object of the present invention to provide a DNA sequence which can be obtained by the so called polymerase chain reaction method ("PCR") by PCR primers designed on the basis of the specifically described DNA sequences of the present invention. It is understood that the so obtained DNA sequences code for phytases with at least the same mutation as the ones from which they are designed and show comparable activity properties.

The principles of the polymerase chain reaction (PCR) method are outlined e.g. by White et al., Trends in Genetics, 5, 185–189 (1989), whereas improved methods are described e.g. in Innis et al. [PCR Protocols: A guide to Methods and Applications, Academic Press, Inc. (1990)].

DNA sequences of the present invention can be constructed starting from genomic or cDNA sequences coding for phytases known in the state of the art [for sequence information see references mentioned above, e.g. EP 684 313 or sequence data bases, for example like Genbank (Intelligenetics, California, USA), European Bioinformatics Institute (Hinston Hall, Cambridge, GB), NBRF (Georgetown University, Medical Centre, Washington DC, USA) and Vecbase (University of Wisconsin, Biotechnology Centre, Madison, Wis., USA) or disclosed in the figures by methods of in vitro mutagenesis [see e.g. Sambrook et al., Molecular Cloning, Cold Spring Harbor Laboratory Press, New York]. A widely used strategy for such "site directed mutagenesis", as originally outlined by Hurchinson and Edgell [J. Virol. 8, 181 (1971)], involves the annealing of a synthetic oligonucleotide carrying the desired nucleotide substitution to a target region of a single-stranded DNA sequence wherein the mutation should be introduced [for review see Smith, Annu. Rev. Genet. 19, 423 (1985) and for improved methods see references 2–6 in Stanssen et al., Nucl. Acid Res., 17, 4441–4454 (1989)]. Another possibility of mutating a given DNA sequence which is also preferred for the practice of the present invention is the mutagenesis by using the polymerase chain reaction (PCR). DNA as starting material can be isolated by methods known in the art and described e.g. in Sambrook et al. (Molecular Cloning) from the respective strains. For strain information see, e.g. EP 684 313 or any depository authority indicated below. *Aspergillus niger* [ATCC 9142], *Myceliophthora thermophila* [ATCC 48102], *Talaromyces thermophilus* [ATCC 20186] and *Aspergillus fumigatus* [ATCC 34625] have been redeposited on Mar. 14, 1997 according to the conditions of the Budapest Treaty at the American Type Culture Cell Collection under the following accession numbers: ATCC 74337, ATCC 74340, ATCC 74338 and ATCC 74339, respectively. It is however, understood that DNA encoding a phytase to be mutated in accordance with the present invention can also be prepared on the basis of a known DNA sequence, e.g. as shown in FIG. 6 in a synthetic manner and described e.g. in EP 747 483 by methods known in the art.

Once complete DNA sequences of the present invention have been obtained they can be integrated into vectors by methods known in the art and described e.g. in Sambrook et al. (s.a.) to overexpress the encoded polypeptide in appropriate host systems. However, a man skilled in the art knows that also the DNA sequences themselves can be used to transform the suitable host systems of the invention to get overexpression of the encoded polypeptide. Appropriate host systems are for example fungi, like Aspergilli, e.g. *Aspergillus niger* [ATCC 9142] or *Aspergillus ficuum* [NRRL 3135] or like Trichoderma, e.g. Trichoderma reesei or yeasts, like Saccharomyces, e.g. Saccharomyces cerevisiae or Pichia, like Pichia pastoris, or Hansenula polymorpha, e.g. H. polymorpha (DSM5215). A man skilled in the art knows that such microorganisms are available from depository authorities, e.g. the American Type Culture Collection (ATCC), the Centraalbureau voor Schimmelcultures (CBS) or the Deutsche Sammlung fair Mikroorganismen und Zellkulturen GmbH (DSM) or any other depository authority as listed in the Journal "Industrial Property" [(1991) 1, pages 29–40]. Bacteria which can be used are e.g. *E. coli*, Bacilli as, e.g. *Bacillus subtilis* or Streptomyces, e.g. *Streptomyces lividans* (see e.g. Anne and Mallaert in FEMS Microbiol. Letters 114, 121 (1993). *E. coli*, which could be used are *E. coli* K12 strains e.g. M15 [described as DZ 291 by Villarejo et al. in J. Bacteriol. 120, 466–474 (1974)], HB 101 [ATCC No. 33694] or *E. coli* SG13009 [Gottesman et al., J. Bacteriol. 148, 265–273 (1981)].

Vectors which can be used for expression in fungi are known in the art and described e.g. in EP 420 358, or by Cullen et al. [Bio/Technology 5, 369–376 (1987)] or Ward in Molecular Industrial Mycology, Systems and Applications for Filamentous Fungi, Marcel Dekker, New York (1991), Upshall et al. [Bio/Technology 5, 1301–1304 (1987)] Gwynne et al. [Bio/Technology 5, 71–79 (1987)], Punt et al. [J. Biotechnol. 17, 19–34 (1991)] and for yeast by Sreekrishna et al. [J. Basic Microbiol. 28, 265–278 (1988), Biochemistry 28, 4117–4125 (1989)], Hitzemann et al. [Nature 293, 717–722 (1981)] or in EP 183 070, EP 183 071, EP 248 227, EP 263 311. Suitable vectors which can be used for expression in *E. coli* are mentioned, e.g. by Sambrook et al. [s.a.] or by Fiers et al. in Procd. 8th Int. Biotechnology Symposium" [Soc. Franc. de Microbiol., Paris (Durand et al., eds.), pp. 680–697 (1988)] or by Bujard et al. in Methods in Enzymology, eds. Wu and Grossmann, Academic Press, Inc. Vol. 155, 416–433 (1987) and Stüber et al. in Immunological Methods, eds. Lefkovits and Pernis, Academic Press, Inc., Vol. IV, 121–152 (1990). Vectors which could be used for expression in Bacilli are known in the art and described, e.g. in EP 405 370, Procd. Natl. Acad. Sci. USA 81, 439 (1984) by Yansura and Henner, Meth. Enzymol. 185, 199–228 (1990) or EP 207 459. Vectors which can be used for the expression in H. Polymorpha are known in the art and described, e.g. in Gellissen et al., Biotechnology 9, 291–295 (1991).

Either such vectors already carry regulatory elements, e.g. promotors, or the DNA sequences of the present invention can be engineered to contain such elements. Suitable promotor elements which can be used are known in the art and are, e.g. for Trichoderma reesei the cbh1- [Haarki et al., Biotechnology 7, 596–600 (1989)] or the pkil-promotor [Schindler et al., Gene 130, 271–275 (1993)], for Aspergillus oryzae the amy-promotor [Christensen et al., Abstr. 19th Lunteren Lectures on Molecular Genetics F23 (1987), Christensen et al., Biotechnology 6, 1419–1422 (1988), Tada et al., Mol. Gen. Genet. 229, 301 (1991)], for *Aspergillus niger* the glaA- [Cullen et al., Bio/Technology 5, 369–376 (1987), Gwynne et al., Bio/Technology 5, 713–719 (1987), Ward in Molecular Industrial Mycology, Systems and Applications for Filamentous Fungi, Marcel Dekker, New York, 83–106 (1991)], alcA- [Gwynne et al., Bio/Technology 5, 718–719 (1987)], suc1- [Boddy et al., Curr. Genet. 24, 60–66 (1993)], aphA- [MacRae et al., Gene 71, 339–348 (1988), MacRae et al., Gene 132, 193–198 (1993)], tpiA- [McKnight et al., Cell 46, 143–147 (1986), Upshall et al., Bio/Technology 5, 1301–1304 (1987)], gpdA-[Punt et al., Gene 69, 49–57 (1988), Punt et al., J. Biotechnol. 17, 19–37 (1991)] and the pkiA-promotor [de Graaff et al., Curr. Genet. 22, 21–27 (1992)]. Suitable promotor elements which could be used for expression in yeast are known in the art and are, e.g. the pho5-promotor [Vogel et al., Mol. Cell. Biol., 2050–2057 (1989); Rudolf and Hinnen, Proc. Natl. Acad. Sci. 84, 1340–1344 (1987)] or the gap-promotor for expression in *Saccharomyces cerevisiae* and for *Pichia pastoris*, e.g. the aoxl-promotor [Koutz et al., Yeast 5, 167–177 (1989); Sreekrishna et al., J. Basic Microbiol. 28, 265–278 (1988)], or the FMD promoter [Hollenberg et al., EPA No. 0299108] or MOX-promotor [Ledeboer et al., Nucleic Acids Res. 13, 3063–3082 (1985)] for H. polymorpha.

Accordingly vectors comprising DNA sequences of the present invention, preferably for the expression of said DNA sequences in bacteria or a fungal or a yeast host and such transformed bacteria or fungal or yeast hosts are also an object of the present invention.

Once such DNA sequences have been expressed in an appropriate host cell in a suitable medium the encoded phytase can be isolated either from the medium in the case the phytase is secreted into the medium or from the host organism in case such phytase is present intracellularly by methods known in the art of protein purification or described, e.g. in EP 420 358 Known methods of protein purification may be used to isolate the phytases of this invention. For example various types of chromatography may be used individually or in combination. Gel purification may also be used. Accordingly a process for the preparation of a polypeptide of the present invention characterized in that transformed bacteria or a host cell as described above is cultured under suitable culture conditions and the polypeptide is recovered therefrom and a polypeptide when produced by such a process or a polypeptide encoded by a DNA sequence of the present invention are also an object of the present invention.

Phytases of the present invention can be also expressed in plants according to methods as described, e.g. by Pen et al. in Bio/Technology 11, 811–814 (1994) or in EP 449 375, preferably in seeds as described, e.g. in EP 449 376.

For example, a DNA sequence encoding a phytase of the present invention can be placed under the control of regulatory sequences from the gene encoding the 12S storage protein cruciferin from *Brassica napus*. The construct is thereafter subcloned into a binary vector such as pMOG23 (in *E. coli* K-12 strain DH5α, deposited at the Centraal Bureau voor Schimmelcultures, Baarn, The Netherlands under accession number CBS 102.90). This vector is introduced into *Agrobacterium tumefaciens* which contains a disarmed Ti plasmid. Bacterial cells containing this contruct are co-cultivated with tissues from tobacco or Brassica plants, and transformed plant cells are selected by nutrient media containing antibiotics and induced to regenerate into differentiated plants on such media. The resulting plants will produce seeds that contain and express the DNA contruct. Or the phytase-encoding DNA sequence can be placed under the control of regulatory sequences from the 35S promoter of Cauliflower Mosaic Virus (CaMV). The contruct is thereafter subcloned into a binary vector. This vector is then introduced into *Agrobacterium tumefaciens* which contains a disarmed Ti plasmid. Bacterial cells containing this construct are cocultivated with tissues from tobacco or Brassica plants, and transformed plant cells are selected by nutrient media containing antibiotics and induced to regenerate into differentiated plants on such media. The resulting plants contain and express the DNA construct constitutively.

The plant or plant part containing phytase can be used directly for the preparation of a feed composition or can be extracted from plants or plant organs by methods known in the art. Accordingly it is also an object of the present invention to provide a process for the production of the phytases of the present invention in plants or plant organs, like seeds, the phytases when produced by such methods, the transformed plants and plant organs, like seeds itself.

Once obtained the polypeptides of the present invention (which include modified phytases as described and active fragments thereof, and fusion proteins which include the phytases or fragments, or proteins which have stabilized by other moieties such as conjugation with polyalkylene glycols and such) can be characterized regarding their properties which make them useful in agriculture any assay known in the art and described e.g. by Simons et al. [Br. J. Nutr. 64, 525–540 (1990)], Schöner et al. [J. Anim. Physiol. a. Anim. Nutr. 66, 248–255 (1991)], Vogt [Arch. Geflügelk. 56, 93–98 (1992)], Jongbloed et al. [J. Anim. Sci., 70, 1159–1168 (1992)], Perney et al. [Poultry Sci. 72, 2106–2114 (1993)], Farrell et al., [J. Anim. Physiol. a. Anim. Nutr. 69, 278–283 (1993), Broz et al., [Br. Poultry Sci. 35, 273–280 (1994)] and Düngelhoef et al. [Animal Feed Sci. Technol. 49, 1–10 (1994)] can be used.

In general the polypeptides of the present invention can be used without being limited to a specific field of application for the conversion of inositol polyphosphates, like phytate to inositol and inorganic phosphate. For example phytases can be used to increase the nutrient value of plant material in animal feed by liberating from it inorganic phosphate which otherwise would otherwise not be accessible to non-ruminants. This reduces the amount of phosphorous which must be added to feed as a supplement and also reduces the amount of phosphorous which is excreted. Thus, phytases of this invention which have improved properties will enhance this process, or impart new benefits.

Furthermore the polypeptides of the present invention can be used in a process for the preparation of compound food or feeds wherein the components of such a composition are mixed with one or more polypeptides of the present invention. Accordingly compound food or feeds comprising one or more polypeptides of the present invention are also an object of the present invention. A person skilled in the art is familiar with their process of preparation. A phytase of this invention may be added to the complete feed preparation or to any component or premix or pelleted component. The effect of the added phytase may be an improvement in food utilization by virtue of the improved property or properties of the phytase. For example a phytase may have improved heat resistance to resist degradation caused by the food preparation process, and/or may have improved specific activity to liberate more phosphorous, and/or to liberate phosphorous in a wider range of conditions. Other properties of the modified phytase which increase the value or stability or other properties of the feed are also contemplated. Such compound foods or feeds can further comprise additives or components generally used for such purpose and known in the state of the art.

It is furthermore an object of the present invention to provide a process for the reduction of levels of phytate in animal manure characterized in that an animal is fed such a feed composition in an amount effective in converting phytate contained in the feedstuff to inositol and inorganic phosphate.

EXAMPLES

Example 1

Homology Modeling of A. fumigatus and A. terreus cbs116.46 Phytase

The amino acid sequences of A. fumigatus [ATCC 13073] (see FIG. 1) and A. terreus cbs116.46 phytase (see FIG. 1) were compared with the sequence of A. niger (ficuum) phytase (see FIG. 1) for which the three-dimensional structure had been determined by X-ray crystallography. Crystallographic data are given in FIG. 8.

A multiple amino acid sequence alignment of A. niger (ficuum) phytase, A. fumigatus phytase and A. terreus cbs116.46 phytase was calculated with the program "PILEUP" (Prog. Menu for the Wisconsin Package, version 8, September 1994, Genetics Computer Group, 575 Science Drive, Madison Wis., USA 53711). The three-dimensional models of A. fumigatus phytase and A. terreus cbs116.46 phytase were built by using the structure of A. niger (ficuum) phytase as template and exchanging the amino acids of A. niger (ficuum) phytase according to the sequence alignment to amino acids of A. fumigatus and A. terreus cbs116.46 phytases, respectively. Model construction and energy optimization were performed by using the program Moloc (Gerber and Müller, 1995). C-alpha positions were kept fixed except for new insertions/deletions and in loop regions distant from the active site.

Only small differences of the modelled structures to the original crystal structure could be observed in external loops. Furthermore the different substrate molecules that mainly occur on the degradation pathway of phytic acid (myo-inositol-hexakisphosphate) by Pseudomonas sp. bacterium phytase and, as far as determined, by A. niger (ficuum) phytase (Cosgrove, 1980; FIG. 1) were constructed and forged into the active site cavity of each phytase structure. Each of these substrates was oriented in a hypothetical binding mode proposed for histidine acid phosphatases (Van Etten, 1982). The scissile phosphate group was oriented towards the catalytically essential His 59 to form the covalent phosphoenzyme intermediate. The oxygen of the substrate phosphoester bond which will be protonated by Asp 339 after cleavage was orientated towards the proton donor. Conformational relaxation of the remaining structural part of the substrates as well as the surrounding active site residues was performed by energy optimization with the program Moloc.

Based on the structure models the residues pointing into the active site cavity were identified. More than half (60%) of these positions were identical between these three phytases, whereas only few positions were not conserved (see FIG. 1). This observation could be extended to four additional phytase sequences (A. nidulans, A. terreus 9A1, Talaromyces thermophilus, Myceliophthora thermophila).

The results coming from sequence alignment and structural information including favourable enzyme-substrate interactions were combined to define the positions for mutational analysis which are shown in Table 1.

References

Gerber, P. and Müller, K. (1995) Moloc molecular modeling software. J. Comput. Aided Mol. Des. 9, 251–268

Van Etten, R. L. (1982) Human prostatic acid phosphatase: a histidine phosphatase. Ann. NY Acad. Sci. 390,27–50

Cosgrove, D. J. (1980) Inositol phosphates—their chemistry, biochemistry and physiology: studies in organic chemistry, chapter 4. Elsevier Scientific Publishing Company, Amsterdam, Oxford, N.Y.

Example 2

Construction of Plasmids pUC18-AfumgDNA and pUC18-AfumcDNA

Plasmids pUC18-AfumgDNA and pUC18-AfumcDNA, the basic constructs for all the A. fumigatus muteins described below were constructed as follows.

pUC18-AfumgDNA: The genomic DNA sequence of the phytase gene of Aspergillus fumigatus was obtained by PCR using the "Expand™ High Fidelity PCR Kit" (Boehringer Mannheim, Mannheim, Germany) with primers #39 and #40 (designed on the basis of the genomic sequence shown in FIG. 6) and genomic DNA of Aspergillus fumigatus [ATCC 13073] from the A. fumigatus (NIH stock 5233) genomic library in a Lambda FixII vector [Stratagene, Lugolla, Calif. 92037, USA; catalog No. 946055].

Primer #39:

```
                BspHI
5' TAT ATC ATG ATT ACT CTG ACT TTC CTG CTT TCG 3'  (SEQ ID NO:16)
         M   I   T   L   T   F   L   L   S         (SEQ ID NO:17)
```

Primer #40:

```
                                        EcoRV
3' CCT CTC ACG AAA TCA ACT CTA TAG ATA TAT 5' (SEQ ID NO:8)
    G   E   C   F   S   *                         (SEQ ID NO:19)
```

The reaction mix included 10 pmol of each primer and 200 ng of template DNA. 35 rounds of amplification were done with the following cycling values: 95° C., 1 min/56° C., 1 min/72° C., 90 sec. The PCR-amplified Aspergillus fumigatus mutein genes had a new BspHI site at the ATG start codon, introduced with primer #39, which resulted in the change of the second amino acid from a valine to an isoleucine. Furthermore, an EcoRV site was created with primer #40 downstream of the TGA termination codon of the gene.

The PCR fragment (approx. 1450 bp) was subsequently cloned into the SmaI site of pUC18 using the "sure clone Kit" (Boehringer Mannheim s.a.) according to the supplier's recommendations. The resulting plasmid was named pUC18-*AfumgDNA*.

pUC18-*AfumcDNA*: This plasmid lacks the intron (small gap letters in FIG. 6) of the *A. fumigatus* phytase gene and was constructed as outlined in FIG. 13. Briefly, using primers Fum28 and Fum11 the 5' end of exon 2 was amplified by PCR (see below), digested with NcoI and EagI (new restriction site introduced with primer Fum28) and ligated together with the linker coding for exon 1 made of primers Fum26 and Fum27 into the XbaI and NcoI sites of pUC18-*AfumgDNA*, thereby resulting in plasmid pUC18-*AfumcDNA*.

Fum28:

```
                                      (SEQ ID NO:20)
5' ATATATCGGCCGAGTGTCTGCGGCACCTAGT 3'
        EagI
```

Fum11:
5' TGAGGTCATCCGCACCCAGAG 3' (SEQ ID NO:20)

Fum26:
5' CTAGAATTCATGGTGACTCTGACTTTC-CTGCTTTCGGCGGCGTATCT GCTTTCC 3'(SEQ ID NO:22)

Fum27:
5' GGC C GGAAAGCAGATACGCCGCCGAAAG-CAGGAAAGTCAGAGTC ACCATGAATT 3' (SEQ ID NO:23)

PCR reaction to get 5' end of exon 2 of the *A. fumigatus* phytase:

| | |
|---|---|
| 2 μl | template: pUC18-AfumgDNA (20 ng) |
| 1 μl | dNTP's-mix (Boehringer Mannheim s.a.) |
| 5 μl | 10x Buffer |
| 1 μl | Taq polymerase (Boehringer Mannheim s.a.) |
| 1.9 μl | Fum11 (= 10 pmol) |
| 2 μl | Fum28 (= 10 pmol) |
| 37,1 μl | H$_2$O |

In total 35 cycles with the temperature profile: 95° C. for 30 sec/56° C. for 30 sec/72° C. for 45 sec were made. The amplified fragment (approx. 330 bp) was extracted once with an equal volume of phenol/chloroform (1:1). To the recovered aqueous phase 0.1 volume of 3 M sodium acetate, pH 4.8 and 2.5 volumes of ethanol were added. The mixture was centrifuged for 10 min at 12000 g and the pellet resuspended in 20 μl of H$_2$O. Subsequently, the purified fragment was digested with NcoI and EagI and processed as outlined above.

Example 3

Construction of Muteins of the Phytase of *Aspergillus fumigatus* for Expression in *A. niger*

Figure 15:
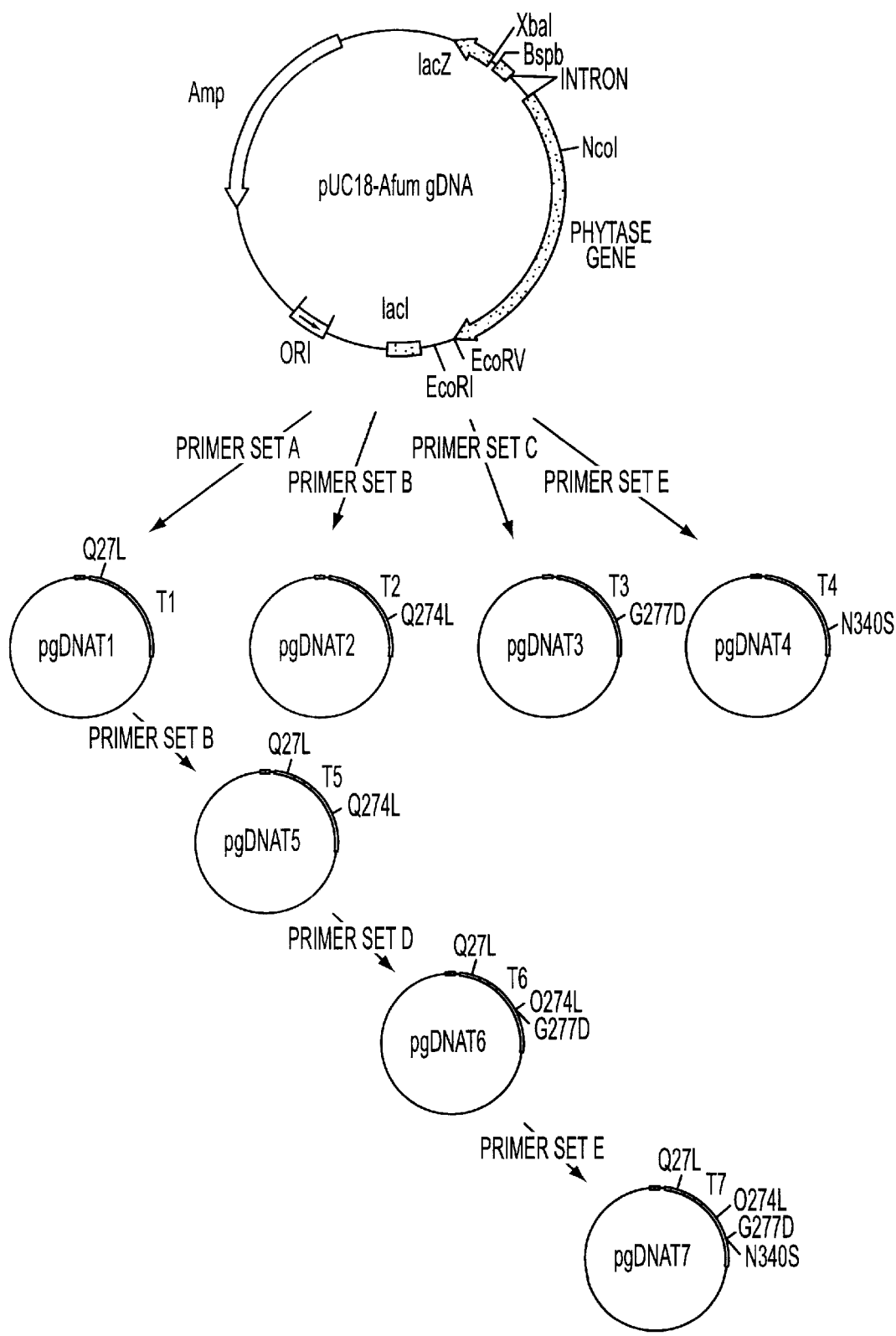
FIG. 15: Construction of plasmids pgDNAT1-pgDNAT7.
Figure 16:
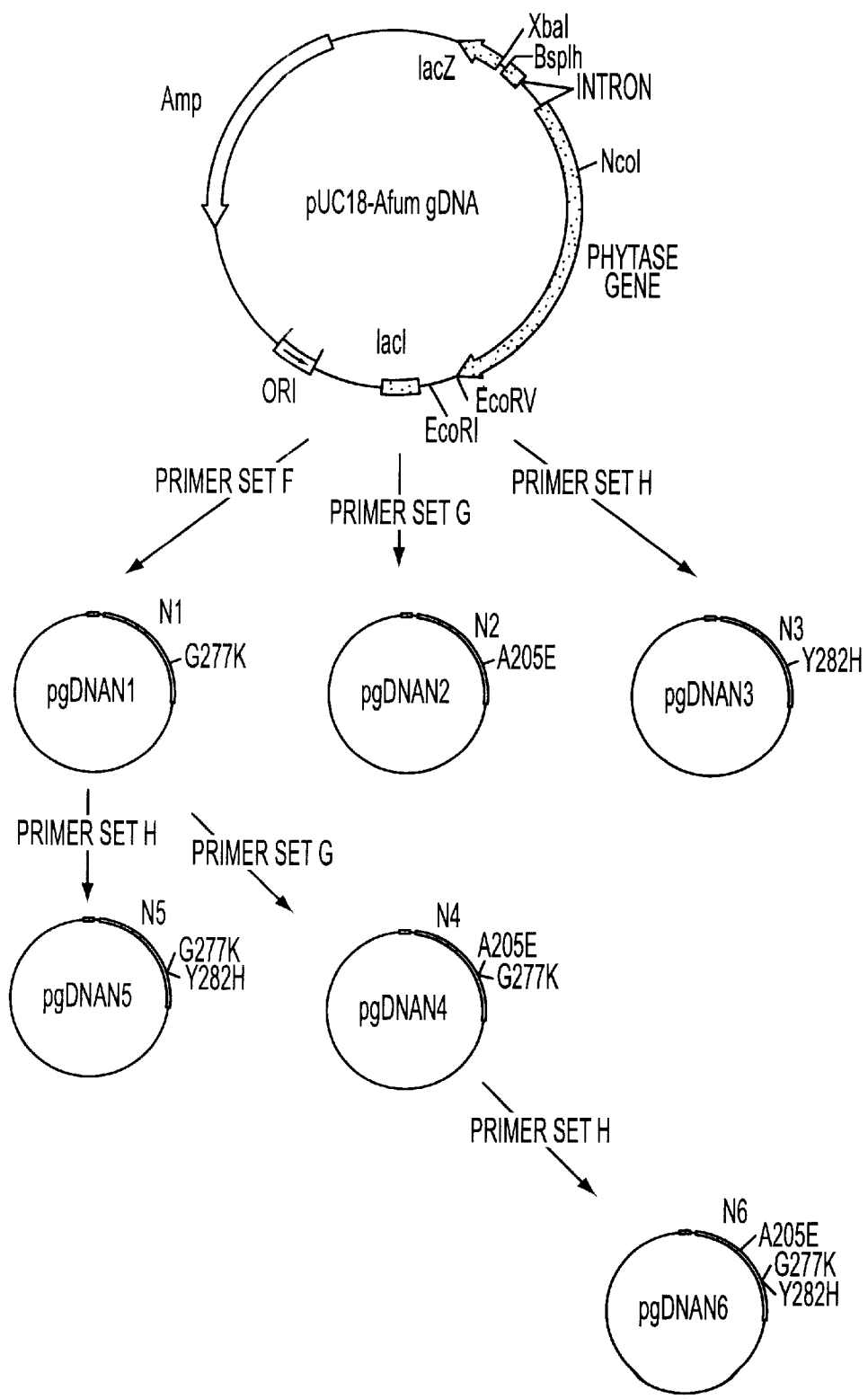
FIG. 16: Construction of plasmids pgDNAN1-pgDNAN6.

To construct all muteins for the expression in *A. niger*, plasmid pUC18-*AfumgDNA* was used as template for site-directed mutagenesis. Mutations were introduced using the "quick exchange site-directed mutagenesis kit" from Stratagene (La Jolla, Calif., USA) following the manufacturer's protocol and using the corresponding primers (FIG. 14). All mutations made are summarized in Table 1A and B wherein T1 to T7 and N1 to N6, respectively, refer to the muteins and "Mutation" to the amino acids replaced at such position. For example T5 refers to a mutein with a double mutation: L at position 27 for Q and L at position 274 for Q. The primer sets (A–H) used to introduce the corresponding mutations are shown in FIG. 14*a*. The newly introduced amino acid is shown in bold and the subscript indicates the position in the mature *Aspergillus fumigatus* enzyme concerning to the numbering of the *A. niger* amino acid sequence. FIGS. 15 and 16 outline the scheme for the construction of different plasmids pgT1–pgT7 and pgN1–pgN6 encoding the muteins carrying only one mutation (T1–T4; N1–N3) or more mutations (T5–T7; N4–N6). Clones harboring the desired mutations were identified by DNA sequence analysis as known in the art. The mutated phytases were verified by complete sequencing of the genes.

Example 4

Construction of Muteins of the Phytase of *Aspergillus fumigatus* for Expression in *Saccharomyces cerevisiae*

Figure 13:
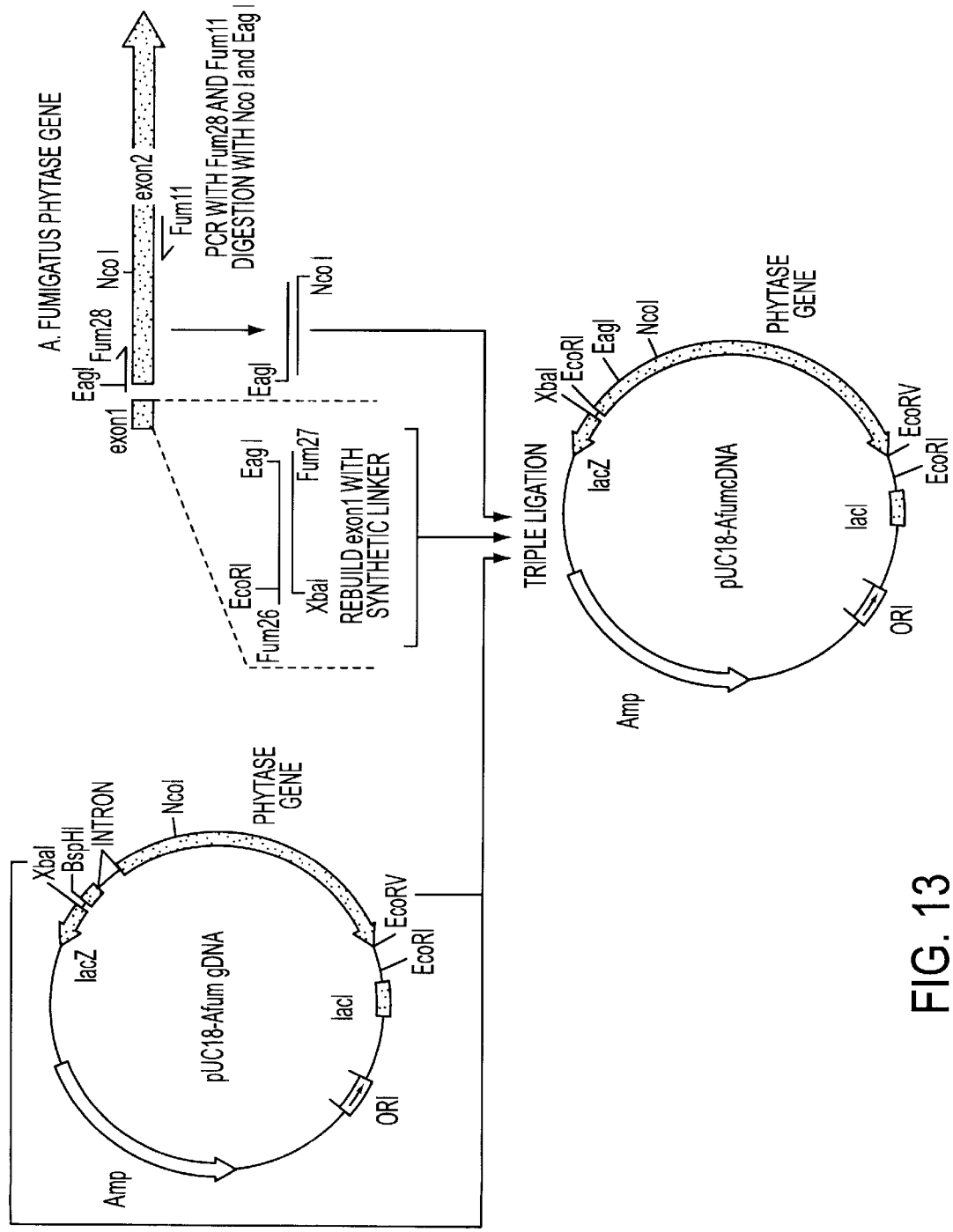
FIG. 13: Construction of the basic plasmids pUC18-*Afum*gDNA and pUC18-*Afum*cDNA for site directed mutagenesis.
Figure 17A:
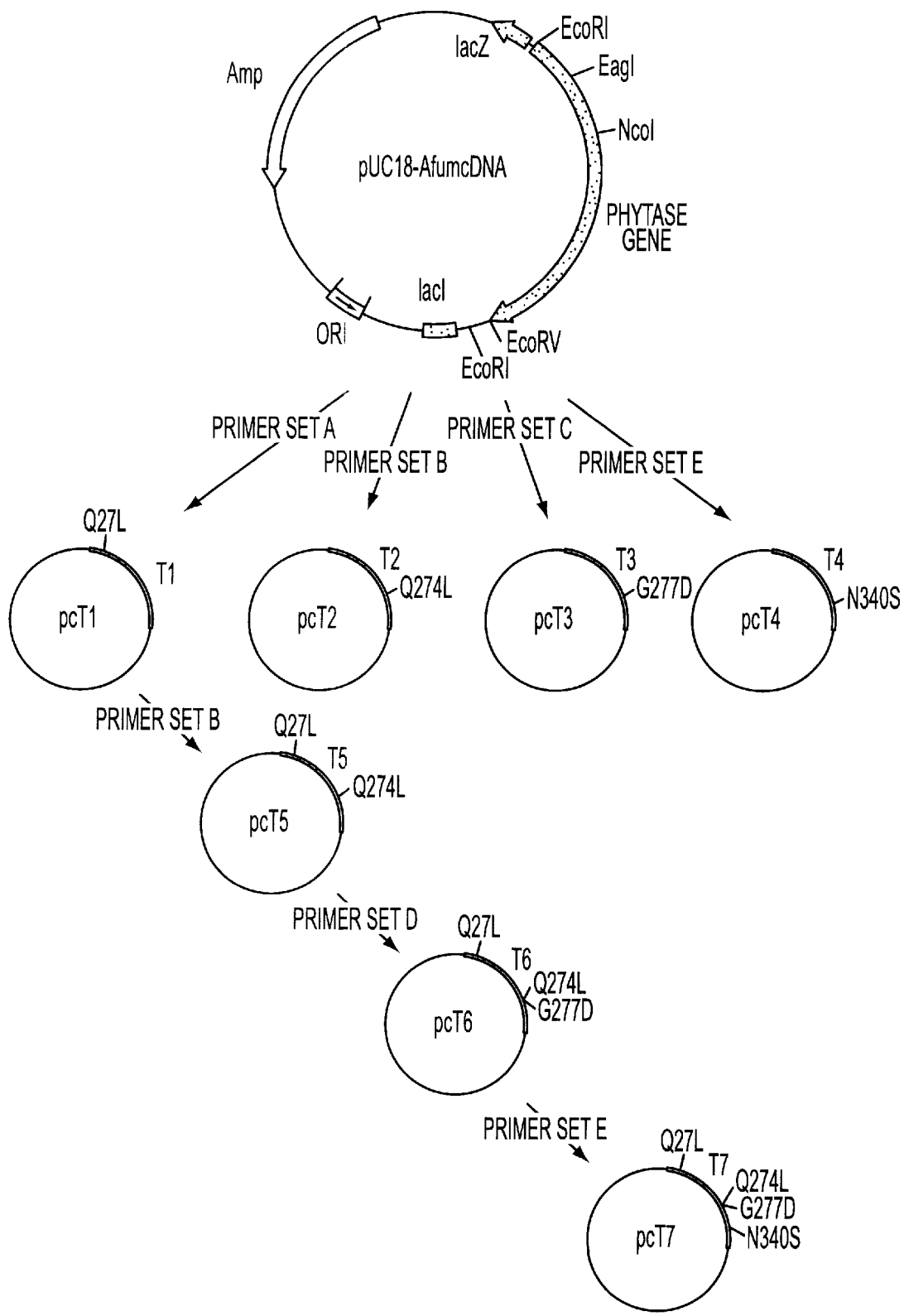
FIG. 17a: Construction of plasmids pcT1-pcT7.
Figure 18:
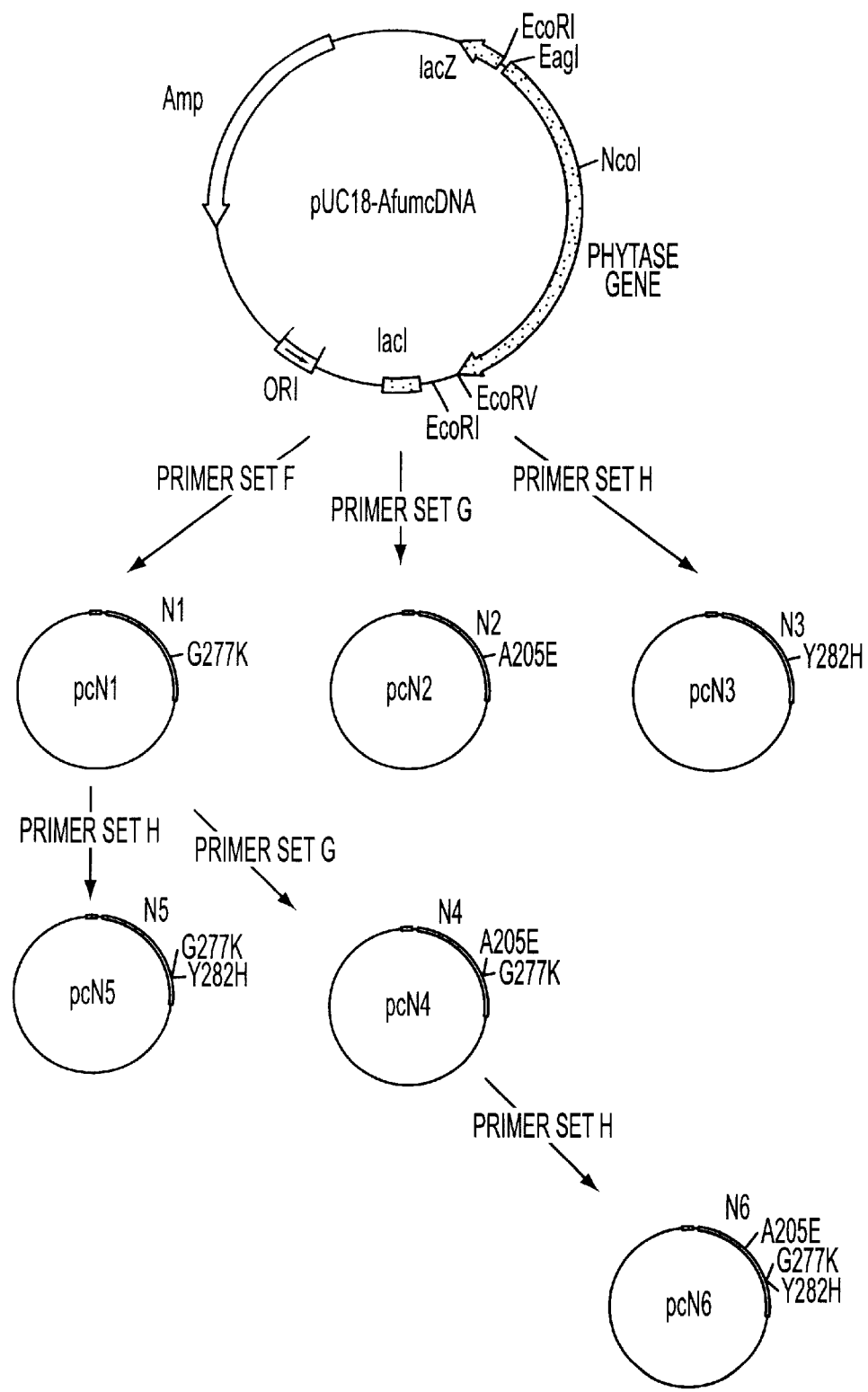
FIG. 18: Construction of plasmids pcN1-pcN6.

Construction of plasmids pcT1–pcT7 (FIG. 17*a*) and pcN1–pcN6 (FIG. 18), respectively, encoding the muteins T1–T7 and N1–N6 for the expression in *S. cerevisiae* was basically done as outlined in Example 3. Instead of using pUC18-*AfumgDNA* as the basic construct to introduce the mutations, plasmid pUC18-*AfumeDNA* was used (FIG. 13).

Figure 17B:
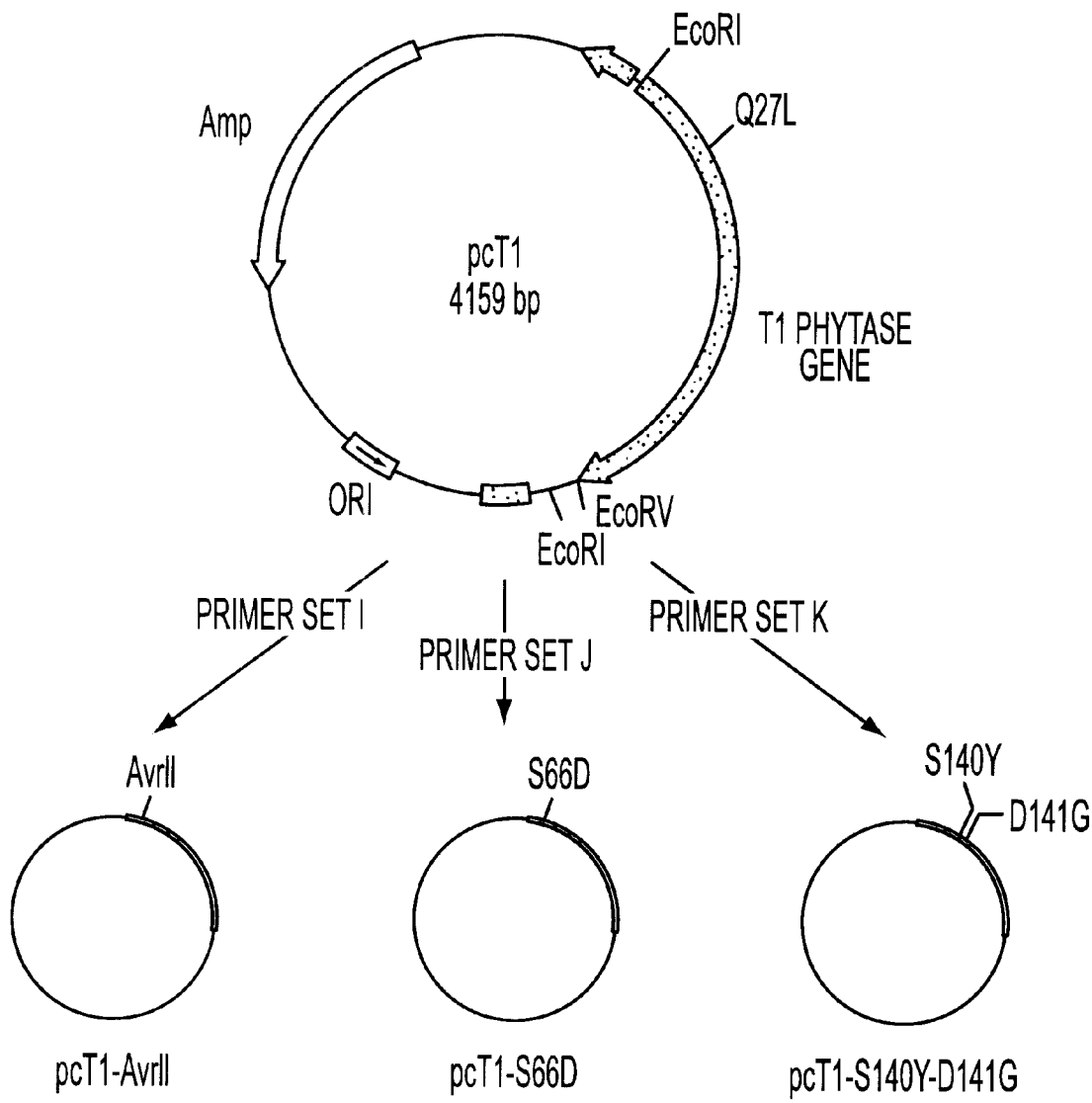
FIG. 17b: Construction of plasmids pcT1-AvrII, pcT1-S66D and pcT1-S140Y-D141G
Figure 17C:
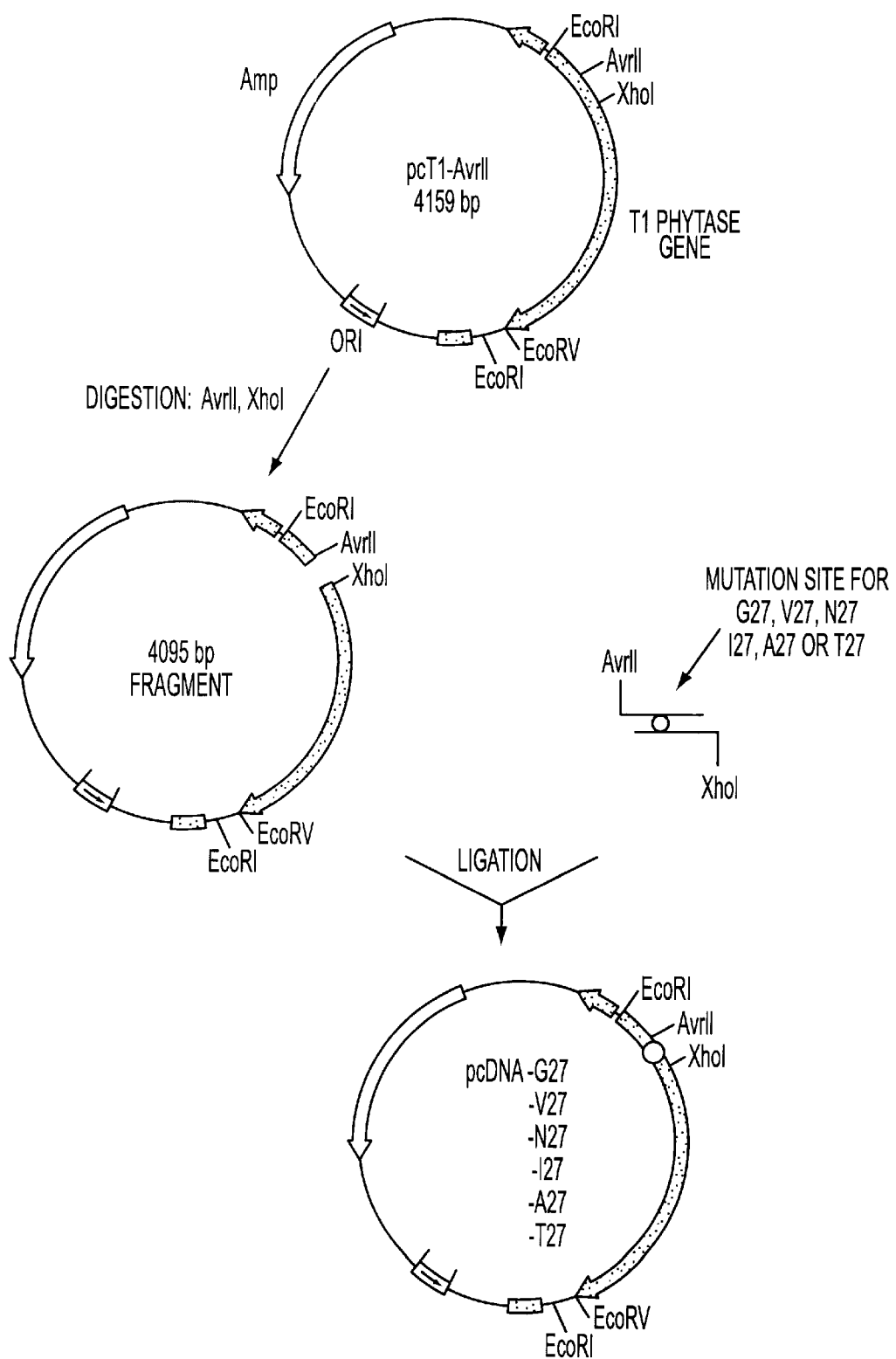
FIG. 17c: Construction of plasmids pcDNA-N27, -T27, -I27, -V27, -A27, -G27 .

The plasmids pcDNA-N27, -G27, -V27, -A27, -I27 and -T27 encoding the muteins N27, G27, V27, A27, I27 and T27 were constructed as follows:

A silent restriction site for AvrII was introduced into plasmid pcT1 by site directed mutagenesis as described in Example 3 using primer set I (FIG. 14*a*; FIG. 17*b*). The *A. fumigatus* phytase gene fragment AvrII/XhoI was then replaced by the linker fragment harbouring the desired mutations (FIG. 17*c*). Each linker fragment was generated by annealing of the respective pairs of synthesized polynucleotides (FIG. 14*b*; sense and antisense strand; 90 ng each) for 3 min at 70 l'C in 9 μl distilled water.

Construction of plasmids pcT1-S66D and pcT1-S140Y–D141G encoding the *A. fumigatus* Q27L-S66D double mutant and the *A. fumigatus* Q27L-S140Y–141G triple mutant was basically carried out as described in Example 3. Plasmid pcT1, harbouring the mutation coding for Q27L, was used as template for site directed mutagenesis together with the corresponding primer sets J andK (FIG. 14*a*; FIG. 17*b*).

All mutations were verified by DNA sequence analysis of the entire gene.

Example 5

Expression in *Aspergillus niger*

Figure 19:
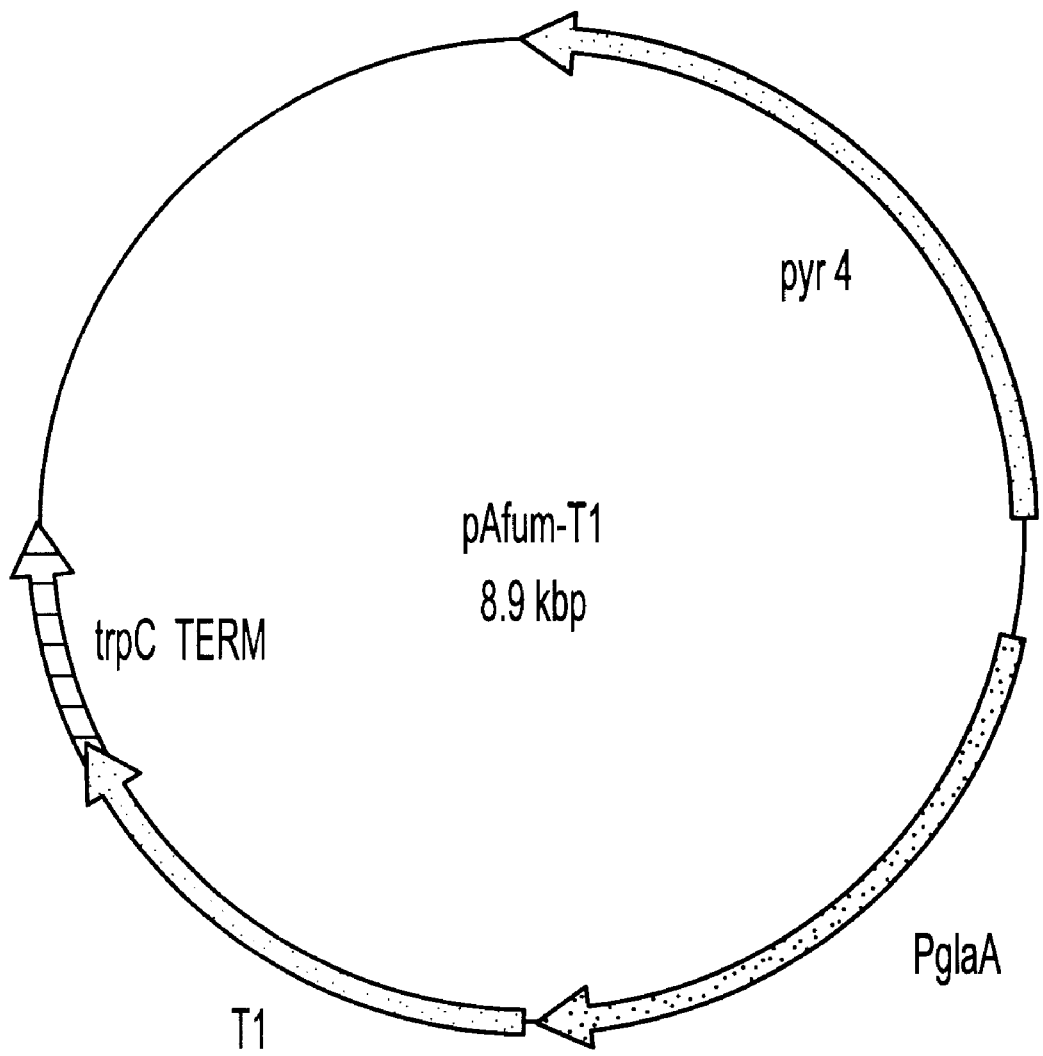
FIG. 19: Plasmid pAfum-T1 for the expression of mutein T1 in *Aspergillus niger*.

The genes encoding the aforementioned *A. fumigatus* wild-type phytase and muteins (FIG. 16) were isolated with BspHI and EcoRV from plasmids pgDNAT1–pgDNAT7 and pgDNAN1–pgDNAN6 and ligated into the NcoI site downstream of the glucoamylase promoter of *Aspergillus niger* (glaA) and the EcoRV site upstream of the *Aspergillus nidulans* tryptophan C terminator (trpC) (Mullaney et al., 1985). The resulting expression plasmids had in addition the orotidine-5'-phosphate decarboxylase gene (pyr4) of *Neurospora crassa* as selection marker. FIG. 19 shows an example for such an expression plasmid carrying the gene encoding mutein T1 (van den Hondel et al., 1991). The basic expression plasmid described above corresponds basically to the pGLAC vector described in example 9 of EP 684 313. Transformation of *Aspergillus niger* and expression of the muteins was done as described in EP 684 313.

The supernatant was concentrated by way of ultrafiltration in Amicon 8400 cells (PM30 membranes) and ultrafree-15 centrifugal filter devices(Biomax-30K, Millipore).

The concentrate (typically 1.5–5 ml) was desalted in aliquots of 1.5 ml on a Fast Desalting HR 10/10 column (Pharmacia Biotech), with 10 mM sodium acetate, pH 5.0, serving as elution buffer. The desalted *A. fumigatus* samples were directly loaded onto a 1.7 ml Poros HS/M cation exchange chromatography column (PerSeptive Biosystems, Framingham, Mass., USA). *A. terreus* cbs116.46 [CBS 220.95] phytase was directly loaded onto a 1.7 ml Poros HQ/M anion exchange chromatography column. In both cases, phytase was eluted in pure form by way of a sodium chloride gradient.

References

Mullaney, E. J., J. E. Hamer, K. A. Roberti, M. M. Yelton, and W. E. Timberlake. 1985. Primary structure of the trpC gene from *Aspergillus nidulans*. Mol. Gen. Genet. 199:37–45.

Van den Hondel, C. A. M. J. J., P. J. Punt, and R. F. M. van Gorcom. 1991. Heterologous gene expression in filamentous fungi. In: More gene manipulations in fungi. pp. 396–428. Bennett, J. W. and Lasure, L. L. (eds.). Academic Press Inc., San Diego, Calif.

Example 6

Expression in *Saccharomyces cerevisiae*

The intron less genes encoding the *A. fumigatus* wild-type phytase and the different muteins (FIGS. 17/18) mentioned above were isolated from the respective plasmids pUC18-AfumcDNA, pcDNAT1–pcDNAT7 and pcDNAN1–pcDNAN6 with EcoRI and EcoRV and subcloned either between the blunt ended XhoI and the EcoRI sites of plasmid pYES2 (Invitrogen, San Diego, Calif., USA) or the shortened GAPFL (glyceraldehyde-3-phosphate dehydrogenase) promoter and the PHO5 terminator as described by Janes et al. (1990). Transformation of *Saccharomyces cerevisiae* strains, e.g. INVSc1 (Invitrogen, San Diego, Calif., USA) was done according to Hinnen et al. (1978). Single colonies harbouring the phytase gene under the control of the GAPFL promoter were picked and cultivated in 5ml selection medium (SD -uracil) (Sherman et al., 1986) at 30Γ C under vigorous shaking (250 rpm) for 1 day. The preculture was then added to 500 ml YPD medium (Sherman et al., 1986) and cultivated under the same conditions. After four days cell broth was centrifuged (7000 rpm, GS3 rotor, 15 min. 5Γ C) and the supernatant was collected. Induction of the GAL1 promotor (plasmid pYES2 from Invitrogen, San Diego, Calif., USA) was done according to the manufacturers instructions. Purification of the muteins was as described in example 5 (s.a.).

References

Janes, M., B. Meyhack, W. Zimmermann and A. Hinnen. 1990. The influence of GAP promoter variants on hirudine production, avarage plasmid copy number and cell growth in *Saccharomyces cerevisiae*. Curr. Genet. 18: 97–103

Hinnen, A., J. B. Hicks and G. R. Fink. 1978. Proc. Natl. Acad. Sci. USA 75: 1929–1933

Sheman, J. P., Finck, G. R. and Hicks, J. B. (1986). Laboratory Course Manual for Methods in Yeast Genetics. Cold Spring Harbor University Press.

Example 7

Determination of Phytase Activity and Substrate Specificity

Phytase activity was measured in an assay mixture containing 0.5% phytic acid (~5 mM), 200 mM sodium acetate, pH 5.0. After 15 min incubation at 37° C., the reaction was stopped by addition of an equal volume of 15% trichloroacetic acid. The liberated phosphate ions were quantified by mixing 100 μl of the assay mixture with 900 μl H$_2$O and 1 ml of 0.6 M H$_2$SO$_4$, 2% ascorbic acid and 0.5% ammonium molybdate. Standard solutions of potassium phosphate were used as reference.

In case of pH optimum curves, purified enzymes were diluted in 10 mM sodium acetate, pH 5.0. Incubations were started by mixing aliquots of the diluted protein with an equal volume of 1% phytic acid (~10 mM) in a series of different buffers: 0.4 M glycine/HCl, pH 2.5; 0.4 M acetate/NaOH, pH 3.0, 3.5, 4.0, 4.5, 5.0, 5.5; 0.4 M imidazole/HCl, pH 6.0, 6.5; 0.4 M Tris/HCl, pH 7.0, 7.5, 8.0, 8.5, 9.0. Control experiments showed that pH was only slightly affected by the mixing step. Incubations were performed for 15 min at 37° C. as described above.

For determination of the substrate specificities of wild-type and mutant *A. fumigatus* phytases, phytic acid in the assay mixture was replaced by 5 mM-concentrations of the respective phosphate compounds. The activity tests were performed as described above.

Figure 2:
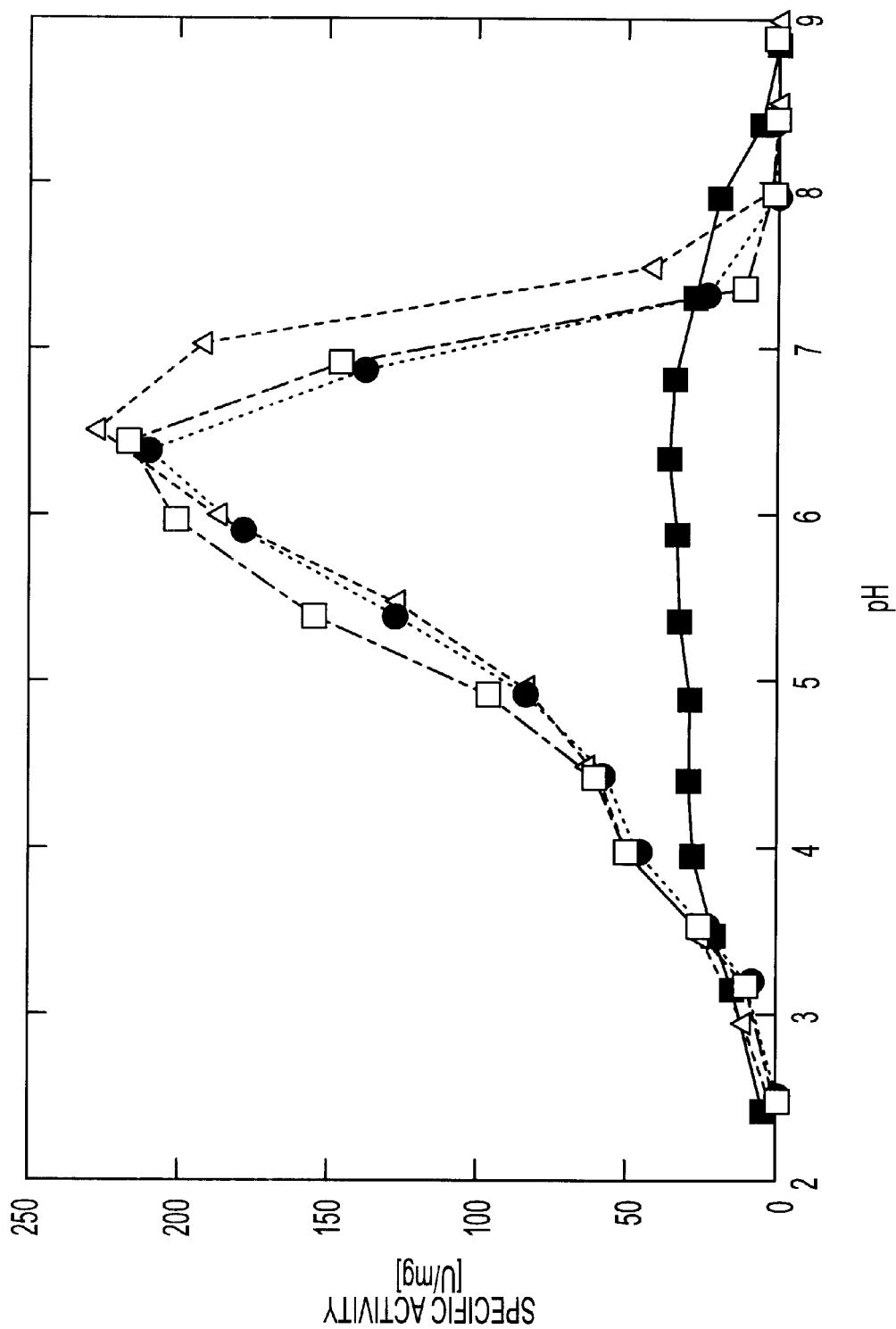
FIG. 2: pH optima curves. Specific activity of wild-type and mutant A. fumigatus phytases is plotted against pH of incubation. Filled squares represent A. fumigatus wild-type phytase; Open triangles represent A. fumigatus Q27L mutant; Filled circles represent A. fumigatus Q27L, Q274L mutant; Open squares represent A. fumigatus Q27L, Q274L, G277D mutant.

Protein concentrations were calculated from the OD at 280 nm, using theoretical absorption values calculated from the known protein sequences with the DNA* software (DNASTAR, Inc., Madison, Wis., USA). An absorption of 1.0 OD at 280 nm corresponds to 0.94 mg/ml *A. fumigatus* phytase and 0.85 mg/ml of *A. terreus* cbs116.46 phytase.

pH profiles of *Aspergillus fumigatus* mutants T1 (Q27L), T5 (Q27L, Q274L) and T6 (Q27L, Q274L, G277D) have drastically changed compared to the wild-type *A. fumigatus* phytase (see FIG. 2). All mutants showed equal pH profiles. Increase in specific activity at pH 5.0 of the muteins as compared to the wild-type phytase of *Aspergillus fumigatus* is shown in Table 2. Enzyme activities were measured under standard assay conditions at pH 5.0. Several individual measurements (n: number of assays) were averaged.

Figure 20:
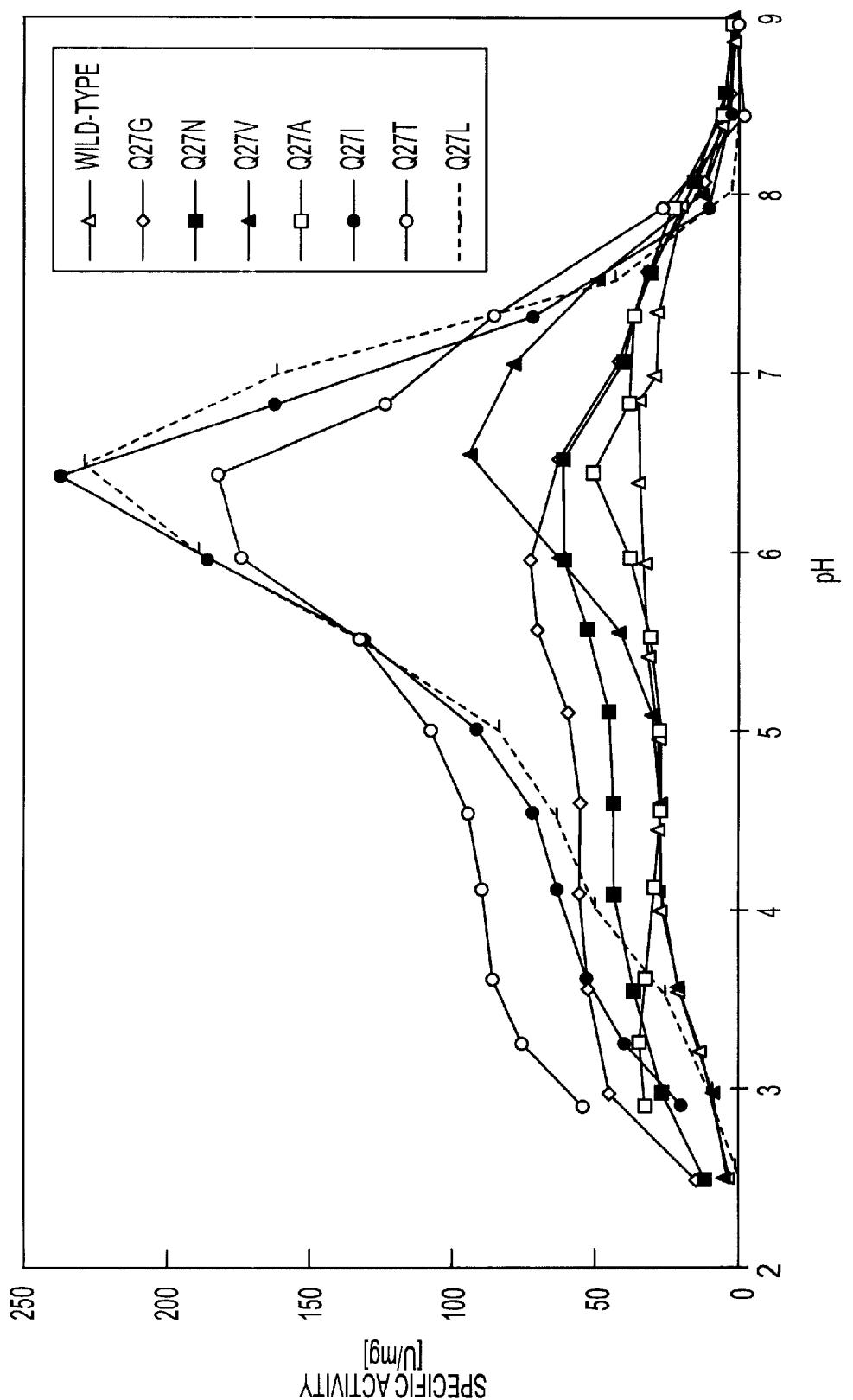
FIG. 20: pH optima curves. Specific activity of wild-type and mutant *A. fumigatus* phytases is plotted against pH of incubation.

The pH profile of *A. fumigatus* phytase mutant Q27A resembles the pH profile of *A. fumigatus* wild-type phytase over nearly the whole pH range (FIG. 20). Whereas the specific activity of wild-type phytase is decreasing at pH values below pH 4.0, the specific activity of the phytase mutant Q27A remains nearly constant down to pH 2.9.

The single amino acid exchanges Q27L, Q27I, Q27V or Q27T have remarkably increased the specific activity over the whole pH range, especially between pH 5.0 and 7.5 (FIG. 20). Maximum values are reached at pH 6.5. In addition, mutation Q27T caused the highest specific activity values for phytic acid at low pH (pH 3.0–5.0).

Higher specific activities are also gained by the single mutations Q27G or Q27N, between pH 2.5 and 7.0, with maximum values at pH 6.0 (FIG. 20). The specific activity decreases at pH values below 3.5.

All single mutants still show a broad substrate specificity which is comparable to that of *A. fumigatus* wild-type phytase (FIG. 21). Some of the mutants show significantly higher specific activities than other mutants for selected substrates, e. g., the Q27T mutant for p-nitrophenyl phosphate and ATP, or the Q27G mutant for phosphoenolpyruvate.

As shown in FIG. 22 the combination of mutation Q27L with S66D or S140Y and D141G led to a shift of the pH profile towards lower pH. The maximum specific activity gained by the single mutation Q27L is further increased by the additional amino acid exchanges.

Figure 3A:
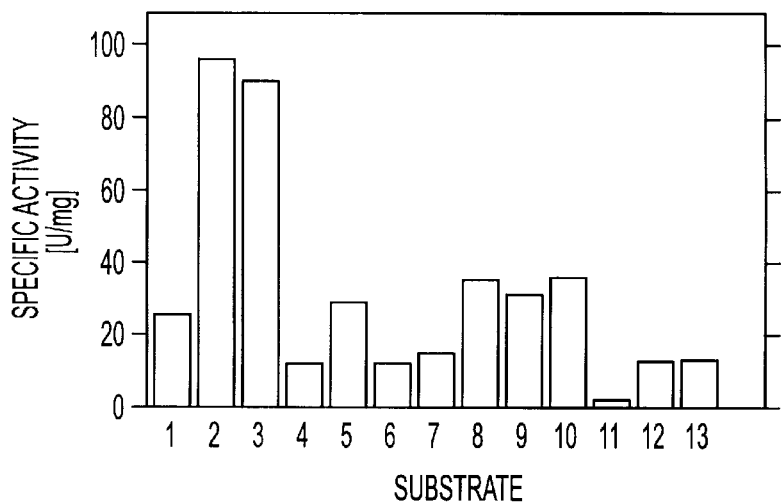
FIG. 3: Substrate specificities of wild-type and mutant *A. fumigatus* phytases. (A) wild-type; (B) Q27L single mutant; (C) Q27L, Q274L, G277D triple mutant. The following substrates were used: (1) phytic acid; (2) p-nitrophenyl phosphate; (3) fructose-1,6-bisphosphate; (4) fructose-6-phosphate; (5) glucose-6-phosphate; (6) ribose-5-phosphate; (7) α-glycerophosphate; (8) β-glycerophosphate; (9) 3-phosphoglycerate; (10) phosphoenolpyruvate; (11) AMP; (12) ADP; (13) ATP.
Figure 3B:
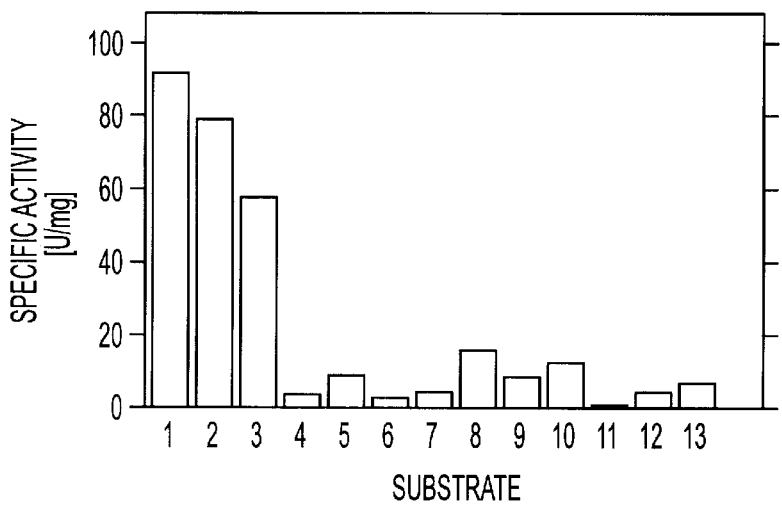
Figure 3C:
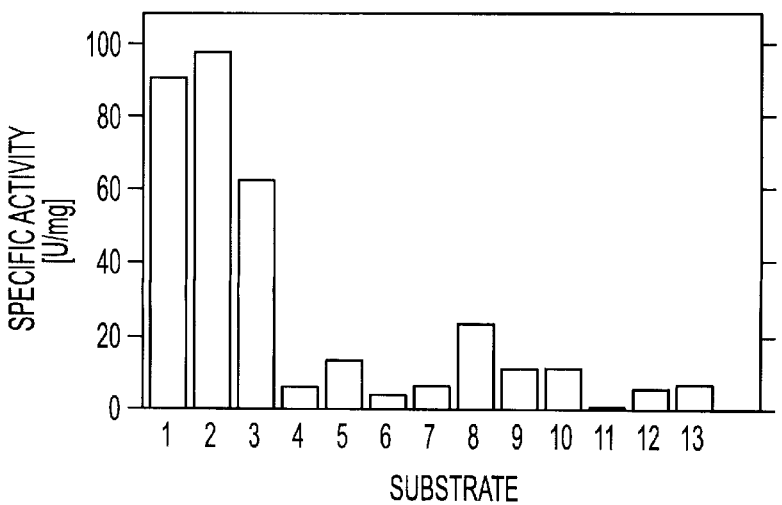

As shown in FIG. 3, *Aspergillus fumigatus* phytase mutant T1 (Q27L) showed no difference in substrate specificity compared to the triple mutant T6 (Q27L, Q274L, G277D).

Figure 10:
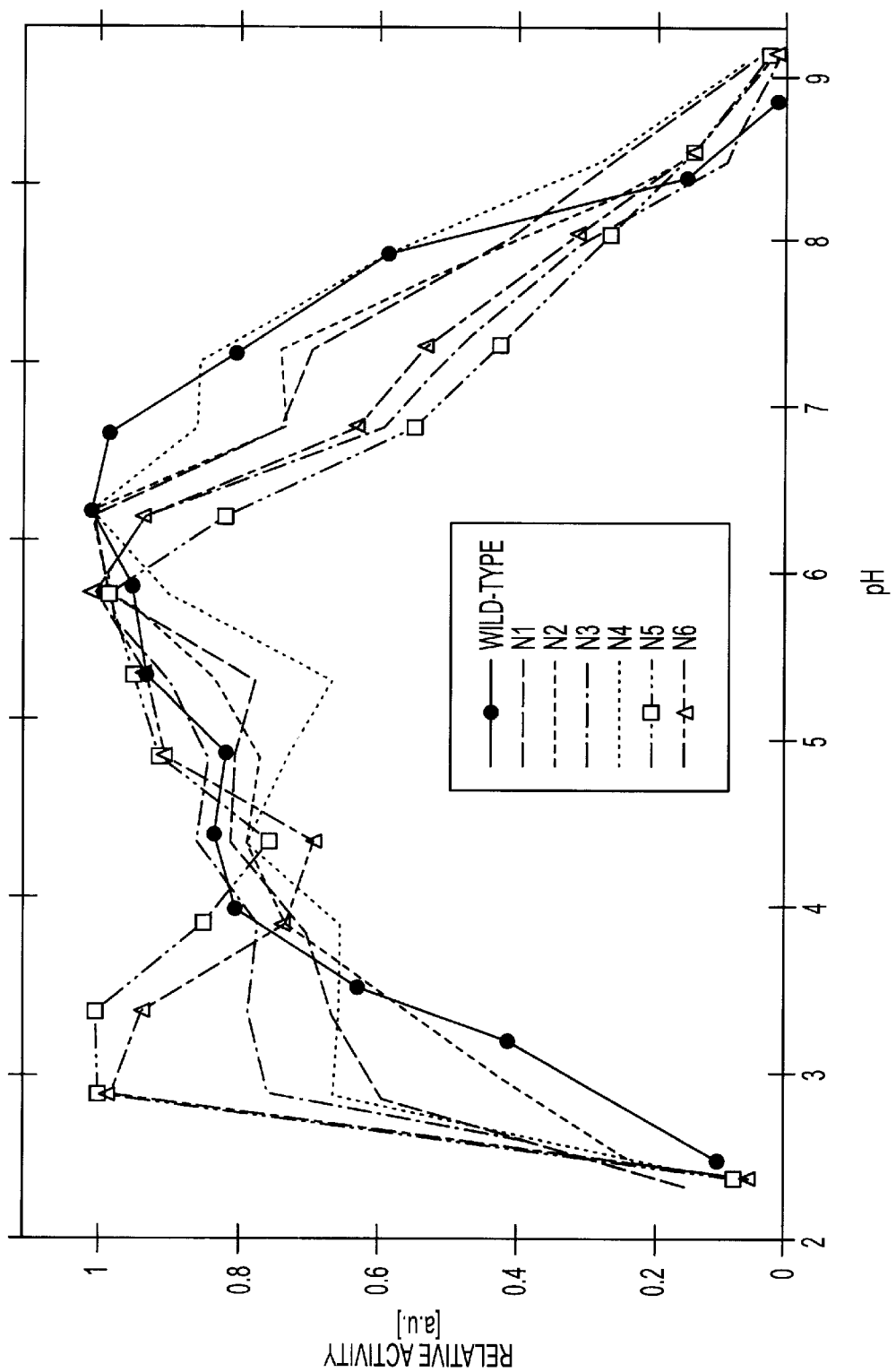
FIG. 10: pH optima curves of further mutant *A. fumigatus* phytases (N1–N6). All activity values were standardized (maximum activity=1.0).
Figure 11A:
FIG. 11a: Stereo picture of the three-dimensional fold of *A. niger* (A. ficuum; NRRL 3135) phytase. The active site is indicated with a circle and the catalytically essential amino acid residues Arg 58 and His 59 are shown in ball-and-stick representation. This figure was prepared with the programs "MOLSCRIPT" [Kraulis, P. J., J. Appl. Cryst. 24, 946–950 (1991)] and "RASTER3D" [Merritt, E. A. & Murphy, M. E. P., Acta Cryst., 869–873 (1994)].
Figure 11B:
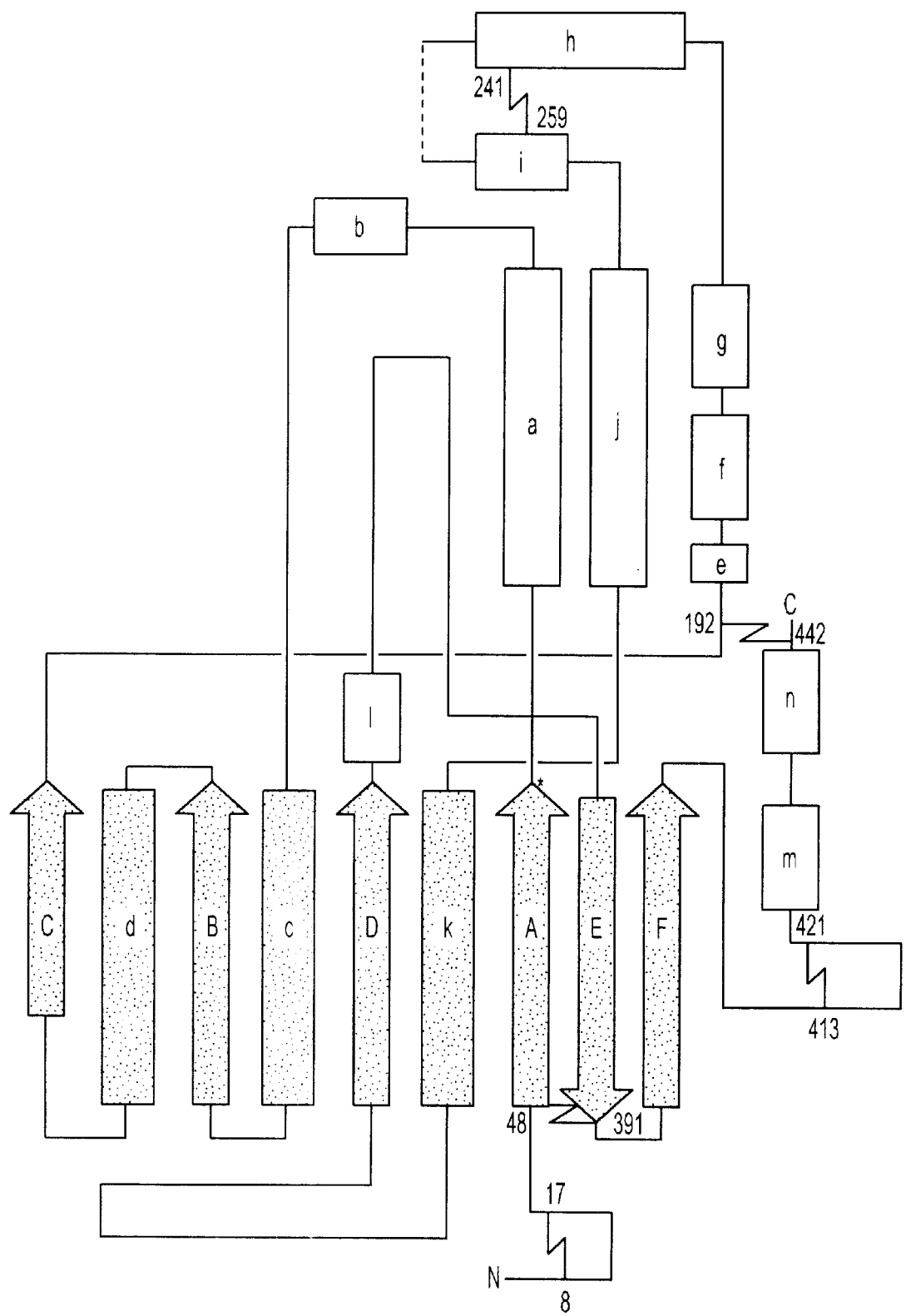
FIG. 11b: Topological sketch, using the same scheme as in (a). The five disulphide bridges are shown as black zigzag lines together with the sequence numbers of the cysteine residues involved. The β-strands are defined with the sequence numbers A:48–58, B:134–138, C: 173–177, D: 332–337, E: 383–391, and F: 398–403. The α-helices are defined with the sequence numbers a: 66–82, b: 88–95, c: 107–123, d: 141–159, e: 193–197, f: 200–210, g: 213–223, h: 231–246, i: 257–261, 264–281, k: 290–305,l: 339–348, m: 423–429, and n: 439–443. The asterisk at the C-terminal end of β-strand A marks the location of the catalytically essential amino acid residues Arg 58 and His 59.
Figure 12:
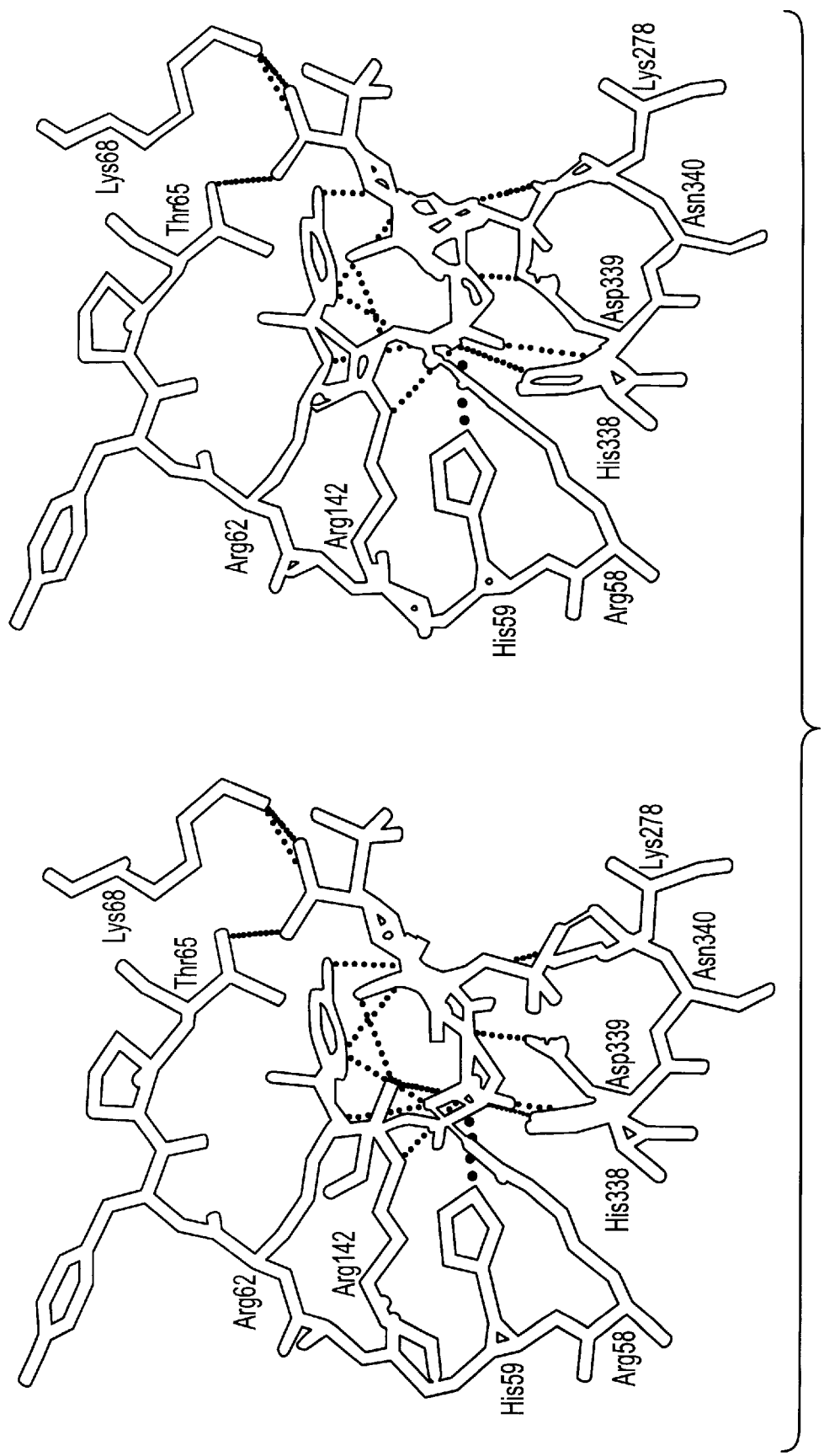
FIG. 12: Stereo picture of the active site of *A. ficuum* (ATCC 13073) phytase with a hypothetical binding mode of the substrate phytate. In this model, the bound crystal water molecules were removed and the protein atom positions were held fixed, except for small adaptations of the side chain torsion angles of Lys 68 in order to interact with the substrate. All the conserved amino acid residues Arg 58, His 59, Arg 62, Arg 142, His 338 and Asp 339 form hydrogen bonds to the scissile 3-phosphate group of phytate, as indicated with lines of small dots. His 59 is in a favorable position to make a nucleophilic attack at the scissile phosphorous, indicated with a line of larger dots, and Asp 339 is in a position to protonate the leaving group.

The pH profiles of the muteins N1–6, except N2 show significant differences compared to the wild-type phytase (FIG. 10). Whereas the pH profile of mutein N4 is expanded towards lower pH, the profiles of muteins N3 to N6 are shifted towards lower pH. The muteins N5, N6 reach maximum activity already at pH 3.0.

Figure 9:
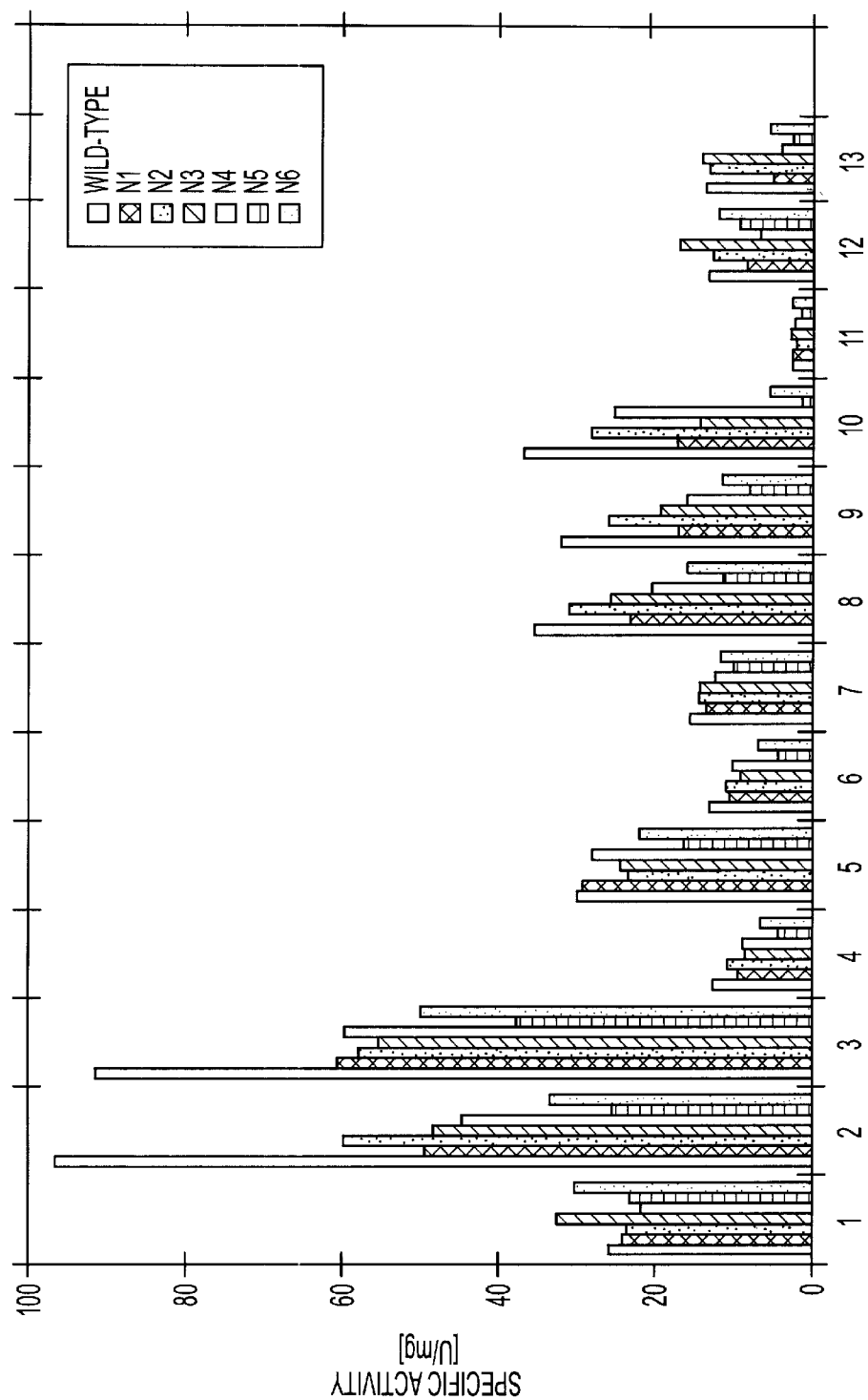
FIG. 9: Substrate specificities of wild-type and mutant *A. fumigatus* phytase (N1-N6). Substrates 1 to 13 are as indicated for FIG. 3.

The muteins N1 to N6 show in almost all cases a drastic reduction in specific activity for all tested substrates, except for phytic acid (FIG. 9). Specific activity for phytic acid remained unchanged compared to the wild-type phytase, whereas mutant N3 and N6 show a tendential higher activity (FIG. 19).

TABLE 1

A) Mutations towards *A. terreus* cbs116.46 phytase

| Mutation | T1 | T2 | T3 | T4 | T5 | T6 | T7 |
|---|---|---|---|---|---|---|---|
| Q27L  | X |   |   |   | X | X | X |
| Q274L |   | X |   |   | X | X | X |
| G277D |   |   | X |   |   | X | X |
| N340S |   |   |   | X |   |   | x |

B) Mutations towards *A. niger* (ficuum) phytase

| Mutation | N1 | N2 | N3 | N4 | N5 | N6 |
|---|---|---|---|---|---|---|
| G277K | X |   |   |   | X |   |
| A205E |   | X |   | X |   | X |
| Y282H |   |   | X |   | X | x |

TABLE 2

|  | U/mg |  |
|---|---|---|
| *A. fumigatus* wild-type phytase | 26.5 ± 5.2 | 22 |
| *A. fumigatus* Q27L | 83.4 | 4 |
| *A. fumigatus* Q27L, Q274L | 88.7 ± 13.5 | 8 |
| *A. fumigatus* Q27L, Q274L, G277D | 92.3 ± 12.0 | 9 |
| *A. terreus* cbs116.46 phytase | 195.8 ± 17.8 | 7 |

TABLE 3

Specific activity under standard assay conditions at pH 5.0. Average standard deviation is 10%.

|  | Specific activity [U/mg] | Number of independent assays |
|---|---|---|
| *A. fumigatus* wild-type phytase | 26.5 | 22 |
| *A. fumigatus* Q27N | 45.5 | 3 |
| *A. fumigatus* Q27T | 106.9 | 3 |
| *A. fumigatus* Q27L | 83.4 | 4 |
| *A. fumigatus* Q27I | 91.2 | 3 |
| *A. fumigatus* Q27V | 35.0 | 3 |
| *A. fumigatus* Q27A | 27.3 | 3 |
| *A. fumigatus* Q27G | 59.6 | 3 |
| *A. fumigatus* Q27L-S66D | 118.5 | 3 |

TABLE 3-continued

Specific activity under standard assay conditions at pH 5.0. Average standard deviation is 10%.

|  | Specific activity [U/mg] | Number of independent assays |
|---|---|---|
| *A. fumigatus* Q27L-S140Y-D141G | 193.0 | 3 |

Example 8

As an alternative approach to obtain phytases with modified characteristics and to get a better idea about the natural variation found in phytase characteristics within a certain species, naturally occurring variants of *A. fumigatus* phytase were analysed. Phytase genes were obtained from six different isolates of *A. fumigatus*. The amino acid sequence of phytase from two of the *A. fumigatus* isolates (ATCC 26934 and ATCC 34625) showed no difference to the original amino acid sequence of wild-type *A. fumigatus* phytase ATCC 13073. Phytase from three other isolates had one or two amino acid substitutions, none of which directly affected the active site. Enzymatic characteristics remained unaffected by these substitutions (not shown). The phytase of isolate of *A. fumigatus* (ATCC 32239) differed in 13 positions in the signal sequence and 51 positions in the mature part of the protein compared to the original wild-type *A. fumigatus* phytase (ATCC 13073). Several of these substitutions affect variable amino acids of the active site cavity. This resulted in an increase in specific activity with phytic acid as substrate (47 U/mg, standard enzyme assay) and in loss of enzymatic activity above pH 7 (FIG. 24). Also in this case, the specific activity against phytic acid was increased relative to the specific activities with other substrates (FIG. 25).

Example 9

Construction of plasmids pc-S130N, pc-R129L–S130N, pc-K167G–R168Q encoding *A. fumigatus* [ATCC 13073] phytase S130N single mutant and R129L–S130N double mutant and *A. nidulans* phytase K167G–R168Q double mutant was basically carried out as described in Example 3. Plasmid pUC18-*Afumc*DNA was used as template for site directed mutagenesis together with the corresponding primer sets L, M and N (FIG. 14*a*; FIG. 26).

All mutations were verified by DNA sequence analysis of the entire gene.

Example 10

When expressed in *A. niger* and stored as concentrated culture supernatants at 4° C., the phytases from *A. fumigatus, A. nidulans* displayed tendency to undergo proteolytic degradation. N-terminal sequencing of fragments suggested that cleavage occured between amino acids S130–V131 and K167–R168 or R168–A169, respectively. Compared with 3D structure of *A. niger* phytase revealed that all cleavage sites are found within surface-exposed loop structures and are therefore accessible to proteases.

Site-directed mutagenesis at protease-sensitive sites of *A. fumigatus* phytase (S130N, R129L-S130N) and*A. nidulans* phytase (K167G–R168Q) yielded mutant proteins with considerably reduced susceptibility to proteolysis.

In contrast to expression in *A. niger*, proteolytic degradation was not observed when the phytases were expressed in Hansenula polymorpha.

What is claimed is:

1. A modified *Aspergillus fumigatus* phytase with a specific activity improved over the specific activity of the corresponding unmodified *Aspergillus fumigatus* phytase wherein the amino acid sequence of the unmodified phytase has been changed at a position corresponding to position 27 of the phytase of *Aspergillus niger* (SEQ ID NO:1), as identified by PILEUP version 8 amino acid sequence alignment program, to an amino acid selected from the group consisting of Ala, Val, Leu, Ile, Thr, Gly, and Asn.

2. A modified *Aspergillus fumigatus* phytase according to claim 1, further comprising an additional mutation selected from the group consisting of S66D, S140Y, D141G, A205E, Q274L, G277D, G277K, Y282H, and N340S.

3. A modified *Aspergillus fumigatis* phytase with a specific activity improved over the specific activity of the corresponding unmodified *Aspergillus fumigatus* phytase wherein the amino acid sequence of the modified *Aspergillus fumigatus* phytase has a mutation selected from the group consisting of S66D, S140Y, D141G, A205E, Q274L, G277D, G277K, Y282H, N340S, and combinations therof, wherein the respective amino acid position of each mutation corresponds to the amino acid position of an *Aspergillus niger* phytase (SEQ ID NO:1) as identified by PILEUP version 8 amino acid alignment program.

4. A modified phytase according to claim 1 wherein the unmodified phytase has the sequence of SEQ ID NO:3.

5. A modified phytase according to claim 4 wherein the amino acid sequence of SEQ ID NO:3 has been changed at a position corresponding to position 27 of the phytase of *Aspergillus niger* to the amino acid Ala.

6. A modified phytase according to claim 4 wherein the amino acid sequence of SEQ ID NO:3 has been changed at a position corresponding to position 27 of the phytase of *Aspergillus niger* to the amino acid Val.

7. A modified phytase according to claim 4 wherein the amino acid sequence of SEQ ID NO:3 has been changed at a position corresponding to position 27 of the phytase of *Aspergillus niger* to the amino acid Leu.

8. A modified phytase according to claim 4 wherein the amino acid sequence of SEQ ID NO:3 has been changed at a position corresponding to position 27 of the phytase of *Aspergillus niger* to the amino acid Ile.

9. A modified phytase according to claim 4 wherein the amino acid sequence of SEQ ID NO:3 has been changed at a position corresponding to position 27 of the phytase of *Aspergillus niger* to the amino acid Thr.

10. A modified phytase according to claim 4 wherein the amino acid sequence of SEQ ID NO:3 has been changed at a position corresponding to position 27 of the phytase of *Aspergillus niger* to the amino acid Asn.

11. A modified phytase according to claim 4 wherein the amino acid sequence of SEQ ID NO:3 has been changed at a position corresponding to position 27 of the phytase of *Aspergillus niger* to the amino acid Gly.

12. A modified phytase according to claim 4 wherein the amino acid sequence of SEQ ID NO:3 has been modified as follows: Q23L and S62D.

13. A modified phytase according to claim 4 wherein the amino acid sequence of SEQ ID NO:3 has been modified as follows: Q23L, S136Y, and D137G.

14. A modified phytase according to claim 3 wherein the unmodified phytase has the sequence of SEQ ID NO:3.

15. A modified phytase according to claim 14 wherein the amino acid sequence of SEQ ID NO:3 has been modified as follows: S62D.

16. A modified phytase according to claim 14 wherein the amino acid sequence of SEQ ID NO:3 has been modified as follows: S136Y.

17. A modified phytase according to claim 14 wherein the amino acid sequence of SEQ ID NO:3 has been modified as follows: D137G.

18. A modified phytase according to claim 14 wherein the amino acid sequence of SEQ ID NO:3 has been modified as follows: A200E.

19. A modified phytase according to claim 3 wherein the amino acid sequence of SEQ ID NO:3 has been modified as follows: Q269L.

20. A modified phytase according to claim 14 wherein the amino acid sequence of SEQ ID NO:3 has been modified as follows: G272D.

21. A modified phytase according to claim 14 wherein the amino acid sequence of SEQ ID NO:3 has been modified as follows: G272K.

22. A modified phytase according to claim 14 wherein the amino acid sequence of SEQ ID NO:3 has been modified as follows: Y277H.

23. A modified phytase according to claim 14 wherein the amino acid sequence of SEQ ID NO:3 has been modified as follows: N335S.

24. A food or feed composition comprising a modified phytase of claim 1.

* * * * *

UNITED STATES PATENT AND TRADEMARK OFFICE
CERTIFICATE OF CORRECTION

PATENT NO. : 6,391,605 B1
DATED : May 21, 2002
INVENTOR(S) : Dirk Kostrewa et al.

It is certified that error appears in the above-identified patent and that said Letters Patent is hereby corrected as shown below:

Column 87,
Line 26, please delete the "," after claim 1;
Line 29, please change "*fumigatis*" to -- *fumigatus* --;

Column 88,
Line 43, please change "claim 3" to -- claim 14 --.

Signed and Sealed this

Seventh Day of January, 2003

JAMES E. ROGAN
*Director of the United States Patent and Trademark Office*

SEQUENCE LISTING

<160> NUMBER OF SEQ ID NOS: 82

<210> SEQ ID NO 1
<211> LENGTH: 444
<212> TYPE: PRT
<213> ORGANISM: Aspergillus niger

<400> SEQUENCE: 1

```
Ala Ser Arg Asn Gln Ser Ser Cys Asp Thr Val Asp Gln Gly Tyr Gln
 1               5                  10                  15

Cys Phe Ser Glu Thr Ser His Leu Trp Gly Gln Tyr Ala Pro Phe Phe
                20                  25                  30

Ser Leu Ala Asn Glu Ser Val Ile Ser Pro Glu Val Pro Ala Gly Cys
            35                  40                  45

Arg Val Thr Phe Ala Gln Val Leu Ser Arg His Gly Ala Arg Tyr Pro
         50                  55                  60

Thr Asp Ser Lys Gly Lys Lys Tyr Ser Ala Leu Ile Glu Glu Ile Gln
 65                  70                  75                  80

Gln Asn Ala Thr Thr Phe Asp Gly Lys Tyr Ala Phe Leu Lys Thr Tyr
                85                  90                  95

Asn Tyr Ser Leu Gly Ala Asp Asp Leu Thr Pro Phe Gly Glu Gln Glu
            100                 105                 110

Leu Val Asn Ser Gly Ile Lys Phe Tyr Gln Arg Tyr Glu Ser Leu Thr
        115                 120                 125

Arg Asn Ile Val Pro Phe Ile Arg Ser Ser Gly Ser Ser Arg Val Ile
130                 135                 140

Ala Ser Gly Lys Lys Phe Ile Glu Gly Phe Gln Ser Thr Lys Leu Lys
145                 150                 155                 160

Asp Pro Arg Ala Gln Pro Gly Gln Ser Ser Pro Lys Ile Asp Val Val
                165                 170                 175

Ile Ser Glu Ala Ser Ser Ser Asn Asn Thr Leu Asp Pro Gly Thr Cys
            180                 185                 190

Thr Val Phe Glu Asp Ser Glu Leu Ala Asp Thr Val Glu Ala Asn Phe
        195                 200                 205

Thr Ala Thr Phe Val Pro Ser Ile Arg Gln Arg Leu Glu Asn Asp Leu
    210                 215                 220

Ser Gly Val Thr Leu Thr Asp Thr Glu Val Thr Tyr Leu Met Asp Met
225                 230                 235                 240

Cys Ser Phe Asp Thr Ile Ser Thr Ser Thr Val Asp Thr Lys Leu Ser
                245                 250                 255

Pro Phe Cys Asp Leu Phe Thr His Asp Glu Trp Ile Asn Tyr Asp Tyr
            260                 265                 270

Leu Gln Ser Leu Lys Lys Tyr Tyr Gly His Gly Ala Gly Asn Pro Leu
        275                 280                 285

Gly Pro Thr Gln Gly Val Gly Tyr Ala Asn Glu Leu Ile Ala Arg Leu
    290                 295                 300

Thr His Ser Pro Val His Asp Asp Thr Ser Ser Asn His Thr Leu Asp
305                 310                 315                 320

Ser Ser Pro Ala Thr Phe Pro Leu Asn Ser Thr Leu Tyr Ala Asp Phe
                325                 330                 335

Ser His Asp Asn Gly Ile Ile Ser Ile Leu Phe Ala Leu Gly Leu Tyr
            340                 345                 350

Asn Gly Thr Lys Pro Leu Ser Thr Thr Thr Val Glu Asn Ile Thr Gln
```

```
                   355                 360                 365
Thr Asp Gly Phe Ser Ser Ala Trp Thr Val Pro Phe Ala Ser Arg Leu
            370                 375                 380

Tyr Val Glu Met Met Gln Cys Gln Ala Glu Gln Glu Pro Leu Val Arg
385                 390                 395                 400

Val Leu Val Asn Asp Arg Val Val Pro Leu His Gly Cys Pro Val Asp
                405                 410                 415

Ala Leu Gly Arg Cys Thr Arg Asp Ser Phe Val Arg Gly Leu Ser Phe
            420                 425                 430

Ala Arg Ser Gly Gly Asp Trp Ala Glu Cys Phe Ala
            435                 440

<210> SEQ ID NO 2
<211> LENGTH: 438
<212> TYPE: PRT
<213> ORGANISM: Aspergillus terreus

<400> SEQUENCE: 2

Ser Asp Cys Thr Ser Val Asp Arg Gly Tyr Gln Cys Phe Pro Glu Leu
  1               5                  10                  15

Ser His Lys Trp Gly Leu Tyr Ala Pro Tyr Phe Ser Leu Gln Asp Glu
                20                  25                  30

Ser Pro Phe Pro Leu Asp Val Pro Asp Asp Cys His Ile Thr Phe Val
            35                  40                  45

Gln Val Leu Ala Arg His Gly Ala Arg Ser Pro Thr Asp Ser Lys Thr
     50                  55                  60

Lys Ala Tyr Ala Ala Thr Ile Ala Ala Ile Gln Lys Asn Ala Thr Ala
 65                  70                  75                  80

Leu Pro Gly Lys Tyr Ala Phe Leu Lys Ser Tyr Asn Tyr Ser Met Gly
                85                  90                  95

Ser Glu Asn Leu Thr Pro Phe Gly Arg Asn Gln Leu Gln Asp Leu Gly
            100                 105                 110

Ala Gln Phe Tyr Arg Arg Tyr Asp Thr Leu Thr Arg His Ile Asn Pro
        115                 120                 125

Phe Val Arg Ala Ala Asp Ser Ser Arg Val His Glu Ser Ala Glu Lys
130                 135                 140

Phe Val Glu Gly Phe Gln Asn Ala Arg Gln Gly Asp Pro His Ala Asn
145                 150                 155                 160

Pro His Gln Pro Ser Pro Arg Val Asp Val Val Ile Pro Glu Gly Thr
                165                 170                 175

Ala Tyr Asn Asn Thr Leu Glu His Ser Ile Cys Thr Ala Phe Glu Ala
            180                 185                 190

Ser Thr Val Gly Asp Ala Ala Asp Asn Phe Thr Ala Val Phe Ala
        195                 200                 205

Pro Ala Ile Ala Lys Arg Leu Glu Ala Asp Leu Pro Gly Val Gln Leu
        210                 215                 220

Ser Ala Asp Asp Val Val Asn Leu Met Ala Met Cys Pro Phe Glu Thr
225                 230                 235                 240

Val Ser Leu Thr Asp Asp Ala His Thr Leu Ser Pro Phe Cys Asp Leu
                245                 250                 255

Phe Thr Ala Ala Glu Trp Thr Gln Tyr Asn Tyr Leu Leu Ser Leu Asp
            260                 265                 270

Lys Tyr Tyr Gly Tyr Gly Gly Asn Pro Leu Gly Pro Val Gln Gly
        275                 280                 285
```

```
Val Gly Trp Ala Asn Glu Leu Ile Ala Arg Leu Thr Arg Ser Pro Val
    290                 295                 300

His Asp His Thr Cys Val Asn Thr Leu Asp Ala Asn Pro Ala Thr
305                 310                 315                 320

Phe Pro Leu Asn Ala Thr Leu Tyr Ala Asp Phe Ser His Asp Ser Asn
                325                 330                 335

Leu Val Ser Ile Phe Trp Ala Leu Gly Leu Tyr Asn Gly Thr Lys Pro
                340                 345                 350

Leu Ser Gln Thr Thr Val Glu Asp Ile Thr Arg Thr Asp Gly Tyr Ala
                355                 360                 365

Ala Ala Trp Thr Val Pro Phe Ala Arg Ala Tyr Ile Glu Met Met
    370                 375                 380

Gln Cys Arg Ala Glu Lys Gln Pro Leu Val Arg Val Leu Val Asn Asp
385                 390                 395                 400

Arg Val Met Pro Leu His Gly Cys Ala Val Asp Asn Leu Gly Arg Cys
                405                 410                 415

Lys Arg Asp Asp Phe Val Glu Gly Leu Ser Phe Ala Arg Ala Gly Gly
                420                 425                 430

Asn Trp Ala Glu Cys Phe
            435

<210> SEQ ID NO 3
<211> LENGTH: 439
<212> TYPE: PRT
<213> ORGANISM: Aspergillus fumigatus

<400> SEQUENCE: 3

Ser Lys Ser Cys Asp Thr Val Asp Leu Gly Tyr Gln Cys Ser Pro Ala
  1               5                  10                  15

Thr Ser His Leu Trp Gly Gln Tyr Ser Pro Phe Phe Ser Leu Glu Asp
                20                  25                  30

Glu Leu Ser Val Ser Ser Lys Leu Pro Lys Asp Cys Arg Ile Thr Leu
            35                  40                  45

Val Gln Val Leu Ser Arg His Gly Ala Arg Tyr Pro Thr Ser Ser Lys
    50                  55                  60

Ser Lys Lys Tyr Lys Lys Leu Val Thr Ala Ile Gln Ala Asn Ala Thr
65                  70                  75                  80

Asp Phe Lys Gly Lys Phe Ala Phe Leu Lys Thr Tyr Asn Tyr Thr Leu
                85                  90                  95

Gly Ala Asp Asp Leu Thr Pro Phe Gly Glu Gln Gln Leu Val Asn Ser
                100                 105                 110

Gly Ile Lys Phe Tyr Gln Arg Tyr Lys Ala Leu Ala Arg Ser Val Val
            115                 120                 125

Pro Phe Ile Arg Ala Ser Gly Ser Asp Arg Val Ile Ala Ser Gly Glu
    130                 135                 140

Lys Phe Ile Glu Gly Phe Gln Gln Ala Lys Leu Ala Asp Pro Gly Ala
145                 150                 155                 160

Thr Asn Arg Ala Ala Pro Ala Ile Ser Val Ile Ile Pro Glu Ser Glu
                165                 170                 175

Thr Phe Asn Asn Thr Leu Asp His Gly Val Cys Thr Lys Phe Glu Ala
                180                 185                 190

Ser Gln Leu Gly Asp Glu Val Ala Ala Asn Phe Thr Ala Leu Phe Ala
            195                 200                 205

Pro Asp Ile Arg Ala Arg Ala Glu Lys His Leu Pro Gly Val Thr Leu
    210                 215                 220
```

```
Thr Asp Glu Asp Val Val Ser Leu Met Asp Met Cys Ser Phe Asp Thr
225                 230                 235                 240

Val Ala Arg Thr Ser Asp Ala Ser Gln Leu Ser Pro Phe Cys Gln Leu
            245                 250                 255

Phe Thr His Asn Glu Trp Lys Lys Tyr Asn Tyr Leu Gln Ser Leu Gly
        260                 265                 270

Lys Tyr Tyr Gly Tyr Gly Ala Gly Asn Pro Leu Gly Pro Ala Gln Gly
        275                 280                 285

Ile Gly Phe Thr Asn Glu Leu Ile Ala Arg Leu Thr Arg Ser Pro Val
    290                 295                 300

Gln Asp His Thr Ser Thr Asn Ser Thr Leu Val Ser Asn Pro Ala Thr
305                 310                 315                 320

Phe Pro Leu Asn Ala Thr Met Tyr Val Asp Phe Ser His Asp Asn Ser
            325                 330                 335

Met Val Ser Ile Phe Phe Ala Leu Gly Leu Tyr Asn Gly Thr Glu Pro
        340                 345                 350

Leu Ser Arg Thr Ser Val Glu Ser Ala Lys Glu Leu Asp Gly Tyr Ser
        355                 360                 365

Ala Ser Trp Val Val Pro Phe Gly Ala Arg Ala Tyr Phe Glu Thr Met
370                 375                 380

Gln Cys Lys Ser Glu Lys Glu Pro Leu Val Arg Ala Leu Ile Asn Asp
385                 390                 395                 400

Arg Val Val Pro Leu His Gly Cys Asp Val Asp Lys Leu Gly Arg Cys
                405                 410                 415

Lys Leu Asn Asp Phe Val Lys Gly Leu Ser Trp Ala Arg Ser Gly Gly
            420                 425                 430

Asn Trp Gly Glu Cys Phe Ser
        435

<210> SEQ ID NO 4
<211> LENGTH: 1931
<212> TYPE: DNA
<213> ORGANISM: Aspergillus nidulans
<220> FEATURE:
<221> NAME/KEY: CDS
<222> LOCATION: (158)..(205)
<221> NAME/KEY: CDS
<222> LOCATION: (260)..(1600)

<400> SEQUENCE: 4
tctgtaaccg atagcggacc gactaggcat cgttgatcca caatatctca gacaatgcaa      60
ctcagtcgaa tatgaagggc tacagccagc atttaaatac ggccgtctag gtcgggctcc     120
ggggatgagg aggagcaggc tcgtgttcat ttcggtc atg gct ttt ttc acg gtc     175
                                         Met Ala Phe Phe Thr Val
                                           1               5 gct ctt tcg ctt tat tac ttg cta tcg agg tgagatctct acaatatctg        225
Ala Leu Ser Leu Tyr Tyr Leu Leu Ser Arg
            10                  15 tctgcttagt tgaattggta cttatctgta caga gtc tct gct cag gcc cca gtg    280
                                     Val Ser Ala Gln Ala Pro Val
                                                     20 gtc cag aat cat tca tgc aat acg gcg gac ggt gga tat caa tgc ttc      328
Val Gln Asn His Ser Cys Asn Thr Ala Asp Gly Gly Tyr Gln Cys Phe
 25                  30                  35 ccc aat gtc tct cat gtt tgg ggt cag tac tcg ccg tac ttc tcc atc      376
Pro Asn Val Ser His Val Trp Gly Gln Tyr Ser Pro Tyr Phe Ser Ile
 40                  45                  50                  55
```

| | |
|---|---|
| gag cag gag tca gct atc tct gag gac gtg cct cat ggc tgt gag gtt<br>Glu Gln Glu Ser Ala Ile Ser Glu Asp Val Pro His Gly Cys Glu Val<br>60                        65                  70 | 424 |
| acc ttt gtg cag gtg ctc tcg cgg cat ggg gct agg tat ccg aca gag<br>Thr Phe Val Gln Val Leu Ser Arg His Gly Ala Arg Tyr Pro Thr Glu<br>75                      80                    85 | 472 |
| tcg aag agt aag gcg tac tcg ggg ttg att gaa gca atc cag aag aat<br>Ser Lys Ser Lys Ala Tyr Ser Gly Leu Ile Glu Ala Ile Gln Lys Asn<br>90                      95                  100 | 520 |
| gct acc tct ttt tgg gga cag tat gct ttt ctg gag agt tat aac tat<br>Ala Thr Ser Phe Trp Gly Gln Tyr Ala Phe Leu Glu Ser Tyr Asn Tyr<br>105                  110               115 | 568 |
| acc ctc ggc gcg gat gac ttg act atc ttc ggc gag aac cag atg gtt<br>Thr Leu Gly Ala Asp Asp Leu Thr Ile Phe Gly Glu Asn Gln Met Val<br>120                  125               130               135 | 616 |
| gat tcg ggt gcc aag ttc tac cga cgg tat aag aat ctc gcc agg aaa<br>Asp Ser Gly Ala Lys Phe Tyr Arg Arg Tyr Lys Asn Leu Ala Arg Lys<br>140                  145               150 | 664 |
| aat act cct ttt atc cgt gca tca ggg tct gac cgt gtc gtt gcg tct<br>Asn Thr Pro Phe Ile Arg Ala Ser Gly Ser Asp Arg Val Val Ala Ser<br>155                  160               165 | 712 |
| gcg gag aag ttc att aat gga ttt cgc aag gct cag ctc cac gac cat<br>Ala Glu Lys Phe Ile Asn Gly Phe Arg Lys Ala Gln Leu His Asp His<br>170                  175               180 | 760 |
| ggc tcc aaa cgt gct acg cca gtt gtc aat gtg att atc cct gaa atc<br>Gly Ser Lys Arg Ala Thr Pro Val Val Asn Val Ile Ile Pro Glu Ile<br>185                  190               195 | 808 |
| gat ggg ttt aac aac acc ctg gac cat agc acg tgc gta tct ttt gag<br>Asp Gly Phe Asn Asn Thr Leu Asp His Ser Thr Cys Val Ser Phe Glu<br>200                  205               210               215 | 856 |
| aat gat gag cgg gcg gat gaa att gaa gcc aat ttc acg gca att atg<br>Asn Asp Glu Arg Ala Asp Glu Ile Glu Ala Asn Phe Thr Ala Ile Met<br>220                  225               230 | 904 |
| gga cct ccg atc cgc aaa cgt ctg gaa aat gac ctc cct ggc atc aaa<br>Gly Pro Pro Ile Arg Lys Arg Leu Glu Asn Asp Leu Pro Gly Ile Lys<br>235                  240               245 | 952 |
| ctt aca aac gag aat gta ata tat ttg atg gat atg tgc tct ttc gac<br>Leu Thr Asn Glu Asn Val Ile Tyr Leu Met Asp Met Cys Ser Phe Asp<br>250                  255               260 | 1000 |
| acc atg gcg cgc acc gcc cac gga acc gag ctg tct cca ttt tgt gcc<br>Thr Met Ala Arg Thr Ala His Gly Thr Glu Leu Ser Pro Phe Cys Ala<br>265                  270               275 | 1048 |
| atc ttc act gaa aag gag tgg ctg cag tac gac tac ctt caa tct cta<br>Ile Phe Thr Glu Lys Glu Trp Leu Gln Tyr Asp Tyr Leu Gln Ser Leu<br>280                  285               290               295 | 1096 |
| tca aag tac tac ggc tac ggt gcc gga agc ccc ctt ggc cca gct cag<br>Ser Lys Tyr Tyr Gly Tyr Gly Ala Gly Ser Pro Leu Gly Pro Ala Gln<br>300                  305               310 | 1144 |
| gga att ggc ttc acc aac gag ctg att gcc cga cta acg caa tcg ccc<br>Gly Ile Gly Phe Thr Asn Glu Leu Ile Ala Arg Leu Thr Gln Ser Pro<br>315                  320               325 | 1192 |
| gtc cag gac aac aca agc acc aac cac act cta gac tcg aac cca gcc<br>Val Gln Asp Asn Thr Ser Thr Asn His Thr Leu Asp Ser Asn Pro Ala<br>330                  335               340 | 1240 |
| aca ttt ccg ctc gac agg aag ctc tac gcc gac ttc tcc cac gac aat<br>Thr Phe Pro Leu Asp Arg Lys Leu Tyr Ala Asp Phe Ser His Asp Asn<br>345                  350               355 | 1288 |
| agc atg ata tcg ata ttc ttc gcc atg ggt ctg tac aac ggc acc cag<br>Ser Met Ile Ser Ile Phe Phe Ala Met Gly Leu Tyr Asn Gly Thr Gln | 1336 |

```
                    360                365                370                375
ccg ctg tca atg gat tcc gtg gag tcg atc cag gag atg gac ggt tac    1384
Pro Leu Ser Met Asp Ser Val Glu Ser Ile Gln Glu Met Asp Gly Tyr
                380                385                390 gcg gcg tct tgg act gtt ccg ttt ggt gcg agg gct tac ttt gag ctc    1432
Ala Ala Ser Trp Thr Val Pro Phe Gly Ala Arg Ala Tyr Phe Glu Leu
            395                400                405 atg cag tgc gag aag aag gag ccg ctt gtg cgg gta tta gtg aat gat    1480
Met Gln Cys Glu Lys Lys Glu Pro Leu Val Arg Val Leu Val Asn Asp
        410                415                420 cgc gtt gtt cct ctt cat ggc tgc gca gtt gac aag ttt gga cgg tgc    1528
Arg Val Val Pro Leu His Gly Cys Ala Val Asp Lys Phe Gly Arg Cys
    425                430                435 act ttg gac gat tgg gta gag ggc ttg aat ttt gca agg agc ggc ggg    1576
Thr Leu Asp Asp Trp Val Glu Gly Leu Asn Phe Ala Arg Ser Gly Gly
440                445                450                455 aac tgg aag act tgt ttt acc cta taaagggcgt tgctcattc ataagtgttg    1630
Asn Trp Lys Thr Cys Phe Thr Leu
                460 tgcaggtata ggaaggttag ggaattagct gtttggcttt actcttatta gaccaagaat    1690 gatttgtttg ttctcaaggc cttctagcat atcgtcaagt gggataaatc acctatcctc    1750 catgtgtagg tgaacccgct cttgcatcaa cctcttgtgt ttcagagtag tttcaccaaa    1810 catatcctcg tgtcctctct tctgctcttc ggtctcatat tacactgttc tctatctata    1870 tcgtcaacaa aactaccacc caaacaccaa atgtcacact ttccagcacg aaatttcttc    1930 g                                                                    1931

<210> SEQ ID NO 5
<211> LENGTH: 16
<212> TYPE: PRT
<213> ORGANISM: Aspergillus nidulans

<400> SEQUENCE: 5

Met Ala Phe Phe Thr Val Ala Leu Ser Leu Tyr Tyr Leu Leu Ser Arg
  1               5                  10                  15

<210> SEQ ID NO 6
<211> LENGTH: 447
<212> TYPE: PRT
<213> ORGANISM: Aspergillus nidulans

<400> SEQUENCE: 6

Val Ser Ala Gln Ala Pro Val Gln Asn His Ser Cys Asn Thr Ala
  1               5                  10                  15

Asp Gly Gly Tyr Gln Cys Phe Pro Asn Val Ser His Val Trp Gly Gln
                 20                  25                  30

Tyr Ser Pro Tyr Phe Ser Ile Glu Gln Glu Ser Ala Ile Ser Glu Asp
             35                  40                  45

Val Pro His Gly Cys Glu Val Thr Phe Val Gln Val Leu Ser Arg His
         50                  55                  60

Gly Ala Arg Tyr Pro Thr Glu Ser Lys Ser Lys Ala Tyr Ser Gly Leu
 65                  70                  75                  80

Ile Glu Ala Ile Gln Lys Asn Ala Thr Ser Phe Trp Gly Gln Tyr Ala
                 85                  90                  95

Phe Leu Glu Ser Tyr Asn Tyr Thr Leu Gly Ala Asp Asp Leu Thr Ile
            100                 105                 110

Phe Gly Glu Asn Gln Met Val Asp Ser Gly Ala Lys Phe Tyr Arg Arg
```

| | | | | 115 | | | | | 120 | | | | | 125 | | |
|---|---|---|---|---|---|---|---|---|---|---|---|---|---|---|---|---|

Tyr Lys Asn Leu Ala Arg Lys Asn Thr Pro Phe Ile Arg Ala Ser Gly
    130                       135                  140

Ser Asp Arg Val Val Ala Ser Ala Glu Lys Phe Ile Asn Gly Phe Arg
145                    150                  155                  160

Lys Ala Gln Leu His Asp His Gly Ser Lys Arg Ala Thr Pro Val Val
                      165                  170                  175

Asn Val Ile Ile Pro Glu Ile Asp Gly Phe Asn Asn Thr Leu Asp His
            180                  185                  190

Ser Thr Cys Val Ser Phe Glu Asn Asp Glu Arg Ala Asp Glu Ile Glu
        195                  200                205

Ala Asn Phe Thr Ala Ile Met Gly Pro Pro Ile Arg Lys Arg Leu Glu
210                    215                  220

Asn Asp Leu Pro Gly Ile Lys Leu Thr Asn Glu Asn Val Ile Tyr Leu
225                    230                235                  240

Met Asp Met Cys Ser Phe Asp Thr Met Ala Arg Thr Ala His Gly Thr
            245                  250                  255

Glu Leu Ser Pro Phe Cys Ala Ile Phe Thr Glu Lys Glu Trp Leu Gln
        260                  265                270

Tyr Asp Tyr Leu Gln Ser Leu Ser Lys Tyr Tyr Gly Tyr Gly Ala Gly
    275                  280                285

Ser Pro Leu Gly Pro Ala Gln Gly Ile Gly Phe Thr Asn Glu Leu Ile
290                    295                  300

Ala Arg Leu Thr Gln Ser Pro Val Gln Asp Asn Thr Ser Thr Asn His
305                    310                315                  320

Thr Leu Asp Ser Asn Pro Ala Thr Phe Pro Leu Asp Arg Lys Leu Tyr
            325                  330                  335

Ala Asp Phe Ser His Asp Asn Ser Met Ile Ser Ile Phe Phe Ala Met
        340                  345                350

Gly Leu Tyr Asn Gly Thr Gln Pro Leu Ser Met Asp Ser Val Glu Ser
    355                  360                365

Ile Gln Glu Met Asp Gly Tyr Ala Ala Ser Trp Thr Val Pro Phe Gly
    370                  375                380

Ala Arg Ala Tyr Phe Glu Leu Met Gln Cys Glu Lys Lys Glu Pro Leu
385                    390                395                  400

Val Arg Val Leu Val Asn Asp Arg Val Val Pro Leu His Gly Cys Ala
            405                  410                415

Val Asp Lys Phe Gly Arg Cys Thr Leu Asp Asp Trp Val Glu Gly Leu
            420                  425                430

Asn Phe Ala Arg Ser Gly Gly Asn Trp Lys Thr Cys Phe Thr Leu
        435                  440                445

<210> SEQ ID NO 7
<211> LENGTH: 1845
<212> TYPE: DNA
<213> ORGANISM: Talaromyces thermophilus
<220> FEATURE:
<221> NAME/KEY: CDS
<222> LOCATION: (288)..(335)
<221> NAME/KEY: CDS
<222> LOCATION: (391)..(1740)

<400> SEQUENCE: 7
ttccacgctg aaagcctgac tgcgatttcc aagctgcatg caggctgctc aactgcctgc    60
ttatcttcat cagacgcaga tacacaacct ggtctgtaga tgcacccatg acggacgaac   120

-continued

```
gcaccgctct cttggcctcc agggacccgg aggtcgaggg cgatgaggtc gcgccctcga     180
cggcctccca gtccctgttg cagttgagat ctcgctgcga acgtcgaccg cagatatggt     240
tgtcttcgac gttttctcgc cttcgaggaa gaattgctgc tgtgacg atg agt ctg       296
                                                   Met Ser Leu
                                                     1 ttg ttg ctg gtg ctg tcc ggc ggg ttg gtc gcg tta tag tatgctcctt       345
Leu Leu Leu Val Leu Ser Gly Gly Leu Val Ala Leu
  5                  10                 15 ctctctggtc atattgtttt ctgctaacgt tctcataatt gaagt gtc tca aga aat    402
                                                  Val Ser Arg Asn
                                                               20 ccg cat gtt gat agc cac tct tgc aat aca gtg gaa gga ggg tat cag      450
Pro His Val Asp Ser His Ser Cys Asn Thr Val Glu Gly Gly Tyr Gln
                 25                  30                  35 tgt cgt cca gaa atc tcc cac tcc tgg ggc cag tat tct cca ttc ttc      498
Cys Arg Pro Glu Ile Ser His Ser Trp Gly Gln Tyr Ser Pro Phe Phe
             40                  45                  50 tcc ctg gca gac cag tcg gag atc tcg cca gat gtc cca cag aac tgc      546
Ser Leu Ala Asp Gln Ser Glu Ile Ser Pro Asp Val Pro Gln Asn Cys
         55                  60                  65 aag att acg ttt gtc cag ctg ctt tct cgt cac ggc gct aga tac cct      594
Lys Ile Thr Phe Val Gln Leu Leu Ser Arg His Gly Ala Arg Tyr Pro
     70                  75                  80 acg tct tcc aag acg gag ctg tat tcg cag ctg atc agt cgg att cag      642
Thr Ser Ser Lys Thr Glu Leu Tyr Ser Gln Leu Ile Ser Arg Ile Gln
 85                  90                  95                 100 aag acg gcg act gcg tac aaa ggc tac tat gcc ttc ttg aaa gac tac      690
Lys Thr Ala Thr Ala Tyr Lys Gly Tyr Tyr Ala Phe Leu Lys Asp Tyr
                105                 110                 115 aga tac cag ctg gga gcg aac gac ctg acg ccc ttt ggg gaa aac cag      738
Arg Tyr Gln Leu Gly Ala Asn Asp Leu Thr Pro Phe Gly Glu Asn Gln
            120                 125                 130 atg atc cag ttg ggc atc aag ttt tat aac cat tac aag agt ctc gcc      786
Met Ile Gln Leu Gly Ile Lys Phe Tyr Asn His Tyr Lys Ser Leu Ala
        135                 140                 145 agg aat gcc gtc cca ttc gtt cgt tgc tcc ggc tct gat cgg gtc att      834
Arg Asn Ala Val Pro Phe Val Arg Cys Ser Gly Ser Asp Arg Val Ile
    150                 155                 160 gcc tcg ggg aga ctt ttc atc gaa ggt ttc cag agc gcc aaa gtg ctg      882
Ala Ser Gly Arg Leu Phe Ile Glu Gly Phe Gln Ser Ala Lys Val Leu
165                 170                 175                 180 gat cct cat tca gac aag cat gac gct cct ccc acg atc aac gtg atc      930
Asp Pro His Ser Asp Lys His Asp Ala Pro Pro Thr Ile Asn Val Ile
                185                 190                 195 atc gag gag ggt ccg tcc tac aat aac acg ctc gac acc ggc agc tgt      978
Ile Glu Glu Gly Pro Ser Tyr Asn Asn Thr Leu Asp Thr Gly Ser Cys
            200                 205                 210 cca gtc ttt gag gac agc agc ggg gga cat gac gca cag gaa aag ttc     1026
Pro Val Phe Glu Asp Ser Ser Gly Gly His Asp Ala Gln Glu Lys Phe
        215                 220                 225 gca aag caa ttc gca cca gct atc ctg gaa aag atc aag gac cat ctt     1074
Ala Lys Gln Phe Ala Pro Ala Ile Leu Glu Lys Ile Lys Asp His Leu
    230                 235                 240 ccc ggc gtg gac ctg gcc gtg tcg gat gta ccg tac ttg atg gac ttg     1122
Pro Gly Val Asp Leu Ala Val Ser Asp Val Pro Tyr Leu Met Asp Leu
245                 250                 255                 260 tgt ccg ttt gag acc ttg gct cgc aac cac aca gac acg ctg tct ccg     1170
Cys Pro Phe Glu Thr Leu Ala Arg Asn His Thr Asp Thr Leu Ser Pro
                265                 270                 275
```

```
ttc tgc gct ctt tcc acg caa gag gag tgg caa gca tat gac tac tac   1218
Phe Cys Ala Leu Ser Thr Gln Glu Glu Trp Gln Ala Tyr Asp Tyr Tyr
            280                 285                 290 caa agt ctg ggg aaa tac tat ggc aat ggc ggg ggt aac ccg ttg ggg   1266
Gln Ser Leu Gly Lys Tyr Tyr Gly Asn Gly Gly Gly Asn Pro Leu Gly
        295                 300                 305 cca gcc caa ggc gtg ggg ttt gtc aac gag ttg att gct cgc atg acc   1314
Pro Ala Gln Gly Val Gly Phe Val Asn Glu Leu Ile Ala Arg Met Thr
    310                 315                 320 cat agc cct gtc cag gac tac acc acg gtc aac cac act ctt gac tcg   1362
His Ser Pro Val Gln Asp Tyr Thr Thr Val Asn His Thr Leu Asp Ser
325                 330                 335                 340 aat ccg gcg aca ttc cct ttg aac gcg acg ctg tac gca gat ttc agc   1410
Asn Pro Ala Thr Phe Pro Leu Asn Ala Thr Leu Tyr Ala Asp Phe Ser
                345                 350                 355 cac gac aac aca atg acg tca att ttc gcg gcc ttg ggc ctg tac aac   1458
His Asp Asn Thr Met Thr Ser Ile Phe Ala Ala Leu Gly Leu Tyr Asn
            360                 365                 370 ggg acc gcg aag ctg tcc acg acc gag atc aag tcc att gaa gag acg   1506
Gly Thr Ala Lys Leu Ser Thr Thr Glu Ile Lys Ser Ile Glu Glu Thr
        375                 380                 385 gac ggc tac tcg gcg gcg tgg acc gtt ccg ttc ggg ggg cga gcc tat   1554
Asp Gly Tyr Ser Ala Ala Trp Thr Val Pro Phe Gly Gly Arg Ala Tyr
    390                 395                 400 atc gag atg atg cag tgt gat gat tcg gat gag cca gtc gtt cgg gtg   1602
Ile Glu Met Met Gln Cys Asp Asp Ser Asp Glu Pro Val Val Arg Val
405                 410                 415                 420 ctg gtc aac gac cgg gtg gtg cca ctg cat ggc tgc gag gtg gac tcc   1650
Leu Val Asn Asp Arg Val Val Pro Leu His Gly Cys Glu Val Asp Ser
                425                 430                 435 ctg ggg cga tgc aaa cga gac gac ttt gtc agg gga ctg agt ttt gcg   1698
Leu Gly Arg Cys Lys Arg Asp Asp Phe Val Arg Gly Leu Ser Phe Ala
            440                 445                 450 cga cag ggt ggg aac tgg gag ggg tgt tac gct gct tct gag           1740
Arg Gln Gly Gly Asn Trp Glu Gly Cys Tyr Ala Ala Ser Glu
        455                 460                 465 taggtttatt cagcgagttt cgacctttct atccttcaaa cactgcacaa agacacactg   1800
catgaaatgg taacaggcct ggagcgtttt agaaggaaaa aagtt                  1845

<210> SEQ ID NO 8
<211> LENGTH: 15
<212> TYPE: PRT
<213> ORGANISM: Talaromyces thermophilus

<400> SEQUENCE: 8

Met Ser Leu Leu Leu Leu Val Leu Ser Gly Gly Leu Val Ala Leu
1               5                   10                  15

<210> SEQ ID NO 9
<211> LENGTH: 450
<212> TYPE: PRT
<213> ORGANISM: Talaromyces thermophilus

<400> SEQUENCE: 9

Val Ser Arg Asn Pro His Val Asp Ser His Ser Cys Asn Thr Val Glu
1               5                   10                  15

Gly Gly Tyr Gln Cys Arg Pro Glu Ile Ser His Ser Trp Gly Gln Tyr
            20                  25                  30

Ser Pro Phe Phe Ser Leu Ala Asp Gln Ser Glu Ile Ser Pro Asp Val
```

-continued

```
                35                  40                  45
Pro Gln Asn Cys Lys Ile Thr Phe Val Gln Leu Leu Ser Arg His Gly
             50                  55                  60

Ala Arg Tyr Pro Thr Ser Ser Lys Thr Glu Leu Tyr Ser Gln Leu Ile
 65                  70                  75                  80

Ser Arg Ile Gln Lys Thr Ala Thr Ala Tyr Lys Gly Tyr Tyr Ala Phe
                 85                  90                  95

Leu Lys Asp Tyr Arg Tyr Gln Leu Gly Ala Asn Asp Leu Thr Pro Phe
                100                 105                 110

Gly Glu Asn Gln Met Ile Gln Leu Gly Ile Lys Phe Tyr Asn His Tyr
            115                 120                 125

Lys Ser Leu Ala Arg Asn Ala Val Pro Phe Val Arg Cys Ser Gly Ser
130                 135                 140

Asp Arg Val Ile Ala Ser Gly Arg Leu Phe Ile Glu Gly Phe Gln Ser
145                 150                 155                 160

Ala Lys Val Leu Asp Pro His Ser Asp Lys His Asp Ala Pro Pro Thr
                165                 170                 175

Ile Asn Val Ile Ile Glu Glu Gly Pro Ser Tyr Asn Asn Thr Leu Asp
            180                 185                 190

Thr Gly Ser Cys Pro Val Phe Glu Asp Ser Ser Gly Gly His Asp Ala
        195                 200                 205

Gln Glu Lys Phe Ala Lys Gln Phe Ala Pro Ala Ile Leu Glu Lys Ile
    210                 215                 220

Lys Asp His Leu Pro Gly Val Asp Leu Ala Val Ser Asp Val Pro Tyr
225                 230                 235                 240

Leu Met Asp Leu Cys Pro Phe Glu Thr Leu Ala Arg Asn His Thr Asp
                245                 250                 255

Thr Leu Ser Pro Phe Cys Ala Leu Ser Thr Gln Glu Glu Trp Gln Ala
            260                 265                 270

Tyr Asp Tyr Tyr Gln Ser Leu Gly Lys Tyr Tyr Gly Asn Gly Gly Gly
        275                 280                 285

Asn Pro Leu Gly Pro Ala Gln Gly Val Gly Phe Val Asn Glu Leu Ile
    290                 295                 300

Ala Arg Met Thr His Ser Pro Val Gln Asp Tyr Thr Thr Val Asn His
305                 310                 315                 320

Thr Leu Asp Ser Asn Pro Ala Thr Phe Pro Leu Asn Ala Thr Leu Tyr
                325                 330                 335

Ala Asp Phe Ser His Asp Asn Thr Met Thr Ser Ile Phe Ala Ala Leu
            340                 345                 350

Gly Leu Tyr Asn Gly Thr Ala Lys Leu Ser Thr Thr Glu Ile Lys Ser
        355                 360                 365

Ile Glu Glu Thr Asp Gly Tyr Ser Ala Ala Trp Thr Val Pro Phe Gly
    370                 375                 380

Gly Arg Ala Tyr Ile Glu Met Met Gln Cys Asp Asp Ser Asp Glu Pro
385                 390                 395                 400

Val Val Arg Val Leu Val Asn Asp Arg Val Pro Leu His Gly Cys
                405                 410                 415

Glu Val Asp Ser Leu Gly Arg Cys Lys Arg Asp Asp Phe Val Arg Gly
            420                 425                 430

Leu Ser Phe Ala Arg Gln Gly Gly Asn Trp Glu Gly Cys Tyr Ala Ala
        435                 440                 445

Ser Glu
450
```

```
<210> SEQ ID NO 10
<211> LENGTH: 1571
<212> TYPE: DNA
<213> ORGANISM: Aspergillus fumigatus
<220> FEATURE:
<221> NAME/KEY: CDS
<222> LOCATION: (43)..(90)
<221> NAME/KEY: CDS
<222> LOCATION: (148)..(1494)

<400> SEQUENCE: 10
agattcaacg acggaggaat cgcaaccct a attgtcggta tc atg gtg act ctg        54
                                           Met Val Thr Leu
                                             1 act ttc ctg ctt tcg gcg gcg tat ctg ctt tct ggg tgagtggctt            100
Thr Phe Leu Leu Ser Ala Ala Tyr Leu Leu Ser Gly
  5              10              15 ggatctattg ctcggatagg gctgtggtgc tgattctgaa acggagt aga gtg tct       156
                                                    Arg Val Ser gcg gca cct agt tct gct ggc tcc aag tcc tgc gat acg gta gac ctc       204
Ala Ala Pro Ser Ser Ala Gly Ser Lys Ser Cys Asp Thr Val Asp Leu
 20                  25                  30                  35 ggg tac cag tgc tcc cct gcg act tct cat cta tgg ggc cag tac tcg       252
Gly Tyr Gln Cys Ser Pro Ala Thr Ser His Leu Trp Gly Gln Tyr Ser
                 40                  45                  50 cca ttc ttt tcg ctc gag gac gag ctg tcc gtg tcg agt aag ctt ccc       300
Pro Phe Phe Ser Leu Glu Asp Glu Leu Ser Val Ser Ser Lys Leu Pro
         55                  60                  65 aag gat tgc cgg atc acc ttg gta cag gtg cta tcg cgc cat gga gcg       348
Lys Asp Cys Arg Ile Thr Leu Val Gln Val Leu Ser Arg His Gly Ala
 70                  75                  80 cgg tac cca acc agc tcc aag agc aaa aag tat aag aag ctt gtg acg       396
Arg Tyr Pro Thr Ser Ser Lys Ser Lys Lys Tyr Lys Lys Leu Val Thr
         85                  90                  95 gcg atc cag gcc aat gcc acc gac ttc aag ggc aag ttt gcc ttt ttg       444
Ala Ile Gln Ala Asn Ala Thr Asp Phe Lys Gly Lys Phe Ala Phe Leu
100                 105                 110                 115 aag acg tac aac tat act ctg ggt gcg gat gac ctc act ccc ttt ggg       492
Lys Thr Tyr Asn Tyr Thr Leu Gly Ala Asp Asp Leu Thr Pro Phe Gly
                120                 125                 130 gag cag cag ctg gtg aac tcg ggc atc aag ttc tac cag agg tac aag       540
Glu Gln Gln Leu Val Asn Ser Gly Ile Lys Phe Tyr Gln Arg Tyr Lys
        135                 140                 145 gct ctg gcg cgc agt gtg gtg ccg ttt att cgc gcc tca ggc tcg gac       588
Ala Leu Ala Arg Ser Val Val Pro Phe Ile Arg Ala Ser Gly Ser Asp
150                 155                 160 cgg gtt att gct tcg gga gag aag ttc atc gag ggg ttc cag cag gcg       636
Arg Val Ile Ala Ser Gly Glu Lys Phe Ile Glu Gly Phe Gln Gln Ala
        165                 170                 175 aag ctg gct gat cct ggc gcg acg aac cgc gcc gct ccg gcg att agt       684
Lys Leu Ala Asp Pro Gly Ala Thr Asn Arg Ala Ala Pro Ala Ile Ser
180                 185                 190                 195 gtg att att ccg gag agc gag acg ttc aac aat acg ctg gac cac ggt       732
Val Ile Ile Pro Glu Ser Glu Thr Phe Asn Asn Thr Leu Asp His Gly
                200                 205                 210 gtg tgc acg aag ttt gag gcg agt cag ctg gga gat gag gtt gcg gcc       780
Val Cys Thr Lys Phe Glu Ala Ser Gln Leu Gly Asp Glu Val Ala Ala
        215                 220                 225 aat ttc act gcg ctc ttt gca ccc gac atc cga gct cgc gcc gag aag       828
Asn Phe Thr Ala Leu Phe Ala Pro Asp Ile Arg Ala Arg Ala Glu Lys
```

```
                    230                 235                  240
cat ctt cct ggc gtg acg ctg aca gac gag gac gtt gtc agt cta atg        876
His Leu Pro Gly Val Thr Leu Thr Asp Glu Asp Val Val Ser Leu Met
    245                 250                  255 gac atg tgt tcg ttt gat acg gta gcg cgc acc agc gac gca agt cag        924
Asp Met Cys Ser Phe Asp Thr Val Ala Arg Thr Ser Asp Ala Ser Gln
260                 265                  270                 275 ctg tca ccg ttc tgt caa ctc ttc act cac aat gag tgg aag aag tac        972
Leu Ser Pro Phe Cys Gln Leu Phe Thr His Asn Glu Trp Lys Lys Tyr
                280                 285                  290 aac tac ctt cag tcc ttg ggc aag tac tac ggc tac ggc gca ggc aac       1020
Asn Tyr Leu Gln Ser Leu Gly Lys Tyr Tyr Gly Tyr Gly Ala Gly Asn
            295                 300                  305 cct ctg gga ccg gct cag ggg ata ggg ttc acc aac gag ctg att gcc       1068
Pro Leu Gly Pro Ala Gln Gly Ile Gly Phe Thr Asn Glu Leu Ile Ala
        310                 315                  320 cgg ttg act cgt tcg cca gtg cag gac cac acc agc act aac tcg act       1116
Arg Leu Thr Arg Ser Pro Val Gln Asp His Thr Ser Thr Asn Ser Thr
    325                 330                  335 cta gtc tcc aac ccg gcc acc ttc ccg ttg aac gct acc atg tac gtc       1164
Leu Val Ser Asn Pro Ala Thr Phe Pro Leu Asn Ala Thr Met Tyr Val
340                 345                  350                 355 gac ttt tca cac gac aac agc atg gtt tcc atc ttc ttt gca ttg ggc       1212
Asp Phe Ser His Asp Asn Ser Met Val Ser Ile Phe Phe Ala Leu Gly
                360                 365                  370 ctg tac aac ggc act gaa ccc ttg tcc cgg acc tcg gtg gaa agc gcc       1260
Leu Tyr Asn Gly Thr Glu Pro Leu Ser Arg Thr Ser Val Glu Ser Ala
            375                 380                  385 aag gaa ttg gat ggg tat tct gca tcc tgg gtg gtg cct ttc ggc gcg       1308
Lys Glu Leu Asp Gly Tyr Ser Ala Ser Trp Val Val Pro Phe Gly Ala
        390                 395                  400 cga gcc tac ttc gag acg atg caa tgc aag tcg aaa aag gag cct ctt       1356
Arg Ala Tyr Phe Glu Thr Met Gln Cys Lys Ser Glu Lys Glu Pro Leu
    405                 410                  415 gtt cgc gct ttg att aat gac cgg gtt gtg cca ctg cat ggc tgc gat       1404
Val Arg Ala Leu Ile Asn Asp Arg Val Val Pro Leu His Gly Cys Asp
420                 425                  430                 435 gtg gac aag ctg ggg cga tgc aag ctg aat gac ttt gtc aag gga ttg       1452
Val Asp Lys Leu Gly Arg Cys Lys Leu Asn Asp Phe Val Lys Gly Leu
                440                 445                  450 agt tgg gcc aga tct ggg ggc aac tgg gga gag tgc ttt agt              1494
Ser Trp Ala Arg Ser Gly Gly Asn Trp Gly Glu Cys Phe Ser
            455                 460                  465 tgagatgtca ttgttatgct atactccaat agaccgttgc ttagccattc acttcacttt    1554
gctcgaaccg cctgccg                                                   1571

<210> SEQ ID NO 11
<211> LENGTH: 16
<212> TYPE: PRT
<213> ORGANISM: Aspergillus fumigatus

<400> SEQUENCE: 11

Met Val Thr Leu Thr Phe Leu Leu Ser Ala Ala Tyr Leu Leu Ser Gly
  1               5                  10                  15

<210> SEQ ID NO 12
<211> LENGTH: 449
<212> TYPE: PRT
<213> ORGANISM: Aspergillus fumigatus
```

-continued

<400> SEQUENCE: 12

| | | | | | | | | | | | | | | |
|---|---|---|---|---|---|---|---|---|---|---|---|---|---|---|
| Arg | Val | Ser | Ala | Ala | Pro | Ser | Ser | Ala | Gly | Ser | Lys | Ser | Cys | Asp | Thr |
| 1 | | | | 5 | | | | | 10 | | | | | 15 | |

Val Asp Leu Gly Tyr Gln Cys Ser Pro Ala Thr Ser His Leu Trp Gly
             20                 25                 30

Gln Tyr Ser Pro Phe Phe Ser Leu Glu Asp Glu Leu Ser Val Ser Ser
        35                     40                 45

Lys Leu Pro Lys Asp Cys Arg Ile Thr Leu Val Gln Val Leu Ser Arg
    50                     55                 60

His Gly Ala Arg Tyr Pro Thr Ser Ser Lys Ser Lys Tyr Lys Lys
65                70                 75                 80

Leu Val Thr Ala Ile Gln Ala Asn Ala Thr Asp Phe Lys Gly Lys Phe
             85                 90                 95

Ala Phe Leu Lys Thr Tyr Asn Tyr Thr Leu Gly Ala Asp Asp Leu Thr
        100                 105             110

Pro Phe Gly Glu Gln Gln Leu Val Asn Ser Gly Ile Lys Phe Tyr Gln
        115                 120             125

Arg Tyr Lys Ala Leu Ala Arg Ser Val Val Pro Phe Ile Arg Ala Ser
130                135                 140

Gly Ser Asp Arg Val Ile Ala Ser Gly Glu Lys Phe Ile Glu Gly Phe
145                150                155              160

Gln Gln Ala Lys Leu Ala Asp Pro Gly Ala Thr Asn Arg Ala Ala Pro
        165                 170             175

Ala Ile Ser Val Ile Ile Pro Glu Ser Glu Thr Phe Asn Asn Thr Leu
            180                 185             190

Asp His Gly Val Cys Thr Lys Phe Glu Ala Ser Gln Leu Gly Asp Glu
        195                 200             205

Val Ala Ala Asn Phe Thr Ala Leu Phe Ala Pro Asp Ile Arg Ala Arg
210                215                 220

Ala Glu Lys His Leu Pro Gly Val Thr Leu Thr Asp Glu Asp Val Val
225                230                235              240

Ser Leu Met Asp Met Cys Ser Phe Asp Thr Val Ala Arg Thr Ser Asp
        245                 250             255

Ala Ser Gln Leu Ser Pro Phe Cys Gln Leu Phe Thr His Asn Glu Trp
        260                 265             270

Lys Lys Tyr Asn Tyr Leu Gln Ser Leu Gly Lys Tyr Tyr Gly Tyr Gly
        275                 280             285

Ala Gly Asn Pro Leu Gly Pro Ala Gln Gly Ile Gly Phe Thr Asn Glu
    290                   295                 300

Leu Ile Ala Arg Leu Thr Arg Ser Pro Val Gln Asp His Thr Ser Thr
305                310                315              320

Asn Ser Thr Leu Val Ser Asn Pro Ala Thr Phe Pro Leu Asn Ala Thr
            325                 330             335

Met Tyr Val Asp Phe Ser His Asp Asn Ser Met Val Ser Ile Phe Phe
        340                 345             350

Ala Leu Gly Leu Tyr Asn Gly Thr Glu Pro Leu Ser Arg Thr Ser Val
    355                   360             365

Glu Ser Ala Lys Glu Leu Asp Gly Tyr Ser Ala Ser Trp Val Val Pro
    370                   375             380

Phe Gly Ala Arg Ala Tyr Phe Glu Thr Met Gln Cys Lys Ser Glu Lys
385                390                395              400

Glu Pro Leu Val Arg Ala Leu Ile Asn Asp Arg Val Val Pro Leu His
        405                 410             415

```
Gly Cys Asp Val Asp Lys Leu Gly Arg Cys Lys Leu Asn Asp Phe Val
            420                 425                 430
Lys Gly Leu Ser Trp Ala Arg Ser Gly Gly Asn Trp Gly Glu Cys Phe
        435                 440                 445
Ser

<210> SEQ ID NO 13
<211> LENGTH: 1567
<212> TYPE: DNA
<213> ORGANISM: Aspergillus terreus
<220> FEATURE:
<221> NAME/KEY: CDS
<222> LOCATION: (78)..(125)
<221> NAME/KEY: CDS
<222> LOCATION: (178)..(1527)

<400> SEQUENCE: 13
acgtcccagg tcggggacta catccgctat gtggtcctct acttcgtcgg aagaatatac    60
tgtctcttgt ggctacc atg ggg gtt ttc gtc gtt cta tta tct atc gcg      110
                  Met Gly Val Phe Val Val Leu Leu Ser Ile Ala
                    1               5                  10 act ctg ttc ggc agg tatgtgcacc gctctaggtt caactcgcct ggtaactgac     165
Thr Leu Phe Gly Arg
            15 aaacagtaca gc aca tcg ggc act gcg ctg ggc ccc cgt gga aat cac agc   216
              Thr Ser Gly Thr Ala Leu Gly Pro Arg Gly Asn His Ser
                                20                  25 gac tgc acc tca gtc gac cgg ggg tat caa tgc ttc cct gag ctc tcc    264
Asp Cys Thr Ser Val Asp Arg Gly Tyr Gln Cys Phe Pro Glu Leu Ser
 30              35                  40                  45 cat aaa tgg ggt ctc tac gcg ccc tat ttc tcc ctc cag gat gaa tct    312
His Lys Trp Gly Leu Tyr Ala Pro Tyr Phe Ser Leu Gln Asp Glu Ser
             50                  55                  60 ccg ttt cct ctg gac gtc ccg gat gac tgc cac atc acc ttt gtg cag    360
Pro Phe Pro Leu Asp Val Pro Asp Asp Cys His Ile Thr Phe Val Gln
         65                  70                  75 gtg ctg gcc cga cat gga gcg cgg tct cca acc gat agc aag aca aag    408
Val Leu Ala Arg His Gly Ala Arg Ser Pro Thr Asp Ser Lys Thr Lys
     80                  85                  90 gcg tat gcc gcg act att gca gcc atc cag aag aat gcc acc gcg ttg    456
Ala Tyr Ala Ala Thr Ile Ala Ala Ile Gln Lys Asn Ala Thr Ala Leu
 95                 100                 105 ccg ggc aaa tac gcc ttc ctg aag tcg tac aat tac tcc atg ggc tcc    504
Pro Gly Lys Tyr Ala Phe Leu Lys Ser Tyr Asn Tyr Ser Met Gly Ser
110             115                 120                 125 gag aac ctg aac ccc ttc ggg cgg aac caa ctg caa gat ctg ggc gcc    552
Glu Asn Leu Asn Pro Phe Gly Arg Asn Gln Leu Gln Asp Leu Gly Ala
            130                 135                 140 cag ttc tac cgt cgc tac gac acc ctc acc cgg cac atc aac cct ttc    600
Gln Phe Tyr Arg Arg Tyr Asp Thr Leu Thr Arg His Ile Asn Pro Phe
        145                 150                 155 gtc cgg gcc gcg gat tcc tcc cgc gtc cac gaa tca gcc gag aag ttc    648
Val Arg Ala Ala Asp Ser Ser Arg Val His Glu Ser Ala Glu Lys Phe
    160                 165                 170 gtc gag ggc ttc caa aac gcc cgc caa ggc gat cct cac gcc aac cct    696
Val Glu Gly Phe Gln Asn Ala Arg Gln Gly Asp Pro His Ala Asn Pro
175                 180                 185 cac cag ccg tcg ccg cgc gtg gat gta gtc atc ccc gaa ggc acc gcc    744
His Gln Pro Ser Pro Arg Val Asp Val Val Ile Pro Glu Gly Thr Ala
190                 195                 200                 205
```

```
tac aac aac acg ctc gag cac agc atc tgc acc gcc ttc gag gcc agc          792
Tyr Asn Asn Thr Leu Glu His Ser Ile Cys Thr Ala Phe Glu Ala Ser
                210                 215                 220 acc gtc ggc gac gcc gcg gca gac aac ttc act gcc gtg ttc gcg ccg          840
Thr Val Gly Asp Ala Ala Ala Asp Asn Phe Thr Ala Val Phe Ala Pro
                225                 230                 235 gcg atc gcc aag cgt ctg gag gcc gat ctg ccc ggc gtg cag ctg tcc          888
Ala Ile Ala Lys Arg Leu Glu Ala Asp Leu Pro Gly Val Gln Leu Ser
                240                 245                 250 gcc gac gac gtg gtc aat ctg atg gcc atg tgt ccg ttc gag acg gtc          936
Ala Asp Asp Val Val Asn Leu Met Ala Met Cys Pro Phe Glu Thr Val
                255                 260                 265 agc ctg acc gac gac gcg cac acg ctg tcg ccg ttc tgc gac ctc ttc          984
Ser Leu Thr Asp Asp Ala His Thr Leu Ser Pro Phe Cys Asp Leu Phe
270                 275                 280                 285 acc gcc gcc gag tgg acg cag tac aac tac ctc tcg ctg gac aag             1032
Thr Ala Ala Glu Trp Thr Gln Tyr Asn Tyr Leu Leu Ser Leu Asp Lys
                290                 295                 300 tac tac ggc tac ggc ggc ggc aat ccg ctg ggc ccc gtg cag ggc gtg         1080
Tyr Tyr Gly Tyr Gly Gly Gly Asn Pro Leu Gly Pro Val Gln Gly Val
                305                 310                 315 ggc tgg gcg aac gag ctg atc gcg cgg ctg acg cgc tcc ccc gtc cac         1128
Gly Trp Ala Asn Glu Leu Ile Ala Arg Leu Thr Arg Ser Pro Val His
                320                 325                 330 gac cac acc tgc gtc aac aac acc ctc gac gcc aac ccg gcc acc ttc         1176
Asp His Thr Cys Val Asn Asn Thr Leu Asp Ala Asn Pro Ala Thr Phe
                335                 340                 345 ccg ctg aac gcc acc ctc tac gcg gac ttt tcg cac gac agt aac ctg         1224
Pro Leu Asn Ala Thr Leu Tyr Ala Asp Phe Ser His Asp Ser Asn Leu
350                 355                 360                 365 gtg tcg atc ttc tgg gcg ctg ggt ctg tac aac ggc acc aag ccc ctg         1272
Val Ser Ile Phe Trp Ala Leu Gly Leu Tyr Asn Gly Thr Lys Pro Leu
                370                 375                 380 tcg cag acc acc gtg gag gat atc acc cgg acg gac ggg tac gcg gcc         1320
Ser Gln Thr Thr Val Glu Asp Ile Thr Arg Thr Asp Gly Tyr Ala Ala
                385                 390                 395 gcc tgg acg gtg ccg ttt gcc gcc cgc gcc tac atc gag atg atg cag         1368
Ala Trp Thr Val Pro Phe Ala Ala Arg Ala Tyr Ile Glu Met Met Gln
                400                 405                 410 tgt cgc gcg gag aag cag ccg ctg gtg cgc gtg ctg gtc aac gac cgt         1416
Cys Arg Ala Glu Lys Gln Pro Leu Val Arg Val Leu Val Asn Asp Arg
                415                 420                 425 gtc atg ccg ctg cac ggc tgc gcg gtg gat aat ctg ggc agg tgt aaa         1464
Val Met Pro Leu His Gly Cys Ala Val Asp Asn Leu Gly Arg Cys Lys
430                 435                 440                 445 cgg gac gac ttt gtg gag gga ctg agc ttt gcg cgg gca gga ggg aac         1512
Arg Asp Asp Phe Val Glu Gly Leu Ser Phe Ala Arg Ala Gly Gly Asn
                450                 455                 460 tgg gcc gag tgt ttc tgatgtacat gctgtagtta gctttgagtc ctgaggtacc         1567
Trp Ala Glu Cys Phe
                465

<210> SEQ ID NO 14
<211> LENGTH: 16
<212> TYPE: PRT
<213> ORGANISM: Aspergillus terreus

<400> SEQUENCE: 14

Met Gly Val Phe Val Leu Leu Ser Ile Ala Thr Leu Phe Gly Arg
1               5                   10                  15
```

```
<210> SEQ ID NO 15
<211> LENGTH: 450
<212> TYPE: PRT
<213> ORGANISM: Aspergillus terreus

<400> SEQUENCE: 15

Thr Ser Gly Thr Ala Leu Gly Pro Arg Gly Asn His Ser Asp Cys Thr
 1               5                  10                  15

Ser Val Asp Arg Gly Tyr Gln Cys Phe Pro Glu Leu Ser His Lys Trp
            20                  25                  30

Gly Leu Tyr Ala Pro Tyr Phe Ser Leu Gln Asp Glu Ser Pro Phe Pro
        35                  40                  45

Leu Asp Val Pro Asp Cys His Ile Thr Phe Val Gln Val Leu Ala
50                  55                  60

Arg His Gly Ala Arg Ser Pro Thr Asp Ser Lys Thr Lys Ala Tyr Ala
65                  70                  75                  80

Ala Thr Ile Ala Ala Ile Gln Lys Asn Ala Thr Ala Leu Pro Gly Lys
                85                  90                  95

Tyr Ala Phe Leu Lys Ser Tyr Asn Tyr Ser Met Gly Ser Glu Asn Leu
            100                 105                 110

Asn Pro Phe Gly Arg Asn Gln Leu Gln Asp Leu Gly Ala Gln Phe Tyr
        115                 120                 125

Arg Arg Tyr Asp Thr Leu Thr Arg His Ile Asn Pro Phe Val Arg Ala
130                 135                 140

Ala Asp Ser Ser Arg Val His Glu Ser Ala Glu Lys Phe Val Glu Gly
145                 150                 155                 160

Phe Gln Asn Ala Arg Gln Gly Asp Pro His Ala Asn Pro His Gln Pro
                165                 170                 175

Ser Pro Arg Val Asp Val Val Ile Pro Glu Gly Thr Ala Tyr Asn Asn
            180                 185                 190

Thr Leu Glu His Ser Ile Cys Thr Ala Phe Glu Ala Ser Thr Val Gly
        195                 200                 205

Asp Ala Ala Asp Asn Phe Thr Ala Val Phe Ala Pro Ala Ile Ala
210                 215                 220

Lys Arg Leu Glu Ala Asp Leu Pro Gly Val Gln Leu Ser Ala Asp Asp
225                 230                 235                 240

Val Val Asn Leu Met Ala Met Cys Pro Phe Glu Thr Val Ser Leu Thr
                245                 250                 255

Asp Asp Ala His Thr Leu Ser Pro Phe Cys Asp Leu Phe Thr Ala Ala
            260                 265                 270

Glu Trp Thr Gln Tyr Asn Tyr Leu Leu Ser Leu Asp Lys Tyr Tyr Gly
        275                 280                 285

Tyr Gly Gly Asn Pro Leu Gly Pro Val Gln Gly Val Gly Trp Ala
290                 295                 300

Asn Glu Leu Ile Ala Arg Leu Thr Arg Ser Pro Val His Asp His Thr
305                 310                 315                 320

Cys Val Asn Asn Thr Leu Asp Ala Asn Pro Ala Thr Phe Pro Leu Asn
                325                 330                 335

Ala Thr Leu Tyr Ala Asp Phe Ser His Asp Ser Asn Leu Val Ser Ile
            340                 345                 350

Phe Trp Ala Leu Gly Leu Tyr Asn Gly Thr Lys Pro Leu Ser Gln Thr
        355                 360                 365

Thr Val Glu Asp Ile Thr Arg Thr Asp Gly Tyr Ala Ala Ala Trp Thr
```

```
              370                 375                 380
Val Pro Phe Ala Ala Arg Ala Tyr Ile Glu Met Met Gln Cys Arg Ala
385                 390                 395                 400

Glu Lys Gln Pro Leu Val Arg Val Leu Val Asn Asp Arg Val Met Pro
                405                 410                 415

Leu His Gly Cys Ala Val Asp Asn Leu Gly Arg Cys Lys Arg Asp Asp
                420                 425                 430

Phe Val Glu Gly Leu Ser Phe Ala Arg Ala Gly Gly Asn Trp Ala Glu
            435                 440                 445

Cys Phe
    450
```

<210> SEQ ID NO 16
<211> LENGTH: 33
<212> TYPE: DNA
<213> ORGANISM: Artificial Sequence
<220> FEATURE:
<223> OTHER INFORMATION: Description of Artificial Sequence: Nucleotide
      Sequence of Primer #39 designed based on Aspergillus fumigatus
      ATCC 13073

<400> SEQUENCE: 16
tatatcatga ttactctgac tttcctgctt tcg                              33

<210> SEQ ID NO 17
<211> LENGTH: 9
<212> TYPE: PRT
<213> ORGANISM: Artificial Sequence
<220> FEATURE:
<223> OTHER INFORMATION: Description of Artificial Sequence: Amino Acid
      Sequence Corresponding to Primer #39

<400> SEQUENCE: 17

Met Ile Thr Leu Thr Phe Leu Leu Ser
  1               5

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Nucleotide
      Sequence of Primer #40 designed based on Aspergillus fumigatus
      ATCC 13073

<400> SEQUENCE: 18
tatatagata tctcaactaa agcactctcc                                  30

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: Amino Acid
      Sequence Corresponding to Primer #40

<400> SEQUENCE: 19

Gly Glu Cys Phe Ser
  1               5

<210> SEQ ID NO 20
<211> LENGTH: 31
<212> TYPE: DNA
<213> ORGANISM: Artificial Sequence
<220> FEATURE:

<223> OTHER INFORMATION: Description of Artificial Sequence: Fum28 PCR
      Primer

<400> SEQUENCE: 20
atatatcggc cgagtgtctg cggcacctag t                                   31

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence: Fum11 PCR
      Primer

<400> SEQUENCE: 21
tgaggtcatc cgcacccaga g                                              21

<210> SEQ ID NO 22
<211> LENGTH: 54
<212> TYPE: DNA
<213> ORGANISM: Artificial Sequence
<220> FEATURE:
<223> OTHER INFORMATION: Description of Artificial Sequence: Fum26 PCR
      Primer

<400> SEQUENCE: 22
ctagaattca tggtgactct gactttcctg ctttcggcgg cgtatctgct ttcc          54

<210> SEQ ID NO 23
<211> LENGTH: 54
<212> TYPE: DNA
<213> ORGANISM: Artificial Sequence
<220> FEATURE:
<223> OTHER INFORMATION: Description of Artificial Sequence: Fum27 PCR
      Primer

<400> SEQUENCE: 23
ggccggaaag cagatacgcc gccgaaagca ggaaagtcag agtcaccatg aatt          54

<210> SEQ ID NO 24
<211> LENGTH: 27
<212> TYPE: DNA
<213> ORGANISM: Artificial Sequence
<220> FEATURE:
<223> OTHER INFORMATION: Description of Artificial Sequence:Primer
      Q27L s

<400> SEQUENCE: 24
catctatggg gcctgtactc gccattc                                        27

<210> SEQ ID NO 25
<211> LENGTH: 27
<212> TYPE: DNA
<213> ORGANISM: Artificial Sequence
<220> FEATURE:
<223> OTHER INFORMATION: Description of Artificial Sequence:Primer
      Q27L as

<400> SEQUENCE: 25
gaatggcgag tacaggcccc atagatg                                        27

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence:Amino Acid Sequence Encoded by Primer Set A

<400> SEQUENCE: 26

His Leu Trp Gly Leu Tyr Ser Pro Phe
 1               5

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence:Primer
      Q274L s

<400> SEQUENCE: 27
tacaactacc ttctgtcctt gggcaag                                          27

<210> SEQ ID NO 28
<211> LENGTH: 27
<212> TYPE: DNA
<213> ORGANISM: Artificial Sequence
<220> FEATURE:
<223> OTHER INFORMATION: Description of Artificial Sequence:Primer
      Q274L as

<400> SEQUENCE: 28
cttgcccaag gacagaaggt agttgta                                          27

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence:Amino Acid
      Sequence Encoded by Primer Set B

<400> SEQUENCE: 29

Tyr Asn Tyr Leu Leu Ser Leu Gly Lys
 1               5

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence:Primer
      G277D s

<400> SEQUENCE: 30
cttcagtcct tggacaagta ctacggc                                          27

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence:Primer
      G277D as

<400> SEQUENCE: 31
gccgtagtac ttgtccaagg actgaag                                          27

<210> SEQ ID NO 32
<211> LENGTH: 9
<212> TYPE: PRT
<213> ORGANISM: Artificial Sequence
<220> FEATURE:

<223> OTHER INFORMATION: Description of Artificial Sequence:Amino Acid
      Sequence encoded by Primer set C

<400> SEQUENCE: 32

Leu Gln Ser Leu Asp Lys Tyr Tyr Gly
  1               5

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence:Primer
      G277D* s

<400> SEQUENCE: 33
cttctgtcct tggacaagta ctacggc                                        27

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence:Primer
      G277D* as

<400> SEQUENCE: 34
gccgtagtac ttgtccaagg acagaag                                        27

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence:Amino Acid
      Sequence Encoded by Primer Set D

<400> SEQUENCE: 35

Leu Leu Ser Leu Asp Lys Tyr Tyr Gly
  1               5

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence:Primer
      N340S s

<400> SEQUENCE: 36
ttttcacacg acagcagcat ggtttcc                                        27

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence:Primer
      N340S as

<400> SEQUENCE: 37
ggaaaccatg ctgctgtcgt gtgaaaa                                        27

<210> SEQ ID NO 38
<211> LENGTH: 9
<212> TYPE: PRT
<213> ORGANISM: Artificial Sequence

```
<220> FEATURE:
<223> OTHER INFORMATION: Description of Artificial Sequence:Amino Acid
      Sequence Encoded by Primer Set E

<400> SEQUENCE: 38

Phe Ser His Asp Ser Ser Met Val Ile
 1               5

<210> SEQ ID NO 39
<211> LENGTH: 31
<212> TYPE: DNA
<213> ORGANISM: Artificial Sequence
<220> FEATURE:
<223> OTHER INFORMATION: Description of Artificial Sequence:Primer
      G277K s

<400> SEQUENCE: 39
ccttcagtcc ttgaagaagt actacggcta c                              31

<210> SEQ ID NO 40
<211> LENGTH: 31
<212> TYPE: DNA
<213> ORGANISM: Artificial Sequence
<220> FEATURE:
<223> OTHER INFORMATION: Description of Artificial Sequence:Primer
      G277K as

<400> SEQUENCE: 40
gtagccgtag tacttcttca aggactgaag g                              31

<210> SEQ ID NO 41
<211> LENGTH: 10
<212> TYPE: PRT
<213> ORGANISM: Artificial Sequence
<220> FEATURE:
<223> OTHER INFORMATION: Description of Artificial Sequence:Amino Acid
      Sequence Encoded by Primer Set F

<400> SEQUENCE: 41

Leu Gln Ser Leu Lys Lys Tyr Tyr Gly Tyr
 1               5                  10

<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence:Primer
      A205E s

<400> SEQUENCE: 42
ggagatgagg ttgaggccaa tttcactg                                  28

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence:Primer
      A205E as

<400> SEQUENCE: 43
cagtgaaatt ggcctcaacc tcatctcc                                  28

<210> SEQ ID NO 44
<211> LENGTH: 9
<212> TYPE: PRT
```

```
<213> ORGANISM: Artificial Sequence
<220> FEATURE:
<223> OTHER INFORMATION: Description of Artificial Sequence:Amino Acid
      Sequence Encoded by Primer Set G

<400> SEQUENCE: 44

Gly Asp Glu Val Glu Ala Asn Phe Thr
  1               5

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence:Primer
      Y282H s

<400> SEQUENCE: 45
aagtactacg gccacggcgc aggcaac                                          27

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence:Primer
      Y282H as

<400> SEQUENCE: 46
gttgcctgcg ccgtggccgt agtactt                                          27

<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence:Amino Acid
      Sequence Encoded by Primer Set H

<400> SEQUENCE: 47

Lys Tyr Tyr Gly His Gly Ala Gly Asn
  1               5

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence:Primer
      AvrII s

<400> SEQUENCE: 48
gatacggtag acctagggta ccagtgc                                          27

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence:Primer
      AvrII as

<400> SEQUENCE: 49
gcactggtac cctaggtcta ccgtatc                                          27

<210> SEQ ID NO 50
<211> LENGTH: 9
```

```
<212> TYPE: PRT
<213> ORGANISM: Artificial Sequence
<220> FEATURE:
<223> OTHER INFORMATION: Description of Artificial Sequence:Amino Acid
      Sequence Encoded by Primer Set I

<400> SEQUENCE: 50

Asp Thr Val Asp Leu Gly Tyr Gln Cys
  1               5

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence:Primer
      S66D s

<400> SEQUENCE: 51
cggtacccaa ccgattcgaa gagcaaaaag                                        30

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence:Primer
      S66D as

<400> SEQUENCE: 52 cttttttgctc ttcgaatcgg ttgggtaccg                                       30

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence:Amino Acid
      Sequence Encoded by Primer Set J

<400> SEQUENCE: 53

Arg Tyr Pro Thr Asp Ser Lys Ser Lys Lys
  1               5                  10

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence:Primer
      S140Y/D141G s

<400> SEQUENCE: 54
gcgcctcagg ctacggccgg gttattgc                                          28

<210> SEQ ID NO 55
<211> LENGTH: 28
<212> TYPE: DNA
<213> ORGANISM: Artificial Sequence
<220> FEATURE:
<223> OTHER INFORMATION: Description of Artificial Sequence:Primer
      S140Y/D141G as

<400> SEQUENCE: 55
gcaataaccc ggccgtagcc tgaggcgc                                          28

<210> SEQ ID NO 56
```

```
<211> LENGTH: 9
<212> TYPE: PRT
<213> ORGANISM: Artificial Sequence
<220> FEATURE:
<223> OTHER INFORMATION: Description of Artificial Sequence:Amino Acid
      Sequence Encoded by Primer Set K

<400> SEQUENCE: 56

Ala Ser Gly Tyr Gly Arg Val Ile Ala
  1               5

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence:Primer
      S130N s

<400> SEQUENCE: 57
ctggcgcgca atgtggtgcc gtttattc                                      28

<210> SEQ ID NO 58
<211> LENGTH: 28
<212> TYPE: DNA
<213> ORGANISM: Artificial Sequence
<220> FEATURE:
<223> OTHER INFORMATION: Description of Artificial Sequence:Primer
      S130N as

<400> SEQUENCE: 58
gaataaacgg caccacattg cgcgccag                                      28

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence:Amino Acid
      Sequence Encoded by Primer Set L

<400> SEQUENCE: 59

Leu Ala Arg Asn Val Val Pro Phe Ile
  1               5

<210> SEQ ID NO 60
<211> LENGTH: 31
<212> TYPE: DNA
<213> ORGANISM: Artificial Sequence
<220> FEATURE:
<223> OTHER INFORMATION: Description of Artificial Sequence:Primer
      R129L/S130N s

<400> SEQUENCE: 60
gctctggcgc tcaatgtggt gccgtttatt c                                  31

<210> SEQ ID NO 61
<211> LENGTH: 31
<212> TYPE: DNA
<213> ORGANISM: Artificial Sequence
<220> FEATURE:
<223> OTHER INFORMATION: Description of Artificial Sequence:Primer
      R129L/S130N as

<400> SEQUENCE: 61
gaataaacgg caccacattg agcgccagag c                                  31
```

```
<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence:Amino Acid
      Sequence Encoded by Primer Set M

<400> SEQUENCE: 62

Ala Leu Ala Leu Asn Val Val Pro Phe Ile
 1               5                  10

<210> SEQ ID NO 63
<211> LENGTH: 28
<212> TYPE: DNA
<213> ORGANISM: Artificial Sequence
<220> FEATURE:
<223> OTHER INFORMATION: Description of Artificial Sequence:Primer
      K167G/R168Q s

<400> SEQUENCE: 63
gaccatggct ccggacaagc tacgccag                                        28

<210> SEQ ID NO 64
<211> LENGTH: 28
<212> TYPE: DNA
<213> ORGANISM: Artificial Sequence
<220> FEATURE:
<223> OTHER INFORMATION: Description of Artificial Sequence:Primer
      K167G/R168Q as

<400> SEQUENCE: 64
ctggcgtagc ttgtccggag ccatggtc                                        28

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence:Amino Acid
      Sequence Encoded by Primer Set N

<400> SEQUENCE: 65

Asp His Gly Ser Gly Gln Ala Thr Pro
 1               5

<210> SEQ ID NO 66
<211> LENGTH: 64
<212> TYPE: DNA
<213> ORGANISM: Artificial Sequence
<220> FEATURE:
<223> OTHER INFORMATION: Description of Artificial Sequence:FumG27-s
      from Primer Set O

<400> SEQUENCE: 66
ctagggtacc agtgctcccc tgcgacttct catctatggg gcggatactc gccattcttt     60
tcgc                                                                  64

<210> SEQ ID NO 67
<211> LENGTH: 64
<212> TYPE: DNA
<213> ORGANISM: Artificial Sequence
<220> FEATURE:
<223> OTHER INFORMATION: Description of Artificial Sequence:FumG27-as
      from Primer Set O

<400> SEQUENCE: 67
```

```
tcgagcgaaa agaatggcga gtatccgccc catagatgag aagtcgcagg ggagcactgg    60
tacc                                                                 64
```

<210> SEQ ID NO 68
<211> LENGTH: 64
<212> TYPE: DNA
<213> ORGANISM: Artificial Sequence
<220> FEATURE:
<223> OTHER INFORMATION: Description of Artificial Sequence:FumV27-s
      from Primer Set P

<400> SEQUENCE: 68

```
ctagggtacc agtgctcccc tgcgacttct catctatggg gcgtgtactc gccattcttt    60
tcgc                                                                 64
```

<210> SEQ ID NO 69
<211> LENGTH: 64
<212> TYPE: DNA
<213> ORGANISM: Artificial Sequence
<220> FEATURE:
<223> OTHER INFORMATION: Description of Artificial Sequence:FumV27-as
      from Primer Set P

<400> SEQUENCE: 69

```
tcgagcgaaa agaatggcga gtacacgccc catagatgag aagtcgcagg ggagcactgg    60
tacc                                                                 64
```

<210> SEQ ID NO 70
<211> LENGTH: 64
<212> TYPE: DNA
<213> ORGANISM: Artificial Sequence
<220> FEATURE:
<223> OTHER INFORMATION: Description of Artificial Sequence:FumN27-s
      from Primer Set Q

<400> SEQUENCE: 70

```
ctagggtacc agtgctcccc tgcgacttct catctatggg gcaactactc gccattcttt    60
tcgc                                                                 64
```

<210> SEQ ID NO 71
<211> LENGTH: 64
<212> TYPE: DNA
<213> ORGANISM: Artificial Sequence
<220> FEATURE:
<223> OTHER INFORMATION: Description of Artificial Sequence:FumN27-as
      from Primer Set Q

<400> SEQUENCE: 71

```
tcgagcgaaa agaatggcga gtagttgccc catagatgag aagtcgcagg ggagcactgg    60
tacc                                                                 64
```

<210> SEQ ID NO 72
<211> LENGTH: 64
<212> TYPE: DNA
<213> ORGANISM: Artificial Sequence
<220> FEATURE:
<223> OTHER INFORMATION: Description of Artificial Sequence:FumI27-s
      from Primer Set R

<400> SEQUENCE: 72

```
ctagggtacc agtgctcccc tgcgacttct catctatggg gcatctactc gccattcttt    60
tcgc                                                                 64
```

<210> SEQ ID NO 73
<211> LENGTH: 64
<212> TYPE: DNA
<213> ORGANISM: Artificial Sequence
<220> FEATURE:
<223> OTHER INFORMATION: Description of Artificial Sequence:FumI27-as
      from Primer Set R

<400> SEQUENCE: 73
tcgagcgaaa agaatggcga gtagatgccc catagatgag aagtcgcagg ggagcactgg     60
tacc                                                                 64

<210> SEQ ID NO 74
<211> LENGTH: 64
<212> TYPE: DNA
<213> ORGANISM: Artificial Sequence
<220> FEATURE:
<223> OTHER INFORMATION: Description of Artificial Sequence:FumA27-s
      from Primer Set S

<400> SEQUENCE: 74
ctagggtacc agtgctcccc tgcgacttct catctatggg gcgcgtactc gccattcttt     60
tcgc                                                                 64

<210> SEQ ID NO 75
<211> LENGTH: 64
<212> TYPE: DNA
<213> ORGANISM: Artificial Sequence
<220> FEATURE:
<223> OTHER INFORMATION: Description of Artificial Sequence:FumA27-as
      from Primer Set S

<400> SEQUENCE: 75
tcgagcgaaa agaatggcga gtacgcgccc catagatgag aagtcgcagg ggagcactgg     60
tacc                                                                 64

<210> SEQ ID NO 76
<211> LENGTH: 64
<212> TYPE: DNA
<213> ORGANISM: Artificial Sequence
<220> FEATURE:
<223> OTHER INFORMATION: Description of Artificial Sequence:FumT27-s
      from Primer Set T

<400> SEQUENCE: 76
ctagggtacc agtgctcccc tgcgacttct catctatggg gcacgtactc gccattcttt     60
tcgc                                                                 64

<210> SEQ ID NO 77
<211> LENGTH: 64
<212> TYPE: DNA
<213> ORGANISM: Artificial Sequence
<220> FEATURE:
<223> OTHER INFORMATION: Description of Artificial Sequence:FumT27-as
      from Primer Set T

<400> SEQUENCE: 77
tcgagcgaaa agaatggcga gtacgtgccc catagatgag aagtcgcagg ggagcactgg     60
tacc                                                                 64

<210> SEQ ID NO 78
<211> LENGTH: 465
<212> TYPE: PRT

-continued

<213> ORGANISM: Aspergillus fumigatus

<400> SEQUENCE: 78

```
Met Val Thr Leu Thr Phe Leu Leu Ser Ala Ala Tyr Leu Leu Ser Gly
 1               5                  10                  15

Arg Val Ser Ala Ala Pro Ser Ala Gly Ser Lys Ser Cys Asp Thr
             20                  25                  30

Val Asp Leu Gly Tyr Gln Cys Ser Pro Ala Thr Ser His Leu Trp Gly
             35                  40                  45

Gln Tyr Ser Pro Phe Phe Ser Leu Glu Asp Glu Leu Ser Val Ser Ser
         50                  55                  60

Lys Leu Pro Lys Asp Cys Arg Ile Thr Leu Val Gln Val Leu Ser Arg
 65                  70                  75                  80

His Gly Ala Arg Tyr Pro Thr Ser Ser Lys Ser Lys Tyr Lys Lys
                 85                  90                  95

Leu Val Thr Ala Ile Gln Ala Asn Ala Thr Asp Phe Lys Gly Lys Phe
                100                 105                 110

Ala Phe Leu Lys Thr Tyr Asn Tyr Thr Leu Gly Ala Asp Asp Leu Thr
            115                 120                 125

Pro Phe Gly Glu Gln Gln Leu Val Asn Ser Gly Ile Lys Phe Tyr Gln
130                 135                 140

Arg Tyr Lys Ala Leu Ala Arg Ser Val Val Pro Phe Ile Arg Ala Ser
145                 150                 155                 160

Gly Ser Asp Arg Val Ile Ala Ser Gly Glu Lys Phe Ile Glu Gly Phe
                165                 170                 175

Gln Gln Ala Lys Leu Ala Asp Pro Gly Ala Thr Asn Arg Ala Ala Pro
            180                 185                 190

Ala Ile Ser Val Ile Ile Pro Glu Ser Glu Thr Phe Asn Asn Thr Leu
            195                 200                 205

Asp His Gly Val Cys Thr Lys Phe Glu Ala Ser Gln Leu Gly Asp Glu
        210                 215                 220

Val Ala Ala Asn Phe Thr Ala Leu Phe Ala Pro Asp Ile Arg Ala Arg
225                 230                 235                 240

Ala Glu Lys His Leu Pro Gly Val Thr Leu Thr Asp Glu Asp Val Val
                245                 250                 255

Ser Leu Met Asp Met Cys Ser Phe Asp Thr Val Ala Arg Thr Ser Asp
            260                 265                 270

Ala Ser Gln Leu Ser Pro Phe Cys Gln Leu Phe Thr His Asn Glu Trp
        275                 280                 285

Lys Lys Tyr Asn Tyr Leu Gln Ser Leu Gly Lys Tyr Tyr Gly Tyr Gly
290                 295                 300

Ala Gly Asn Pro Leu Gly Pro Ala Gln Gly Ile Gly Phe Thr Asn Glu
305                 310                 315                 320

Leu Ile Ala Arg Leu Thr Arg Ser Pro Val Gln Asp His Thr Ser Thr
                325                 330                 335

Asn Ser Thr Leu Val Ser Asn Pro Ala Thr Phe Pro Leu Asn Ala Thr
            340                 345                 350

Met Tyr Val Asp Phe Ser His Asp Asn Ser Met Val Ser Ile Phe Phe
            355                 360                 365

Ala Leu Gly Leu Tyr Asn Gly Thr Glu Pro Leu Ser Arg Thr Ser Val
        370                 375                 380

Glu Ser Ala Lys Glu Leu Asp Gly Tyr Ser Ala Ser Trp Val Val Pro
385                 390                 395                 400
```

```
Phe Gly Ala Arg Ala Tyr Phe Glu Thr Met Gln Cys Lys Ser Glu Lys
            405                 410                 415

Glu Pro Leu Val Arg Ala Leu Ile Asn Asp Arg Val Val Pro Leu His
            420                 425                 430

Gly Cys Asp Val Asp Lys Leu Gly Arg Cys Lys Leu Asn Asp Phe Val
            435                 440                 445

Lys Gly Leu Ser Trp Ala Arg Ser Gly Gly Asn Trp Gly Glu Cys Phe
            450                 455                 460

Ser
465

<210> SEQ ID NO 79
<211> LENGTH: 465
<212> TYPE: PRT
<213> ORGANISM: Aspergillus fumigatus

<400> SEQUENCE: 79

Met Val Thr Leu Thr Phe Leu Leu Ser Ala Ala Tyr Leu Leu Ser Gly
  1               5                  10                  15

Arg Val Ser Ala Ala Pro Ser Ser Ala Gly Ser Lys Ser Cys Asp Thr
             20                  25                  30

Val Asp Leu Gly Tyr Gln Cys Ser Pro Ala Thr Ser His Leu Trp Gly
         35                  40                  45

Gln Tyr Ser Pro Phe Phe Ser Leu Glu Asp Glu Leu Ser Val Ser Ser
     50                  55                  60

Lys Leu Pro Lys Asp Cys Arg Ile Thr Leu Val Gln Val Leu Ser Arg
 65                  70                  75                  80

His Gly Ala Arg Tyr Pro Thr Ser Ser Lys Ser Lys Tyr Lys Lys
                 85                  90                  95

Leu Val Thr Ala Ile Gln Ala Asn Ala Thr Asp Phe Lys Gly Lys Phe
            100                 105                 110

Ala Phe Leu Lys Thr Tyr Asn Tyr Thr Leu Gly Ala Asp Asp Leu Thr
            115                 120                 125

Pro Phe Gly Glu Gln Gln Leu Val Asn Ser Gly Ile Lys Phe Tyr Gln
        130                 135                 140

Arg Tyr Lys Ala Leu Ala Arg Ser Val Val Pro Phe Ile Arg Ala Ser
145                 150                 155                 160

Gly Ser Asp Arg Val Ile Ala Ser Gly Glu Lys Phe Ile Glu Gly Phe
                165                 170                 175

Gln Gln Ala Lys Leu Ala Asp Pro Gly Ala Thr Asn Arg Ala Ala Pro
            180                 185                 190

Ala Ile Ser Val Ile Ile Pro Glu Ser Glu Thr Phe Asn Asn Thr Leu
            195                 200                 205

Asp His Gly Val Cys Thr Lys Phe Glu Ala Ser Gln Leu Gly Asp Glu
        210                 215                 220

Val Ala Ala Asn Phe Thr Ala Leu Phe Ala Pro Asp Ile Arg Ala Arg
225                 230                 235                 240

Ala Glu Lys His Leu Pro Gly Val Thr Leu Thr Asp Glu Asp Val Val
                245                 250                 255

Ser Leu Met Asp Met Cys Ser Phe Asp Thr Val Ala Arg Thr Ser Asp
            260                 265                 270

Ala Ser Gln Leu Ser Pro Phe Cys Gln Leu Phe Thr His Asn Glu Trp
        275                 280                 285

Lys Lys Tyr Asn Tyr Leu Gln Ser Leu Gly Lys Tyr Tyr Gly Tyr Gly
        290                 295                 300
```

```
Ala Gly Asn Pro Leu Gly Pro Ala Gln Gly Ile Gly Phe Thr Asn Glu
305                 310                 315                 320

Leu Ile Ala Arg Leu Thr Arg Ser Pro Val Gln Asp His Thr Ser Thr
            325                 330                 335

Asn Ser Thr Leu Val Ser Asn Pro Ala Thr Phe Pro Leu Asn Ala Thr
            340                 345                 350

Met Tyr Val Asp Phe Ser His Asp Asn Ser Met Val Ser Ile Phe Phe
            355                 360                 365

Ala Leu Gly Leu Tyr Asn Gly Thr Glu Gly Leu Ser Arg Thr Ser Val
    370                 375                 380

Glu Ser Ala Lys Glu Leu Asp Gly Tyr Ser Ala Ser Trp Val Val Pro
385                 390                 395                 400

Phe Gly Ala Arg Ala Tyr Phe Glu Thr Met Gln Cys Lys Ser Glu Lys
            405                 410                 415

Glu Pro Leu Val Arg Ala Leu Ile Asn Asp Arg Val Val Pro Leu His
            420                 425                 430

Gly Cys Asp Val Asp Lys Leu Gly Arg Cys Lys Leu Asn Asp Phe Val
            435                 440                 445

Lys Gly Leu Ser Trp Ala Arg Ser Gly Gly Asn Trp Gly Glu Cys Phe
    450                 455                 460

Ser
465

<210> SEQ ID NO 80
<211> LENGTH: 465
<212> TYPE: PRT
<213> ORGANISM: Aspergillus fumigatus

<400> SEQUENCE: 80

Met Val Thr Leu Thr Phe Leu Leu Ser Ala Ala Tyr Leu Leu Ser Gly
1               5                   10                  15

Arg Val Ser Ala Ala Pro Ser Ser Ala Gly Ser Lys Ser Cys Asp Thr
            20                  25                  30

Val Asp Leu Gly Tyr Gln Cys Ser Pro Ala Thr Ser His Leu Trp Gly
        35                  40                  45

Gln Tyr Ser Pro Phe Phe Ser Leu Glu Asp Glu Leu Ser Val Ser Ser
    50                  55                  60

Lys Leu Pro Lys Asp Cys Arg Ile Thr Leu Val Gln Val Leu Ser Arg
65                  70                  75                  80

His Gly Ala Arg Tyr Pro Thr Ser Ser Lys Ser Lys Tyr Lys Lys
                85                  90                  95

Leu Val Thr Ala Ile Gln Ala Asn Ala Thr Asp Phe Lys Gly Lys Phe
            100                 105                 110

Ala Phe Leu Lys Thr Tyr Asn Tyr Thr Leu Gly Ala Asp Asp Leu Thr
            115                 120                 125

Pro Phe Gly Glu Gln Gln Leu Val Asn Ser Gly Ile Lys Phe Tyr Gln
    130                 135                 140

Arg Tyr Lys Ala Leu Ala Arg Ser Val Val Pro Phe Ile Arg Ala Ser
145                 150                 155                 160

Gly Ser Asp Arg Val Ile Ala Ser Gly Glu Lys Phe Ile Glu Gly Phe
                165                 170                 175

Gln Gln Ala Lys Leu Ala Asp Pro Gly Ala Thr Asn Arg Ala Ala Pro
            180                 185                 190

Ala Ile Ser Val Ile Ile Pro Glu Ser Glu Thr Phe Asn Asn Thr Leu
```

```
                      195                 200                 205
Asp His Gly Val Cys Thr Lys Phe Glu Ala Ser Gln Leu Gly Asp Glu
    210                 215                 220

Val Ala Ala Asn Phe Thr Ala Leu Phe Ala Pro Asp Ile Arg Ala Arg
225                 230                 235                 240

Ala Glu Lys His Leu Pro Gly Val Thr Leu Thr Asp Glu Asp Val Val
                245                 250                 255

Ser Leu Met Asp Met Cys Ser Phe Asp Thr Val Ala Arg Thr Ser Asp
                260                 265                 270

Ala Ser Gln Leu Ser Pro Phe Cys Gln Leu Phe Thr His Asn Glu Trp
            275                 280                 285

Lys Lys Tyr Asn Tyr Leu Gln Ser Leu Gly Lys Tyr Tyr Gly Tyr Gly
    290                 295                 300

Ala Gly Asn Pro Leu Gly Pro Ala Gln Gly Ile Gly Phe Thr Asn Glu
305                 310                 315                 320

Leu Ile Ala Arg Leu Thr Arg Ser Pro Val Gln Asp His Thr Ser Thr
                325                 330                 335

Asn Ser Thr Leu Val Ser Asn Pro Ala Thr Phe Pro Leu Asn Ala Thr
                340                 345                 350

Met Tyr Val Asp Phe Ser His Asp Asn Ser Met Val Ser Ile Phe Phe
            355                 360                 365

Ala Leu Gly Leu Tyr Asn Gly Thr Glu Pro Leu Ser Arg Thr Ser Val
    370                 375                 380

Glu Ser Ala Lys Glu Leu Asp Gly Tyr Ser Ala Ser Trp Val Val Pro
385                 390                 395                 400

Phe Gly Ala Arg Ala Tyr Phe Glu Thr Met Gln Cys Lys Ser Glu Lys
                405                 410                 415

Glu Ser Leu Val Arg Ala Leu Ile Asn Asp Arg Val Val Pro Leu His
                420                 425                 430

Gly Cys Asp Val Asp Lys Leu Gly Arg Cys Lys Leu Asn Asp Phe Val
            435                 440                 445

Lys Gly Leu Ser Trp Ala Arg Ser Gly Gly Asn Trp Gly Glu Cys Phe
    450                 455                 460

Ser
465

<210> SEQ ID NO 81
<211> LENGTH: 465
<212> TYPE: PRT
<213> ORGANISM: Aspergillus fumigatus

<400> SEQUENCE: 81

Met Val Thr Leu Thr Phe Leu Leu Ser Ala Ala Tyr Leu Leu Ser Gly
  1               5                  10                  15

Arg Val Ser Ala Ala Pro Ser Ser Ala Gly Ser Lys Ser Cys Asp Thr
                20                  25                  30

Val Asp Leu Gly Tyr Gln Cys Ser Pro Ala Thr Ser His Leu Trp Gly
            35                  40                  45

Gln Tyr Ser Pro Phe Phe Ser Leu Glu Asp Glu Leu Ser Val Ser Ser
     50                  55                  60

Lys Leu Pro Lys Asp Cys Arg Ile Thr Leu Val Gln Val Leu Ser Arg
 65                  70                  75                  80

His Gly Ala Arg Tyr Pro Thr Ser Ser Lys Ser Lys Tyr Lys Lys
                85                  90                  95
```

```
Leu Val Thr Ala Ile Gln Ala Asn Ala Thr Asp Phe Lys Gly Lys Phe
            100                 105                 110

Ala Phe Leu Lys Thr Tyr Asn Tyr Thr Leu Gly Ala Asp Asp Leu Thr
            115                 120                 125

Ala Phe Gly Glu Gln Gln Leu Val Asn Ser Gly Ile Lys Phe Tyr Gln
            130                 135                 140

Arg Tyr Lys Ala Leu Ala Arg Ser Val Val Pro Phe Ile Arg Ala Ser
145                 150                 155                 160

Gly Ser Asp Arg Val Ile Ala Ser Gly Glu Lys Phe Ile Glu Gly Phe
                165                 170                 175

Gln Gln Ala Lys Leu Ala Asp Pro Gly Ala Thr Asn Arg Ala Ala Pro
                180                 185                 190

Ala Ile Ser Val Ile Ile Pro Glu Ser Glu Thr Phe Asn Asn Thr Leu
                195                 200                 205

Asp His Gly Val Cys Thr Lys Phe Glu Ala Ser Gln Leu Gly Asp Glu
            210                 215                 220

Val Ala Ala Asn Phe Thr Ala Leu Phe Ala Pro Asp Ile Arg Ala Arg
225                 230                 235                 240

Ala Lys Lys His Leu Pro Gly Val Thr Leu Thr Asp Glu Asp Val Val
                245                 250                 255

Ser Leu Met Asp Met Cys Ser Phe Asp Thr Val Ala Arg Thr Ser Asp
            260                 265                 270

Ala Ser Gln Leu Ser Pro Phe Cys Gln Leu Phe Thr His Asn Glu Trp
            275                 280                 285

Lys Lys Tyr Asn Tyr Leu Gln Ser Leu Gly Lys Tyr Tyr Gly Tyr Gly
        290                 295                 300

Ala Gly Asn Pro Leu Gly Pro Ala Gln Gly Ile Gly Phe Thr Asn Glu
305                 310                 315                 320

Leu Ile Ala Arg Leu Thr Arg Ser Pro Val Gln Asp His Thr Ser Thr
                325                 330                 335

Asn Ser Thr Leu Val Ser Asn Pro Ala Thr Phe Pro Leu Asn Ala Thr
            340                 345                 350

Met Tyr Val Asp Phe Ser His Asp Asn Ser Met Val Ser Ile Phe Phe
            355                 360                 365

Ala Leu Gly Leu Tyr Asn Gly Thr Glu Pro Leu Ser Arg Thr Ser Val
            370                 375                 380

Glu Ser Ala Lys Glu Leu Asp Gly Tyr Ser Ala Ser Trp Val Val Pro
385                 390                 395                 400

Phe Gly Ala Arg Ala Tyr Phe Glu Thr Met Gln Cys Lys Ser Glu Lys
                405                 410                 415

Glu Pro Leu Val Arg Ala Leu Ile Asn Asp Arg Val Val Pro Leu His
            420                 425                 430

Gly Cys Asp Val Asp Lys Leu Gly Arg Cys Lys Leu Asn Asp Phe Val
            435                 440                 445

Lys Gly Leu Ser Trp Ala Arg Ser Gly Gly Asn Trp Gly Glu Cys Phe
        450                 455                 460

Ser
465

<210> SEQ ID NO 82
<211> LENGTH: 469
<212> TYPE: PRT
<213> ORGANISM: Aspergillus fumigatus

<400> SEQUENCE: 82
```

-continued

```
Met Gly Ala Leu Thr Phe Leu Leu Ser Val Met Tyr Leu Leu Ser Gly
 1               5                  10                  15

Val Ala Gly Ala Pro Ser Ser Gly Cys Ser Ala Gly Ser Gly Ser Lys
             20                  25                  30

Ala Cys Asp Thr Val Glu Leu Gly Tyr Gln Cys Ser Pro Gly Thr Ser
             35                  40                  45

His Leu Trp Gly Gln Tyr Ser Pro Phe Phe Ser Leu Glu Asp Glu Leu
         50                  55                  60

Ser Val Ser Ser Asp Leu Pro Lys Asp Cys Arg Val Thr Phe Val Gln
 65                  70                  75                  80

Val Leu Ser Arg His Gly Ala Arg Tyr Pro Thr Ala Ser Lys Ser Lys
                 85                  90                  95

Lys Tyr Lys Lys Leu Val Thr Ala Ile Gln Lys Asn Ala Thr Glu Phe
                100                 105                 110

Lys Gly Lys Phe Ala Phe Leu Glu Thr Tyr Asn Tyr Thr Leu Gly Ala
            115                 120                 125

Asp Asp Leu Thr Pro Phe Gly Glu Gln Gln Met Val Asn Ser Gly Ile
        130                 135                 140

Lys Phe Tyr Gln Lys Tyr Lys Ala Leu Ala Gly Ser Val Val Pro Phe
145                 150                 155                 160

Ile Arg Ser Ser Gly Ser Asp Arg Val Ile Ala Ser Gly Glu Lys Phe
                165                 170                 175

Ile Glu Gly Phe Gln Gln Ala Asn Val Ala Asp Pro Gly Ala Thr Asn
            180                 185                 190

Arg Ala Ala Pro Val Ile Ser Val Ile Ile Pro Glu Ser Glu Thr Tyr
        195                 200                 205

Asn Asn Thr Leu Asp His Ser Val Cys Thr Asn Phe Glu Ala Ser Glu
210                 215                 220

Leu Gly Asp Glu Val Glu Ala Asn Phe Thr Ala Leu Phe Ala Pro Ala
225                 230                 235                 240

Ile Arg Ala Arg Ile Glu Lys His Leu Pro Gly Val Gln Leu Thr Asp
                245                 250                 255

Asp Asp Val Val Ser Leu Met Asp Met Cys Ser Phe Asp Thr Val Ala
            260                 265                 270

Arg Thr Ala Asp Ala Ser Glu Leu Ser Pro Phe Cys Ala Ile Phe Thr
        275                 280                 285

His Asn Glu Trp Lys Lys Tyr Asp Tyr Leu Gln Ser Leu Gly Lys Tyr
290                 295                 300

Tyr Gly Tyr Gly Ala Gly Asn Pro Leu Gly Pro Ala Gln Gly Ile Gly
305                 310                 315                 320

Phe Thr Asn Glu Leu Ile Ala Arg Leu Thr Asn Ser Pro Val Gln Asp
                325                 330                 335

His Thr Ser Thr Asn Ser Thr Leu Asp Ser Asp Pro Ala Thr Phe Pro
            340                 345                 350

Leu Asn Ala Thr Ile Tyr Val Asp Phe Ser His Asp Asn Gly Met Ile
        355                 360                 365

Pro Ile Phe Phe Ala Met Gly Leu Tyr Asn Gly Thr Glu Pro Leu Ser
370                 375                 380

Gln Thr Ser Glu Glu Ser Thr Lys Glu Ser Asn Gly Tyr Ser Ala Ser
385                 390                 395                 400

Trp Ala Val Pro Phe Gly Ala Arg Ala Tyr Phe Glu Thr Met Gln Cys
                405                 410                 415
```

```
Lys Ser Glu Lys Glu Pro Leu Val Arg Ala Leu Ile Asn Asp Arg Val
        420             425             430

Val Pro Leu His Gly Cys Ala Val Asp Lys Leu Gly Arg Cys Lys Leu
        435             440             445

Lys Asp Phe Val Lys Gly Leu Ser Trp Ala Arg Ser Gly Gly Asn Ser
    450             455             460

Glu Gln Ser Phe Ser
465
```